United States Patent
Šimo et al.

(10) Patent No.: US 8,067,423 B2
(45) Date of Patent: Nov. 29, 2011

(54) POLYMORPHS OF DASATINIB ISOPROPYL ALCOHOL AND PROCESS FOR PREPARATION THEREOF

(75) Inventors: Ondrej Šimo, Trnava (SK); Jiří Filipčík, Rýmařov (CZ); Alexandr Martaus, Ostrava (CZ); Alexandr Jegorov, Dobrá Voda (CZ); Aleš Gavenda, Ostrava-Lhotka (CZ); Judith Aronhime, Rehovot (IL); Pavel Vraspir, Rýmařov (CZ); Tamás Koltai, Netanya (IL); Jiří Faustmann, Opava (CZ); Roman Gabriel, Olomouc (CZ)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 40 days.

(21) Appl. No.: 12/257,338

(22) Filed: Oct. 23, 2008

(65) Prior Publication Data

US 2009/0118297 A1 May 7, 2009

Related U.S. Application Data

(60) Provisional application No. 60/999,998, filed on Oct. 23, 2007, provisional application No. 61/008,699, filed on Dec. 20, 2007, provisional application No. 61/019,106, filed on Jan. 4, 2008, provisional application No. 61/039,011, filed on Mar. 24, 2008, provisional application No. 61/041,384, filed on Apr. 1, 2008, provisional application No. 61/052,513, filed on May 12, 2008, provisional application No. 61/055,309, filed on May 22, 2008, provisional application No. 61/056,876, filed on May 29, 2008, provisional application No. 61/061,054, filed on Jun. 12, 2008, provisional application No. 61/073,628, filed on Jun. 18, 2008, provisional application No. 61/079,548, filed on Jul. 10, 2008, provisional application No. 61/080,382, filed on Jul. 14, 2008, provisional application No. 61/091,607, filed on Aug. 25, 2008.

(51) Int. Cl.
*A01N 43/54* (2006.01)

(52) U.S. Cl. ......... 514/256; 544/328; 544/359; 548/202

(58) Field of Classification Search .................. 514/256; 544/328, 359; 548/202
See application file for complete search history.

(56) References Cited

U.S. PATENT DOCUMENTS

| | | | |
|---|---|---|---|
| 4,728,653 A | 3/1988 | Campbell et al. | |
| 5,250,534 A | 10/1993 | Bell et al. | |
| 6,333,198 B1 | 12/2001 | Edmeades et al. | |
| 6,596,746 B1 | 7/2003 | Das et al. | |
| 6,976,694 B1 | 12/2005 | Rayl et al. | |
| 7,091,223 B2 | 8/2006 | Das et al. | |
| 7,125,875 B2 | 10/2006 | Das et al. | |
| 7,153,856 B2 | 12/2006 | Barrish et al. | |
| 7,189,854 B2 | 3/2007 | Das et al. | |
| 7,408,069 B2 | 8/2008 | Schaefer et al. | |
| 7,491,725 B2 | 2/2009 | Lajeunesse et al. | |
| 2005/0176965 A1 | 8/2005 | Chen et al. | |
| 2005/0215795 A1 | 9/2005 | Chen et al. | |
| 2006/0004067 A1 | 1/2006 | Chen et al. | |
| 2006/0211705 A1 | 9/2006 | Arora et al. | |
| 2007/0037978 A1 | 2/2007 | Schaefer et al. | |
| 2007/0219370 A1 | 9/2007 | Sun et al. | |
| 2009/0149650 A1 | 6/2009 | Chen et al. | |

FOREIGN PATENT DOCUMENTS

| | | |
|---|---|---|
| EP | 463756 | 4/1995 |
| WO | WO 00/62778 | 10/2000 |
| WO | WO 2004/085388 | 10/2004 |
| WO | WO 2005/076990 | 8/2005 |
| WO | WO 2005/077945 | 8/2005 |
| WO | WO 2007/019210 | 2/2007 |
| WO | WO 2007/035874 | 3/2007 |

OTHER PUBLICATIONS

Zhao, et al., "A new facile synthesis of 2-aminothiazole-5-carboxylates," Tetrahedron Letters, 42: 2102-02 (2001).
Caira, "Crystalline Polymorphism of Organic Compounds", Topics in Current Chemistry, Springer, Berlin, DE, Jan. 1, 1998, vol. 198, p. 163-208.
Das et al., "2-aminothiazole as a Novel Kinase Inhibitor Template. Structure-Activity Relationship Studies Toward the Discovery of N-(2-Chloro-6-methylphenyl)-2-[[6-[4-(2-hydroxyethyl)-1-piperazinyl)]2-methyl-4-pyrimidinyl]amino)]-1,3-thiazole-5-carboxamide (Dasatinib, BMS-354825) as a Potent pan-Src Kinase Inh", Journal of Medicinal Chemistry, Nov. 2006, vol. 49, No. 23, p. 6819-6832.
Strobel et al., Chemical Instrumentation: A Systematic Approach, 3rd ed., Wiley & Sons: New York, p. 391-393, 879,894, 922, 924, 925, 953 (1989).
Snyder et al., Introduction to Modern Liquid Chromatography, 2nd ed., John Wiley & Sons, New York, p. 571-572, 549, 552 (1979).
International Search Report and Written Opinion of ISA, dated Oct. 15, 2009, from corresponding International Patent Application PCT/IB2008/003862.

*Primary Examiner* — James O. Wilson
*Assistant Examiner* — Douglas M Willis
(74) *Attorney, Agent, or Firm* — Kenyon & Kenyon LLP

(57) ABSTRACT

The invention provides crystalline forms of isopropyl alcohol solvate of dasatinib, methods for their preparation, and pharmaceutical compositions thereof.

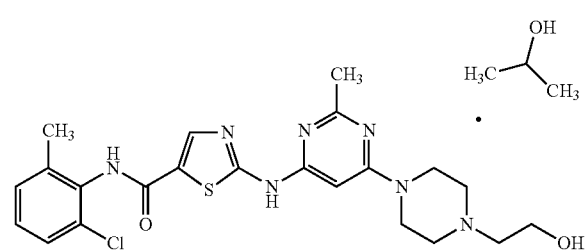

20 Claims, 68 Drawing Sheets

Calculated (top) and observed XRPD diffractogram (bottom) of Dasatinib IPA solvate (Form A3).

PXRD pattern of Dasatinib form BA

Microscope image of dasatinib form A3

Microscope image of dasatinib form A21

US 8,067,423 B2

POLYMORPHS OF DASATINIB ISOPROPYL ALCOHOL AND PROCESS FOR PREPARATION THEREOF

CROSS REFERENCE TO RELATED APPLICATIONS

The present invention claims the benefit of the following United States Provisional Patent Application Nos. 60/999,998, filed Oct. 23, 2007; 61/008,699, filed Dec. 20, 2007; 61/019,106, filed Jan. 4, 2008; 61/039,011, filed Mar. 24, 2008; 61/041,384, filed Apr. 1, 2008; 61/052,513, filed May 12, 2008; 61/055,309, filed May 22, 2008; 61/056,876, filed May 29, 2008; 61/061,054, filed Jun. 12, 2008; 61/073,628, filed Jun. 18, 2008; 61/079,548, filed Jul. 10, 2008; 61/080,382, filed Jul. 14, 2008; and 61/091,607, filed Aug. 25, 2008. The contents of these applications are incorporated herein by reference.

FIELD OF THE INVENTION

The present invention relates to polymorphs of dasatinib, process for preparing said polymorphs, and pharmaceutical compositions thereof.

BACKGROUND OF THE INVENTION

Dasatinib, N-(2-chloro-6-methylphenyl)-2-[[6-[4-(2-hydroxyethyl)-1-piperazinyl]-2-methyl-4-pyrimidinyl]amino]-5-thiazole carboxamide a compound having the following chemical structure:

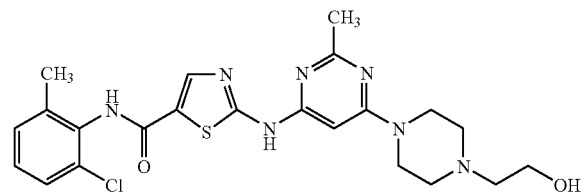

also known as BMS-354825, is a drug produced by Bristol-Myers Squibb and sold under the trade name Sprycel®. Dasatinib is an oral dual BCR/ABL and Src family tyrosine kinases inhibitor approved for use in patients with chronic yelogenous leukemia (CML) after imatinib treatemant and Philadelphia chromosome-positive acute lymphoblastic leukemia (Ph+ ALL). It is also being assessed for use in metastatic melanoma.

A Preparation of dasatinib is described in U.S. Pat. No. 6,596,746 B1; where the process is done by reacting compound 1 of the following formula:

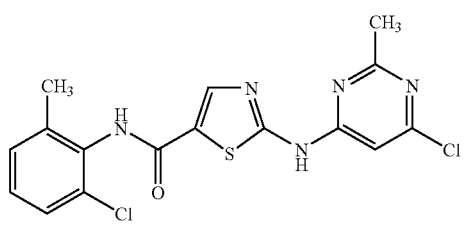

with N-(2-hydroxyethyl)piperazine at 80° C. Several crystalline forms are described in the literature, these were designated forms H1-7, BU-2, E2-1, N-6, T1H1-7, and T1E2-1. Crystalline dasatinib monohydrate (H1-7) and butanol solvate (BU-2) along with the processes for their preparation are described in WO2005/077945A2. In addition US2006/0004067A1, which is continuation of WO 2005/077945 A2 also describes two ethanol solvates (E2-1; T1E2-1) and two anhydrous forms (N-6; T1H1-7)

The present invention describes the preparation of new forms of dasatinib.

Polymorphism, the occurrence of different crystal forms, is a property of some compounds and compound complexes. A single compound, like dasatinib, may give rise to a variety of crystalline forms having distinct crystal structures and physical characteristics like melting point, x-ray diffraction pattern, infrared absorption fingerprint, and solid state NMR spectrum. One crystalline form may give rise to thermal behavior different from that of another crystalline form. Thermal behavior can be measured in the laboratory by such techniques as capillary melting point, thermogravimetric analysis ("TGA"), and differential scanning calorimetry ("DSC") as well as content of solvent in the crystalline form, which have been used to distinguish polymorphic forms.

The difference in the physical properties of different crystalline forms results from the orientation and intermolecular interactions of adjacent molecules or complexes in the bulk solid. Accordingly, polymorphs are distinct solids sharing the same molecular formula yet having distinct advantageous physical properties compared to other crystalline forms of the same compound or complex.

One of the most important physical properties of pharmaceutical compounds is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. Different crystalline forms or polymorphs of the same pharmaceutical compounds can and reportedly do have different aqueous solubilities.

The discovery of new polymorphic forms and solvates of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. Therefore, there is a need for additional solid state forms of dasatinib.

BRIEF SUMMARY OF THE INVENTION

In one embodiment the present invention encompasses a solvate of dasatinib selected from the group consisting of: an n-propanol-dimethylsulfoxide ("DMSO") solvate of dasatinib, a DMSO solvate of dasatinib, a hemi tetrahydrofuran ("THF") solvate of dasatinib, a 2-methyl-tetrahydrofuran ("2-methyl THF") solvate of dasatinib, a hemi 1,4-dioxane solvate of dasatinib, a pyridine solvate of dasatinib, a toluene solvate of dasatinib, a methyl isobutyl ketone ("MIBK") solvate of dasatinib, a mono acetone solvate of dasatinib, an iso-propanol ("IPA")-DMSO solvate of dasatinib, a 2-butanol-DMSO solvate of dasatinib, an IPA-DMF solvate of dasatinib, an IPA solvate of dasatinib, an n-propanol-DMF solvate of dasatinib, an n-propanol solvate of dasatinib, a 2-butanol-DMF solvate of dasatinib, a 2-butanol solvate of dasatinib, an n-butanol-DMSO solvate of dasatinib, a DMF-water solvate of dasatinib, a DMF solvate of dasatinib, a methyl isopropyl ketone ("MIPK") solvate of dasatinib, a dimethoxyethane solvate of dasatinib, a cellosolve solvate of dasatinib, a methylacetate solvate of dasatinib, a methanol solvate of dasatinib, an ethylacetate solvate of dasatinib, a 2-pentanole solvate of dasatinib, a dimethyl carbonate solvate of dasatinib, an isopropylacetate solvate of dasatinib, a ethyleneglycol solvate of dasatinib, a dichloromethane solvate of dasatinib, a methylformate solvate of dasatinib, a tert-butanol solvate of dasatinib, a dimethoxyethane solvate of dasatinib, a methylethylketone ("MEK") solvate of dasatinib, a monochlorobenzene solvate of dasatinib, a propylene glycol monoethyl ether ("PGME") solvate of dasatinib, a glycerol solvate of dasatinib, a cyclopentyl methyl ether solvate of dasatinib, a methyl tert butyl ether ("MTBE") solvate of dasatinib, an amylalcohol solvate of dasatinib, and a glycerol formal solvate of dasatinib.

In one embodiment, the present invention encompasses an IPA solvate of dasatinib characterized by data selected from the group consisting of: a PXRD pattern having any 3 peaks selected from the list consisting of: 6.0, 11.9, 12.0, 14.9, 17.9, 18.3, 18.8, 21.4, 22.9, 24.2 and 24.7±0.2 degrees 2-theta, a powder XRD pattern as depicted in FIG. 18, a solid-state $^{13}$C NMR spectrum having signals at about 139.2 and 127.6±0.2 ppm; a solid-state $^{13}$C NMR spectrum having chemical shifts differences between the signal exhibiting the lowest chemical shift and another in the chemical shift range of 100 to 180 ppm of about 14.2 and 2.6±0.1 ppm; a unit cell with parameters as determined by crystal structure determination using synchrotron powder diffraction data approximately equal to the following:

| Cell dimensions: | |
|---|---|
| Cell length a | 14.9942(5) Å |
| Cell length b | 8.45434(22) Å |
| Cell length c | 22.6228(16) Å |
| Cell angle alpha | 90.0° |
| Cell angle beta | 95.890(4)° |
| Cell angle gamma | 90.0° |
| Cell volume | 2852.67(21) Å$^3$ |
| Symmetry cell setting | monoclinic |
| Symmetry space group name | P 2$_1$/c, | a PXRD pattern and calculated PXRD pattern as depicted in FIG. 96; and a combination thereof. This form can be designated as form A3.

In another embodiment, the present invention encompasses a process for preparing the IPA solvate of dasatinib characterized by data selected from the group consisting of: a PXRD pattern having any 3 peaks selected from the list consisting of: 6.0, 11.9, 12.0, 14.9, 17.9, 18.3, 18.8, 21.4, 22.9, 24.2 and 24.7±0.2 degrees 2-theta, a powder XRD pattern as depicted in FIG. 18, and combination thereof comprising crystallizing dasatinib from a mixture of IPA and water.

In one embodiment the present invention encompasses an Isopropanol ("IPA")-DMSO solvate of dasatinib characterized by data selected from the group consisting of: a PXRD pattern having any 3 peaks selected from the group consisting of: 6.0, 12.0, 15.0, 18.0, 18.3, 18.9, 21.2, 21.5, 22.9, 24.1, and 24.6±0.1 degrees 2-theta, a powder XRD pattern as depicted in FIG. 11, and a combination thereof. The peak positions are calibrated by means of silicon internal standard.

In another embodiment the present invention encompasses a process for preparing the iso-propanol ("IPA")-DMSO solvate of dasatinib characterized by data selected from the group consisting of: a PXRD pattern having any 3 peaks selected from the group consisting of: 6.0, 12.0, 15.0, 18.0, 18.3, 18.9, 21.2, 21.5, 22.9, 24.1, and 24.6±0.1 degrees 2-theta, a powder XRD pattern as depicted in FIG. 11, and a combination thereof comprising crystallizing dasatinib from a mixture comprising the compound of formula 1, N-(2-hydroxyethyl) piperazine of the following formula;

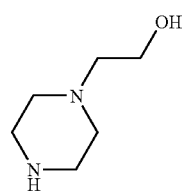

N-ethyldiisopropylamine of the following formula;

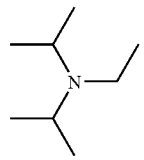

and a mixture of DMSO and IPA by reacting compound 1, N-(2-hydroxyethyl) piperazine, and N-ethyldiisopropylamine in DMSO at a temperature of about 76° C. to about 85° C. to obtain a solution comprising dasatinib, and adding IPA to obtain a suspension comprising said crystalline form.

In one embodiment the present invention encompasses an IPA-DMSO solvate of dasatinib characterized by data selected from the group consisting of: a PXRD pattern having any 3 peaks selected from the list consisting of: 6.0, 11.8, 18.2, 20.8, 23.8, 24.3 and 25.5±0.1 degrees 2-theta, a powder XRD pattern as depicted in FIG. 118, a solid-state $^{13}$C NMR spectrum having signals at about 139.5 and 127.9±0.2 ppm; and a solid-state $^{13}$C NMR spectrum having chemical shifts differences between the signal exhibiting the lowest chemical shift and another in the chemical shift range of 100 to 180 ppm of about 14.4 and 2.8±0.1 ppm; and a combination thereof. The peak positions are calibrated by means of silicon internal standard.

In another embodiment the present invention encompasses a process for preparing the IPA-DMSO solvate of dasatinib characterized by data selected from the group consisting of: a PXRD pattern having peaks at about 6.0, 20.8 and 24.3±0.1 degrees 2-theta, a powder XRD pattern as depicted in FIG. 118, and combination thereof comprising crystallizing dasatinib from a mixture comprising the compound 1, N-(2-hydroxyethyl) piperazine, N-ethyldiisopropylamine and a mixture of DMSO and IPA by reacting compound 1, N-(2-hydroxyethyl)piperazine, and N-ethyldiisopropylamine in DMSO at a temperature of about 65° C. to about 75° C. to obtain a solution comprising dasatinib, and adding IPA to obtain a suspension comprising said crystalline form.

In one embodiment the present invention encompasses an anhydrous dasatinib characterized by data selected from the group consisting of: a PXRD pattern having any 5 peaks selected from the group consisting of: 7.2, 11.9, 14.4, 16.5, 17.3, 19.1, 20.8, 22.4, 23.8, 25.3 and 29.1±0.2 degrees 2-theta, a powder XRD pattern as depicted in FIG. 2, and a combination thereof.

In another embodiment the present invention encompasses a process for preparing the anhydrous dasatinib characterized by data selected from the group consisting of: a PXRD pattern having any 5 peaks selected from the group consisting of: 7.2, 11.9, 14.4, 16.5, 17.3, 19.1, 20.8, 22.4, 23.8, 25.3 and 29.1±0.2 degrees 2-theta, a powder XRD pattern as depicted in FIG. 2, and a combination thereof comprising crystallizing dasatinib from a mixture comprising the compound 1, N-(2-hydroxyethyl) piperazine N-ethyldiisopropylamine, and a mixture of DMSO, methanol and water.

In another embodiment the present invention encompasses a process for preparing the anhydrous dasatinib characterized by data selected from the group consisting of: a PXRD pattern having any 5 peaks selected from the group consisting of: 7.2, 11.9, 14.4, 16.5, 17.3, 19.1, 20.8, 22.4, 23.8, 25.3 and 29.1±0.2 degrees 2-theta, a powder XRD pattern as depicted in FIG. 2, and a combination thereof comprising crystallizing dasatinib from a mixture comprising ethanol and water.

In yet another embodiment the present invention encompasses a process for preparing the anhydrous dasatinib characterized by data selected from the group consisting of: a PXRD pattern having any 5 peaks selected from the group consisting of: 7.2, 11.9, 14.4, 16.5, 17.3, 19.1, 20.8, 22.4, 23.8, 25.3 and 29.1±0.2 degrees 2-theta, a powder XRD pattern as depicted in FIG. 2, and a combination thereof comprising providing an opalescent solution of dasatinib in methanol, and precipitating said crystalline form to obtain a suspension.

In another embodiment, the present invention encompasses an n-propanol-DMSO solvate of dasatinib characterized by data selected from the group consisting of: a PXRD pattern having any 3 peaks selected from the group consisting of: 6.0, 11.9, 12.0, 14.9, 17.8, 18.3, 18.7, 21.4, 22.9, 24.2 and 24.7±0.2 degrees 2-theta, a powder XRD pattern as depicted in FIG. 1, and a combination thereof.

In another embodiment the present invention encompasses a DMSO solvate of dasatinib characterized by data selected from the group consisting of: a PXRD pattern having any 3 peaks selected from the group consisting of: 6.1, 11.8, 15.1, 16.6, 18.2, 19.3, 20.8, 21.6, 23.0, 23.8, 24.3, 24.8 and 25.5±0.2 degrees 2-theta, a powder XRD pattern as depicted in FIG. 3, a solid-state $^{13}$C NMR spectrum having signals at about 139.1 and 128.1±0.2 ppm; a solid-state $^{13}$C NMR spectrum having chemical shifts differences between the signal exhibiting the lowest chemical shift and another in the chemical shift range of 100 to 180 ppm of about 13.9 and 2.9±0.1 ppm; and a combination thereof.

In another embodiment the present invention encompasses a THF solvate of dasatinib characterized by data selected from the group consisting of: a PXRD pattern having any 3 peaks selected from the group consisting of: 5.9, 11.8, 12.2, 14.8, 18.3, 18.6, 21.5, 21.8, 24.5, 25.0, and 26.1±0.2 degrees 2-theta, a powder XRD pattern as depicted in FIG. 4, and a combination thereof.

In another embodiment the present invention encompasses a 2-methyl-THF solvate of dasatinib characterized by data selected from the group consisting of: PXRD pattern having any 3 peaks selected from the group consisting of: 6.0, 11.7, 12.8, 13.2, 17.5, 18.0, 18.4, 20.2, 22.8, 26.3 and 27.0±0.2 degrees 2-theta, a powder XRD pattern as depicted in FIG. 5, and a combination thereof.

In another embodiment the present invention encompasses a 1,4-dioxane solvate of dasatinib characterized by data selected from the group consisting of: PXRD pattern having any 3 peaks selected from the group consisting of: 6.0, 12.0, 14.9, 17.9, 18.2, 18.8, 20.8, 21.2, 22.8, 24.1 24.1, 24.6 and 25.7±0.2 degrees 2-theta, a powder XRD pattern as depicted in FIG. 6, and a combination thereof.

In another embodiment the present invention encompasses a pyridine solvate of dasatinib characterized by data selected from the group consisting of: PXRD pattern having any 3 peaks selected from the group consisting of: 5.9, 11.7, 12.3, 14.0, 18.3, 21.4, 22.0, 22.7, 24.7, and 25.2±0.2 degrees 2-theta, a powder XRD pattern as depicted in FIG. 7, and a combination thereof.

In another embodiment the present invention encompasses a toluene solvate of dasatinib characterized by data selected from the group consisting of: PXRD pattern having any 3 peaks selected from the group consisting of: 6.0, 12.0, 15.0, 15.4, 16.9, 19.3, 21.3, 21.7, 23.4, 24.1 and 24.8±0.2 degrees 2-theta, a powder XRD pattern as depicted in FIG. 8, and a combination thereof.

In another embodiment the present invention encompasses an MIBK solvate of dasatinib characterized by data selected from the group consisting of: PXRD pattern having any 3 peaks selected from the group consisting of: 5.8, 10.2, 11.4, 12.5, 17.3, 17.8, 20.0, 21.9, 22.6, 25.8 and 26.2±0.2 degrees 2-theta, a powder XRD pattern as depicted in FIG. 9, and a combination thereof.

In another embodiment the present invention encompasses a mono acetone solvate of dasatinib characterized by data selected from the group consisting of: PXRD pattern having any 3 peaks selected from the group consisting of: 5.9, 11.7, 12.3, 14.7, 17.6, 18.5, 21.4, 22.1, 22.8, 24.7 and 25.2±0.2 degrees 2-theta, a powder XRD pattern as depicted in FIG. 10, and a combination thereof.

In another embodiment the present invention encompasses a 2-butanol-DMSO solvate of dasatinib characterized by data selected from the group consisting of: PXRD pattern having any 3 peaks selected from the group consisting of: 6.0, 12.0, 14.9, 17.9, 18.2, 18.9, 21.1, 22.8, 24.0, 24.5, 25.6 and 26.1±0.2 degrees 2-theta, a powder XRD pattern as depicted in FIG. 12, and a combination thereof.

The present invention encompasses an amorphous dasatinib.

The present invention encompasses an amorphous dasatinib characterized by data selected from the group consisting of: a powder XRD pattern as depicted in FIG. 16, a powder XRD pattern as depicted in FIG. 99, and a combination thereof.

In another embodiment, the present invention encompasses an IPA-DMF solvate of dasatinib characterized by data selected from the group consisting of: PXRD pattern having any 3 peaks selected from the list consisting of: 5.9, 11.8, 12.0, 14.9, 17.8, 18.2, 18.7, 21.4, 22.8, 24.2 and 24.7±0.2 degrees 2-theta, a powder XRD pattern as depicted in FIG. 17, and a combination thereof.

In another embodiment, the present invention encompasses an n-propanol-DMF solvate of dasatinib characterized by data selected from the group consisting of: PXRD pattern having any 3 peaks selected from the list consisting of: 5.9, 11.8, 12.2, 14.9, 17.7, 18.3, 18.6, 21.4, 21.7, 24.4 and 24.9±0.2 degrees 2-theta, a powder XRD pattern as depicted in FIG. 19, and a combination thereof.

In another embodiment, the present invention encompasses an n-propanol solvate of dasatinib characterized by data selected from the group consisting of: PXRD pattern having any 3 peaks selected from the list consisting of: 5.9, 11.8, 12.1, 14.9, 17.8, 18.3, 18.7, 21.5, 21.6, 22.8, 24.3 and 24.8±0.2 degrees 2-theta, a powder XRD pattern as depicted in FIG. 20, and a combination thereof.

In another embodiment, the present invention encompasses a 2-butanol-DMF solvate of dasatinib characterized by data selected from the group consisting of: PXRD pattern having any 3 peaks selected from the list consisting of: 5.9, 11.7, 12.0, 14.7, 17.6, 18.1, 18.6, 21.4, 22.6, 24.1, 24.6 and 25.7±0.2 degrees 2-theta, a powder XRD pattern as depicted in FIG. 21, and a combination thereof.

In one embodiment, the present invention encompasses a 2-butanol solvate of dasatinib characterized by data selected from the group consisting of: PXRD pattern having any 3 peaks selected from the list consisting of: 5.9, 11.8, 12.0, 14.7, 17.7, 18.1, 18.7, 21.3, 22.6, 24.1 and 24.6±0.2 degrees 2-theta, a powder XRD pattern as depicted in FIG. 22, and a combination thereof.

In another embodiment, the present invention encompasses a n-butanol-DMSO solvate of dasatinib characterized by data selected from the group consisting of: PXRD pattern having any 3 peaks selected from the list consisting of: 5.9, 11.9, 12.0, 14.8, 17.8, 18.2, 18.7, 21.3, 22.7, 24.1 and 24.6±0.2 degrees 2-theta, a powder XRD pattern as depicted in FIG. 23, and a combination thereof.

In another embodiment, the present invention encompasses a DMF-water solvate of dasatinib characterized by data selected from the group consisting of: PXRD pattern having any 3 peaks selected from the list consisting of: 5.4, 10.8, 12.1, 14.8, 16.4, 21.4, 22.1, 24.2, 24.8 and 25.4±0.2 degrees 2-theta, a powder XRD pattern as depicted in FIG. 24, and a combination thereof.

In another embodiment, the present invention encompasses a DMF solvate of dasatinib characterized by data selected from the group consisting of: PXRD pattern having any 3 peaks selected from the list consisting of: 5.8, 11.5, 12.3, 14.6, 17.3, 18.2, 21.2, 22.1, 22.6, 24.7 and 25.2±0.2 degrees 2-theta, a powder XRD pattern as depicted in FIG. 25, and a combination thereof.

In another embodiment, the present invention encompasses a MIPK solvate of dasatinib characterized by data selected from the group consisting of: PXRD pattern having any 3 peaks selected from the list consisting of: 5.7, 12.0, 14.6, 18.0, 18.2, 22.4 and 24.6±0.2 degrees 2-theta, a powder XRD pattern as depicted in FIG. 26, and a combination thereof.

In another embodiment, the present invention encompasses a dimethoxyethane solvate of dasatinib characterized by data selected from the group consisting of: PXRD pattern having any 3 peaks selected from the list consisting of: 5.7, 6.0, 11.4, 16.8, 19.7 and 24.1±0.2 degrees 2-theta, a powder XRD pattern as depicted in FIG. 27, and a combination thereof.

In another embodiment, the present invention encompasses a cellosolve solvate of dasatinib characterized by data selected from the group consisting of: PXRD pattern having any 3 peaks selected from the list consisting of: 5.5, 11.1, 11.6, 15.7, 16.8 and 23.4±0.2 degrees 2-theta, a powder XRD pattern as depicted in FIG. 28, and a combination thereof.

In another embodiment, the present invention encompasses a methylacetate solvate of dasatinib characterized by data selected from the group consisting of: PXRD pattern having any 3 peaks selected from the list consisting of: 5.9, 11.8, 12.1, 14.8, 17.7, 18.2 and 21.6±0.2 degrees 2-theta, a powder XRD pattern as depicted in FIG. 29, and a combination thereof.

In another embodiment, the present invention encompasses a methanol solvate of dasatinib characterized by data selected from the group consisting of: PXRD pattern having any 3 peaks selected from the list consisting of: 7.1, 11.9, 12.7, 14.3, 16.0, 19.1 and 21.6±0.2 degrees 2-theta, a powder XRD pattern as depicted in FIG. 30, and a combination thereof.

In another embodiment, the present invention encompasses an ethylacetate solvate of dasatinib characterized by data selected from the group consisting of: PXRD pattern having any 3 peaks selected from the list consisting of: 6.0, 8.9, 11.8, 12.4, 16.1, 22.3 and 25.4±0.2 degrees 2-theta, a powder XRD pattern as depicted in FIG. 31, and a combination thereof.

In another embodiment, the present invention encompasses a 2-pentanole solvate of dasatinib characterized by data selected from the group consisting of: PXRD pattern having any 3 peaks selected from the list consisting of: 5.6, 11.3, 17.1, 17.3 and 21.9±0.2 degrees 2-theta, a powder XRD pattern as depicted in FIG. 32, and a combination thereof.

In another embodiment, the present invention encompasses a dimethyl carbonate solvate of dasatinib characterized by data selected from the group consisting of: PXRD pattern having any 3 peaks selected from the list consisting of: 12.1, 17.3, 18.3, 24.5, 24.7 and 26.5±0.2 degrees 2-theta, a powder XRD pattern as depicted in FIG. 33, and a combination thereof.

In another embodiment, the present invention encompasses an isopropylacetate solvate of dasatinib characterized by data selected from the group consisting of: PXRD pattern having any 3 peaks selected from the list consisting of: 5.8, 10.3, 12.3, 17.3, 21.9 and 24.4±0.2 degrees 2-theta, a powder XRD pattern as depicted in FIG. 34, and a combination thereof.

In another embodiment, the present invention encompasses a dichloromethane solvate of dasatinib characterized by data selected from the group consisting of: PXRD pattern having any 3 peaks selected from the list consisting of: 5.9, 7.1, 11.8, 14.4, 14.8, 18.3 and 22.9±0.2 degrees 2-theta, a powder XRD pattern as depicted in FIG. 36, and a combination thereof.

In another embodiment, the present invention encompasses a methylformate solvate of dasatinib characterized by data selected from the group consisting of: PXRD pattern having any 3 peaks selected from the list consisting of: 6.0, 7.1, 11.9, 14.3, 16.0, 24.2 and 25.1±0.2 degrees 2-theta, a powder XRD pattern as depicted in FIG. 37, and a combination thereof.

In another embodiment, the present invention encompasses a tert-butanol solvate of dasatinib characterized by data selected from the group consisting of: PXRD pattern having any 3 peaks selected from the list consisting of: 5.9, 11.8, 12.0, 15.0, 17.7, 18.1 and 26.3±0.2 degrees 2-theta, a powder XRD pattern as depicted in FIG. 38, and a combination thereof.

In another embodiment, the present invention encompasses a dimethoxyethane solvate of dasatinib characterized by data selected from the group consisting of: PXRD pattern having any 3 peaks selected from the list consisting of: 6.1, 12.1, 15.3, 21.0, 23.1 and 24.4±0.2 degrees 2-theta, a powder XRD pattern as depicted in FIG. 39, and a combination thereof.

In another embodiment, the present invention encompasses a MEK solvate of dasatinib characterized by data selected from the group consisting of: PXRD pattern having any 3 peaks selected from the list consisting of: 5.9, 12.2, 14.7, 15.1, 21.7, 24.5 and 24.9±0.2 degrees 2-theta, a powder XRD pattern as depicted in FIG. 40, and a combination thereof.

In another embodiment, the present invention encompasses a monochlorobenzene solvate of dasatinib characterized by data selected from the group consisting of: PXRD pattern having any 3 peaks selected from the list consisting of:

6.2, 12.4, 15.8, 18.7, 23.6 and 26.8±0.2 degrees 2-theta, a powder XRD pattern as depicted in FIG. 41, and a combination thereof.

In another embodiment, the present invention encompasses a PGME solvate of dasatinib characterized by data selected from the group consisting of: PXRD pattern having any 3 peaks selected from the list consisting of: 5.7, 11.5, 17.0, 17.4, 22.0, 23.1 and 24.3±0.2 degrees 2-theta, a powder XRD pattern as depicted in FIG. 42, and a combination thereof.

In another embodiment, the present invention encompasses a cyclopentyl methyl ether solvate of dasatinib characterized by data selected from the group consisting of: PXRD pattern having any 3 peaks selected from the list consisting of: 5.8, 14.6, 17.5, 21.1, 22.4, 23.9 and 24.3±0.2 degrees 2-theta, a powder XRD pattern as depicted in FIG. 44, and a combination thereof.

In another embodiment, the present invention encompasses a MTBE solvate of dasatinib characterized by data selected from the group consisting of: PXRD pattern having any 3 peaks selected from the list consisting of: 5.8, 10.0, 19.2, 19.6, 22.4, 25.7 and 26.1±0.2 degrees 2-theta, a powder XRD pattern as depicted in FIG. 45, and a combination thereof.

In another embodiment, the present invention encompasses an amylalcohol solvate of dasatinib characterized by data selected from the group consisting of: PXRD pattern having any 3 peaks selected from the list consisting of: 5.6, 10.4, 11.2, 21.7, 23.1 and 26.1±0.2 degrees 2-theta, a powder XRD pattern as depicted in FIG. 46, and a combination thereof.

In one embodiment, the present invention encompasses a dimethyl carbonate solvate of dasatinib characterized by data selected from the group consisting of: PXRD pattern having any 3 peaks selected from the list consisting of: 12.5, 13.6, 16.2, 21.7 and 25.6±0.2 degrees 2-theta, a powder XRD pattern as depicted in FIG. 47, and a combination thereof.

In one embodiment, the present invention encompasses an ethylene glycol solvate of dasatinib characterized by data selected from the group consisting of: PXRD pattern having any 3 peaks selected from the list consisting of: 7.5, 12.3, 14.7 and 16.4±0.2 degrees 2-theta, a powder XRD pattern as depicted in FIG. 48, and a combination thereof.

In one embodiment, the present invention encompasses an anhydrous form of dasatinib characterized by data selected from the group consisting of: PXRD pattern having peaks at about 5.1 and 10.2±0.2 degrees 2-theta and any 3 peaks selected from the list consisting of: 6.0, 20.3, 20.5, 23.5 and 26.8±0.2 degrees 2-theta, a powder XRD pattern as depicted in FIG. 97, and a combination thereof.

In one embodiment, the present invention encompasses a monochlorobenzene solvate of dasatinib characterized by data selected from the group consisting of: PXRD pattern having any 3 peaks selected from the list consisting of: 5.9, 12.0, 15.3, 17.9, 24.3 and 26.2±0.2 degrees 2-theta, a powder XRD pattern as depicted in FIG. 98, and a combination thereof.

In one embodiment, the present invention encompasses dimethyl carbonate solvate of dasatinib characterized by data selected from the group consisting of: PXRD pattern having any 3 peaks selected from a list consisting of: 12.0, 16.7, 19.1, 21.0, 21.6, 23.0 and 24.5±0.2 degrees 2-theta, a powder XRD pattern as depicted in FIG. 109, and a combination thereof.

In one embodiment, the present invention encompasses a methyl isopropyl ketone ("MIPK") solvate of dasatinib characterized by data selected from the group consisting of: PXRD pattern having any 3 peaks selected from the list consisting of: 10.1, 12.1, 12.7, 17.5, 17.9, 19.9 and 25.9±0.2 degrees 2-theta, a powder XRD pattern as depicted in FIG. 110, and a combination thereof.

In one embodiment, the present invention encompasses a monochlorobenzene solvate of dasatinib characterized by a data selected from the group consisting of: PXRD pattern having any 3 peaks selected from the list consisting of: 5.6, 10.3, 11.3, 17.3, 22.3 and 26.1±0.2 degrees 2-theta, a powder XRD pattern as depicted in FIG. 111, and a combination thereof.

In one embodiment, the present invention encompasses a glycerol formal solvate of dasatinib characterized by a data selected from the group consisting of: PXRD pattern having any 3 peaks selected from the list consisting of: 5.9, 11.8, 17.8, 18.6, 20.5, 23.8 and 24.3±0.2 degrees 2-theta, a powder XRD pattern as depicted in FIG. 125, and a combination thereof.

In one embodiment, the present invention encompasses a crystalline form of dasatinib characterized by data selected from the group consisting of: PXRD pattern having peaks at about 6.4 and 14.0±0.2 degrees 2-theta and any 3 peaks selected from the list consisting of: 6.4, 12.7, 14.0, 19.0, 21.7 and 25.0±0.2 degrees 2-theta, a powder XRD pattern as depicted in FIG. 131, and a combination thereof.

In yet another embodiment, the invention encompasses a pharmaceutical composition comprising at least one of the above-described polymorphs of dasatinib, and at least one pharmaceutically acceptable excipient.

In one embodiment, the present invention also encompasses a pharmaceutical composition comprising at least one of the above described polymorphs of dasatinib prepared according to the processes of the present invention, and at least one pharmaceutically acceptable excipient.

In another embodiment, the invention encompasses a process for preparing a pharmaceutical composition comprising at least one of the above polymorphs of dasatinib, and at least one pharmaceutically acceptable excipient.

In another embodiment, the invention encompasses a method of treating chronic yelogenous leukemia after imatinib treatemant, and Philadelphia chromosome-positive acute lymphoblastic leukemia comprising administering a pharmaceutical composition comprising at least one of the above polymorphs of dasatinib to a patient in need thereof.

One embodiment of the invention provides the use of the above crystalline forms of dasatinib of the present invention for the manufacture of a pharmaceutical composition.

BRIEF DESCRIPTION OF THE FIGURES

FIG. 42 shows a powder XRD pattern of crystalline dasatinib form AS

FIG. 80 shows a TGA thermogram of crystalline Dasatinib form AS

FIG. 81 shows a DSC thermogram of crystalline Dasatinib form AS

FIG. 82 shows a TGA thermogram of crystalline Dasatinib form AT

FIG. 83 shows a DSC thermogram of crystalline Dasatinib form AT

FIG. 122 shows a detailed solid state $^{13}$C NMR spectrum of crystalline dasatinib form A3

FIG. 123 shows a full-width solid state $^{13}$C NMR spectrum of crystalline dasatinib form A21

FIG. 124 shows a detailed solid state $^{13}$C NMR spectrum of crystalline dasatinib form A21

FIG. 125 shows a powder XRD pattern of crystalline dasatinib form BL

FIG. 126 shows a TGA thermogram of crystalline dasatinib form BL

FIG. 127 shows a DSC thermogram of crystalline dasatinib form BL

FIG. 128 shows a microscope image of crystalline dasatinib form A3

FIG. 129 shows a microscope image of crystalline dasatinib form A21

FIG. 130 shows a powder XRD pattern of crystalline Dasatinib form N-6 (anhydrous).

FIG. 131 shows a powder XRD pattern of crystalline Dasatinib form BM.

DETAILED DESCRIPTION OF THE INVENTION

Figure 1:
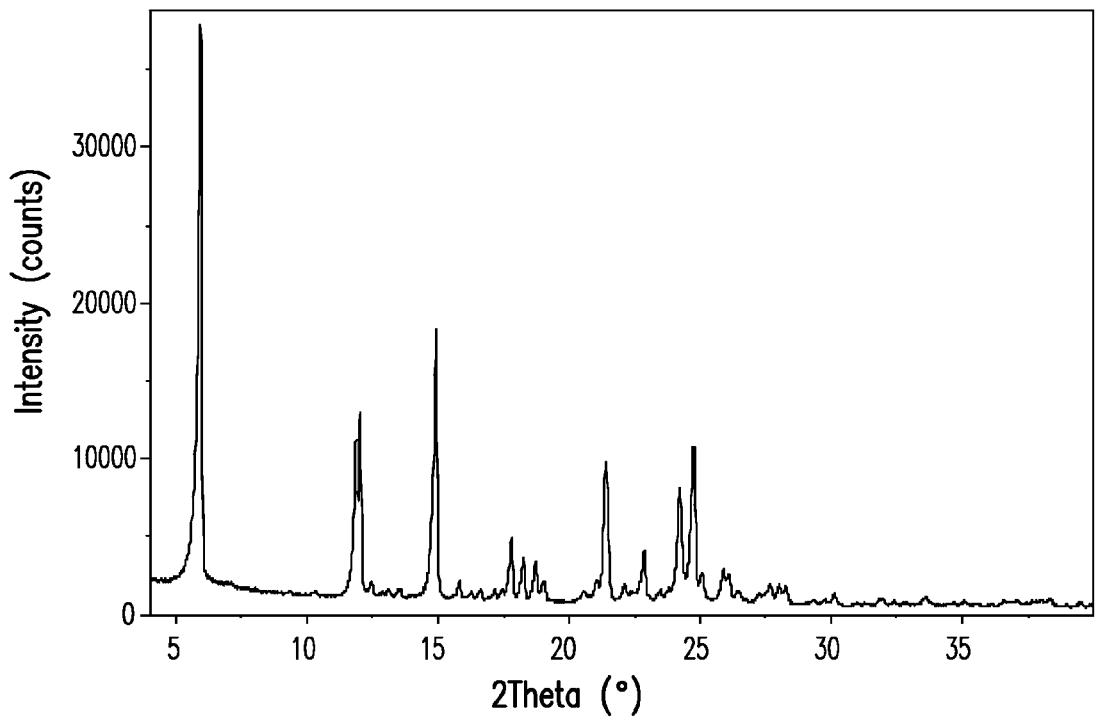
FIG. 1 shows a powder XRD pattern of crystalline dasatinib form K2.

The present invention relates to polymorphs of dasatinib, process for preparing said polymorphs, and pharmaceutical compositions thereof.

As used herein, the term "Room temperature" refers to a temperature between about 20° C. and about 30° C., preferably about 25° C.

As used herein, the term "Overnight" refers to a period of between about 11 and about 13 hours, preferably about 12 hours.

As used herein, unless otherwise defined, the term "N-6" when referring to crystalline form of dasatinib means any hydrous form of dasatinib that exhibits an X-ray powder diffraction pattern having characteristic peaks expressed in degrees 2-theta at approximately 6.9, 12.4, 13.2, 13.8, 16.8, 17.2, 21.1, 24.4, 24.9 and 27.8±0.2 degrees 2-theta.

As used herein, unless otherwise defined, the term "H1-7" when referring to crystalline form of dasatinib means monohydrate form of dasatinib that exhibits an X-ray powder diffraction pattern having characteristic peaks expressed in degrees 2-theta at approximately 4.6, 9.2, 11.2, 13.8, 15.2, 17.9, 19.5, 23.1, 23.6, 25.9 and 28.0±0.2 degrees 2-theta.

As used herein, unless otherwise defined, the term "BU-2" when referring to crystalline form of dasatinib means solvate of dasatinib that exhibits an X-ray powder diffraction pattern having characteristic peaks expressed in degrees 2-theta at approximately 5.9, 11.7, 12.0, 14.7, 17.6, 18.1, 18.6, 21.3, 24.1 and 24.6±0.2 degrees 2-theta.

As used herein, unless otherwise defined, the term "T1E2-1" means solvate of dasatinib that exhibits an X-ray powder diffraction pattern having characteristic peaks expressed in degrees 2-theta at approximately 7.2, 11.9, 14.3, 16.0, 18.7, 19.1, 20.7, 21.5, 24.2 and 25.0±0.2 degrees 2-theta.

As used herein, the term "glycerol formal solvate" refers to a mixture of 5-hydroxy-1,3-dioxane and 4-hydroxymethyl-1,3-dioxolane (60:40), both of which are cyclic ether compounds having 2 oxygen atoms in the ring structure and substituted by alcohol group.

In one embodiment the present invention encompasses a solvate of dasatinib selected from the group consisting of: a n-propanol-dimethylsulfoxide ("DMSO") solvate of dasatinib, a DMSO solvate of dasatinib, a hemi tetrahydrofuran ("THF") solvate of dasatinib, a 2-methyl-tetrahydrofuran ("2-methyl THF") solvate of dasatinib, a hemi 1,4-dioxane solvate of dasatinib, a pyridine solvate of dasatinib, a toluene solvate of dasatinib, a methyl isobutyl ketone ("MIBK") solvate of dasatinib, a mono acetone solvate of dasatinib, an iso-propanol ("IPA")-DMSO solvate of dasatinib, a 2-butanol-DMSO solvate of dasatinib, an IPA-DMF solvate of dasatinib, an IPA solvate of dasatinib, an n-propanol-DMF solvate of dasatinib, an n-propanol solvate of dasatinib, a 2-butanol-DMF solvate of dasatinib, a 2-butanol solvate of dasatinib, an n-butanol-DMSO solvate of dasatinib, a DMF-water solvate of dasatinib, a DMF solvate of dasatinib, a methyl isopropyl ketone ("MIPK") solvate of dasatinib, a dimethoxyethane solvate of dasatinib, a cellosolve solvate of dasatinib, a methylacetate solvate of dasatinib, a methanol solvate of dasatinib, an ethylacetate solvate of dasatinib, a 2-pentanole solvate of dasatinib, a dimethyl carbonate solvate of dasatinib, an isopropylacetate solvate of dasatinib, a ethyleneglycol solvate of dasatinib, a dichloromethane solvate of dasatinib, a methylformate solvate of dasatinib, a tert-butanol solvate of dasatinib, a dimethoxyethane solvate of dasatinib, a methylethylketone ("MEK") solvate of dasatinib, a monochlorobenzene solvate of dasatinib, a propylene glycol monoethyl ether ("PGME") solvate of dasatinib, a glycerol solvate of dasatinib, a cyclopentyl methyl ether solvate of dasatinib, a methyl tert butyl ether ("MTBE") solvate of dasatinib, an amylalcohol solvate of dasatinib, and a glycerol formal solvate of dasatinib.

Figure 18:
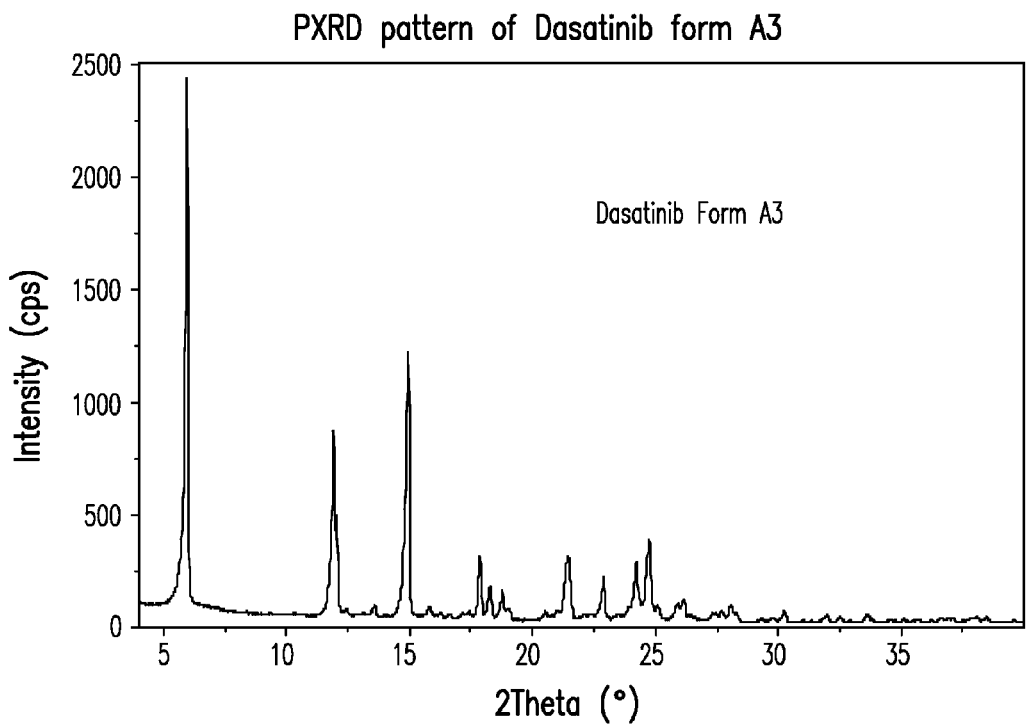
FIG. 18 shows a powder XRD pattern of crystalline dasatinib form A3.
Figure 96:
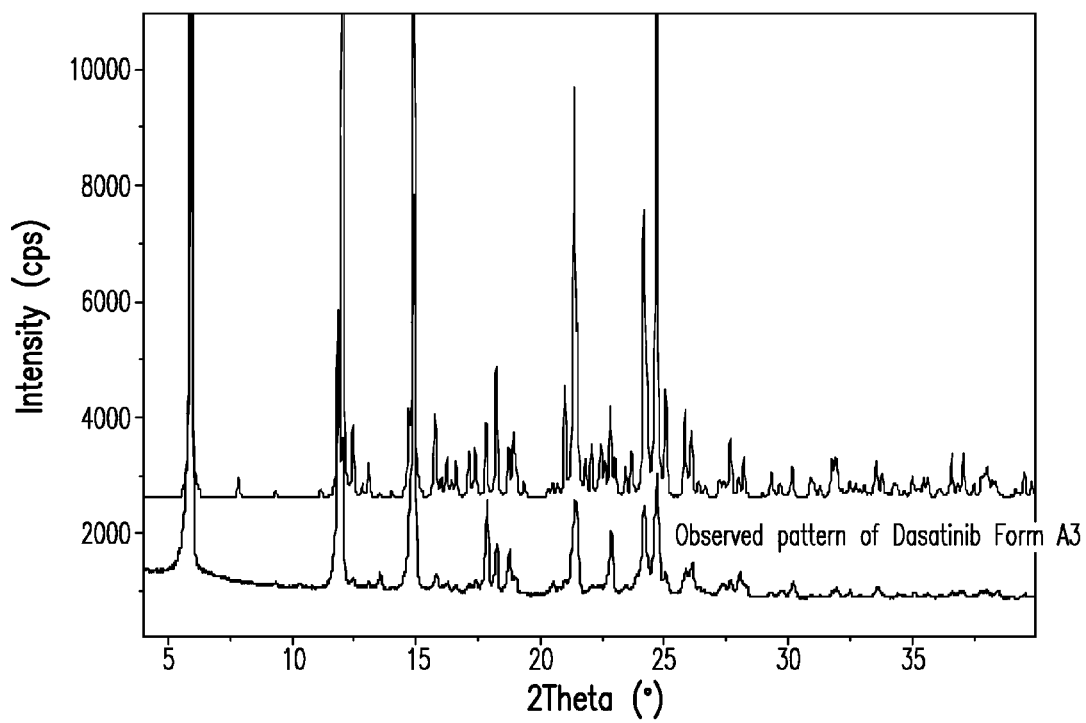
FIG. 96 shows comparison of calculated and observed XRPD diffractogram of crystalline Dasatinib IPA solvate (Form A3).

In another embodiment, the present invention encompasses an IPA solvate of dasatinib characterized by data selected from the group consisting of: a PXRD pattern having any 3 peaks selected from the list consisting of: 6.0, 11.9, 12.0, 14.9, 17.9, 18.3, 18.8, 21.4, 22.9, 24.2 and 24.7±0.2 degrees 2-theta, a powder XRD pattern as depicted in FIG. 18, a solid-state $^{13}C$ NMR spectrum having signals at about 139.2 and 127.6±0.2 ppm; a solid-state $^{13}C$ NMR spectrum having chemical shifts differences between the signal exhibiting the lowest chemical shift at 125±1.0 ppm and another in the chemical shift range of 100 to 180 ppm of about 14.2 and 2.6±0.1 ppm; a unit cell with parameters as determined by crystal structure determination using synchrotron powder diffraction data approximately equal to the following:

| Cell dimensions: | |
|---|---|
| Cell length a | 14.9942(5) Å |
| Cell length b | 8.45434(22) Å |
| Cell length c | 22.6228(16) Å |
| Cell angle alpha | 90.0° |
| Cell angle beta | 95.890(4)° |
| Cell angle gamma | 90.0° |
| Cell volume | 2852.67(21) Å$^3$ |
| Symmetry cell setting | monoclinic |
| Symmetry space group name | P 2$_1$/c | a PXRD pattern and calculated PXRD pattern as depicted in FIG. 96, and a combination thereof. The signal exhibiting the lowest chemical shift in the chemical shift range of 100 to 180 ppm is typically at about 125±1 ppm. This form can be designated as form A3.

In a preferred embodiment, the present invention encompasses an IPA solvate of dasatinib designated Form A3, characterized by a PXRD pattern having any 5 peaks selected from the list consisting of: 6.0, 11.9, 12.0, 14.9, 17.9, 18.3, 18.8, 21.4, 22.9, 24.2 and 24.7±0.2 degrees 2-theta.

The IPA solvate of dasatinib can also be characterized by a PXRD pattern having peaks at about 6.0 and 17.9±0.2 degrees 2-theta and any 3 peaks at positions selected from the group consisting of: 11.9, 14.9, 21.4, 24.2 and 24.7±0.2 degrees 2-theta. The peak positions are calibrated by means of silicon internal standard.

The above IPA solvate of dasatinib designated Form A3 can be further characterized by data selected from the group consisting of: a powder XRD pattern with peaks at about 6.0, 11.9, 12.0, 14.9, 17.9 and 18.3±0.2 degrees 2-theta; a powder XRD pattern with peaks at about 11.9, 12.0, 21.4, 22.9 and 24.7±0.2 degrees 2-theta; a content of IPA of about 9% to about 13% by weight, as measured by GC. Preferably, the IPA content is about 10% to 12% by weight as measured by GC. Theoretical content of IPA in an IPA solvate is typically about 11% by weight.

In addition, crystalline Dasatinib Form A3 has less than about 15% by weight, preferably, less about than 10% by weight, more preferably, less than about 5% by weight of crystalline Dasatinib forms: N-6 and H1-7 or any other form.

Typically, the amount of form N-6 in form A3 is measured by PXRD using any peaks selected from the group consisting of peaks at: 6.9, 13.2, 13.8 and 16.8 deg±0.2 degrees 2-theta and the amount of form H1-7 in form A3 is measured by PXRD using any peaks selected from the group consisting of peaks at: 4.6, 9.2, 11.2, 15.2 and 19.5 deg±0.2 degrees 2-theta.

Figure 128:
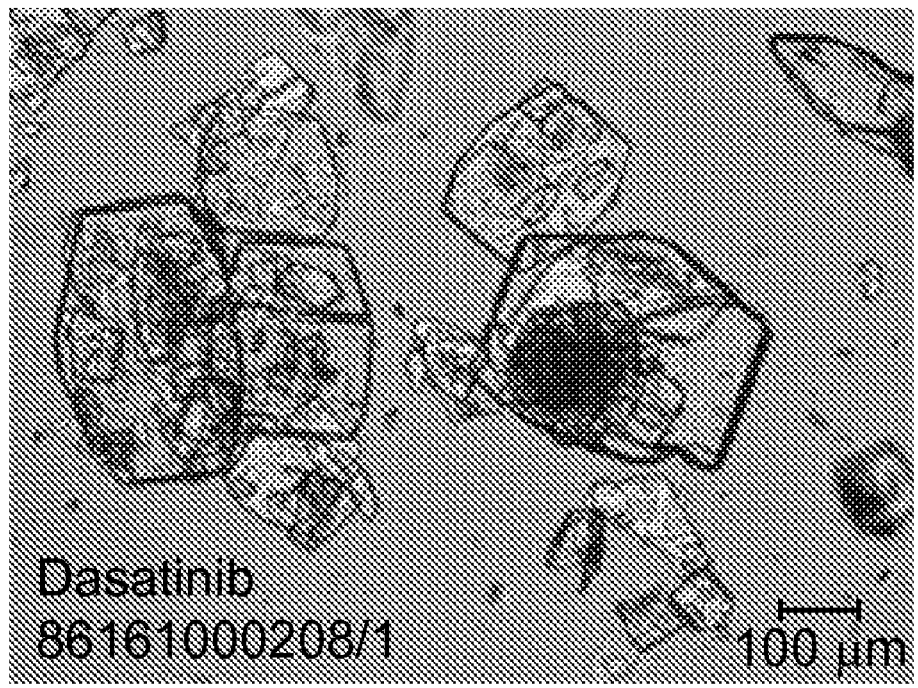
Figure 128:
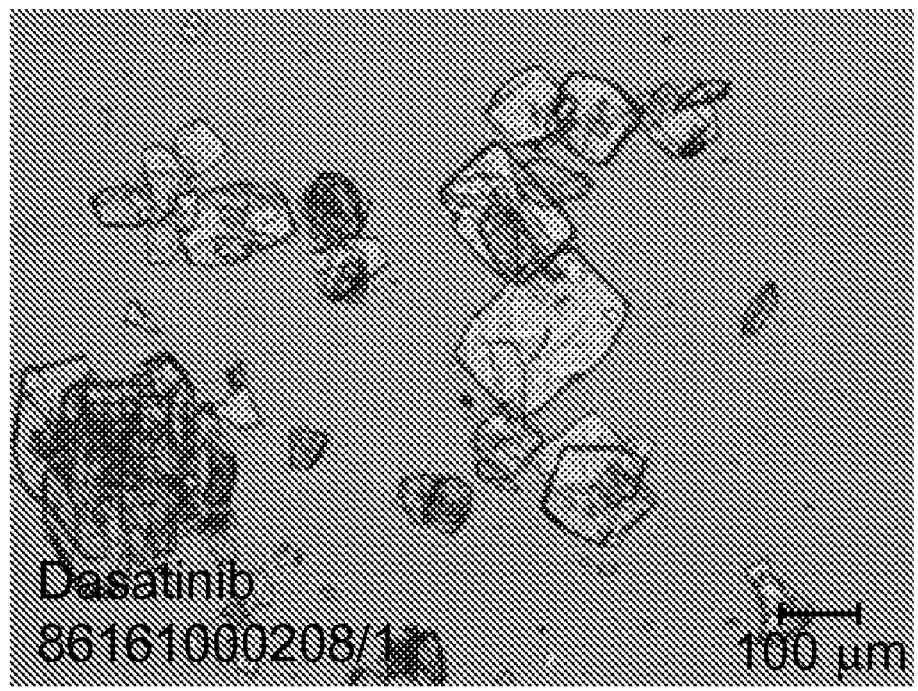

The advantage of form A3 is a size and shape of crystals that allows easier processing such as filtration or pouring of a bulk material. The crystals are of size of about 50 μm to about 300 μm having typically a plate shape. Typical crystals are depicted in FIG. 128.

Form A3 of dasatinib can be prepared by a process comprising crystallizing dasatinib from a mixture of IPA and water.

The crystallization comprises providing a solution of dasatinib in a mixture of IPA and water, and precipitating said crystalline form to obtain a suspension.

Preferably, the solution is provided by combining dasatinib, IPA and water, and heating the combination. Preferably, heating is to about reflux temperature.

Preferably, precipitation is obtained by cooling the solution. Preferably, cooling is to a temperature of about 20° C. to about 0° C., more preferably, for about 5° C. to about 0° C.

The process for preparing form A3 of dasatinib can further comprise recovering said form. The recovery can be done for example, by filtering the suspension and drying.

Figure 11:
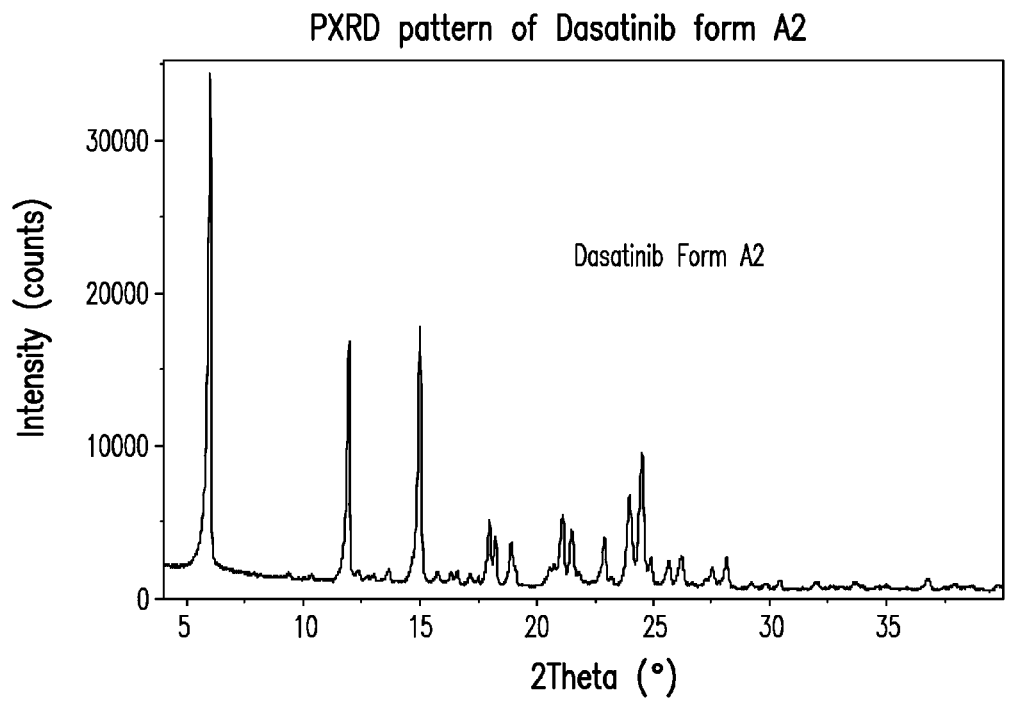
FIG. 11 shows a powder XRD pattern of crystalline dasatinib form A2.

In another embodiment the present invention encompasses an IPA-DMSO solvate of dasatinib characterized by data selected from the group consisting of: a PXRD pattern having any 3 peaks selected from the list consisting of: 6.0, 12.0, 15.0, 18.0, 18.3, 18.9, 21.2, 21.5, 22.9, 24.1, and 24.6±0.1 degrees 2-theta, a powder XRD pattern as depicted in FIG. 11, and combination thereof. The peak positions are calibrated by means of silicon internal standard. This form can be designated as form A2.

In a preferred embodiment the present invention encompasses an IPA-DMSO solvate of dasatinib designated Form A2 characterized by a PXRD pattern having any 5 peaks selected from the list consisting of: 6.0, 12.0, 15.0, 18.0, 18.3, 18.9, 21.2, 21.5, 22.9, 24.1, and 24.6±0.1 degrees 2-theta.

The above IPA-DMSO solvate of dasatinib designated Form A2 can be further characterized by data selected from the group consisting of: a powder XRD pattern with peaks at about 6.0, 12.0, 15.0, 21.2, and 24.6±0.1 degrees 2-theta, a content of IPA of about 6-9% by weight as measured by GC, and a content of DMSO of about 3-5% by weight as measured by GC.

In addition, crystalline Dasatinib Form A2 has less than about 15% by weight, preferably, less about than 10% by weight, more preferably, less than about 5% by weight of crystalline Dasatinib form N-6.

Typically, the amount of form N-6 in form A2 is measured by PXRD using any peaks selected from the group consisting of peaks at: 6.9, 13.2, 13.8 and 16.8 deg±0.1 degrees 2-theta.

Form A2 can be prepared by a process comprising crystallizing dasatinib from a mixture comprising the compound 1 of the following formula

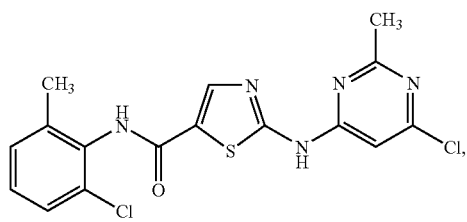

N-(2-hydroxyethyl) piperazine of the following formula;

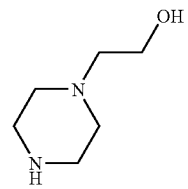

N-ethyldiisopropylamine of the following formula;

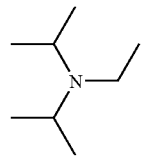

and a mixture of DMSO and IPA by reacting compound 1, N-(2-hydroxyethyl)piperazine, and N-ethyldiisopropylamine in DMSO at a temperature of about 76° C. to about 85° C. to obtain a solution comprising dasatinib, and adding IPA to obtain a suspension comprising said crystalline form.

Preferably, the reaction of a mixture of compound 1, N-(2-hydroxyethyl)piperazine, and N-ethyldiisopropylamine in DMSO is done at a temperature of about 76° C. to about 85° C., more preferably, at a temperature of about 80° C. to about 85° C., most preferably, at about 80° C. Preferably, the reaction is done upon stirring. Preferably, stirring is done for about 1 hour to about 2 hours.

Preferably, IPA is added at a temperature of about 80° C., providing the suspension. Typically, the suspension is cooled to increase the yield of the precipitated crystalline form. Preferably, cooling is to about room temperature to about 0° C., more preferably, to about 20° C. to about 10° C.

The process for preparing form A2 of dasatinib can further comprise recovering said crystalline form. The recovery can be done for example, by filtering the suspension and drying.

Figure 118:
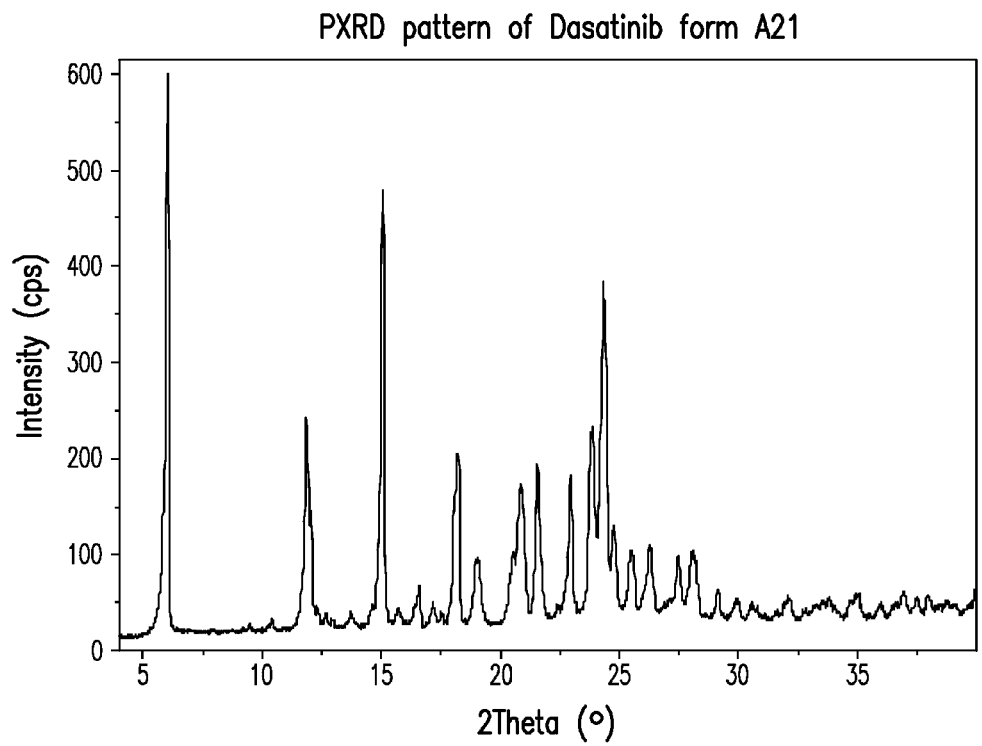
FIG. 118 shows a powder XRD pattern of crystalline dasatinib form A21
Figure 119:
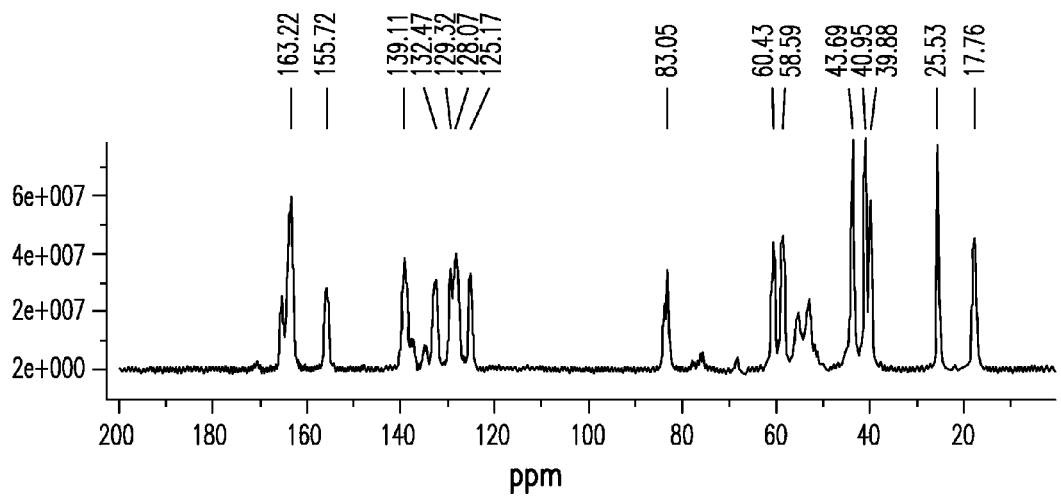
FIG. 119 shows a full-width solid state $^{13}$C NMR spectrum of crystalline dasatinib form C
Figure 120:
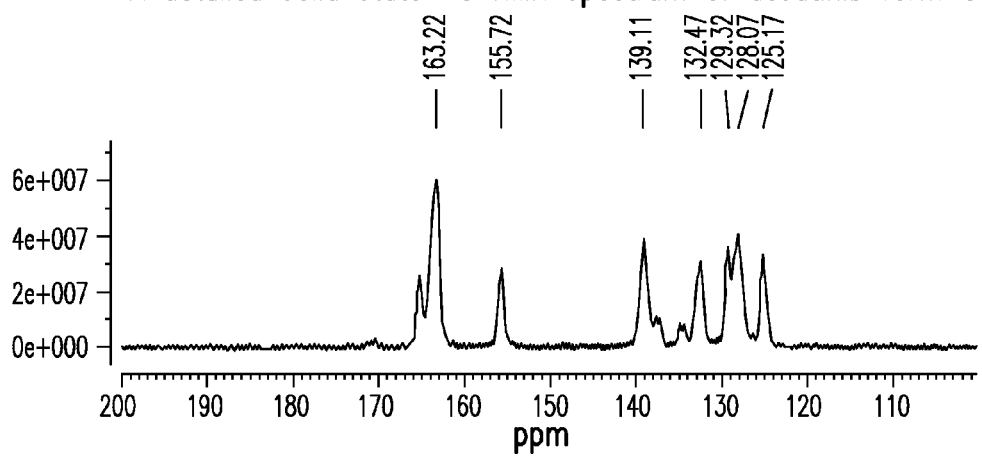
FIG. 120 shows a detailed solid state $^{13}$C NMR spectrum of crystalline dasatinib form C
Figure 121:
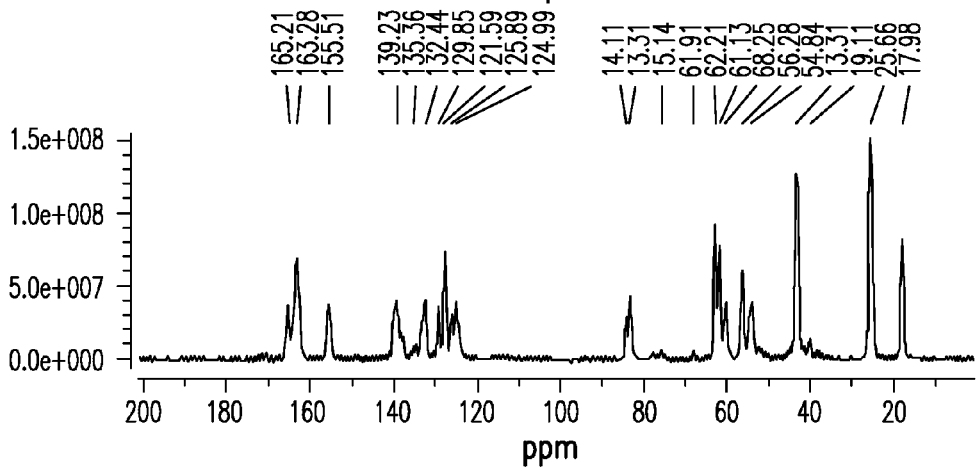
FIG. 121 shows a full-width solid state $^{13}$C NMR spectrum of crystalline dasatinib form A3
Figure 122:
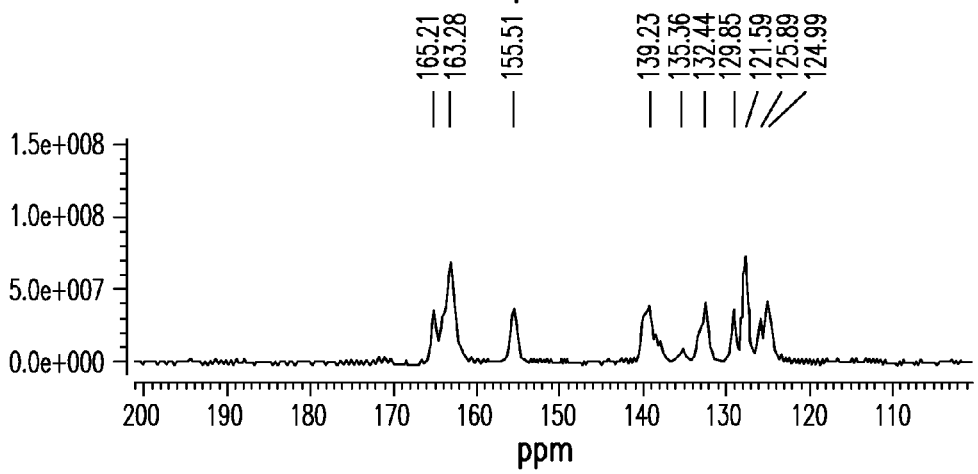
Figure 123:
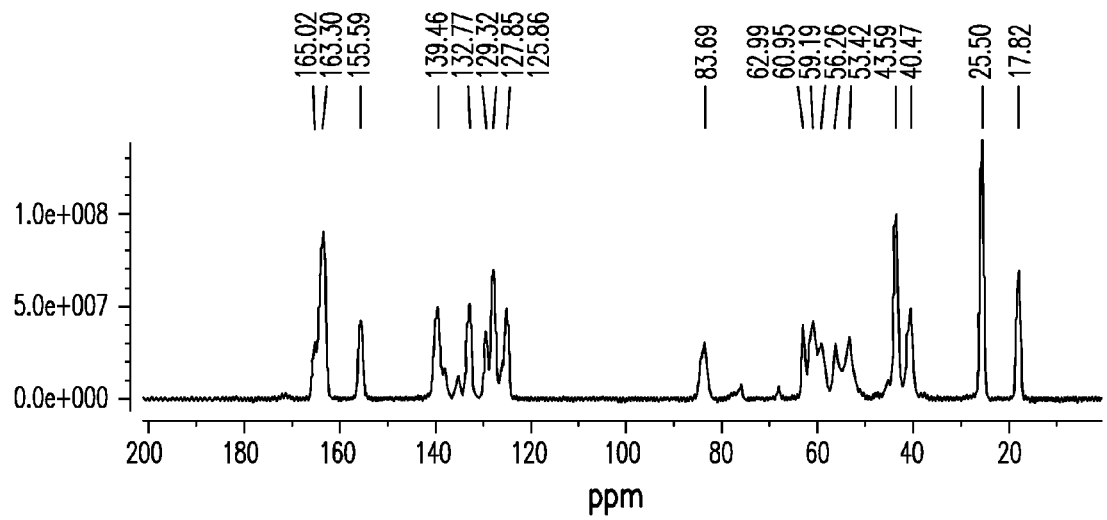
Figure 124:
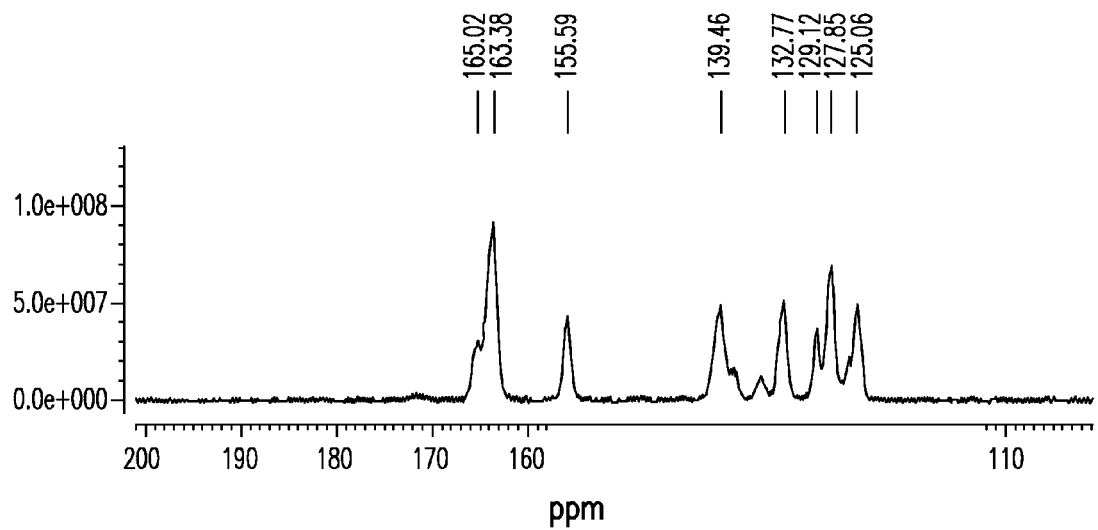

In another embodiment the present invention encompasses an IPA-DMSO solvate of dasatinib characterized by data selected from the group consisting of: a PXRD pattern having any 3 peaks at positions selected from the group consisting of: 6.0, 11.8, 18.2, 20.8, 23.8, 24.3 and 25.5±0.1 degrees 2-theta, a powder XRD pattern as depicted in FIG. 118, a solid-state $^{13}$C NMR spectrum having signals at about 139.5 and 127.9±0.2 ppm; and a solid-state $^{13}$C NMR spectrum having chemical shifts differences between the signal exhibiting the lowest chemical shift at 125±1.0 ppm and another in the chemical shift range of 100 to 180 ppm of about 14.4 and 2.8±0.1 ppm; and combination thereof. The signal exhibiting the lowest chemical shift in the chemical shift range of 100 to 180 ppm is typically at about 125±1 ppm. The peak positions are calibrated by means of silicon internal standard. This form can be designated as form A21.

In a preferred embodiment the present invention encompasses an IPA-DMSO solvate of dasatinib designated Form A21 characterized by a PXRD pattern having peaks at about 6.0 and 20.8±0.1 degrees 2-theta and any 3 peaks at positions selected from the group consisting of: 11.8, 18.2, 23.8, 24.3 and 25.5±0.2 degrees 2-theta The above IPA-DMSO solvate of dasatinib designated Form A21 can be further characterized by data selected from the group consisting of: a powder XRD pattern with peaks at about 6.0, 20.8, 23.9, 24.3 and 25.5±0.2 degrees 2-theta; a powder XRD pattern with peaks at about 11.9, 18.2, 20.8, 23.9 and 24.3±0.2 degrees 2-theta; a content of IPA of about 5-7% by weight as measured by GC, and a content of DMSO of about 5-7% by weight as measured by GC.

In addition, crystalline Dasatinib Form A21 has less than about 15% by weight, preferably, less about than 10% by weight, more preferably, less than about 5% by weight of crystalline Dasatinib forms: N-6 and H1-7 or any other form.

Typically, the amount of form N-6 in form A21 is measured by PXRD using any peaks selected from the group consisting of peaks at: 6.9, 13.2 and 16.8 deg±0.2 degrees 2-theta and the amount of form H1-7 in form A21 is measured by PXRD using any peaks selected from the group consisting of peaks at: 4.6, 9.2, 11.2, 15.2 and 19.5 deg±0.2 degrees 2-theta.

Figure 129:
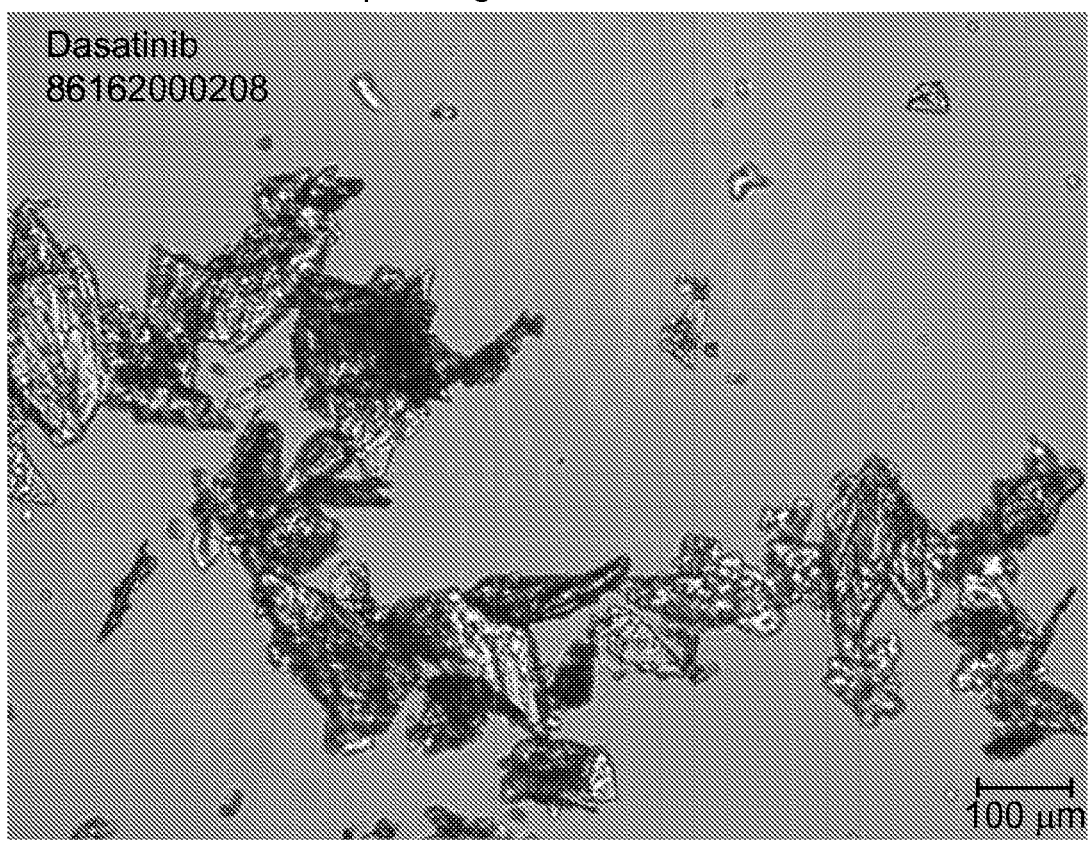
Figure 130:
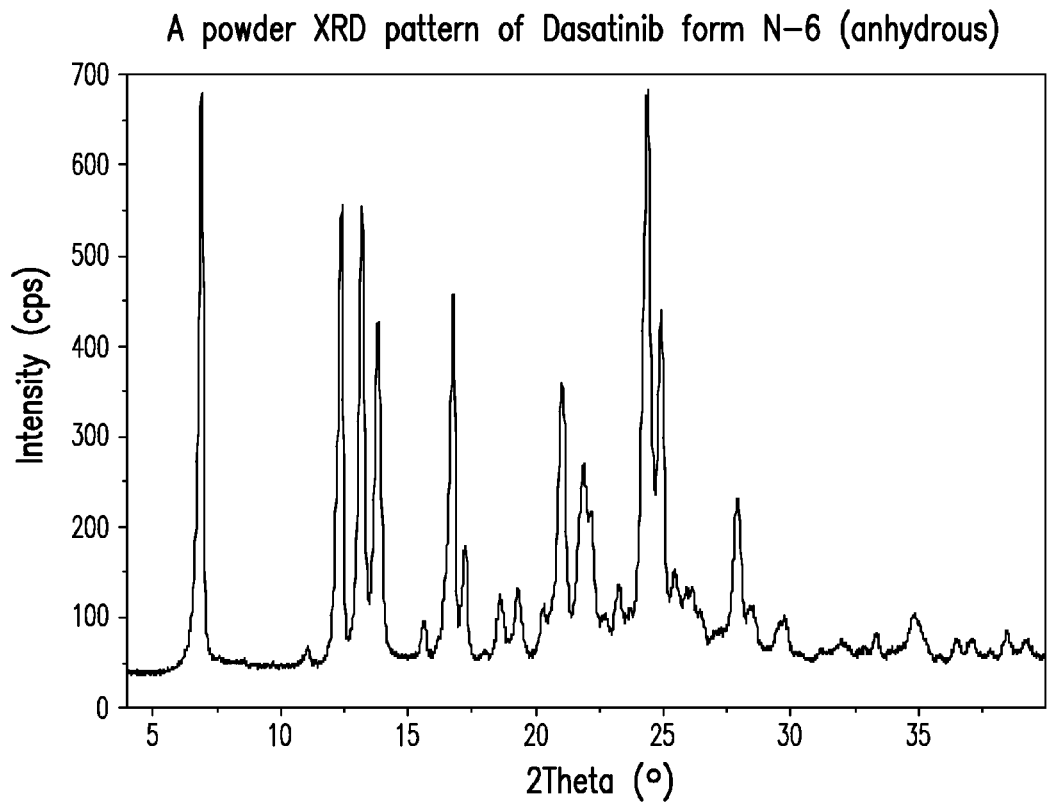

The advantage of form A21 is the size and shape of its crystals that allows easier processing such as filtration or pouring of a bulk material. The crystals are of size of about 50 μm to about 200 μm having typically an oblong plate shape. Typical crystals of form A21 are depicted in FIG. 129.

Form A21 can be prepared by a process comprising crystallizing dasatinib from a mixture comprising the compound 1, N-(2-hydroxyethyl) piperazine, N-ethyldiisopropylamine and a mixture of DMSO and IPA by reacting compound 1, N-(2-hydroxyethyl)piperazine, and N-ethyldiisopropylamine in DMSO at a temperature of about 65° C. to about 75° C. to obtain a solution comprising dasatinib, and adding IPA to obtain a suspension comprising said crystalline form.

Preferably, the reaction of a mixture of compound 1, N-(2-hydroxyethyl)piperazine, and N-ethyldiisopropylamine in DMSO is done at a temperature of about 65° C. to about 75° C., more preferably, at about 70° C. Preferably, the reaction is done upon stirring. Preferably, stirring is done for about 3 hours.

Preferably, IPA is added at a temperature of about 70° C. to about 75° C., more preferably at about 70° C., providing the suspension. Typically, the suspension is cooled to increase the yield of the precipitated crystalline form. Preferably, cooling is to about room temperature to about 0° C., more preferably, to about 20° C. to about 10° C.

Preferably, the suspension is stirred prior to the recovery step. Preferably, stirring is for about 0.5 hours to about 2 hours, preferably about 1 hour.

The process for preparing form A21 of dasatinib can further comprise recovering said crystalline form. The recovery can be done for example, by filtering the suspension and drying.

Figure 2:
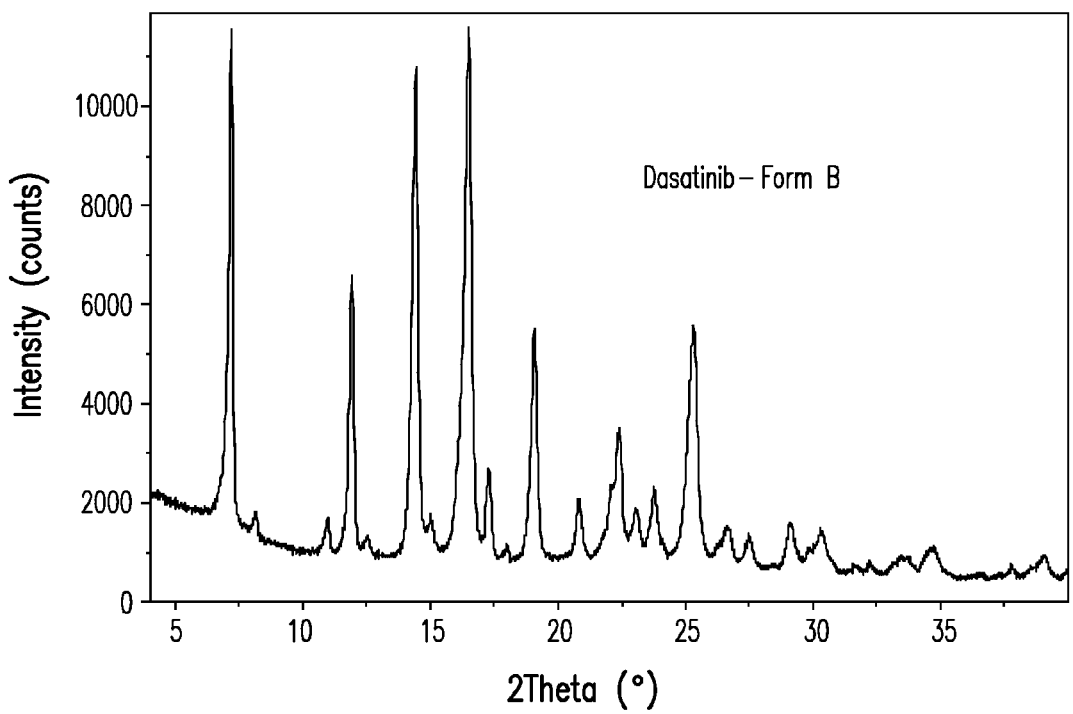
FIG. 2 shows a powder XRD pattern of crystalline dasatinib form B.

In one embodiment, the present invention encompasses an anhydrous form of dasatinib characterized by data selected from the group consisting of: a PXRD pattern having any 5 peaks selected from the list consisting of: 7.2, 11.9, 14.4, 16.5, 17.3, 19.1, 20.8, 22.4, 23.8, 25.3 and 29.1±0.2 degrees 2-theta, a powder XRD pattern as depicted in FIG. 2, and combination thereof. This form can be designated as form B.

The above form B of dasatinib can be also characterized by a PXRD pattern having peaks at about 7.2 and 14.4±0.2 degrees 2-theta and any 3 peaks at positions selected from the group consisting of: 11.9, 16.5, 17.3, 19.1, 22.4 and 25.3±0.2 degrees 2-theta. The peaks position is calibrated by means of silicon internal standard.

The above anhydrous form of dasatinib designated Form B can be further characterized by data selected from the group consisting of: a powder XRD pattern with peaks at about 7.2, 11.9, 14.4, 16.5, and 25.3±0.2 degrees 2-theta; a powder XRD pattern with peaks at about 7.5, 14.4, 16.5, 19.1 and 22.4±0.2 degrees 2-theta; a powder XRD pattern with peaks at about 7.2, 14.4, 16.5, 19.1 and 25.3±0.2 degrees 2-theta, a content of water of about 0.5% by weight as measured by KF; and a content of residual solvents of about 0.5% by weight as measured by GC.

In addition, crystalline Dasatinib Form B has less than about 15% by weight, preferably, less about than 10% by weight, more preferably, less than about 5% by weight of crystalline Dasatinib forms N-6 and H1-7 or mixtures thereof.

Typically, the amount of form N-6 in form B is measured by PXRD using any peaks selected from the group consisting of peaks at: 6.9, 12.4, 13.2, 13.8 and 24.4 deg±0.2 degrees 2-theta, the amount of form H1-7 in form B is measured by PXRD using any peaks selected from the group consisting of peaks at: 4.6, 9.2, 15.2 and 19.6 deg±0.2 degrees 2-theta.

In addition anhydrous form B is relatively stable at a temperature of about 20° C. and below. As exemplified in example 91 and 92, form N6 is converted to form B when slurried at a temperature of about 20° C. to about 0° C. for 2 days.

Form B can be prepared by a process comprising crystallizing dasatinib from a mixture comprising the compound 1, N-(2-hydroxyethyl) piperazine, N-ethyldiisopropylamine and a mixture of DMSO, methanol and water.

Typically, the crystallization comprises reacting compound 1, N-(2-hydroxyethyl)piperazine, and N-ethyldiisopropylamine in DMSO to obtain a solution comprising dasatinib, adding methanol and then water to said solution to obtain a second solution, and precipitating said crystalline form to obtain a suspension.

Preferably, the reaction of compound 1, N-(2-hydroxyethyl)piperazine, and N-ethyldiisopropylamine in DMSO is done at a temperature of about 40° C. to about 150° C., more preferably, of about 40° C. to about 100° C., most preferably, of about 60° C. to about 65° C. Preferably, the reaction is done upon stirring. Preferably, stirring is done for about 2 hours.

Preferably, methanol and water are added at a temperature of about 60° C. to about 65° C.

Preferably, precipitation is done by cooling the solution. Preferably, cooling is to a temperature of about 5° C. to about 0° C.

The process for preparing form B of dasatinib can further comprise recovering the crystalline form. The recovery can be done for example, by filtering the suspension and drying.

Form B can also be prepared by another process comprising crystallizing dasatinib from a mixture comprising ethanol and water.

Typically, the crystallization comprises providing a solution of dasatinib in a mixture of ethanol and water, and precipitating said crystalline form to obtain a suspension.

Preferably, the solution is provided by combining dasatinib and a mixture of ethanol and water, and heating the combination. Preferably, heating is to a temperature of about 75° C. to about 80° C. Preferably, an additional amount of water is added prior to precipitating the crystalline form, providing a solution. Preferably, the additional amount of water is added at a temperature of about 75° C. to about 80° C. to obtain a solution.

Preferably, the solution can be maintained prior to precipitating the crystalline form. Preferably, the solution is maintained at a temperature of about 70° C. Preferably, the solution is maintained for about 1 hour.

Preferably, precipitation is done by cooling the second solution to a temperature of about 5° C. to about 0° C. Preferably, cooling can be done over a period of about 1.5 hours to about 4 hours, more preferably, for a period of about 2 hours.

Typically, the suspension can be further maintained to increase the yield of the precipitated crystalline form. Preferably, the suspension can be further maintained at a temperature of about 5° C. to about 0° C.

Form B can also be prepared by another process comprising providing an opalescent solution of dasatinib in methanol, and precipitating said crystalline form to obtain a suspension.

Preferably, the opalescent solution is provided by combining dasatinib and methanol, and heating the combination. Preferably, heating is to a temperature of about 65° C.

Preferably, the opalescent solution is maintained at a temperature of about 65° C. Preferably, the solution is maintained for about 1 hour.

Preferably, precipitation is done by cooling the opalescent solution to a temperature of about 5° C. to about 0° C. Preferably, cooling can be done over a period of about 1.5 hours to about 4 hours, more preferably, for a period of about 1 hour.

The process for preparing form B of dasatinib can further comprise recovering said crystalline form. The recovery can be done for example, by filtering the suspension and drying.

In another embodiment, the present invention encompasses a n-propanol-DMSO solvate of dasatinib characterized by data selected from the group consisting of: a PXRD pattern having any 3 peaks selected from the list consisting of: 6.0, 11.9, 12.0, 14.9, 17.8, 18.3, 18.7, 21.4, 22.9, 24.2 and 24.7±0.2 degrees 2-theta, a powder XRD pattern as depicted in FIG. 1, and a combination thereof. This form can be designated as form K2.

In a preferred embodiment, the present invention encompasses a n-propanol-DMSO solvate of dasatinib designated Form K2, characterized by a PXRD pattern having any 5 peaks selected from the list consisting of: 6.0, 11.9, 12.0, 14.9, 17.8, 18.3, 18.7, 21.4, 22.9, 24.2 and 24.7±0.2 degrees 2-theta.

The above n-propanol-DMSO solvate of dasatinib designated Form K2, can be further characterized by data selected from the group consisting of: a powder XRD pattern with peaks at about 6.0, 12.0, 14.9, 17.8, and 18.3±0.2 degrees 2-theta; a powder XRD pattern with peaks at about 11.9, 12.0, 21.4, 22.9 and 24.7±0.2 degrees 2-theta, a content of n-propanol of typically 9% by weight as measured by GC, and a content of DMSO of typically 5% by weight as measured by GC.

In addition, crystalline Dasatinib Form K2 has less than about 15% by weight, preferably, less about than 10% by weight, more preferably, less than about 5% by weight of crystalline Dasatinib form N-6.

Typically, the amount of form N-6 in form K2 is measured by PXRD using any peaks selected from the group consisting of: 6.9, 12.4, 13.8 and 16.8 deg±0.2 degrees 2-theta.

Form K2 can be prepared by a process comprising crystallizing dasatinib from a mixture comprising the compound 1 of the following structure

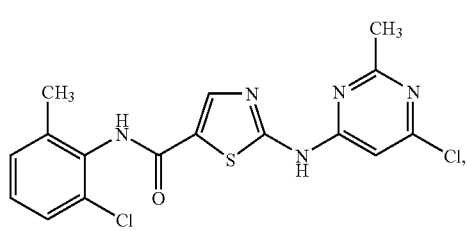

N-(2-hydroxyethyl) piperazine, N-ethyldiisopropylamine and a mixture of DMSO and n-propylalcohol.

Typically, the crystallization comprises reacting the compound of formula 1, N-(2-hydroxyethyl)piperazine, and N-thyldiisopropylamine in DMSO to obtain a solution comprising dasatinib and adding n-propyl alcohol to said solution to obtain a suspension comprising said crystalline form.

Preferably, the reaction of a mixture of the compound 1, N-(2-hydroxyethyl)piperazine, and N-ethyldiisopropylamine in DMSO is done at a temperature of about 40° C. to about 150° C., more preferably, of about 40° C. to about 100° C., most preferably, of about 60° C. to about 80° C.

Preferably, the reaction time is about 1 to about 2 hours. Preferably, when the reaction is done at about 60° C. the reaction time takes about 2 h, and when done at about 80° C. the reaction time takes about 1 h.

Preferably, the reaction is done upon stirring. Preferably, stirring is done for about 1 hour to about 3 hours depending on the reaction temperature, more preferably, for about 2.75 hours.

Preferably, n-propanol is added at a temperature of about 80° C.

Typically, the suspension is cooled to increase the yield of the precipitated crystalline form. Preferably, cooling is to about room temperature.

Preferably, cooling can be conducted slowly, more preferably, over a period of about 90 minutes.

The process for preparing form K2 of dasatinib can further comprise recovering said crystalline form. The recovery can be done for example, by filtering the suspension and drying.

Figure 3:
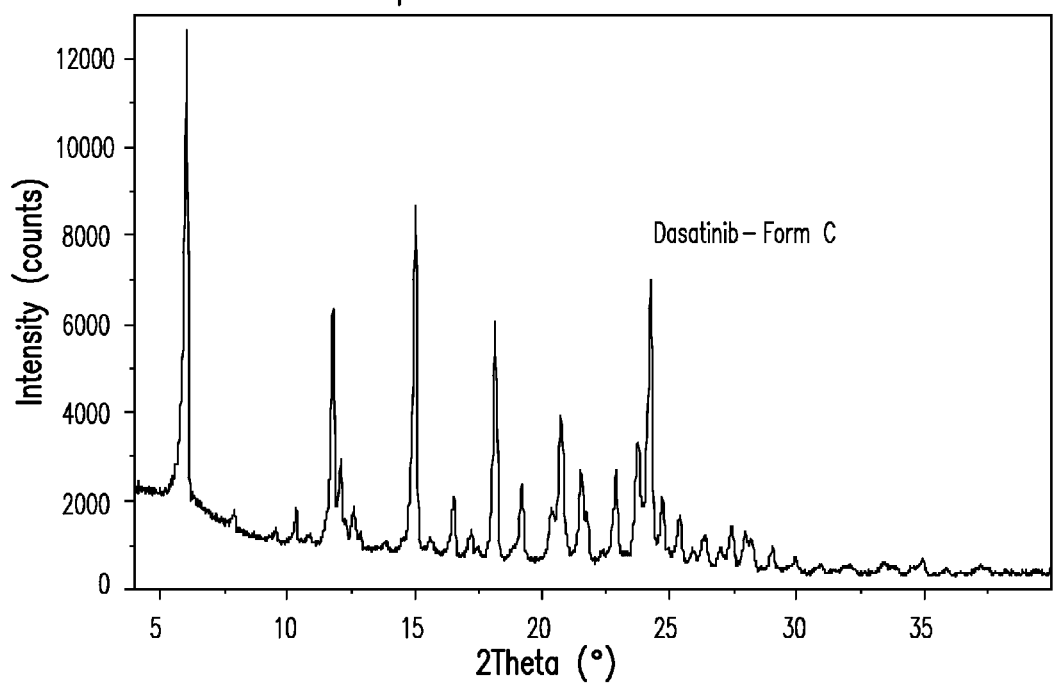
FIG. 3 shows a powder XRD pattern of crystalline dasatinib form C.

In another embodiment the present invention encompasses a DMSO solvate of dasatinib characterized by data selected from the group consisting of: a PXRD pattern having any 3 peaks selected from the list consisting of: 6.1, 11.8, 15.1, 16.6, 18.2, 19.3, 20.8, 21.6, 23.0, 23.8, 24.3, 24.8 and 25.5±0.2 degrees 2-theta, a powder XRD pattern as depicted in FIG. 3; a solid-state $^{13}$C NMR spectrum having signals at about 139.1 and 128.1±0.2 ppm; a solid-state $^{13}$C NMR spectrum having chemical shifts differences between the signal exhibiting the lowest chemical shift at 125±1.0 ppm and another in the chemical shift range of 100 to 180 ppm of about 13.9 and 2.9±0.1 ppm; and combination thereof. The signal exhibiting the lowest chemical shift in the chemical shift range of 100 to 180 ppm is typically at about 125±1 ppm. This form can be designated as form C.

In a preferred embodiment the present invention encompasses a DMSO solvate of dasatinib designated form C, characterized by a PXRD pattern having any 5 peaks selected from the list consisting of: 6.1, 11.8, 15.1, 16.6, 18.2, 19.3, 20.8, 21.6, 23.0, 23.8, 24.3, 24.8 and 25.5±0.2 degrees 2-theta.

The above DMSO solvate of dasatinib can also be characterized by a PXRD pattern having peaks at about 6.1 and 20.8±0.2 degrees 2-theta and any 3 peaks at positions selected from the group consisting of: 11.8, 15.1, 18.2, 19.3 and 23.8±0.2 degrees 2-theta. The peak positions are calibrated by means of silicon internal standard.

The above DMSO solvate of dasatinib designated Form C can be further characterized by data selected from the group consisting of: a powder XRD pattern with peaks at about 6.1, 11.8, 15.1, 18.2, and 24.3±0.2 degrees 2-theta; a powder XRD pattern with peaks at about 6.1, 15.1, 18.2, 24.3 and 25.5±0.2 degrees 2-theta; a powder XRD pattern with peaks at about 11.8, 15.1, 18.2, 19.3 and 24.3±0.2 degrees 2-theta; and a content of DMSO of about 11% to about 13% by weight, preferably about 12% by weight as measured by GC; and a content of water of about 1% by weight as measured by KF.

In addition, crystalline Dasatinib Form C has less than about 15% by weight, preferably, less about than 10% by weight, more preferably, less than about 5% by weight of crystalline dasatinib forms N-6 and H1-7.

Typically, the amount of form N-6 in form C is measured by PXRD using any peaks selected from the group consisting of peaks at: 6.9, 13.3 and 21.2 deg±0.2 degrees 2-theta, the amount of form H1-7 in form C is measured by PXRD using any peaks selected from the group consisting of peaks at: 4.6, 9.2, 11.2, 13.8 and 19.6 deg±0.2 degrees 2-theta.

Form C can be prepared by a process comprising crystallizing dasatinib from a mixture comprising the compound of formula 1, N-(2-hydroxyethyl) piperazine, N-ethyldiisopropylamine and a mixture of DMSO and water.

The crystallization comprises reacting compound 1, N-(2-hydroxyethyl)piperazine, and N-ethyldiisopropylamine in DMSO to obtain a solution comprising dasatinib, adding water, and precipitating said crystalline form to obtain a suspension.

Preferably, the reaction of a mixture of compound 1, N-(2-hydroxyethyl)piperazine, and N-ethyldiisopropylamine in DMSO is done at a temperature of about 40° C. to about 150° C., more preferably, of about 40° C. to about 100° C., most preferably, of about 40° C. to about 60° C. Preferably, the reaction is done upon stirring. Preferably, stirring is done for about 1 hour to about 4 hours, preferably, for about 2 hours to about 3 hours.

Preferably, water is added at a temperature of about 40° C. to about 60° C., providing a second solution.

Preferably, precipitation is done by cooling the second solution. Preferably, cooling is to a temperature of about 5° C. to about 0° C.

Optionally, the second solution can be further maintained prior to precipitating the crystalline form. Preferably, the second solution is further maintained at a temperature of about 40° C. to about 60° C., preferably of about 50° C. to about 60° C. Preferably, the second solution is further maintained for about 30 minutes.

The process for preparing form C of dasatinib can further comprise recovering the said crystalline form. The recovery can be done for example, by filtering the suspension and drying.

Figure 4:
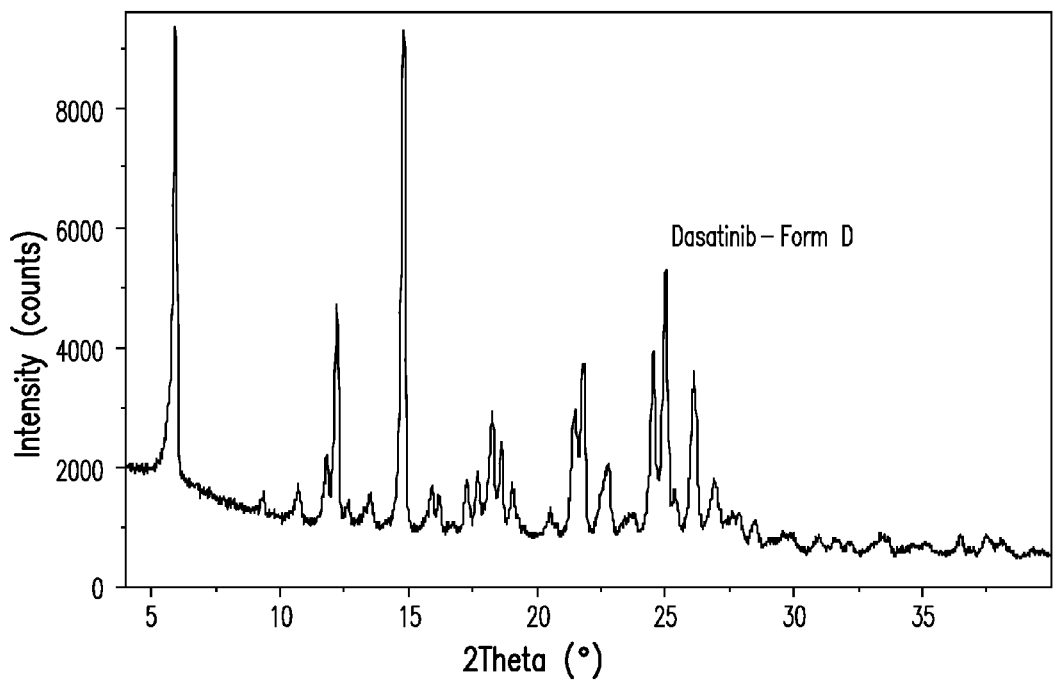
FIG. 4 shows a powder XRD pattern of crystalline dasatinib form D.

In another embodiment the present invention encompasses a THF solvate of dasatinib characterized by data selected from the group consisting of: a PXRD pattern having any 3 peaks selected from the list consisting of: 5.9, 11.8, 12.2, 14.8, 18.3, 18.6, 21.5, 21.8, 24.5, 25.0, and 26.1±0.2 degrees 2-theta, a powder XRD pattern as depicted in FIG. 4, and a combination thereof. This form can be designated as form D.

In a preferred embodiment the present invention encompasses THF solvate of dasatinib designated form D, characterized by a PXRD pattern having any 5 peaks selected from the list consisting of: 5.9, 11.8, 12.2, 14.8, 18.3, 18.6, 21.5, 21.8, 24.5, 25.0, and 26.1±0.2 degrees 2-theta.

The above THF of dasatinib designated Form D can be further characterized by data selected from the group consisting of: a powder XRD pattern with peaks at about 5.9, 12.2, 14.8, 25.0, and 26.1±0.2 degrees 2-theta; a powder XRD pattern with peaks at about 5.9, 18.3, 21.8, 24.5 and 26.1±0.2 degrees 2-theta, and a content of THF of about 7% to about 9% by weight, preferably about 8% by weight as measured by GC.

In addition, crystalline Dasatinib Form D has less than about 15% by weight, preferably, less about than 10% by weight, more preferably, less than about 5% by weight of crystalline Dasatinib form N-6.

Typically, the amount of form N-6 in form D is measured by PXRD using any peaks selected from the group consisting of peaks at: 6.9, 13.2, 13.8, 16.8 and 21.1 deg±0.2 degrees 2-theta.

Form D can be prepared by a process comprising crystallizing dasatinib from a mixture comprising the compound of formula 1, N-(2-hydroxyethyl) piperazine, N-ethyldiisopropylamine and THF.

The crystallization comprises reacting compound 1, N-(2-hydroxyethyl)piperazine, and N-ethyldiisopropylamine in THF to obtain a solution comprising dasatinib, and precipitating said crystalline form to obtain a suspension Preferably, the reaction of a mixture of compound 1, N-(2-hydroxyethyl)piperazine, and N-ethyldiisopropylamine in THF is done at reflux temperature. Preferably, reaction is done for about 8 hours.

Preferably, precipitation is done by cooling the solution. Preferably, cooling is to a temperature of about 5° C. to about 0° C.

The process for preparing form D of dasatinib can further comprise recovering said crystalline form. The recovery can be done for example, by filtering the suspension and drying.

Figure 5:
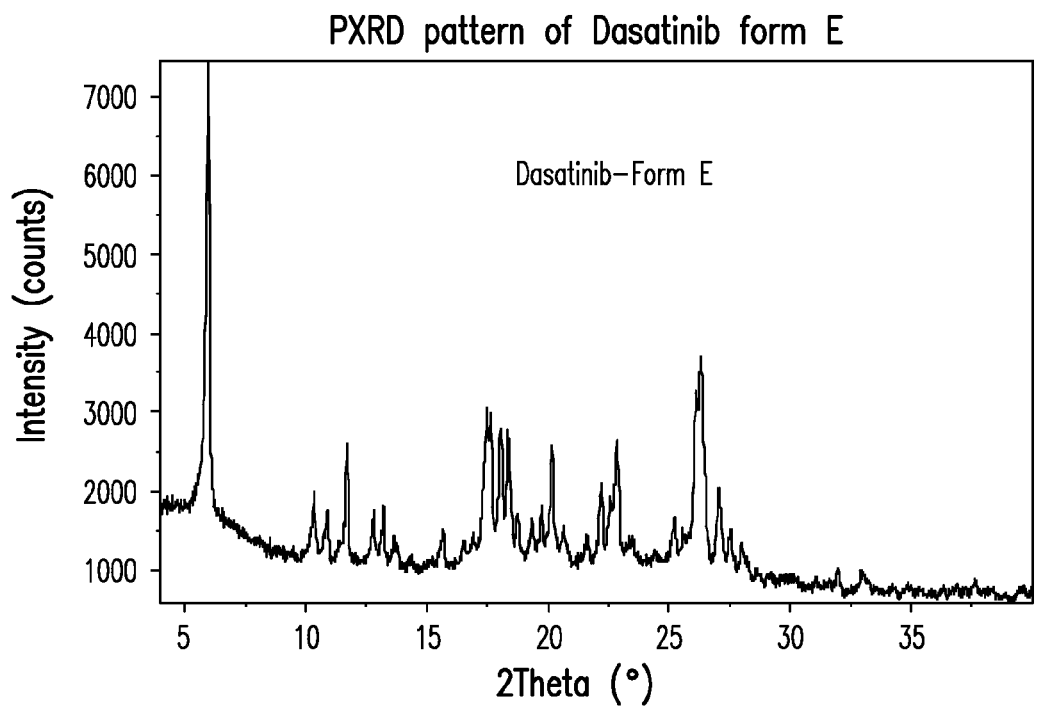
FIG. 5 shows a powder XRD pattern of crystalline dasatinib form E.

In another embodiment the present invention encompasses a 2-methyl-THF solvate of dasatinib characterized by data selected from the group consisting of: a PXRD pattern having any 3 peaks selected from the list consisting of: 6.0, 11.7, 12.8, 13.2, 17.5, 18.0, 18.4, 20.2, 22.8, 26.3 and 27.0±0.2 degrees 2-theta, a powder XRD pattern as depicted in FIG. 5, and combination thereof. This form can be designated as form E.

In a preferred embodiment the present invention encompasses a 2-methyl-THF solvate of dasatinib designated form E characterized by a PXRD pattern having any 5 peaks selected from the list consisting of: 6.0, 11.7, 12.8, 13.2, 17.5, 18.0, 18.4, 20.2, 22.8, 26.3 and 27.0±0.2 degrees 2-theta.

The above 2-methyl-THF solvate of dasatinib designated Form E can be further characterized by data selected from the group consisting of: a powder XRD pattern with peaks at about 6.0, 11.7, 17.5, 20.2, and 26.3±0.2 degrees 2-theta; a powder XRD pattern with peaks at about 6.0, 11.7, 18.0, 20.2 and 22.8±0.2 degrees 2-theta, and a content of 2-methyl-THF of about 3% to about 5%, preferably about 4% by weight as measured by GC.

In addition, crystalline Dasatinib Form E has less than about 15% by weight, preferably, less about than 10% by weight, more preferably, less than about 5% by weight of crystalline Dasatinib form N-6.

Typically, the amount of form N-6 in form E is measured by PXRD using any peaks selected from the group consisting of peaks at: 6.9, 12.4, 16.8, 21.1, 24.4 and 24.9 deg±0.2 degrees 2-theta.

Form E can be prepared by a process comprising crystallizing dasatinib from a mixture comprising the compound of formula 1, N-(2-hydroxyethyl) piperazine, N-ethyldiisopropylamine and 2-methyl-THF.

The crystallization comprises reacting compound 1, N-(2-hydroxyethyl)piperazine, and N-ethyldiisopropylamine in 2-methyl-THF to obtain a solution comprising dasatinib, and precipitating said crystalline form to obtain a suspension Preferably, the reaction of compound 1, N-(2-hydroxyethyl)piperazine, and N-ethyldiisopropylamine in 2-methyl-THF is done at reflux temperature. Preferably, the reaction is done for about 2 hours to about 4 hours, more preferably for about 3 hours.

Preferably, precipitation is done by cooling the solution. Preferably, cooling is to a temperature of about 5° C. to about 0° C.

The process for preparing form E of dasatinib can further comprise recovering said crystalline form. The recovery can be done for example, by filtering the suspension and drying.

Figure 6:
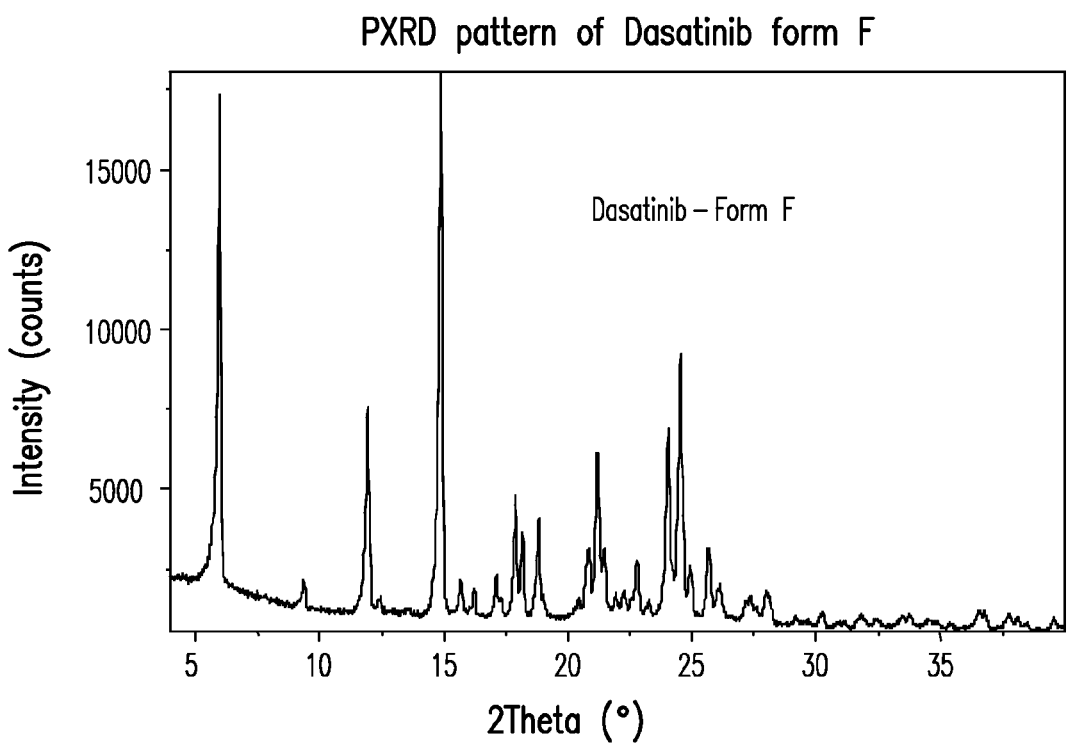
FIG. 6 shows a powder XRD pattern of crystalline dasatinib form F.

In another embodiment the present invention encompasses a 1,4-dioxane solvate of dasatinib characterized by data selected from the group consisting of: a PXRD pattern having any 3 peaks selected from the list consisting of: 6.0, 12.0, 14.9, 17.9, 18.2, 18.8, 20.8, 21.2, 22.8, 24.1 24.1, 24.6 and 25.7±0.2 degrees 2-theta, a powder XRD pattern as depicted in FIG. 6, and a combination thereof. This form can be designated as form F.

In a preferred embodiment the present invention encompasses a 1,4-dioxane solvate of dasatinib designated form F characterized by a PXRD pattern having any 5 peaks selected from the list consisting of: 6.0, 12.0, 14.9, 17.9, 18.2, 18.8, 20.8, 21.2, 22.8, 24.1 24.1, 24.6 and 25.7±0.2 degrees 2-theta.

The above 1,4-dioxane solvate of dasatinib designated Form F can be further characterized by data selected from the group consisting of: a powder XRD pattern with peaks at about 6.0, 12.0, 14.9, 24.1, and 24.6±0.2 degrees 2-theta; a powder XRD pattern with peaks at about 6.0, 14.9, 17.9, 18.8 and 21.2±0.2 degrees 2-theta, and a content of 1,4-dioxane of about 10% to about 12%, preferably about 11% by weight as measured by GC.

In addition, crystalline Dasatinib Form F has less than about 15% by weight, preferably, less about than 10% by weight, more preferably, less than about 5% by weight of crystalline Dasatinib form N-6.

Typically, the amount of form N-6 in form F is measured by PXRD using any peaks selected from the group consisting of peaks at: 6.9, 12.4, 13.2, 13.8 and 16.8 deg±0.2 degrees 2-theta.

Form F can be prepared by a process comprising precipitating dasatinib from a mixture comprising the compound of formula 1, N-(2-hydroxyethyl) piperazine, N-ethyldiisopropylamine and 1,4-dioxane.

The precipitation comprises reacting compound 1, N-(2-hydroxyethyl)piperazine, and N-ethyldiisopropylamine in 1,4-dioxane to obtain a suspension comprising said crystalline dasatinib.

Preferably, the reaction of a mixture of compound 1, N-(2-hydroxyethyl)piperazine, and N-ethyldiisopropylamine in 1,4-dioxane is done at reflux temperature. Preferably, the reaction is done for about 2 hours to about 4 hours, more preferably for about 3 hours.

Typically, the suspension can be cooled to increase the yield of the precipitated crystalline form. Preferably, the suspension is cooled at a temperature of about 5° C. to about 0° C.

The process for preparing form F of dasatinib can further comprise recovering said crystalline form. The recovery can be done for example, by filtering the suspension and drying.

Figure 7:
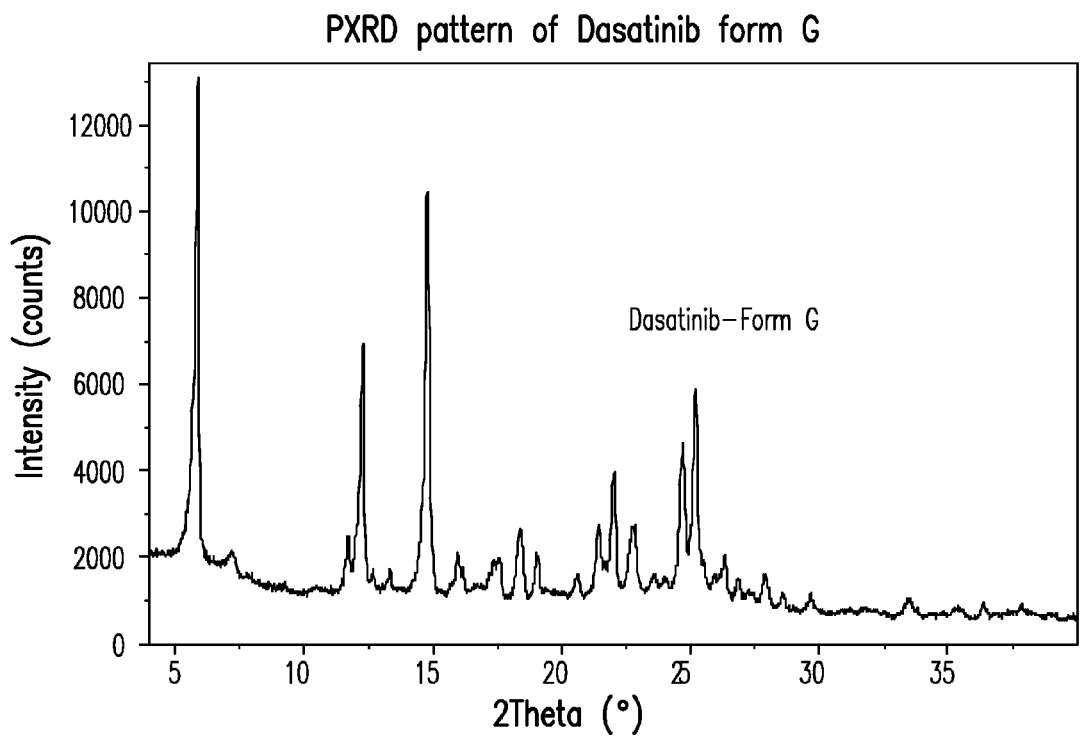
FIG. 7 shows a powder XRD pattern of crystalline dasatinib form G.

In another embodiment the present invention encompasses a pyridine solvate of dasatinib characterized by data selected from the group consisting of: a PXRD pattern having any 3 peaks selected from the list consisting of: 5.9, 11.7, 12.3, 14.0, 18.3, 21.4, 22.0, 22.7, 24.7, and 25.2±0.2 degrees 2-theta, a powder XRD pattern as depicted in FIG. 7, and combination thereof. This form can be designated as form G.

In a preferred embodiment the present invention encompasses a pyridine solvate of dasatinib designated form G characterized by a PXRD pattern having any 5 peaks selected from the list consisting of: 5.9, 11.7, 12.3, 14.0, 18.3, 21.4, 22.0, 22.7, 24.7, and 25.2±0.2 degrees 2-theta.

The above pyridine solvate of dasatinib designated Form G can be further characterized by data selected from the group consisting of: a powder XRD pattern with peaks at about 5.9, 12.3, 14.0, 24.7, and 25.2±0.2 degrees 2-theta; a powder XRD pattern with peaks at about 5.9, 12.3, 14.0, 22.4 and 25.2±0.2 degrees 2-theta, and a content of pyridine of about 4% to about 6% by weight, preferably about 5% by weight as measured by GC.

In addition, crystalline Dasatinib Form G has less than about 15% by weight, preferably, less about than 10% by weight, more preferably, less than about 5% by weight of crystalline Dasatinib form N-6.

Typically, the amount of form N-6 in form G is measured by PXRD using any peaks selected from the group consisting of peaks at: 6.9, 13.2 and 16.8 deg±0.2 degrees 2-theta.

Form G can be prepared by a process comprising crystallizing dasatinib from a mixture comprising the compound of formula 1, N-(2-hydroxyethyl) piperazine, N-ethyldiisopropylamine and a solvent selected from the group consisting of: a mixture of pyridine and acetone and a mixture of pyridine and ethylacetate.

The crystallization comprises reacting compound of formula 1, N-(2-hydroxyethyl)piperazine, and N-ethyldiisopropylamine in pyridine to obtain a solution comprising dasatinib, and adding acetone or ethylacetate to obtain a suspension comprising said crystalline form.

Preferably, the reaction of a mixture of compound 1, N-(2-hydroxyethyl)piperazine, and N-ethyldiisopropylamine in pyridine is done at a temperature of about 80° C. to about 100° C., more preferably, of about 90° C. to about 100° C. Preferably, the reaction is done upon stirring. Preferably, stirring is done for about 2.5 to about 5 hours, more preferably, for about 2.5 to about 3 hours.

Preferably, acetone or ethylacetate are added at a temperature of about 90° C. to about 100° C., providing the suspension.

Typically, the suspension can be cooled to increase the yield of the precipitated crystalline form. Preferably, suspension is cooled to a room temperature.

The process for preparing form G of dasatinib can further comprise recovering said crystalline form. The recovery can be done for example, by filtering the suspension and drying.

Figure 8:
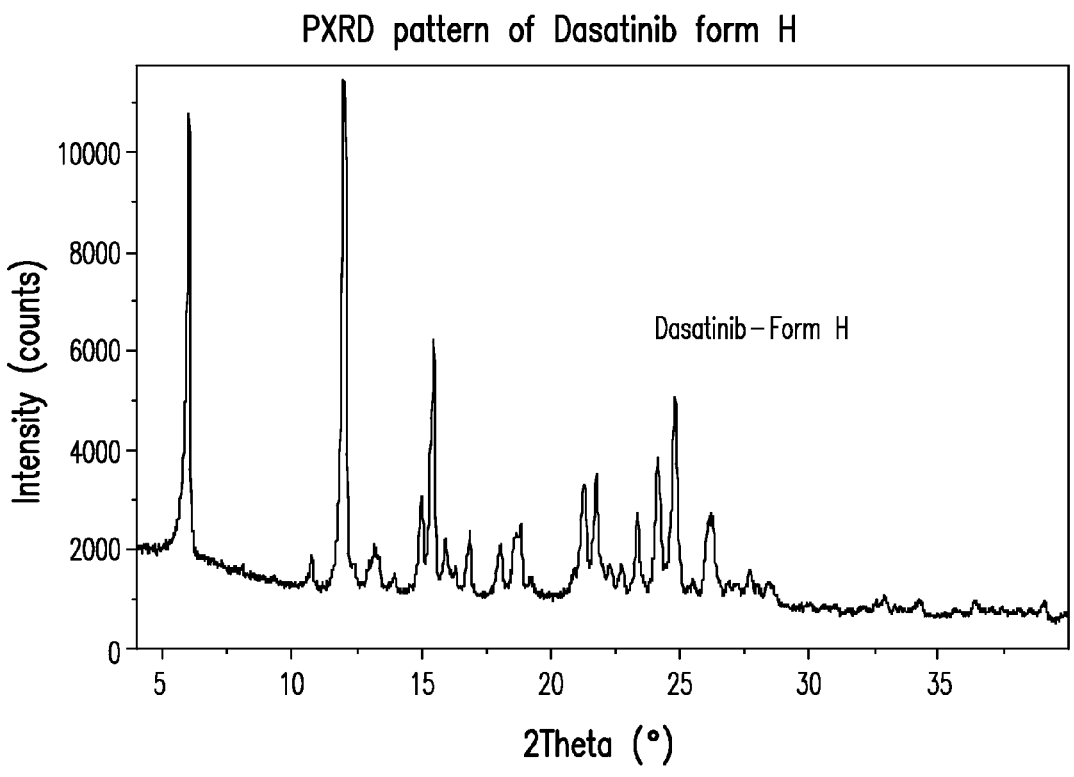
FIG. 8 shows a powder XRD pattern of crystalline dasatinib form H.

In another embodiment the present invention encompasses a toluene solvate of dasatinib characterized by data selected from the group consisting of: a PXRD pattern having any 3 peaks selected from the list consisting of: 6.0, 12.0, 15.0, 15.4, 16.9, 19.3, 21.3, 21.7, 23.4, 24.1 and 24.8±0.2 degrees 2-theta, a powder XRD pattern as depicted in FIG. 8, and a combination thereof. This form can be designated as form H.

In a preferred embodiment the present invention encompasses a toluene solvate of dasatinib designated form H characterized by a PXRD pattern having any 5 peaks selected from the list consisting of: 6.0, 12.0, 15.0, 15.4, 16.9, 19.3, 21.3, 21.7, 23.4, 24.1 and 24.8±0.2 degrees 2-theta.

The above toluene of dasatinib designated Form H can be further characterized by data selected from the group consisting of: a powder XRD pattern with peaks at about 6.0, 12.0, 15.4, 21.7, and 24.8±0.2 degrees 2-theta; a powder XRD pattern with peaks at about 6.0, 12.0, 15.4, 24.1 and 24.8±0.2 degrees 2-theta, and a content of toluene of about 5% to about 7% by weight, preferably about 6% by weight as measured by GC.

In addition, crystalline Dasatinib Form H has less than about 15% by weight, preferably, less about than 10% by weight, more preferably, less than about 5% by weight of crystalline Dasatinib form N-6.

Typically, the amount of form N-6 in form H is measured by PXRD using any peaks from selected the group consisting of peaks at: 6.9 and 13.8 deg±0.2 degrees 2-theta.

Form H can be prepared by a process comprising precipitating dasatinib from a mixture comprising the compound 1, N-(2-hydroxyethyl) piperazine, N-ethyldiisopropylamine and toluene.

The precipitation comprises reacting compound 1, N-(2-hydroxyethyl)piperazine, and N-ethyldiisopropylamine in toluene to obtain a suspension comprising said crystalline dasatinib.

Preferably, the reaction of a mixture of compound 1, N-(2-hydroxyethyl)piperazine, and N-ethyldiisopropylamine in toluene is done at reflux temperature, preferably, reflux temperature is at about 110° C. to about 111° C. Preferably, reaction is done for about 8 hours to about 12 hours, more preferably about 9 hours.

Typically, the suspension can be cooled to increase the yield of the precipitated crystalline form. Preferably, the suspension is cooled at a temperature of about 5° C. to about 0° C.

The process for preparing form H of dasatinib can further comprise recovering said crystalline form. The recovery can be done for example, by filtering the suspension and drying.

Figure 9:
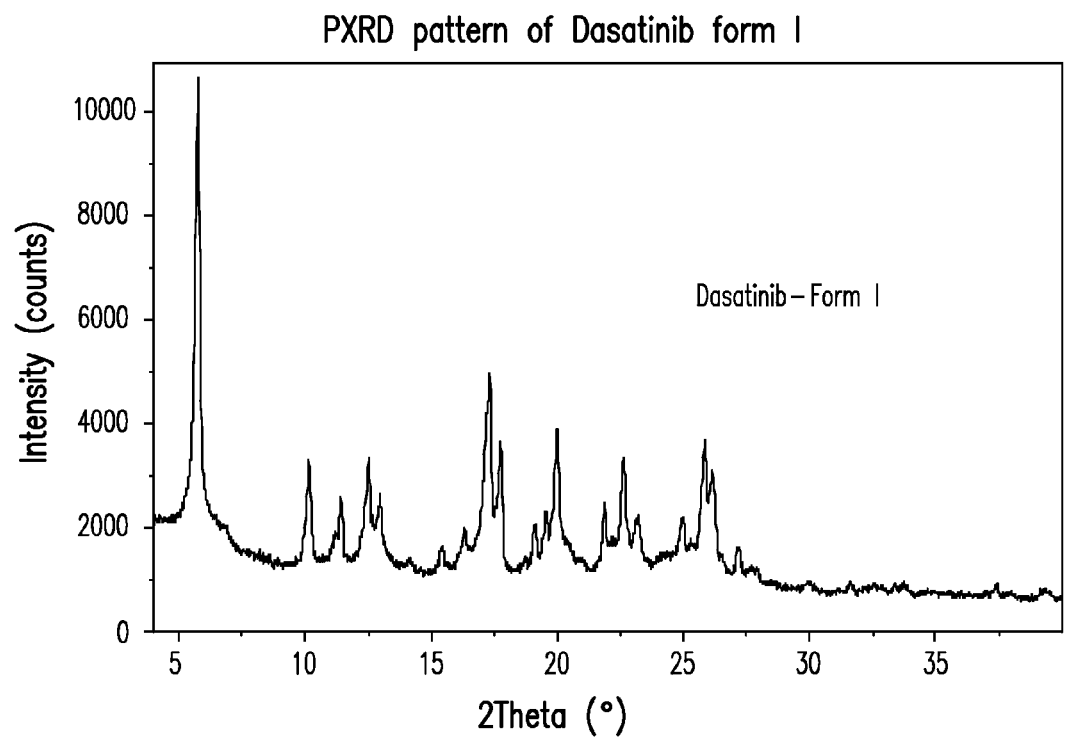
FIG. 9 shows a powder XRD pattern of crystalline dasatinib form I.

In another embodiment the present invention encompasses a MIBK solvate of dasatinib characterized by data selected from the group consisting of: a PXRD pattern having any 3 peaks selected from the list consisting of: 5.8, 10.2, 11.4, 12.5, 17.3, 17.8, 20.0, 21.9, 22.6, 25.8 and 26.2±0.2 degrees 2-theta, a powder XRD pattern as depicted in FIG. 9, and combination thereof. This form can be designated as form I.

In a preferred embodiment the present invention encompasses a MIBK solvate of dasatinib designated Form I characterized by a PXRD pattern having any 5 peaks selected from the list consisting of: 5.8, 10.2, 11.4, 12.5, 17.3, 17.8, 20.0, 21.9, 22.6, 25.8 and 26.2±0.2 degrees 2-theta.

The above MIBK solvate of dasatinib designated Form I can be further characterized by data selected from the group consisting of: a powder XRD pattern with peaks at about 5.8, 10.2, 17.3, 20.0, and 25.8±0.2 degrees 2-theta; a powder XRD pattern with peaks at about 5.8, 10.2, 20.0, 22.6 and 25.8±0.2 degrees 2-theta, and a content of MIBK of about 8% to about 10% by weight, preferably about 9% by weight as measured by GC.

In addition, crystalline Dasatinib Form I has less than about 15% by weight, preferably, less about than 10% by weight, more preferably, less than about 5% by weight of crystalline Dasatinib form N-6.

Typically, the amount of form N-6 in form I is measured by PXRD using any peaks selected from the group consisting of peaks at: 6.9, 13.2, 13.8, 16.8, 21.1 and 24.4 deg±0.2 degrees 2-theta.

Form I can be prepared by a process comprising crystallizing dasatinib from a mixture comprising the compound of formula 1, N-(2-hydroxyethyl) piperazine, N-ethyldiisopropylamine and a mixture of pyridine and MIBK.

The crystallization comprises reacting compound 1, N-(2-hydroxyethyl)piperazine, and N-ethyldiisopropylamine in pyridine to obtain a solution comprising dasatinib, and adding MIBK to obtain a suspension comprising said crystalline form.

Preferably, the reaction of a mixture of compound 1, N-(2-hydroxyethyl)piperazine, and N-ethyldiisopropylamine in pyridine is done at a temperature of about 80° C. to about 100° C., more preferably, at about 100° C. Preferably, the reaction is done upon stirring. Preferably, stirring is done for about 2.5 hours to about 5 hours depending on the reaction temperature, more preferably, for about 2.5 hours.

Preferably, MIBK is added at a temperature of about 100° C., providing the suspension.

Typically, the suspension can be cooled to increase the yield of the precipitated crystalline form. Preferably, the suspension is cooled to a temperature of about room temperature to about 0° C., more preferably, to about room temperature.

The process for preparing form I of dasatinib can further comprise recovering said crystalline form. The recovery can be done for example, by filtering the suspension and drying.

Figure 10:
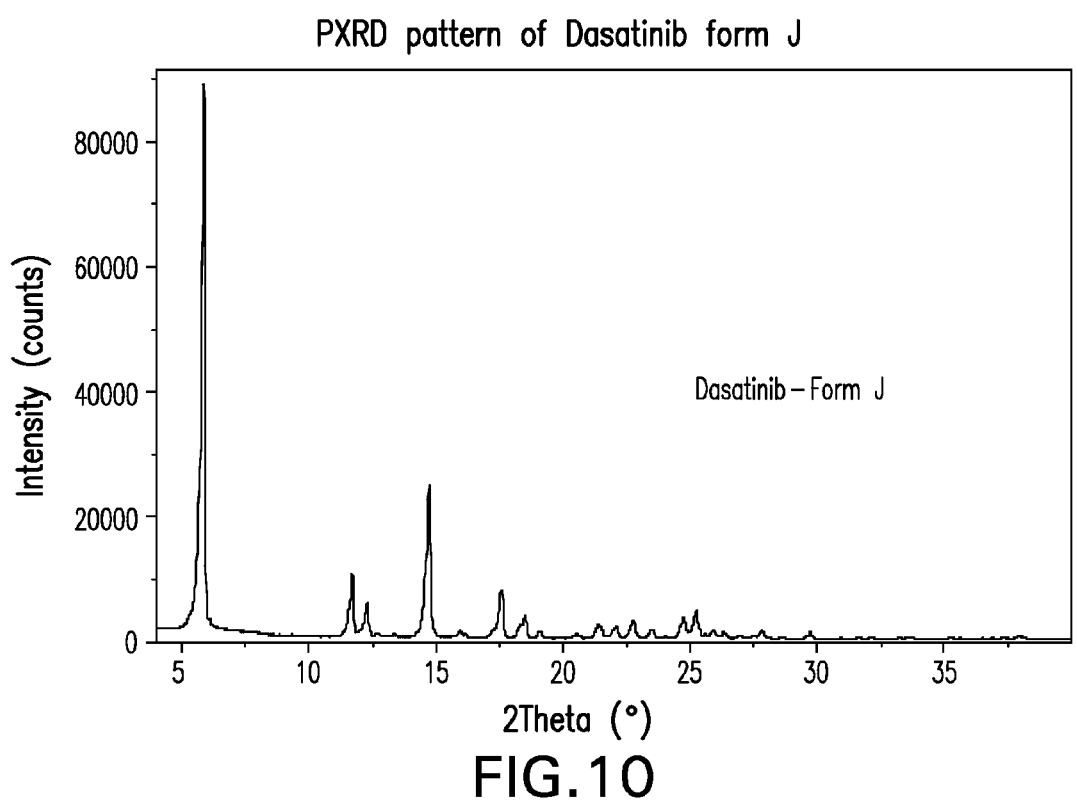
FIG. 10 shows a powder XRD pattern of crystalline dasatinib form J.

In another embodiment the present invention encompasses a mono acetone solvate of dasatinib characterized by data selected from the group consisting of: a PXRD pattern having any 3 peaks selected from the list consisting of: 5.9, 11.7, 12.3, 14.7, 17.6, 18.5, 21.4, 22.1, 22.8, 24.7 and 25.2±0.2 degrees 2-theta, a powder XRD pattern as depicted in FIG. 10, and combination thereof. This form can be designated as form J.

In a preferred embodiment the present invention encompasses a mono acetone solvate of dasatinib designated Form J characterized by a PXRD pattern having any 5 peaks selected from the list consisting of: 5.9, 11.7, 12.3, 14.7, 17.6, 18.5, 21.4, 22.1, 22.8, 24.7 and 25.2±0.2 degrees 2-theta.

The above mono acetone solvate of dasatinib designated Form J can be further characterized by data selected from the group consisting of: a powder XRD pattern with peaks at about 5.9, 11.7, 12.3, 14.7, and 17.6±0.2 degrees 2-theta, and a content of acetone of about 8% to about 10% by weight, preferably about 9% by weight as measured by GC; and a water content of up to 0.5% by weight as measured by Karl-Fischer.

In addition, crystalline Dasatinib Form J has less than about 15% by weight, preferably, less about than 10% by weight, more preferably, less than about 5% by weight of crystalline Dasatinib form N-6.

Typically, the amount of form N-6 in form J is measured by PXRD using any peaks selected from the group consisting of peaks at: 6.9, 13.2, 13.8, 16.8, and 24.4 deg±0.2 degrees 2-theta.

Form J can be prepared by a process comprising crystallizing dasatinib from a mixture comprising the compound 1, N-(2-hydroxyethyl) piperazine, N-ethyldiisopropylamine and a solvent selected from the group consisting of: mixture of DMSO and acetone, and a mixture of DMF and acetone.

The crystallization comprises reacting compound 1, N-(2-hydroxyethyl)piperazine, and N-ethyldiisopropylamine in DMSO or in DMF to obtain a solution comprising dasatinib, and adding acetone to obtain a suspension comprising said crystalline form.

Preferably, the reaction of a mixture of compound 1, N-(2-hydroxyethyl)piperazine, and N-ethyldiisopropylamine in DMSO or in DMF is done at a temperature of about 40° C. to about 150° C. Preferably, the reaction with DMSO is done at a temperature of about 40° C. to about 150° C., preferably, at about 40° C. to about 100° C., more preferably, at about 60° C. to about 80° C. Preferably, the reaction with DMF is done at a temperature of about 90° C. to about 100° C. Preferably, the reaction is done upon stirring. Preferably, stirring is done for about 1 hour to about 3 hours. Preferably, the reaction in DMSO, is stirred for about 1 hour to about 2 hours. Preferably, the reaction with DMF, is stirred for about 2.5 hour to about 3 hours.

Preferably, acetone is added at a temperature of about 60° C. to about 100° C., providing the suspension.

Typically, the suspension is cooled to increase the yield of the precipitated crystalline form. Preferably, cooling is to about room temperature.

Optionally, when the solvent mixture is DMSO and acetone, water can be added to the suspension providing a second solution. Preferably, water is added at a temperature of about 60° C. to about 80° C. Preferably, the second solution is cooled to obtain said suspension. Preferably, cooling is to a temperature of about 5° C. to about 0° C.

The process for preparing form J of dasatinib can further comprise recovering the said crystalline form. The recovery can be done for example, by filtering the suspension and drying.

Figure 12:
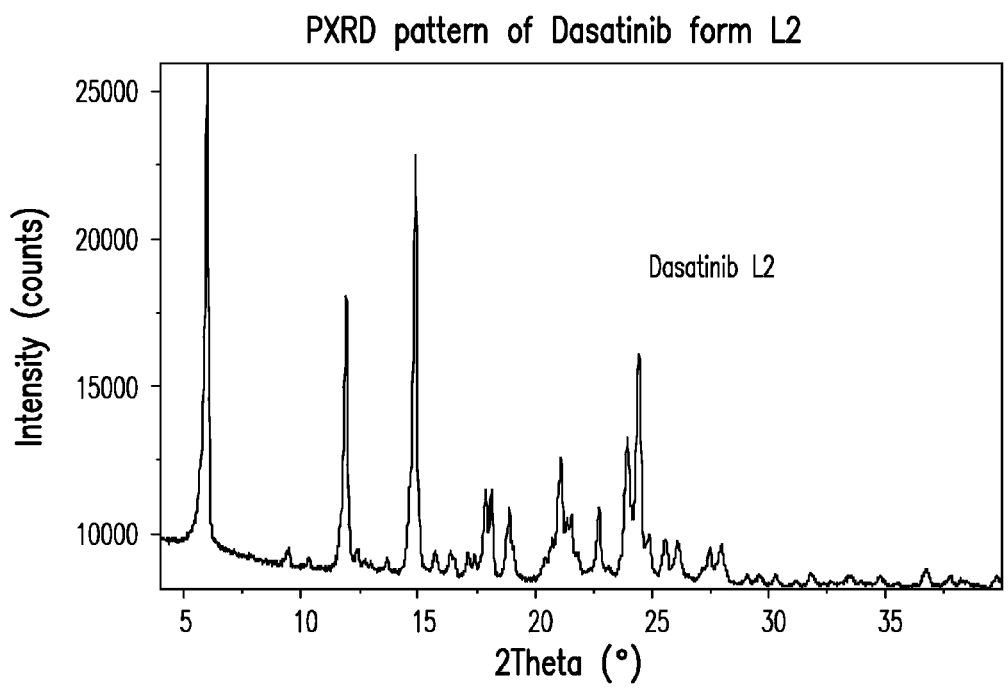
FIG. 12 shows a powder XRD pattern of crystalline dasatinib form L2.

In another embodiment the present invention encompasses a 2-butanol-DMSO solvate of dasatinib characterized by data selected from the group consisting of: a PXRD pattern having any 3 peaks selected from the list consisting of: 6.0, 12.0, 14.9, 17.9, 18.2, 18.9, 21.1, 22.8, 24.0, 24.5, 25.6 and 26.1±0.2 degrees 2-theta, a powder XRD pattern as depicted in FIG. 12, and a combination thereof. This form can be designated as form L2.

In a preferred embodiment the present invention encompasses a 2-butanol-DMSO solvate of dasatinib designated Form L2 characterized by a PXRD pattern having any 5 peaks selected from the list consisting of: 6.0, 12.0, 14.9, 17.9, 18.2, 18.9, 21.1, 22.8, 24.0, 24.5, 25.6 and 26.1±0.2 degrees 2-theta.

The above 2-butanol-DMSO solvate of dasatinib designated Form L2 can be further characterized by data selected from the group consisting of: a powder XRD pattern with peaks at about 6.0, 12.0, 14.9, 21.1 and 24.5±0.2 degrees 2-theta; a powder XRD pattern with peaks at about 14.9, 17.9, 21.1, 24.0 and 24.9±0.2 degrees 2-theta, a content of 2-butanol of typically 9% to about 11%, preferably about 10% by weight as measured by GC, and a content of DMSO of about 4% to about 6%, preferably about 5% by weight as measured by GC.

In addition, crystalline Dasatinib Form L2 has less than about 15% by weight, preferably, less about than 10% by weight, more preferably, less than about 5% by weight of crystalline Dasatinib form N-6.

Typically, the amount of form N-6 in form L2 is measured by PXRD using any peaks selected from the group consisting of peaks at: 6.9, 13.2, 13.8 and 16.8 deg±0.2 degrees 2-theta.

Form L2 can be prepared by a process comprising crystallizing dasatinib from a mixture comprising the compound 1, N-(2-hydroxyethyl) piperazine, N-ethyldiisopropylamine and a mixture of DMSO and 2-butanol.

The crystallization comprises reacting compound 1, N-(2-hydroxyethyl)piperazine, and N-ethyldiisopropylamine in DMSO to obtain a solution comprising dasatinib, adding 2-butanol, and precipitating said crystalline form to obtain a suspension comprising said crystalline form.

Preferably, the reaction of a mixture of compound 1, N-(2-hydroxyethyl)piperazine, and N-ethyldiisopropylamine in DMSO is done at a temperature of about 40° C. to about 150° C., more preferably, at about 40° C. to about 100° C., more preferably, at about 60° C. to about 80° C., most preferably, at about 80° C. to about 85° C. Preferably, the reaction is done for about 1 hour to about 2 hours depending on the reaction temperature.

Preferably, 2-butanol is added at a temperature of about 80° C. to about 85° C., providing a second solution.

Preferably, precipitation is induced by cooling the second solution. Preferably, cooling is to a temperature of about 5° C. to about 0° C.

The process for preparing form L2 of dasatinib can further comprise recovering said crystalline form. The recovery can be done for example, by filtering the suspension and drying.

Also described by the present invention is a mixture of a hydrate form of dasatinib, designated form M characterized by a PXRD pattern having any 5 peaks selected from the list consisting of: 5.5, 10.8, 16.0, 22.3, 25.4, and 27.1±0.2 degrees 2-theta; and a pyridine solvate, designated form G characterized by a PXRD pattern having any 5 peaks selected from the list consisting of: 5.9, 11.7, 12.3, 14.0, 18.3, 21.4, 22.0, 22.7, 24.7, and 25.2±0.2 degrees 2-theta.

Figure 13:
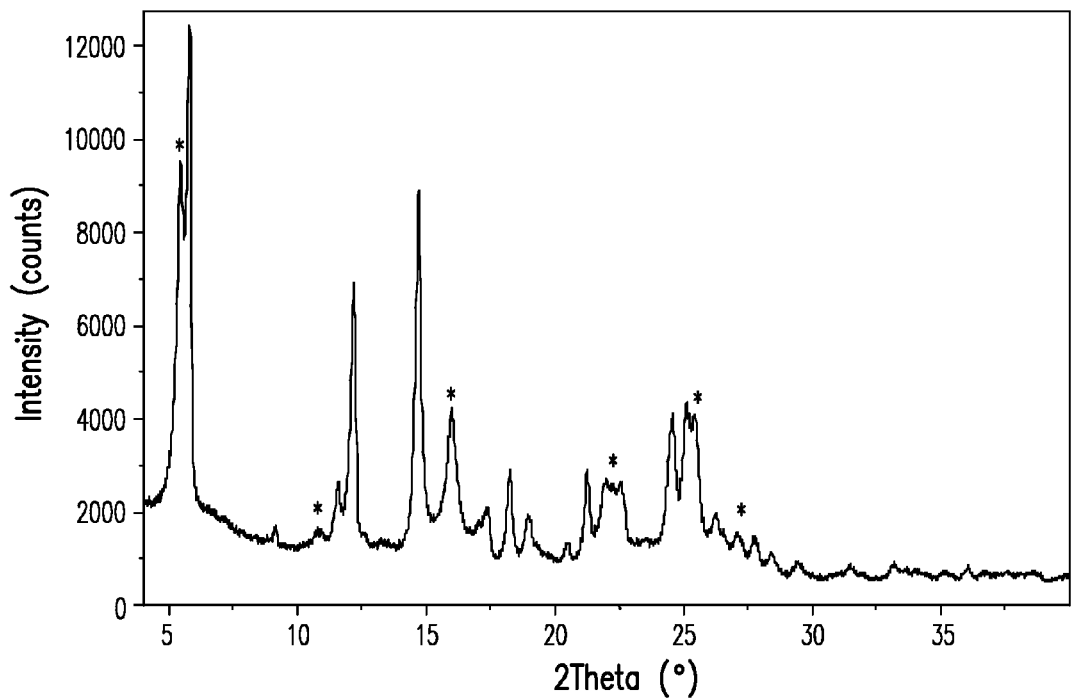
FIG. 13 shows a powder XRD pattern of crystalline dasatinib form G and M.
Figure 14:
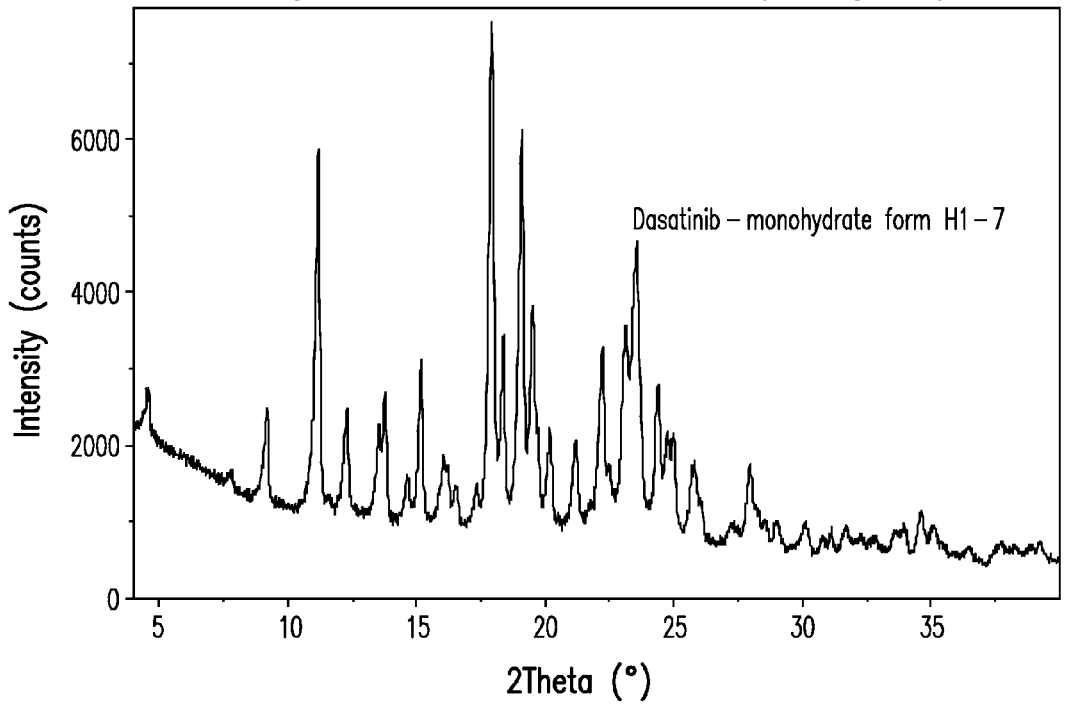
FIG. 14 shows a powder XRD pattern of Dasatinib form H1-7 (monohydrate) obtained in example 21.
Figure 15:
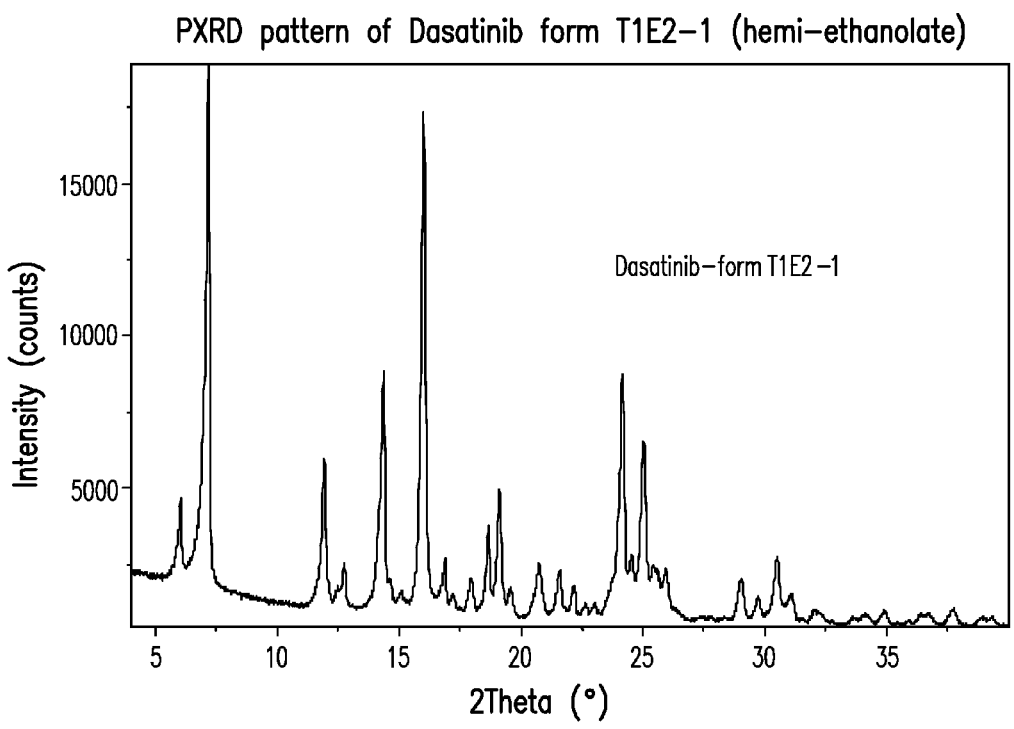
FIG. 15 shows a powder XRD pattern of Dasatinib form T1E2-1 (hemi-ethanolate) obtained in examples 24 and 25.

This mixture of hydrate form of dasatinib, designated form M, and a pyridine solvate, designated form G is characterized by a powder XRD pattern as depicted in FIG. 13.

Form M can be further characterized by a powder XRD pattern with peaks at about 5.5, 16.0, 22.3, 25.4 and 27.1±0.2 degrees 2-theta The mixture of hydrate form of dasatinib, designated form M, and a pyridine solvate, designated form G can be further characterized by a water content of about 3% by weight as measured by KF and a pyridine content of about 6% to about 8% by weight, preferably about 7% by weight as measured by GC.

In addition, crystalline Dasatinib Form M has less than about 15% by weight, preferably, less about than 10% by weight, more preferably, less than about 5% by weight of crystalline Dasatinib forms: N-6 and H1-7.

Typically, the amount of form N-6 in form M is measured by PXRD using any peaks selected from the group consisting of peaks at: 6.9, 13.2, 13.8 and 16.8 deg±0.2 degrees 2-theta and the amount of form H1-7 in form M is measured by PXRD using any peaks selected from the group consisting of peaks at: 4.6, 11.2, 15.2, 18.0 and 19.5 deg±0.2 degrees 2-theta.

The mixture of Forms G and M can be prepared by a process comprising crystallizing dasatinib from a mixture comprising the compound 1, N-(2-hydroxyethyl) piperazine, N-ethyldiisopropylamine and a mixture of pyridine and water.

The crystallization comprises reacting compound 1, N-(2-hydroxyethyl)piperazine, and N-ethyldiisopropylamine in pyridine to obtain a solution comprising dasatinib, and adding water to obtain a suspension comprising said mixture of crystalline forms.

Preferably, the reaction of a mixture of compound 1, N-(2-hydroxyethyl)piperazine, and N-ethyldiisopropylamine in pyridine is done at a temperature of about 80° C. to about 100° C., preferably, at a temperature of about 80° C. Preferably, the reaction is done for about 2.5 hours to about 5 hours, more preferably for about 3 hours to about 4 hours, depending on the reaction temperature.

Preferably, water is added at a temperature of about 80° C., providing the suspension.

Typically, the suspension is cooled to increase the yield of the precipitated mixture of crystalline forms. Preferably, cooling is to about room temperature.

The process for preparing the mixture of crystalline forms G and M of dasatinib can further comprise recovering said mixture of crystalline forms. The recovery can be done for example, by filtering the suspension and drying.

The present invention encompasses amorphous dasatinib.

Figure 16:
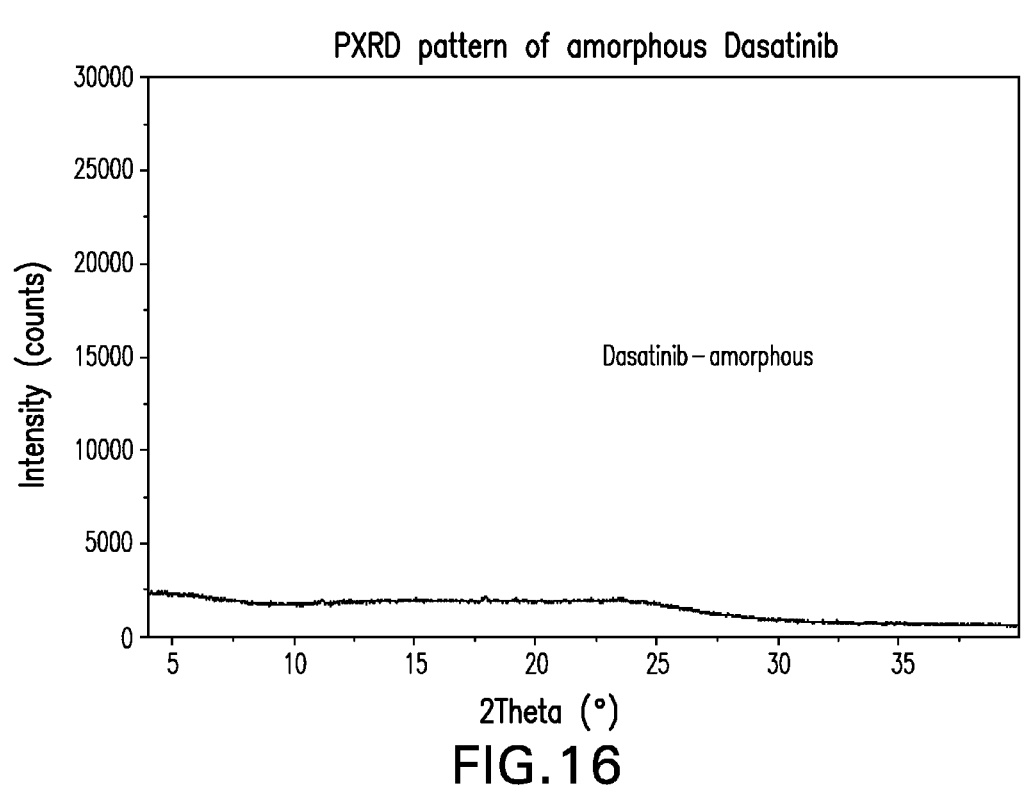
FIG. 16 shows a powder XRD pattern of amorphous Dasatinib.
Figure 35:
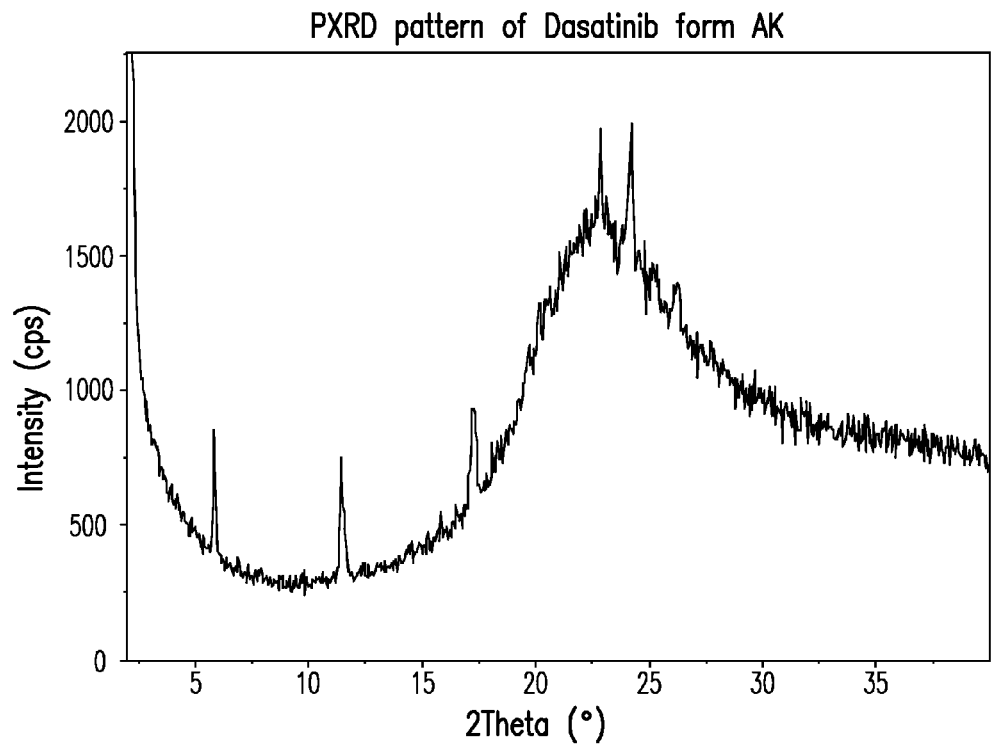
FIG. 35 shows a powder XRD pattern of amorphous dasatinib.
Figure 43:
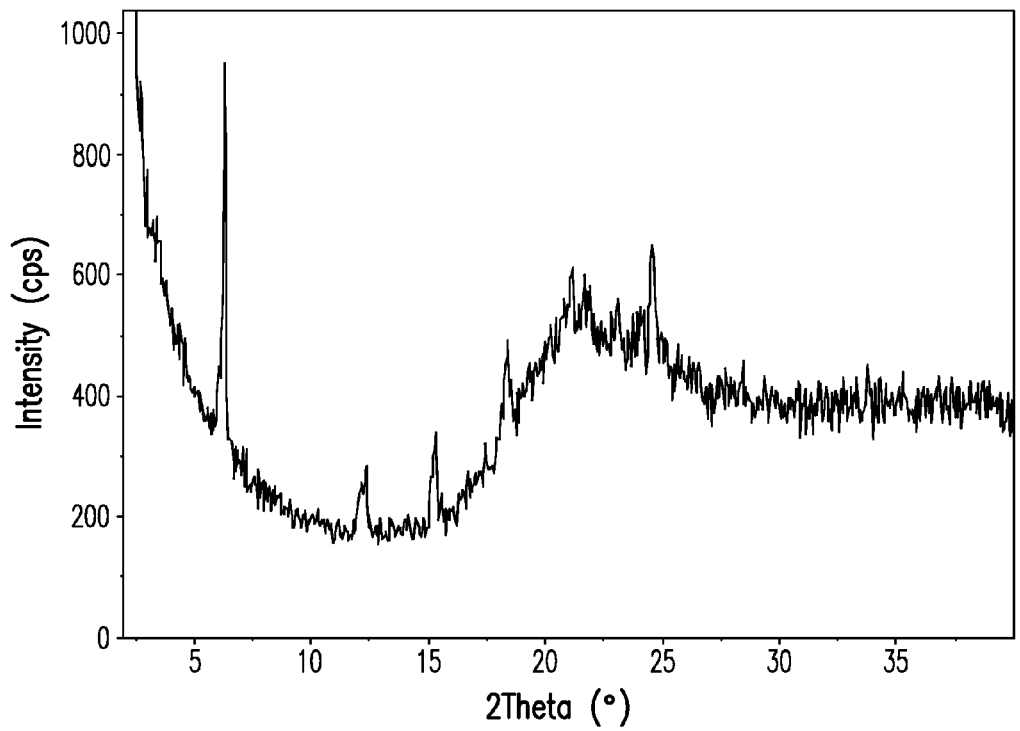
FIG. 43 shows a powder XRD pattern of amorphous dasatinib.
Figure 99:
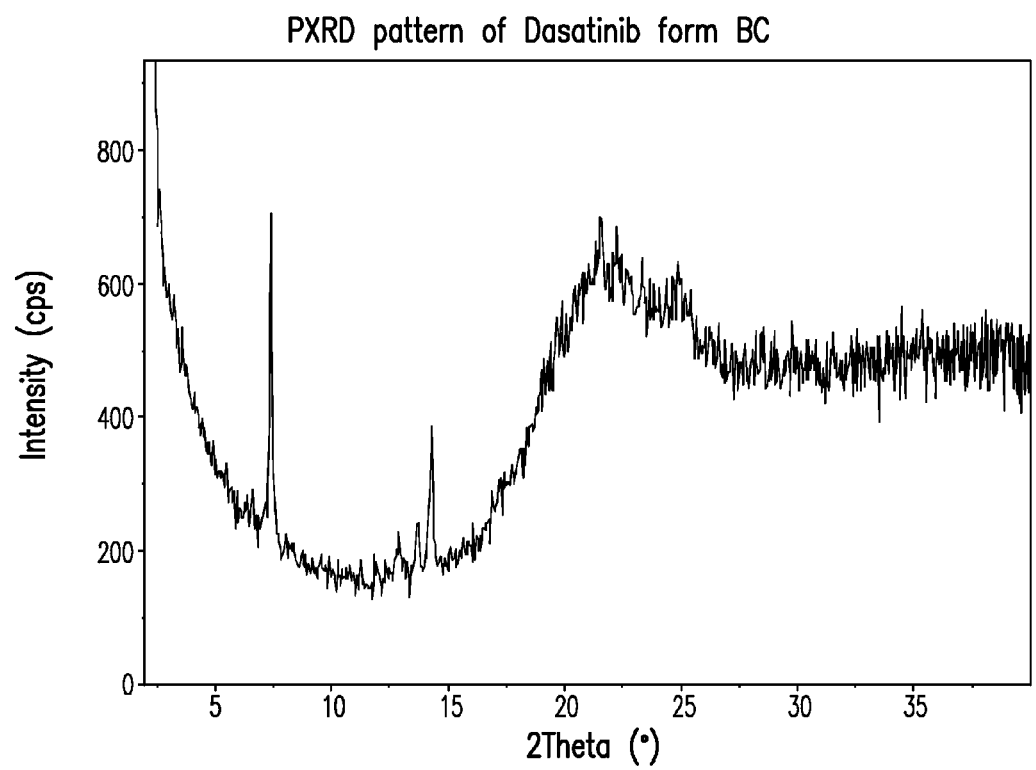
FIG. 99 shows a powder XRD pattern of amorphous dasatinib.
Figure 100:
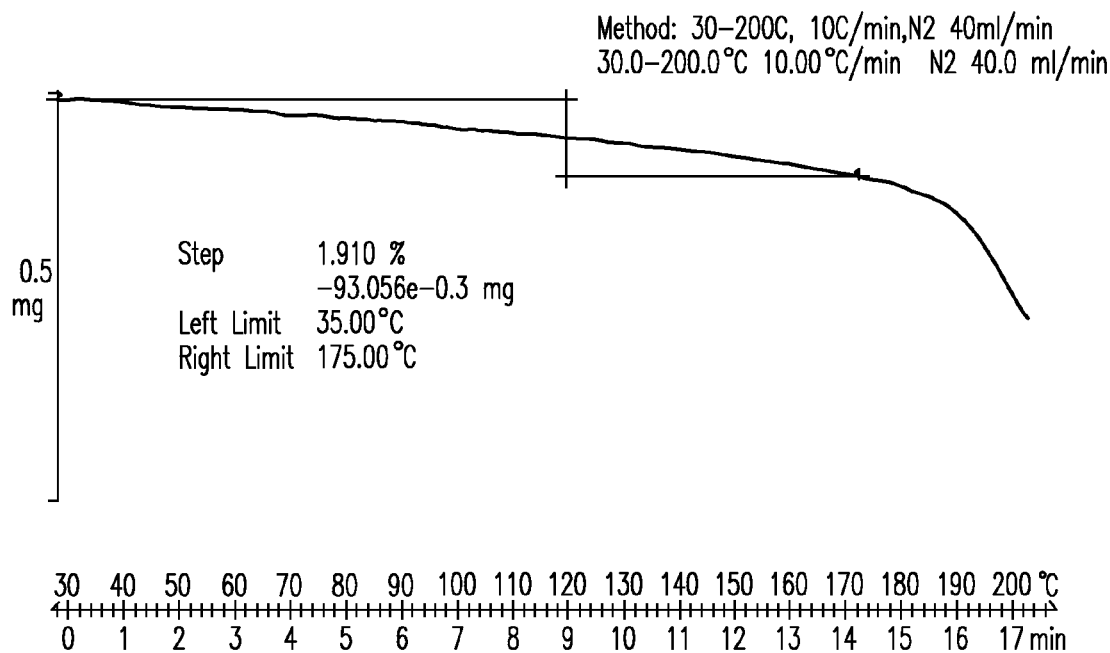
FIG. 100 shows a TGA thermogram of crystalline Dasatinib form BA
Figure 101:
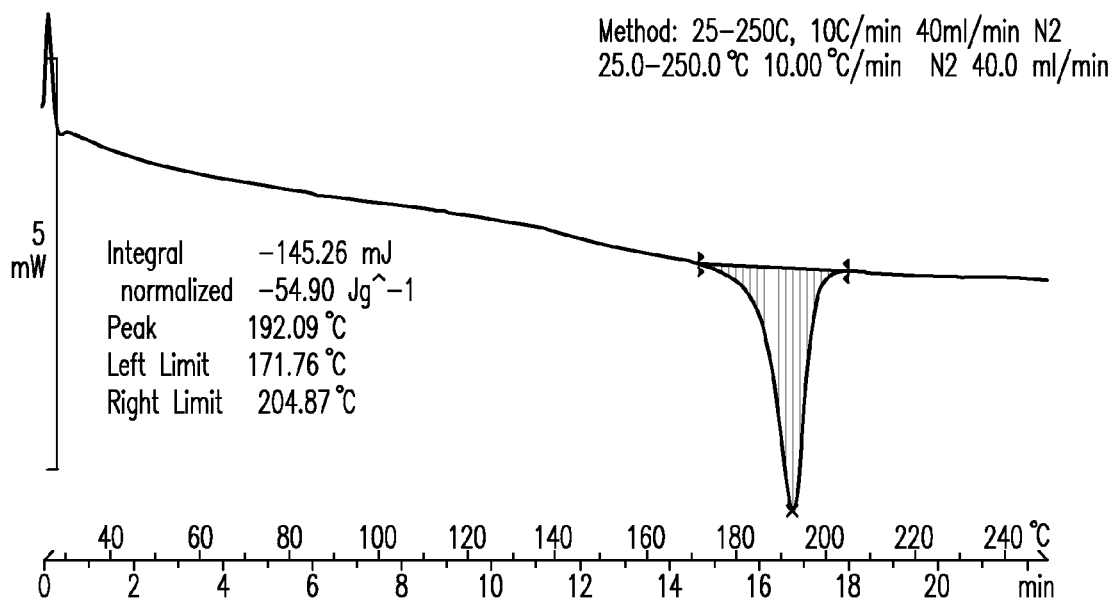
FIG. 101 shows a DSC thermogram of crystalline Dasatinib form BA
Figure 102:
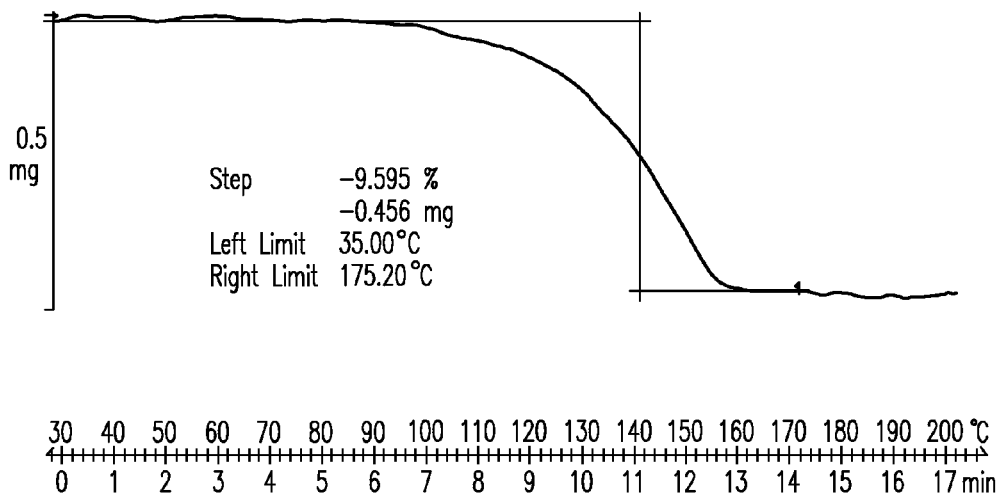
FIG. 102 shows a TGA thermogram of crystalline Dasatinib form BB
Figure 103:
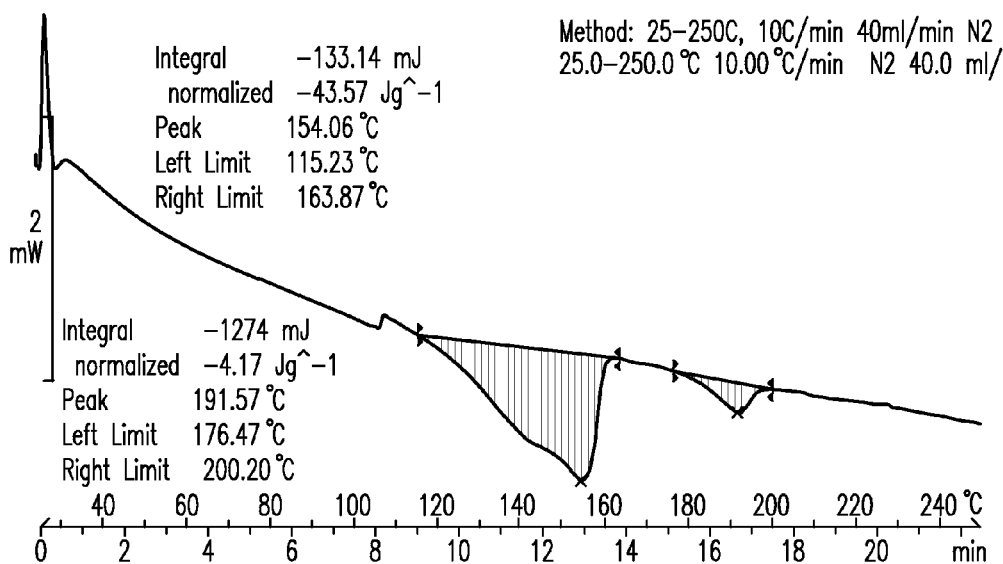
FIG. 103 shows a DSC thermogram of crystalline Dasatinib form BB
Figure 104:
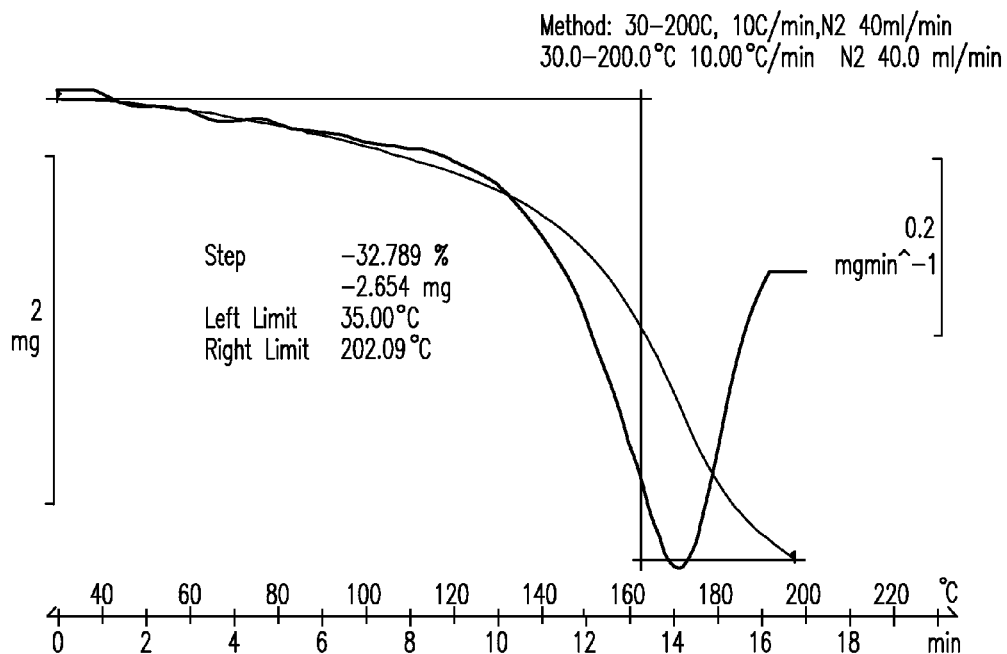
FIG. 104 shows a TGA thermogram of crystalline Dasatinib form BC
Figure 105:
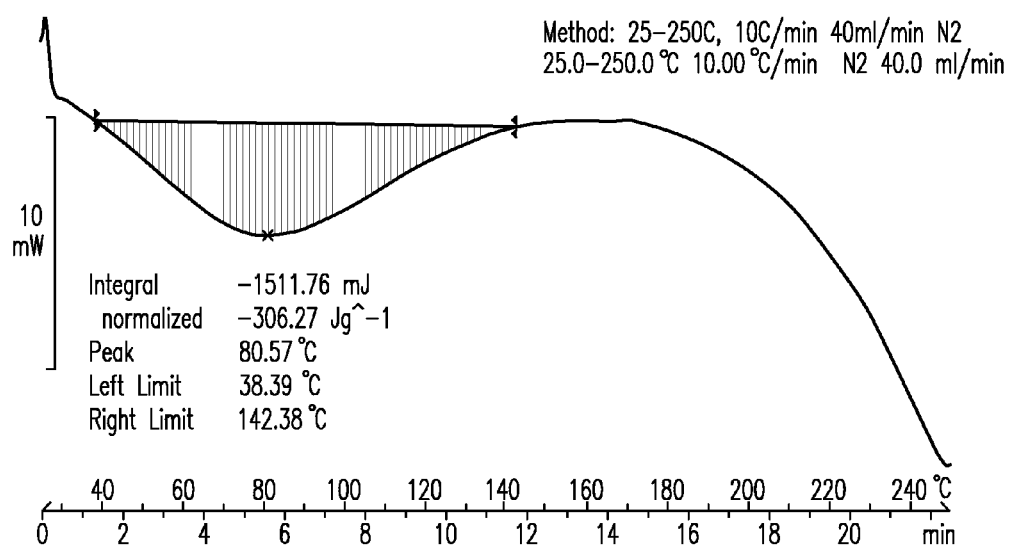
FIG. 105 shows a DSC thermogram of crystalline Dasatinib form BC

The present invention encompasses an amorphous dasatinib characterized by data selected from the group consisting of: a powder XRD pattern as depicted in FIG. 16, a powder XRD pattern as depicted in FIG. 99, a powder XRD pattern as depicted in FIG. 35, a powder XRD pattern as depicted in FIG. 43, and a combination thereof.

In addition, crystalline Dasatinib amorphous has less than about 15% by weight, preferably, less about than 10% by weight, more preferably, less than about 5% by weight of crystalline Dasatinib forms: N-6 and H1-7.

Typically, the amount of form N-6 in amorphous is measured by PXRD using any peaks selected from the group consisting of peaks at: 6.9, 12.4, 13.2, 13.8, 16.8, 21.1, 24.4 and 24.9 deg±0.2 degrees 2-theta and the amount of form H1-7 in amorphous is measured by PXRD using any peaks selected from the group consisting of peaks at: 4.6, 9.2, 11.2, 15.2, 18.0 and 19.5 deg±0.2 degrees 2-theta.

The amorphous form of dasatinib can be prepared by a process comprising reacting compound 1, N-(2-hydroxyethyl)piperazine, and N-ethyldiisopropylamine in DMF to obtain a solution comprising dasatinib, cooling the solution, and adding water to obtain a suspension comprising said amorphous form.

Preferably, the reaction of a mixture of compound 1, N-(2-hydroxyethyl)piperazine, and N-ethyldiisopropylamine in DMF is done at a temperature of about 90° C. to about 100° C., preferably, at a temperature of about 90° C. Preferably, the reaction is done for about 2.5 hours to about 3 hours, more preferably, for about 2.5 hours.

Preferably, the cooling is to a temperature of about 0° C.

Preferably, water is added at a temperature of about 0° C., providing the suspension.

The process for preparing the amorphous form of dasatinib can further comprise recovering said form. The recovery can be done for example, by filtering the suspension and drying.

Amorphous dasatinib can also be prepared by a process comprising suspending dasatinib form A21 in a solvent selected from the group consisting of 1,2-dichlorobenzene, propylene glycol, or mixtures thereof.

Preferably, the suspension is heated to a temperature of about 50° C. Preferably, the suspension is maintained at this temperature for about 6 hours.

The heated suspension is then cooled and maintained for overnight. Preferably, the heated suspension is cooled and maintained at a temperature of about 25° C.

The amorphous form can then be recovered from the suspension by evaporating the solvent. Preferably, the solvent is removed at about room temperature. Preferably, the solvent is removed at atmospheric pressure.

Preferably, the amorphous form is maintained at atmospheric pressure, preferably, at about room temperature, preferably, for a period of overnight.

The amorphous as depicted in FIG. 35 can be prepared by a process comprising suspending form A21 of dasatinib in ethyleneglycol.

Preferably, the suspension is heated to a temperature of about 40° C. to about 60° C., preferably to about 50° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 15° C. to about 30° C., preferably of about 25° C.

The amorphous can then be recovered from the suspension by evaporating the solvent. Preferably, the solvent is removed at about room temperature. Preferably, the solvent is removed at atmospheric pressure.

Preferably, the amorphous is maintained at atmospheric pressure, preferably, at about room temperature, preferably, for a period of overnight.

The amorphous as depicted in FIG. 43 can be prepared by a process comprising suspending form A21 of dasatinib in glycerol.

Preferably, the process further comprises heating the suspension to a temperature of about 40° C. to about 60° C., preferably of about 50° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 15° C. to about 30° C., preferably of about 25° C.

The amorphous can then be recovered from the suspension by evaporating the solvent. Preferably, the solvent is removed at about room temperature. Preferably, the solvent is removed at atmospheric pressure.

Preferably, the removal of the solvent is done by maintaining The amorphous at atmospheric pressure, preferably, at about room temperature, preferably, for a period of overnight.

Figure 17:
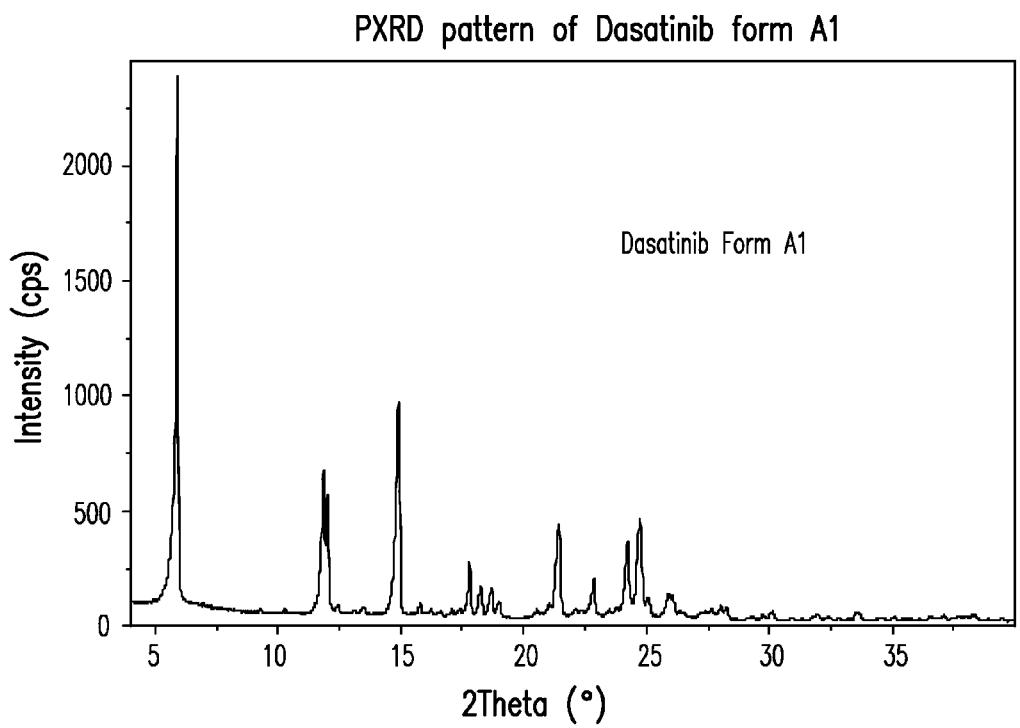
FIG. 17 shows a powder XRD pattern of crystalline dasatinib form A1.

In another embodiment, the present invention encompasses an IPA-DMF solvate of dasatinib characterized by data selected from the group consisting of: a PXRD pattern having any 3 peaks selected from the list consisting of: 5.9, 11.8, 12.0, 14.9, 17.8, 18.2, 18.7, 21.4, 22.8, 24.2 and 24.7±0.2 degrees 2-theta, a powder XRD pattern as depicted in FIG. 17, and a combination thereof. This form can be designated as form A1.

In a preferred embodiment, the present invention encompasses an IPA-DMF solvate of dasatinib designated Form A1, characterized by a PXRD pattern having any 5 peaks selected from the list consisting of: 5.9, 11.8, 12.0, 14.9, 17.8, 18.2, 18.7, 21.4, 22.8, 24.2 and 24.7±0.2 degrees 2-theta.

The above IPA-DMF solvate of dasatinib designated Form A1 can be further characterized by data selected from the group consisting of: a powder XRD pattern with peaks at about 5.9, 11.8, 14.9, 17.8, and 18.2±0.2 degrees 2-theta; a powder XRD pattern with peaks at about 11.8, 11.8, 21.4, 22.8 and 24.7±0.2 degrees 2-theta, a content of IPA of about 8% to about 10% by weight, preferably about 9% by weight as measured by GC, and a content of DMF of about 2% to about 4% by weight, preferably about 3% by weight as measured by GC.

In addition, crystalline Dasatinib Form A1 has less than about 15% by weight, preferably, less about than 10% by weight, more preferably, less than about 5% by weight of crystalline Dasatinib form N-6.

Typically, the amount of form N-6 in form A1 is measured by PXRD using any peaks selected from the group consisting of peaks at: 6.9, 13.2, 13.8 and 16.8 deg±0.2 degrees 2-theta.

Form A1 of dasatinib can be prepared by a process comprising crystallizing dasatinib from a mixture comprising the compound 1, N-(2-hydroxyethyl) piperazine, N-ethyldiisopropylamine and a mixture of DMF and IPA.

The crystallization comprises reacting compound 1, N-(2-hydroxyethyl)piperazine, and N-ethyldiisopropylamine in DMF to obtain a solution comprising dasatinib, and adding IPA to obtain a suspension comprising said crystalline form.

Preferably, the reaction of a mixture of compound 1, N-(2-hydroxyethyl)piperazine, and N-ethyldiisopropylamine in DMF is done at a temperature of about 90° C. to about 100° C., preferably, at a temperature of about 90° C. Preferably, the reaction is done for about 2.5 hours to about 4 hours, more preferably, for about 2.5 hours.

Preferably, IPA is added at a temperature of about 100° C., providing the suspension.

Typically, the suspension is cooled to increase the yield of the precipitated crystalline form. Preferably, cooling is to about room temperature to about 0° C., more preferably, to about 20° C. to about 0° C.

The process for preparing form A1 of dasatinib can further comprise recovering said form. The recovery can be done for example, by filtering the suspension and drying.

Figure 19:
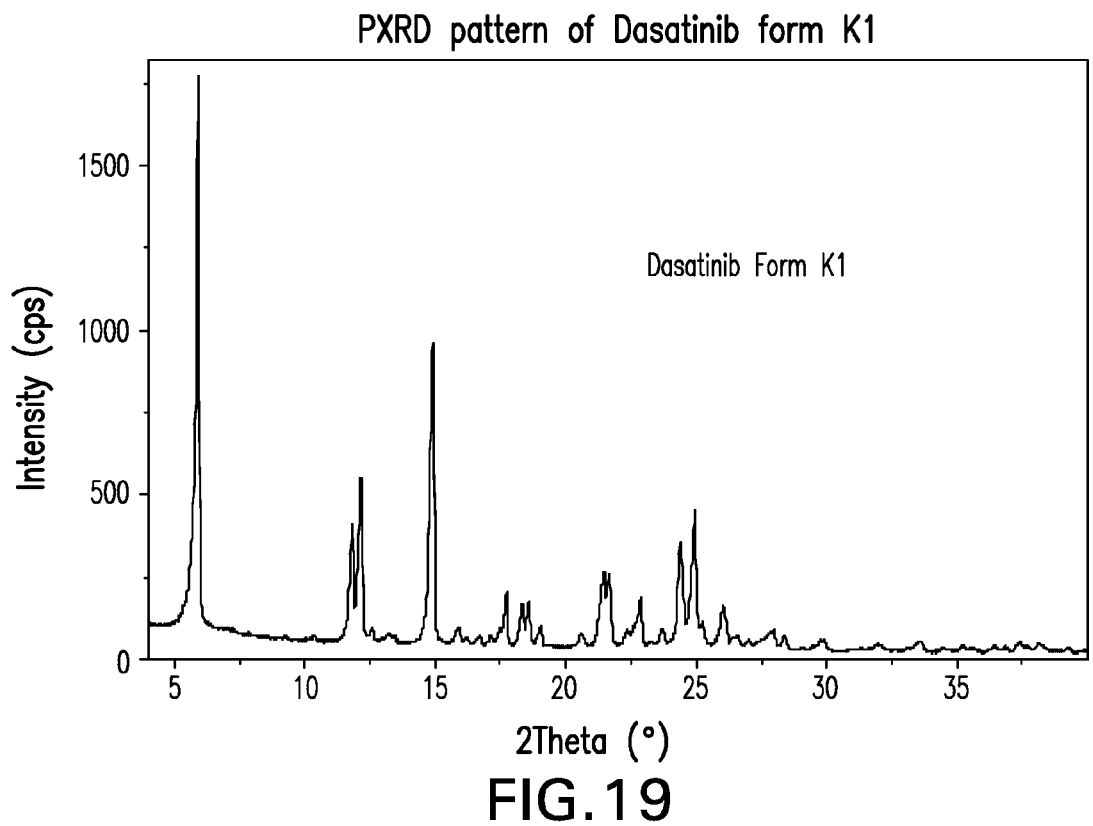
FIG. 19 shows a powder XRD pattern of crystalline dasatinib form K1

In another embodiment, the present invention encompasses a n-propanol-DMF solvate of dasatinib characterized by data selected from the group consisting of: a PXRD pattern having any 3 peaks selected from the list consisting of: 5.9, 11.8, 12.2, 14.9, 17.7, 18.3, 18.6, 21.4, 21.7, 24.4 and 24.9±0.2 degrees 2-theta, a powder XRD pattern as depicted in FIG. 19, and combination thereof. This form can be designated as form K1.

In a preferred embodiment, the present invention encompasses a n-propanol-DMF solvate of dasatinib designated Form K1, characterized by a PXRD pattern having any 5 peaks selected from the list consisting of: 5.9, 11.8, 12.2, 14.9, 17.7, 18.3, 18.6, 21.4, 21.7, 24.4 and 24.9±0.2 degrees 2-theta.

The above n-propanol-DMF solvate of dasatinib designated Form K1 can be further characterized by data selected from the group consisting of: a powder XRD pattern with peaks at about 5.9, 11.8, 12.2, 14.9, 17.7 and 18.3±0.2 degrees 2-theta; a powder XRD pattern with peaks at about 11.8, 12.2, 21.4, 22.7 and 24.9±0.2 degrees 2-theta, a content of n-propanol of about 8% to about 10%, preferably about 9% by weight as measured by GC, and a content of DMF of about 2% to about 4%, preferably about 3% by weight as measured by GC.

In addition, crystalline Dasatinib Form K1 has less than about 15% by weight, preferably, less about than 10% by weight, more preferably, less than about 5% by weight of crystalline Dasatinib form N-6.

Typically, the amount of form N-6 in form K1 is measured by PXRD using any peaks selected from the group consisting of peaks at: 6.9, 13.8 and 21.1 deg±0.2 degrees 2-theta.

Form K1 of dasatinib can be prepared by a process comprising crystallizing dasatinib from a mixture comprising the compound 1, N-(2-hydroxyethyl) piperazine, N-ethyldiisopropylamine and a mixture of DMF and n-propanol.

The crystallization comprises reacting compound 1, N-(2-hydroxyethyl)piperazine, and N-ethyldiisopropylamine in DMF to obtain a solution comprising dasatinib, and adding n-propanol to obtain a suspension comprising said crystalline form.

Preferably, the reaction of a mixture of compound 1, N-(2-hydroxyethyl)piperazine, and N-ethyldiisopylamine in DMF is done at a temperature of about 90° C. to about 100° C., more preferably, at about 100° C. Preferably, the reaction is done for about 2.5 hours to about 4 hours, more preferably, for about 2.5 hours.

Preferably, n-propanol is added at a temperature of about 100° C., providing the suspension.

Typically, the suspension is cooled to increase the yield of the precipitated crystalline form. Preferably, cooling is to a temperature of about 20° C. to about 0° C., more preferably, to about room temperature.

The process for preparing form K1 of dasatinib can further comprise recovering said form. The recovery can be done for example, by filtering the suspension and drying.

Figure 20:
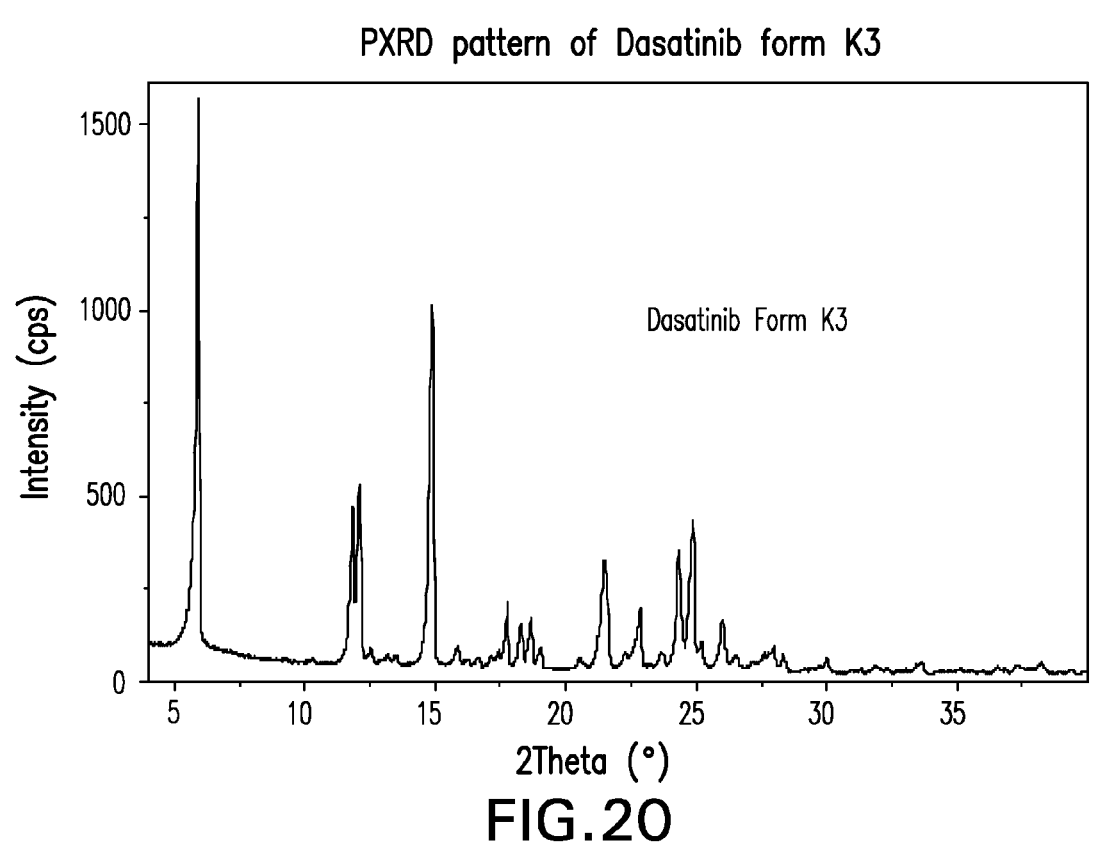
FIG. 20 shows a powder XRD pattern of crystalline dasatinib form K3

In another embodiment, the present invention encompasses a n-propanol solvate of dasatinib characterized by data selected from the group consisting of: a PXRD pattern having any 3 peaks selected from the list consisting of: 5.9, 11.8, 12.1, 14.9, 17.8, 18.3, 18.7, 21.5, 21.6, 22.8, 24.3 and 24.8±0.2 degrees 2-theta, a powder XRD pattern as depicted in FIG. 20, and a combination thereof. This form can be designated as form K3.

In a preferred embodiment, the present invention encompasses a n-propanol solvate of dasatinib designated Form K3, characterized by a PXRD pattern having any 5 peaks selected from the list consisting of: 5.9, 11.8, 12.1, 14.9, 17.8, 18.3, 18.7, 21.5, 21.6, 22.8, 24.3 and 24.8±0.2 degrees 2-theta.

The above n-propanol solvate of dasatinib designated Form K3 can be further characterized by data selected from the group consisting of: a powder XRD pattern with peaks at about 5.9, 11.8, 12.1, 14.9, 17.8 and 18.3±0.2 degrees 2-theta; a powder XRD pattern with peaks at about 11.8, 12.1, 21.5, 22.8 and 24.8±0.2 degrees 2-theta, and a content of n-propanol of about 10% to about 12% by weight, preferably about 11% by weight as measured by GC.

In addition, crystalline Dasatinib Form K3 has less than about 15% by weight, preferably, less about than 10% by weight, more preferably, less than about 5% by weight of crystalline Dasatinib forms: N-6 and H1-7.

Typically, the amount of form N-6 in form K3 is measured by PXRD using any peaks selected from the group consisting of peaks at: 6.9, 12.4, 13.8, 16.8 and 21.1 deg±0.2 degrees 2-theta and the amount of form H1-7 in form K3 is measured by PXRD using any peaks selected from the group consisting of peaks at: 4.6, 9.2, 11.2, 15.2 and 19.5 deg±0.2 degrees 2-theta.

Form K3 of dasatinib can be prepared by a process comprising crystallizing dasatinib from a mixture of n-propanol and water.

The crystallization comprises providing a solution of dasatinib in a mixture of n-propanol and water, and precipitating said crystalline form to obtain a suspension.

Preferably, the solution is provided by combining dasatinib, n-propanol and water, and heating the combination. Preferably, heating is to about reflux temperature.

Preferably, precipitation is obtained by cooling the solution. Preferably, cooling is to a temperature of about 20° C. to about 0° C., more preferably, to a temperature of about 5° C. to about 0° C.

The process for preparing form K3 of dasatinib can further comprise recovering said form. The recovery can be done for example, by filtering the suspension and drying.

Form K3 of dasatinib can also be prepared by a process comprising suspending form A21 of dasatinib in n-propanol.

Preferably, the suspension is heated to a temperature of about 40° C. to about 60° C., preferably about 50° C. Preferably, the suspension is maintained at this temperature for about 4 to about 8 hours, preferably about 6 hours.

Preferably, the heated suspension is then cooled and maintained for about 10 hours to about 14 hours, preferably overnight. Preferably, the heated suspension is cooled and maintained at a temperature of about 20° C. to about 30° C., preferably about 25° C.

Form K3 can then be recovered from the suspension by evaporating the solvent. Preferably, the solvent is removed at about room temperature. Preferably, the solvent is removed at atmospheric pressure.

Figure 21:
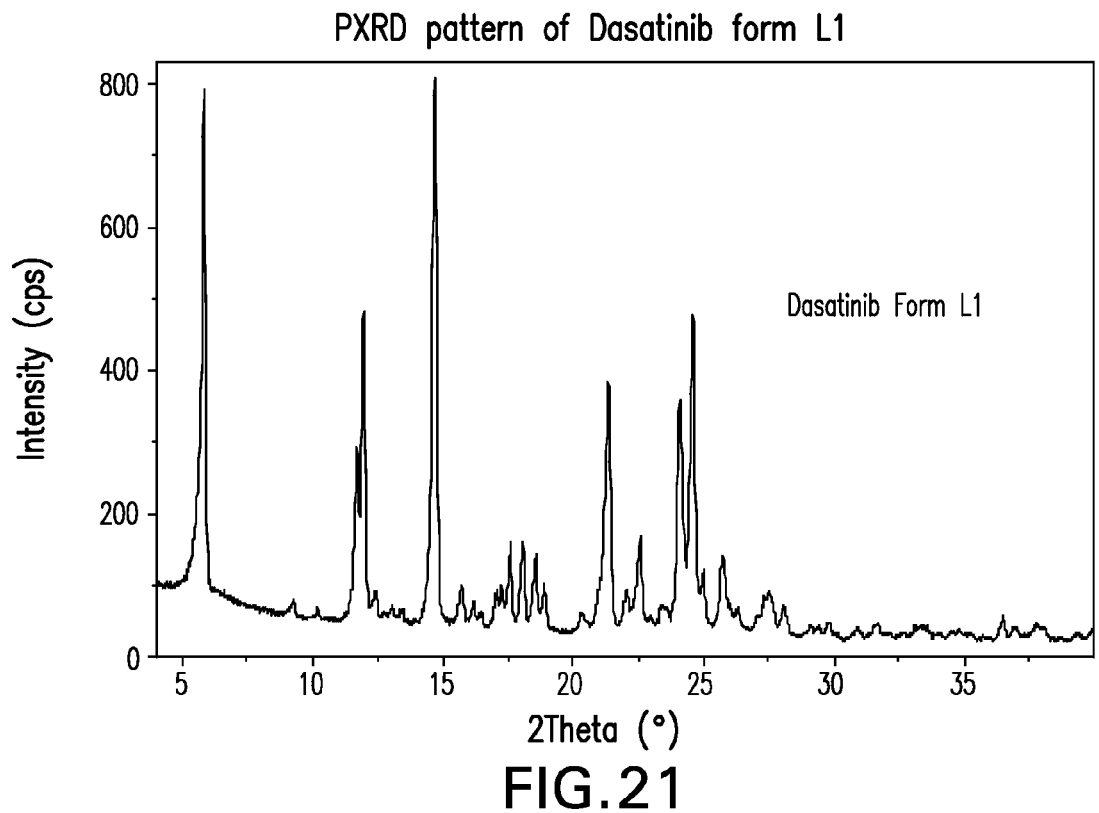
FIG. 21 shows a powder XRD pattern of crystalline dasatinib form L1

In another embodiment, the present invention encompasses a 2-butanol-DMF solvate of dasatinib characterized by data selected from the group consisting of: a PXRD pattern having any 3 peaks selected from the list consisting of: 5.9, 11.7, 12.0, 14.7, 17.6, 18.1, 18.6, 21.4, 22.6, 24.1, 24.6 and 25.7±0.2 degrees 2-theta, a powder XRD pattern as depicted in FIG. 21, and a combination thereof. This form can be designated as form L1.

In a preferred embodiment, the present invention encompasses a 2-butanol-DMF solvate of dasatinib designated Form L1, characterized by a PXRD pattern having any 5 peaks selected from the list consisting of: 5.9, 11.7, 12.0, 14.7, 17.6, 18.1, 18.6, 21.4, 22.6, 24.1, 24.6 and 25.7±0.2 degrees 2-theta.

The above 2-butanol-DMF solvate of dasatinib designated Form L1 can be further characterized by data selected from the group consisting of: a powder XRD pattern with peaks at about 5.9, 12.0, 14.7 and 17.6±0.2 degrees 2-theta; a powder XRD pattern with peaks at about 11.7, 12.0, 21.4, 22.6 and 24.6±0.2 degrees 2-theta, a content of 2-butanol of about 10% to about 12% by weight, preferably about 11% by weight as measured by GC, and a content of DMF of about 2% to about 4% by weight, preferably about 3% by weight as measured by GC.

In addition, crystalline Dasatinib Form L1 has less than about 15% by weight, preferably, less about than 10% by weight, more preferably, less than about 5% by weight of crystalline Dasatinib forms: N-6 and H1-7.

Typically, the amount of form N-6 in form L1 is measured by PXRD using any peaks selected from the group consisting of peaks at: 6.9, 13.3, 13.8 and 16.8 deg ±0.2 degrees 2-theta.

Form L1 of dasatinib can be prepared by a process comprising crystallizing dasatinib from a mixture comprising the compound 1, N-(2-hydroxyethyl) piperazine, N-ethyldiisopropylamine and a mixture of DMF and 2-butanol.

The crystallization comprises reacting compound 1, N-(2-hydroxyethyl)piperazine, and N-ethyldiisopropylamine in DMF to obtain a solution comprising dasatinib, and adding 2-butanol to obtain a suspension comprising said crystalline form.

Preferably, the reaction of a mixture of compound 1, N-(2-hydroxyethyl)piperazine, and N-ethyldiisopropylamine in DMF is done at a temperature of about 90° C. to about 100° C., more preferably, to about 100° C. Preferably, the reaction is done for about 2.5 hours to about 4 hours, more preferably, for about 4 hours.

Preferably, 2-butanol is added at a temperature of about 100° C., providing the suspension.

Typically, the suspension is cooled to increase the yield of the precipitated crystalline form. Preferably, cooling is to a temperature of about 20° C. to about 0° C., more preferably, of about 5° C. to about 0° C.

The process for preparing form L1 of dasatinib can further comprise recovering said form. The recovery can be done for example, by filtering the suspension and drying.

Figure 22:
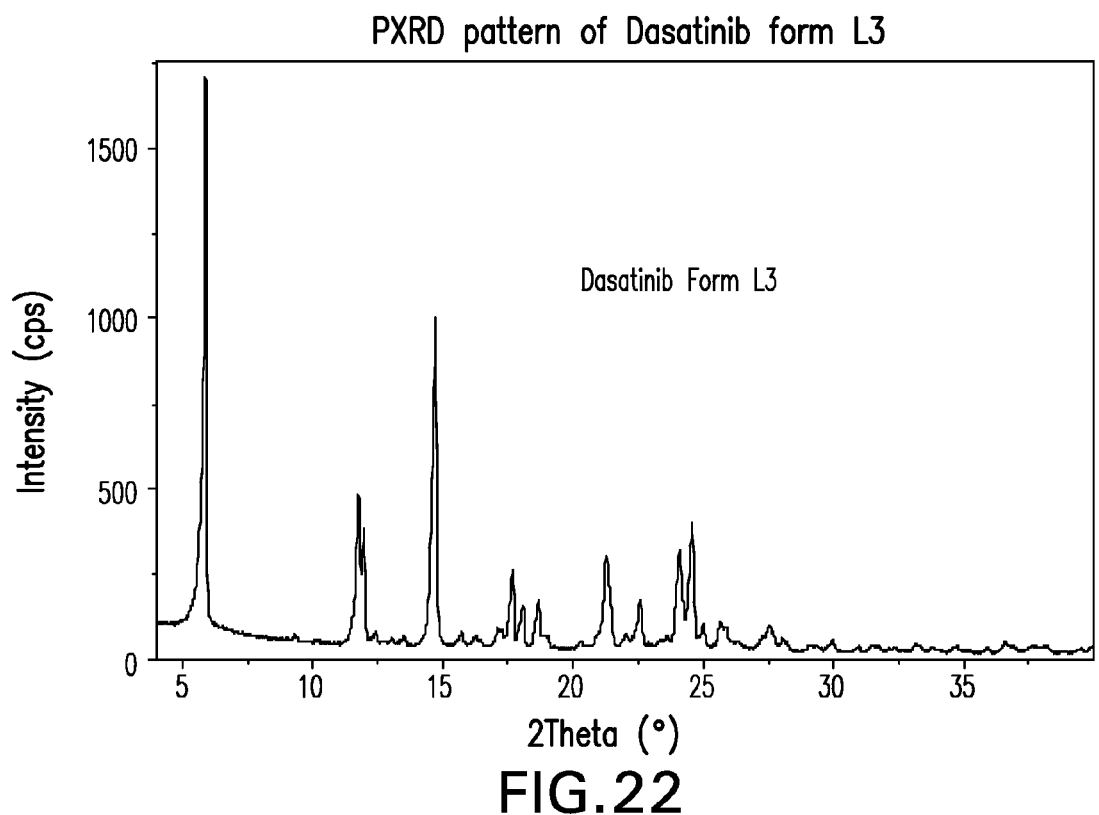
FIG. 22 shows a powder XRD pattern of crystalline dasatinib form L3

In one embodiment, the present invention encompasses a 2-butanol solvate of dasatinib characterized by data selected from the group consisting of: a PXRD pattern having any 3 peaks selected from the list consisting of: 5.9, 11.8, 12.0, 14.7, 17.7, 18.1, 18.7, 21.3, 22.6, 24.1 and 24.6±0.2 degrees 2-theta, a powder XRD pattern as depicted in FIG. 22, and a combination thereof. This form can be designated as form L3.

In a preferred embodiment, the present invention encompasses a 2-butanol solvate of dasatinib designated Form L3, characterized by a PXRD pattern having any 5 peaks selected from the list consisting of: 5.9, 11.8, 12.0, 14.7, 17.7, 18.1, 18.7, 21.3, 22.6, 24.1 and 24.6±0.2 degrees 2-theta.

The above 2-butanol solvate of dasatinib designated Form L3 can be further characterized by data selected from the group consisting of: a powder XRD pattern with peaks at about 5.9, 12.0, 14.7, 17.7 and 18.7±0.2 degrees 2-theta; a powder XRD pattern with peaks at about 11.8, 12.0, 21.3, 22.6 and 24.6±0.2 degrees 2-theta, and a content of 2-butanol of about 12% to about 14% by weight, preferably about 13% by weight as measured by GC.

In addition, crystalline Dasatinib Form L3 has less than about 15% by weight, preferably, less about than 10% by weight, more preferably, less than about 5% by weight of crystalline Dasatinib forms: N-6 and H1-7.

Typically, the amount of form N-6 in form L3 is measured by PXRD using any peaks selected from the group consisting of peaks at: 6.9, 13.3, 13.8, and 16.8 deg ±0.2 degrees 2-theta and the amount of form H1-7 in form L3 is measured by PXRD using any peaks selected from the group consisting of peaks at: 4.6, 11.2, 15.2 and 19.5 deg±0.2 degrees 2-theta.

Form L3 of dasatinib can be prepared by a process comprising crystallizing dasatinib from a mixture of 2-butanol and water.

The crystallization comprises providing a solution of dasatinib in a mixture of 2-butanol and water, and precipitating said crystalline form to obtain a suspension.

Preferably, the solution is provided by combining dasatinib and 2-butanol, heating the combination and adding water. Preferably, the combination of dasatinib and 2-butanol provides a suspension. Preferably, the suspension is heated to a temperature of about reflux. To the heated suspension is then added water, providing the solution.

Preferably, the solution is further maintained prior to precipitation of the said crystalline form. Preferably, the solution is further maintained at about reflux temperature. Preferably, the solution is further maintained for about 20 minutes to about 60 minutes, more preferably, for about an hour.

Preferably, precipitation is obtained by cooling the solution. Preferably, cooling is to a temperature of about 20° C. to about 0° C., more preferably, of about 5° C. to about 0° C.

The process for preparing form L3 of dasatinib can further comprise recovering said form. The recovery can be done for example, by filtering the suspension and drying.

Figure 23:
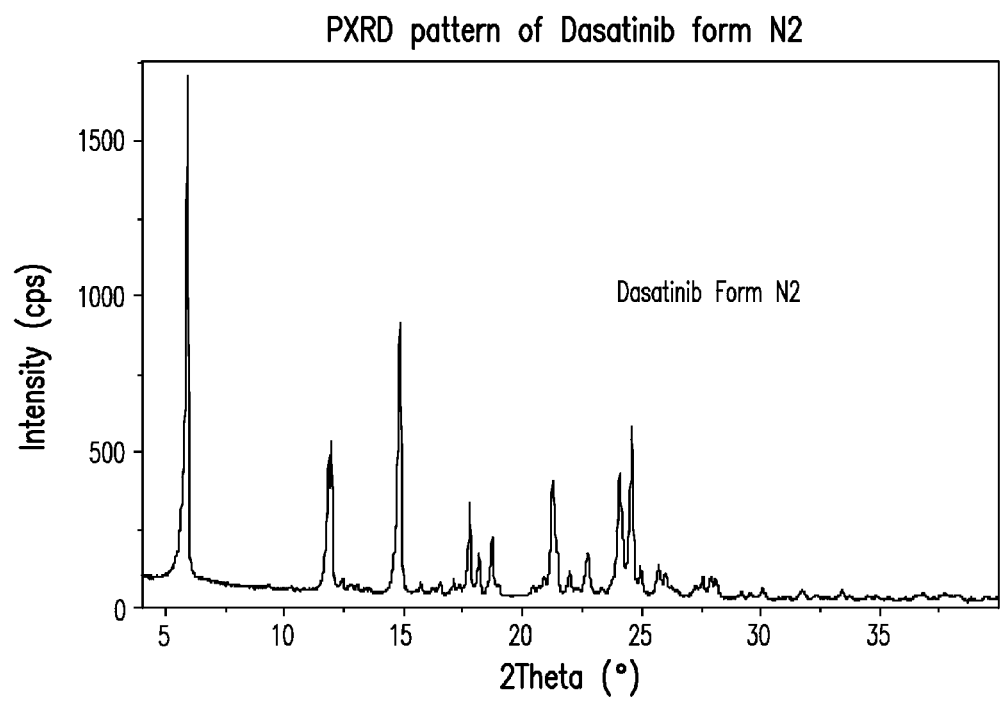
FIG. 23 shows a powder XRD pattern of crystalline dasatinib form N2

In another embodiment, the present invention encompasses a n-butanol-DMSO solvate of dasatinib characterized by data selected from the group consisting of: a PXRD pattern having any 3 peaks selected from the list consisting of: 5.9, 11.9, 12.0, 14.8, 17.8, 18.2, 18.7, 21.3, 22.7, 24.1 and 24.6±0.2 degrees 2-theta, a powder XRD pattern as depicted in FIG. 23, and a combination thereof. This form can be designated as form N2.

In a preferred embodiment, the present invention encompasses a n-butanol-DMSO solvate of dasatinib designated Form N2, characterized by a PXRD pattern having any 5 peaks selected from the list consisting of: 5.9, 11.9, 12.0, 14.8, 17.8, 18.2, 18.7, 21.3, 22.7, 24.1 and 24.6±0.2 degrees 2-theta.

The above n-butanol-DMSO solvate of dasatinib designated Form N2 can be further characterized by data selected from the group consisting of: a powder XRD pattern with peaks at about 5.9, 12.0, 14.8, 17.8 and 18.7±0.2 degrees 2-theta; a powder XRD pattern with peaks at about 11.9, 12.0, 21.3, 22.7 and 24.6±0.2 degrees 2-theta, a content of n-butanol of about 10% as measured by GC, and a content of DMSO of about 5% [please provide range if possible] by weight as measured by GC.

In addition, crystalline Dasatinib Form N2 has less than about 15% by weight, preferably, less about than 10% by weight, more preferably, less than about 5% by weight of crystalline Dasatinib form N-6.

Typically, the amount of form N-6 in form N2 is measured by PXRD using any peaks selected from the group consisting of peaks at: 6.9, 13.3, 13.8, and 16.8 deg±0.2 degrees 2-theta.

Form N2 of dasatinib can be prepared by a process comprising crystallizing dasatinib from a mixture comprising the compound 1, N-(2-hydroxyethyl) piperazine, N-ethyldiisopropylamine and a mixture of DMSO and n-butanol.

The crystallization comprises reacting compound 1, N-(2-hydroxyethyl)piperazine, and N-ethyldiisopropylamine in DMSO to obtain a solution comprising dasatinib, adding n-butanol, and precipitating said crystalline form to obtain a suspension.

Preferably, the reaction of a mixture of compound 1, N-(2-hydroxyethyl)piperazine, and N-ethyldiisopropylamine in DMSO is done at a temperature of about 40° C. to about 150° C., more preferably, at about 40° C. to about 100° C., more preferably, at about 60° C. to about 80° C., most preferably, at about 80° C. to about 85° C. Preferably, the reaction is done for about 1 hour to about 2 hours depending on the reaction temperature.

Preferably, 2-butanol is added at a temperature of about 80° C. to about 85° C., providing a second solution.

Preferably, precipitation is achieved by cooling the second solution. Preferably, cooling is to a temperature of about 20° C. to about 0° C., more preferably, of about 5° C. to about 0° C.

The process for preparing form N2 of dasatinib can further comprise recovering said form. The recovery can be done for example, by filtering the suspension and drying.

Figure 24:
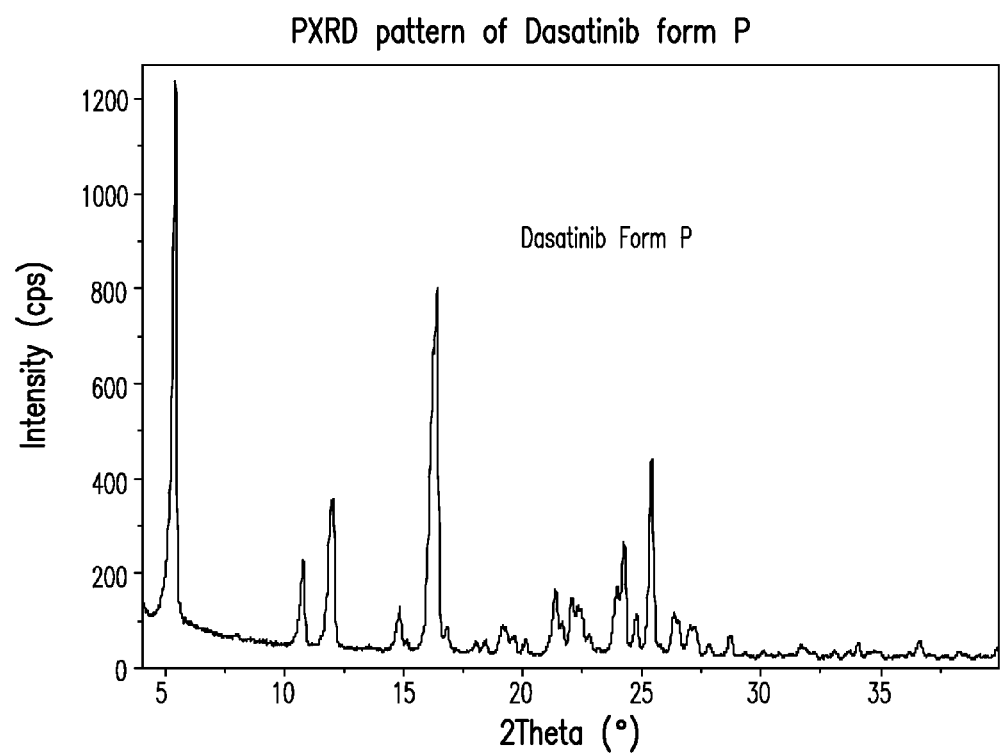
FIG. 24 shows a powder XRD pattern of crystalline dasatinib form P

In another embodiment, the present invention encompasses a DMF-water solvate of dasatinib characterized by data selected from the group consisting of: a PXRD pattern having any 3 peaks selected from the list consisting of: 5.4, 10.8, 12.1, 14.8, 16.4, 21.4, 22.1, 24.2, 24.8 and 25.4±0.2 degrees 2-theta, a powder XRD pattern as depicted in FIG. 24, and combination thereof. This form can be designated as form P.

In a preferred embodiment, the present invention encompasses a DMF-water solvate of dasatinib designated Form P, characterized by a PXRD pattern having any 5 peaks selected from the list consisting of: 5.4, 10.8, 12.1, 14.8, 16.4, 21.4, 22.1, 24.2, 24.8 and 25.4±0.2 degrees 2-theta.

The above DMF-water solvate of dasatinib designated Form P can be further characterized by data selected from the group consisting of: a powder XRD pattern with peaks at about 5.4, 10.8, 12.1, 16.4 and 25.4±0.2 degrees 2-theta; a powder XRD pattern with peaks at about 5.4, 12.1, 16.4, 24.2 and 25.4±0.2 degrees 2-theta, a content of water of about 6 to about 7% by weight as measured by KF, and a content of DMF of about 11% to about 13% by weight, preferably about 12% by weight as measured by TGA.

Form P can be prepared by a process comprising dissolving datatinib in DMF and admixing the solution with water to obtain a suspension comprising said crystalline form.

Preferably, the dissolution is done at about 100° C. Preferably, water is added to the solution. Preferably, the addition of water is done at about 100° C.

Typically, the suspension is cooled to increase the yield of the precipitated crystalline form. Preferably, the cooling is to about room temperature.

The process to prepare crystalline form P can further comprise recovering said crystalline form from the suspension. The recovery can be done for example by filtering the suspension and drying the filtered product.

Figure 25:
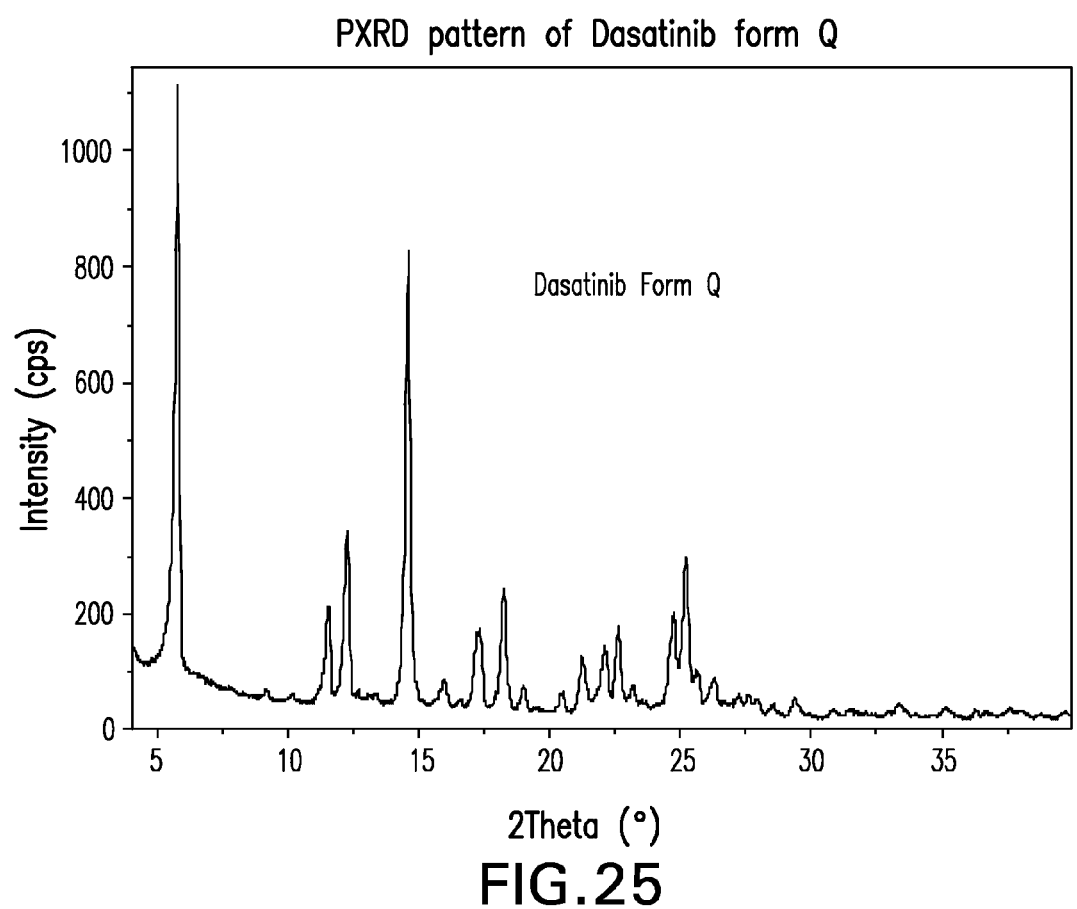
FIG. 25 shows a powder XRD pattern of crystalline dasatinib form Q

In another embodiment, the present invention encompasses a DMF solvate of dasatinib characterized by data selected from the group consisting of: a PXRD pattern having any 3 peaks selected from the list consisting of: 5.8, 11.5, 12.3, 14.6, 17.3, 18.2, 21.2, 22.1, 22.6, 24.7 and 25.2±0.2 degrees 2-theta, a powder XRD pattern as depicted in FIG. 25, and a combination thereof. This form can be designated as form Q.

In a preferred embodiment, the present invention encompasses a DMF solvate of dasatinib designated Form Q, characterized by a PXRD pattern having any 5 peaks selected from the list consisting of: 5.8, 11.5, 12.3, 14.6, 17.3, 18.2, 21.2, 22.1, 22.6, 24.7 and 25.2±0.2 degrees 2-theta.

The above DMF solvate of dasatinib designated Form Q can be further characterized by data selected from the group consisting of: a powder XRD pattern with peaks at about 5.8, 12.3, 14.6, 18.2 and 25.2±0.2 degrees 2-theta; a powder XRD pattern with peaks at about 5.8, 12.3, 14.6, 17.3 and 22.6±0.2 degrees 2-theta, a content of water of about 1% by weight as measured by KF, and a content of DMF of about 11% to about 13% by weight, preferably about 12% by weight as measured by TGA.

Form Q can be prepared by a process comprising heating dasatinib form P to a temperature of about 70° C. at atmospheric pressure.

Figure 26:
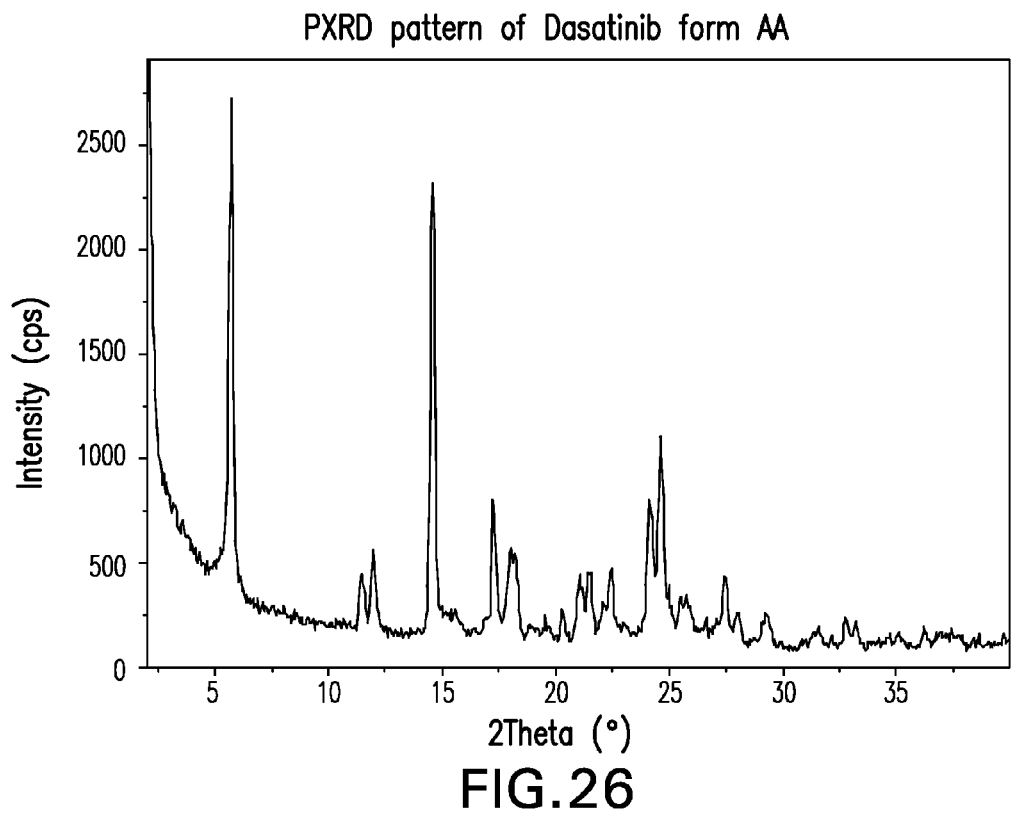
FIG. 26 shows a powder XRD pattern of crystalline dasatinib form AA

In another embodiment, the present invention encompasses a MIPK solvate of dasatinib characterized by data selected from the group consisting of: a PXRD pattern any 3 peaks selected from the list consisting of: 5.7, 12.0, 14.6, 18.0, 18.2, 22.4 and 24.6±0.2 degrees 2-theta, a powder XRD pattern as depicted in FIG. 26, and a combination thereof. This form can be designated as form AA.

In a preferred embodiment, the present invention encompasses a MIPK solvate of dasatinib designated form AA characterized by a PXRD pattern having peaks at about 14.6 and 24.6±0.2 degrees 2-theta and any 3 peaks selected from the list consisting of: 5.7, 12.0, 18.0, 18.2 and 22.4±0.2 degrees 2-theta.

The above MIPK solvate of dasatinib designated Form AA can be further characterized by data selected from the group consisting of: a powder XRD pattern with peaks at about 5.7, 12.0, 14.6, 18.0 and 18.2±0.2 degrees 2-theta; a powder XRD pattern with peaks at about 14.6, 18.0, 18.2, 22.4 and 24.6±0.2 degrees 2-theta; and a weight loss on drying of about 15% by weight as measured by TGA.

Form AA can be prepared by a process comprising suspending form A21 of dasatinib in methyl-isopropylketone at a temperature of about 50° C. for a period of about 6 hours, and cooling the suspension to a temperature of about of 25° C. for a period of about overnight.

Form AA can then be recovered from the suspension by evaporating the solvent. Preferably, the solvent is removed at about room temperature. Preferably, the solvent is removed at atmospheric pressure.

Preferably, form AA is maintained at atmospheric pressure, preferably, at about room temperature, preferably, for a period of overnight.

Figure 27:
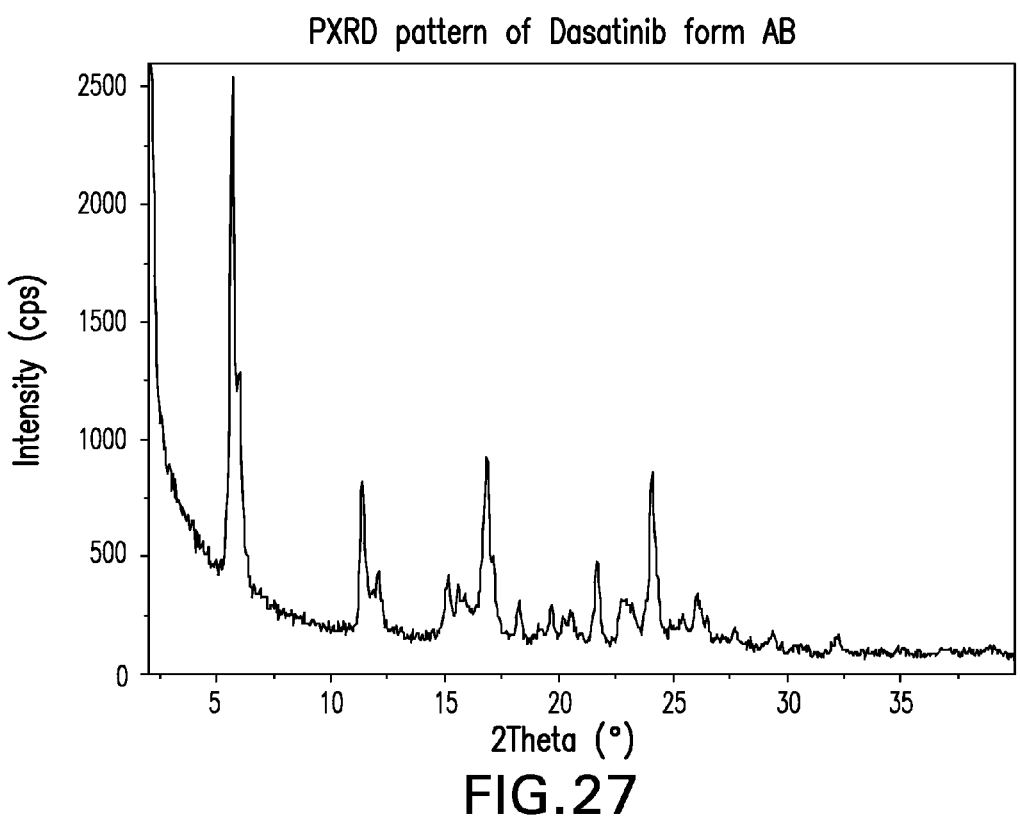
FIG. 27 shows a powder XRD pattern of crystalline dasatinib form AB

In another embodiment, the present invention encompasses a dimethoxyethane solvate of dasatinib characterized by data selected from the group consisting of: a PXRD pattern having any 3 peaks selected from the list consisting of: 5.7, 6.0, 11.4, 16.8, 19.7 and 24.1±0.2 degrees 2-theta, a powder XRD pattern as depicted in FIG. 27, and a combination thereof. This form can be designated as form AB.

In another embodiment, the present invention encompasses a dimethoxyethane solvate of dasatinib designated form AB characterized by PXRD pattern having peaks at about 5.7 and 11.4±0.2 degrees 2-theta and any 3 peaks selected from the list consisting of: 6.0, 16.8, 19.7 and 24.1±0.2 degrees 2-theta.

The above dimethoxyethane solvate of dasatinib designated Form AB can be further characterized by data selected from the group consisting of: a powder XRD pattern with peaks at about 5.7, 6.0, 11.4, 19.7 and 24.1±0.2 degrees 2-theta; a powder XRD pattern with peaks at about 5.7, 11.4, 16.8, 19.7 and 24.1±0.2 degrees 2-theta; and a weight loss on drying of about 14% to about 16%, preferably about 15% by weight as measured by TGA.

Form AB can be prepared by a process comprising suspending form A21 of dasatinib in dimethoxyethane.

Preferably, the suspension is heated to a temperature of about 40° C. to about 60° C., preferably to about 50° C. Preferably, the suspension is maintained at this temperature for about 4 hours to about 12 hours, preferably for about 6 hours.

The heated suspension is then cooled and maintained for an overnight period. Preferably, the heated suspension is cooled and maintained at a temperature of about 15° C. to about 30° C., preferably of about 25° C.

Form AB can then be recovered from the suspension by evaporating the solvent. Preferably, the solvent is removed at about room temperature. Preferably, the solvent is removed at atmospheric pressure.

Preferably, form AB is maintained at atmospheric pressure, preferably, at about room temperature, preferably, for a period of overnight.

Figure 28:
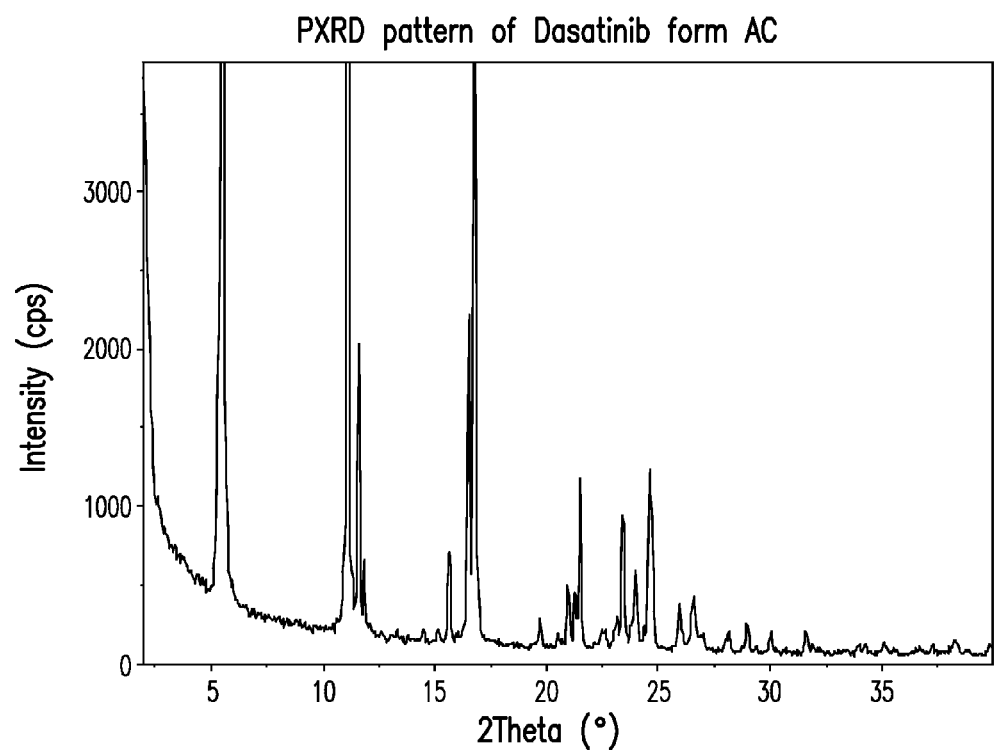
FIG. 28 shows a powder XRD pattern of crystalline dasatinib form AC

In another embodiment, the present invention encompasses a cellosolve solvate of dasatinib characterized by data selected from the group consisting of: a PXRD pattern having any 3 peaks selected from the list consisting of: 5.5, 11.1, 11.6, 15.7, 16.8 and 23.4±0.2 degrees 2-theta, a powder XRD pattern as depicted in FIG. 28, and a combination thereof. This form can be designated as form AC.

In a preferred embodiment, the present invention encompasses a cellosolve solvate of dasatinib designated Form AC characterized by a PXRD pattern having peaks at about 5.5 and 11.1±0.2 degrees 2-theta and any 3 peaks selected from the list consisting of: 11.6, 15.7, 16.8 and 23.4±0.2 degrees 2-theta.

In another embodiment, the present invention encompasses a cellosolve solvate of dasatinib designated Form AC, characterized by a powder XRD pattern as depicted in FIG. 28.

The above cellosolve solvate of dasatinib designated Form AC can be further characterized by data selected from the group consisting of: a powder XRD pattern with peaks at about 5.5, 11.6, 15.7 and 16.8±0.2 degrees 2-theta; a powder XRD pattern with peaks at about 11.1, 11.6, 16.8 and 23.4±0.2 degrees 2-theta; and a weight loss on drying of about 40% to about 50% by weight, preferably about 45% by weight, as measured by TGA.

Form AC can be prepared by a process comprising suspending form A21 of dasatinib in cellosolve.

Preferably, the suspension is heated to a temperature of about 40° C. to about 60° C., preferably to about 50° C. Preferably, the suspension is maintained at this temperature for about 4 hours to about 12 hours, preferably for about 6 hours.

The heated suspension is then cooled and maintained for an overnight period. Preferably, the heated suspension is cooled and maintained at a temperature of about 15° C. to about 30° C., preferably to about 25° C.

Form AC can then be recovered from the suspension by evaporating the solvent. Preferably, the solvent is removed at about room temperature. Preferably, the solvent is removed at atmospheric pressure.

Preferably, form AC is maintained at atmospheric pressure, preferably, at about room temperature, preferably, for a period of overnight.

Figure 29:
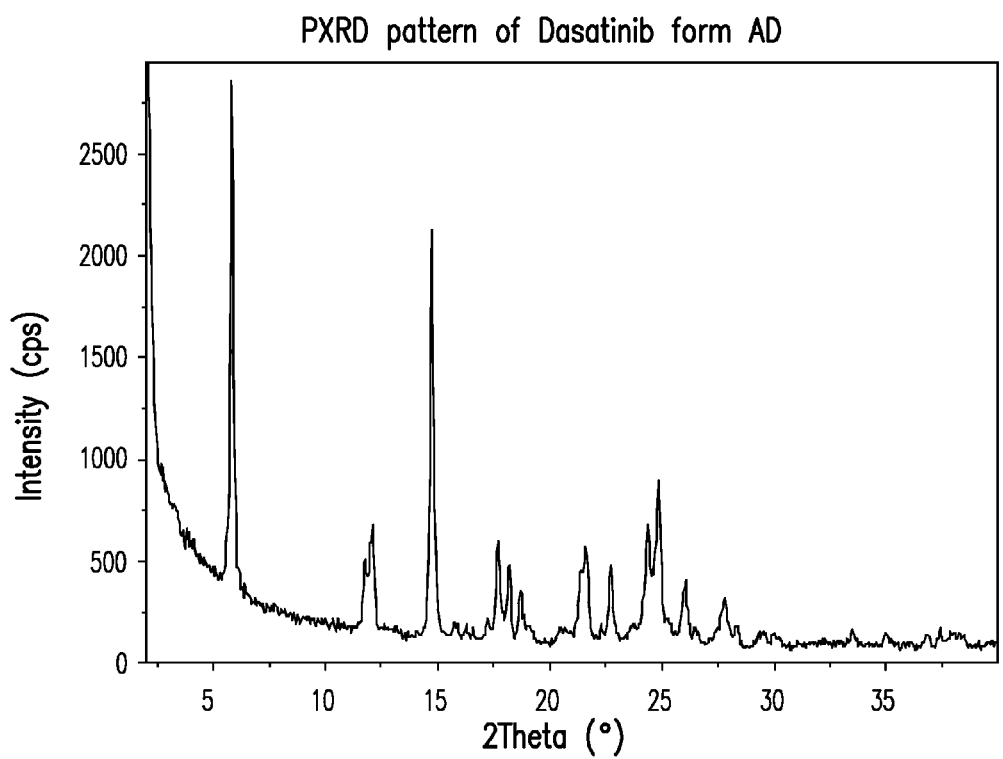
FIG. 29 shows a powder XRD pattern of crystalline dasatinib form AD

In another embodiment, the present invention encompasses a methylacetate solvate of dasatinib characterized by data selected from the group consisting of: a PXRD pattern having any 3 peaks selected from the list consisting of: 5.9, 11.8, 12.1, 14.8, 17.7, 18.2 and 21.6±0.2 degrees 2-theta, a powder XRD pattern as depicted in FIG. 29, and a combination thereof. This form can be designated as form AD.

In a preferred embodiment, the present invention encompasses a methylacetate solvate of dasatinib designated Form AD characterized by a PXRD pattern having peaks at about 12.1 and 21.6±0.2 degrees 2-theta and any 3 peaks selected from the list consisting of: 5.9, 11.8, 14.8, 17.7 and 18.2±0.2 degrees 2-theta.

The above methylacetate solvate of dasatinib designated Form AD can be further characterized by data selected from the group consisting of: a powder XRD pattern with peaks at about 5.9, 12.1, 14.8 and 17.7±0.2 degrees 2-theta; a powder XRD pattern with peaks at about 12.1, 14.8, 18.2 and 21.6±0.2 degrees 2-theta; and a weight loss on drying of about 9% to about 11% by weight, preferably about 10% by weight, as measured by TGA.

Form AD can be prepared by a process comprising suspending form A21 of dasatinib in methylacetate.

Preferably, the suspension is heated to a temperature of about 40° C. to about 60° C., preferably to about 50° C. Preferably, the suspension is maintained at this temperature for about 4 hours to about 12 hours, preferably for about 6 hours.

The heated suspension is then cooled and maintained for an overnight period. Preferably, the heated suspension is cooled and maintained at a temperature of about 15° C. to about 30° C., preferably at about 25° C.

Form AD can then be recovered from the suspension by evaporating solvent. Preferably, the solvent is removed at about room temperature. Preferably, the solvent is removed at atmospheric pressure.

Preferably, form AD is maintained at atmospheric pressure, preferably, at about room temperature, preferably, for a period of overnight.

Figure 30:
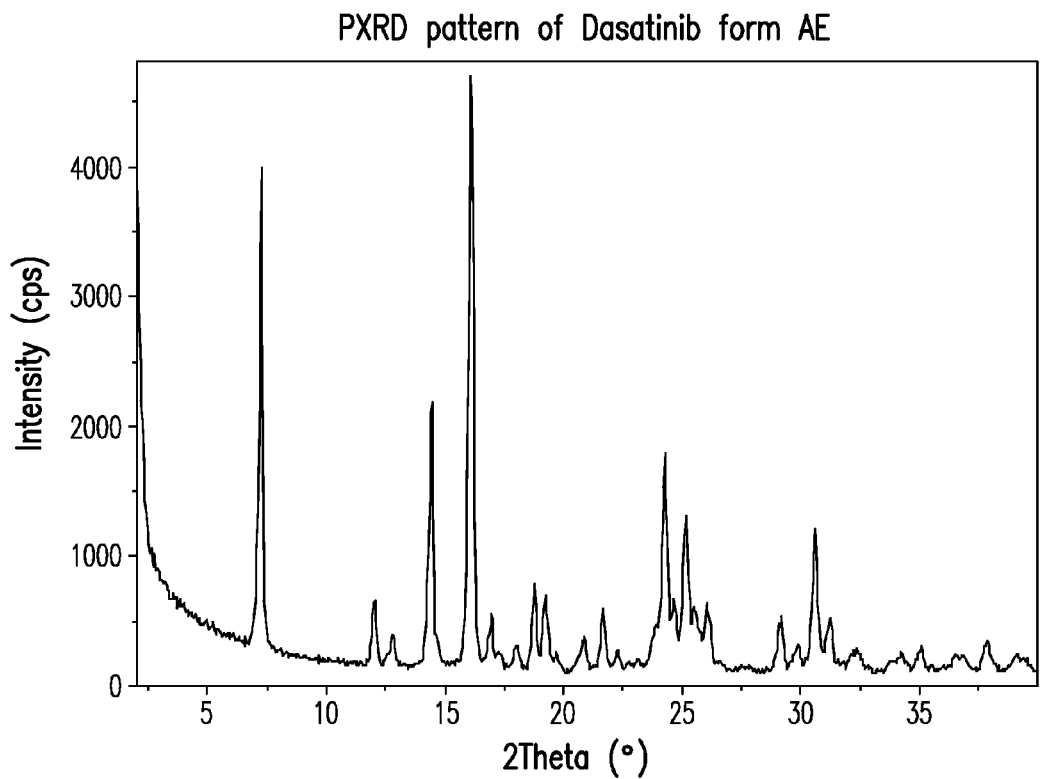
FIG. 30 shows a powder XRD pattern of crystalline dasatinib form AE

In another embodiment, the present invention encompasses a methanol solvate of dasatinib characterized by data selected from the group consisting of: a PXRD pattern having any 3 peaks selected from the list consisting of: 7.1, 11.9, 12.7, 14.3, 16.0, 19.1 and 21.6±0.2 degrees 2-theta, a powder XRD pattern as depicted in FIG. 30, and a combination thereof. This form can be designated as form AE.

In a preferred embodiment, the present invention encompasses a methanol solvate of dasatinib designated Form AE characterized by a PXRD pattern having peaks at about 7.1 and 14.3±0.2 degrees 2-theta and any 3 peaks selected from the list consisting of: 11.9, 12.7, 16.0, 19.1 and 21.6±0.2 degrees 2-theta.

The above methanol solvate of dasatinib designated Form AE can be further characterized by data selected from the group consisting of: a powder XRD pattern with peaks at about 7.1, 11.9, 16.0, 19.1 and 21.6±0.2 degrees 2-theta; a powder XRD pattern with peaks at about 7.1, 12.7, 14.3, 16.0 and 19.1±0.2 degrees 2-theta; and a weight loss on drying of about 2% to about 4%, preferably about 3% by weight as measured by TGA Form AE can be prepared by a process comprising providing a solution of dasatinib in methanol, and precipitating said crystalline form by cooling to a temperature of about 5° C. to about 0° C. to obtain a suspension.

Form A21 is dissolved in methanol, and the solution is heated.

Preferably, the solution is heated to a temperature of about 60° C. to about 70°, preferably about 65° C. Preferably, the solution is maintained at this temperature for about 0.5 hours to about 2 hours, preferably for about 1 hours.

The heated solution is then cooled and maintained for overnight. Preferably, the heated solution is cooled and maintained at a temperature of about 5° C.

Form AE can then be recovered from the suspension by filtering the precipitated crystalline form and washing it with methanol.

Form AE can also be prepared by a process comprising providing a solution of dasatinib in DMSO, transforming the solution into a first suspension and combining the first suspension with methanol providing a second suspension comprising said crystalline form.

Preferably, dasatinib is dissolved in DMSO at a temperature of about 40° C. to about 60° C., preferably of about 50° C. providing the solution. The solution is transformed to the first suspension, preferably, by heating the solution to a temperature of about 60° C. to about 70° C., preferably to about 65° C.

Preferably, methanol is added to the first suspension providing the second suspension.

The second suspension is then cooled. Preferably, the cooling is to a temperature of about 0° C. to about 5° C.

Form AE can then be recovered by filtering the second suspension and washing the filtered precipitate with methanol.

Figure 31:
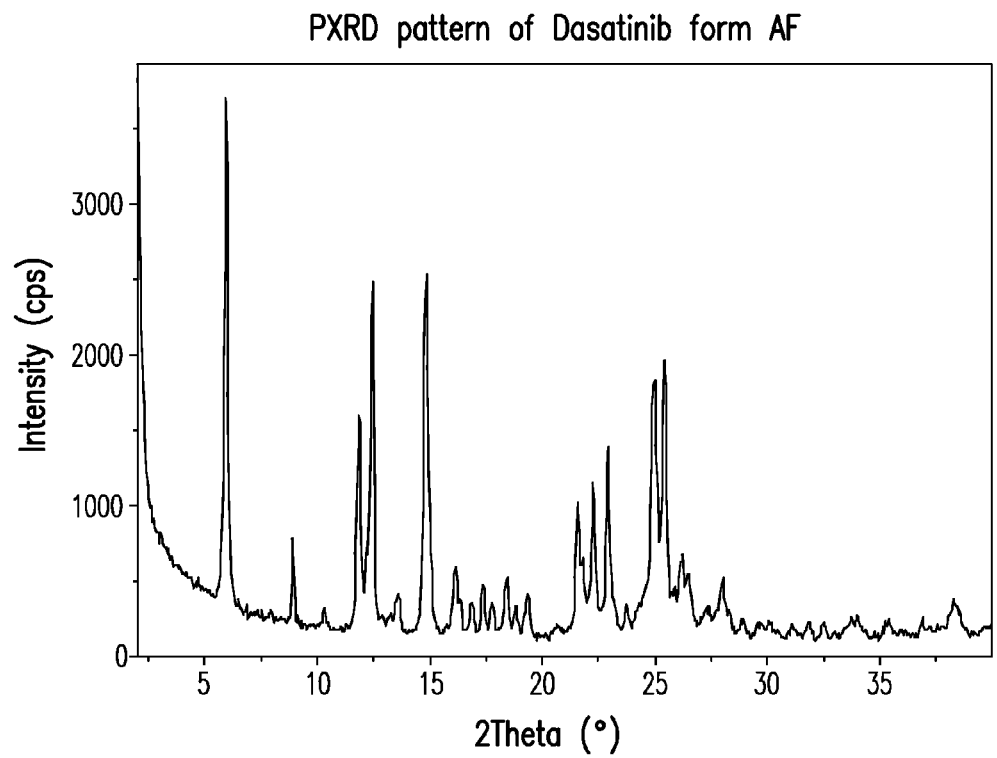
FIG. 31 shows a powder XRD pattern of crystalline dasatinib form AF

In another embodiment, the present invention encompasses an ethylacetate solvate of dasatinib characterized by data selected from the group consisting of: a PXRD pattern having any 3 peaks selected from the list consisting of: 6.0, 8.9, 11.8, 12.4, 16.1, 22.3 and 25.4±0.2 degrees 2-theta, a powder XRD pattern as depicted in FIG. 31, and a combination thereof. This form can be designated as form AF.

In a preferred embodiment, the present invention encompasses an ethylacetate solvate of dasatinib designated Form AF characterized by a PXRD pattern having peaks at about 8.9 and 12.4±0.2 degrees 2-theta and any 3 peaks selected from the list consisting of: 6.0, 11.8, 16.1, 22.3 and 25.4±0.2 degrees 2-theta.

The above ethylacetate solvate of dasatinib designated Form AF can be further characterized by data selected from the group consisting of: a powder XRD pattern with peaks at about 6.0, 8.9, 11.8, 16.1 and 25.4±0.2 degrees 2-theta; a powder XRD pattern with peaks at about 8.9, 11.8, 12.4, 16.1 and 22.3±0.2 degrees 2-theta; and a weight loss on drying of about 9% to about 11% by weight, preferably about 10% by weight, as measured by TGA Form AF can be prepared by a process comprising suspending form A21 of dasatinib in ethylacetate.

Preferably, the suspension is heated to a temperature of about 40° C. to about 60° C., preferably about 50° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 15° C. to about 30° C., preferably about 25° C.

Form AF can then be recovered from the suspension by evaporating the solvent. Preferably, the solvent is removed at about room temperature. Preferably, the solvent is removed at atmospheric pressure.

Preferably, form AF is maintained at atmospheric pressure, preferably, at about room temperature, preferably, for a period of overnight.

Figure 32:
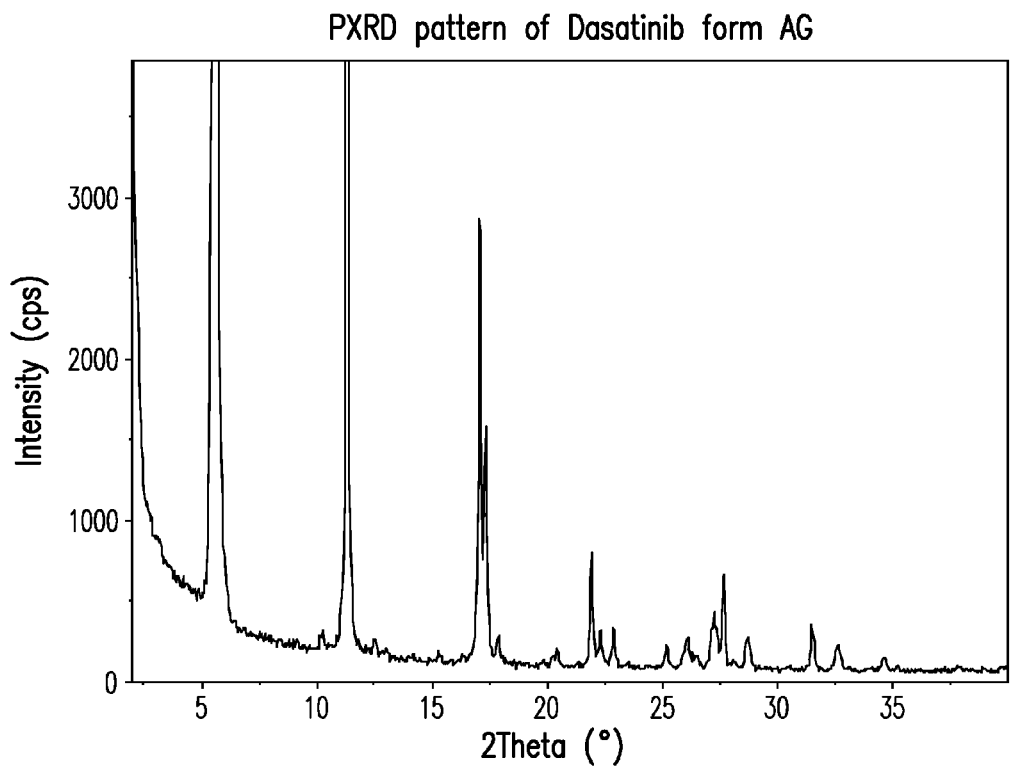
FIG. 32 shows a powder XRD pattern of crystalline dasatinib form AG

In another embodiment, the present invention encompasses a 2-pentanole solvate of dasatinib characterized by data selected from the group consisting of: a PXRD pattern having any 3 peaks selected from the list consisting of: 5.6, 11.3, 17.1, 17.3 and 21.9±0.2 degrees 2-theta, a powder XRD pattern as depicted in FIG. 32, and a combination thereof. This form can be designated as form AG.

In a preferred embodiment, the present invention encompasses a 2-pentanole solvate of dasatinib designated Form AG characterized by a PXRD pattern having peaks at about 5.6, 11.3, 17.1, 17.3 and 21.9±0.2 degrees 2-theta.

The above 2-pentanole solvate of dasatinib designated Form AG can be further characterized by data selected from the group consisting of: a powder XRD pattern with peaks at about 5.6, 11.3, 17.1 and 17.3±0.2 degrees 2-theta; a powder XRD pattern with peaks at about 5.6, 11.3, 17.1 and 21.9±0.2 degrees 2-theta; and a weight loss on drying in two steps, one of about 52% and the second of about 6%, as measured by TGA.

Form AG can be prepared by a process comprising suspending form A21 of dasatinib in 2-pentanole.

Preferably, the suspension is heated to a temperature of about 40° C. to about 60° C., preferably about 50° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 15° C. to about 30° C., preferably to about 25° C.

Form AG can then be recovered from the suspension by evaporating the solvent. Preferably, the solvent is removed at about room temperature. Preferably, the solvent is removed at atmospheric pressure.

Preferably, form AG is maintained at atmospheric pressure, preferably, at about room temperature, preferably, for a period of overnight.

Figure 33:
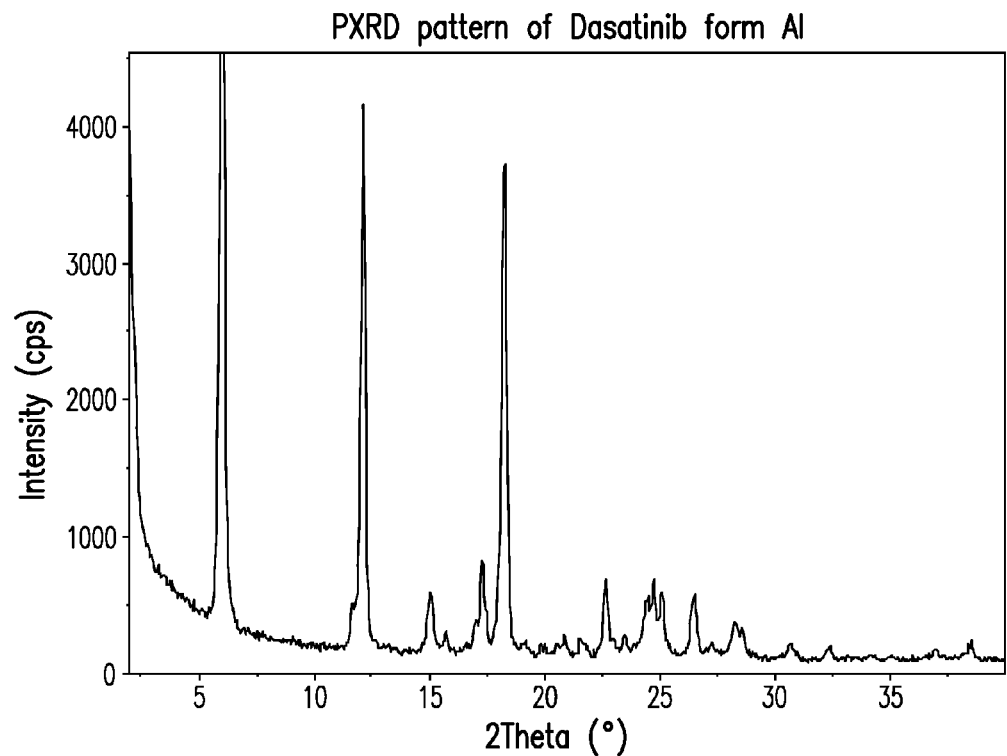
FIG. 33 shows a powder XRD pattern of crystalline dasatinib form AI

In another embodiment, the present invention encompasses a dimethyl carbonate solvate of dasatinib characterized by data selected from the group consisting of: a PXRD pattern having any 3 peaks selected from the list consisting of: 12.1, 17.3, 18.3, 24.5, 24.7 and 26.5±0.2 degrees 2-theta, a powder XRD pattern as depicted in FIG. 33, and combination thereof. This form can be designated as form AI.

In a preferred embodiment, the present invention encompasses a dimethyl carbonate solvate of dasatinib designated Form AI characterized by a PXRD pattern having peaks at about 18.3 and 24.7±0.2 degrees 2-theta and any 3 peaks selected from the list consisting of: 12.1, 17.3, 24.5, and 26.5±0.2 degrees 2-theta.

The above dimethyl carbonate solvate of dasatinib designated Form A1 can be further characterized by data selected from the group consisting of: a powder XRD pattern with peaks at about 12.1, 17.3, 18.3 and 26.5±0.2 degrees 2-theta; a powder XRD pattern having a double peak at about 24.5 and 24.7±0.2 degrees 2-theta; and a weight loss on drying in two steps one of about 66% and the second of about 13%, as measured by TGA.

Form AI can be prepared by a process comprising suspending form A21 of dasatinib in dimethyl carbonate at a temperature of about 50° C. for a period of about 6 hours, and cooling the suspension to a temperature of about 25° C. for a period of about overnight.

Form AI can then be recovered from the suspension by evaporating the solvent. Preferably, the solvent is removed at about room temperature. Preferably, the solvent is removed at atmospheric pressure.

Preferably, form AI is maintained at atmospheric pressure, preferably, at about room temperature, preferably, for a period of overnight.

Figure 34:
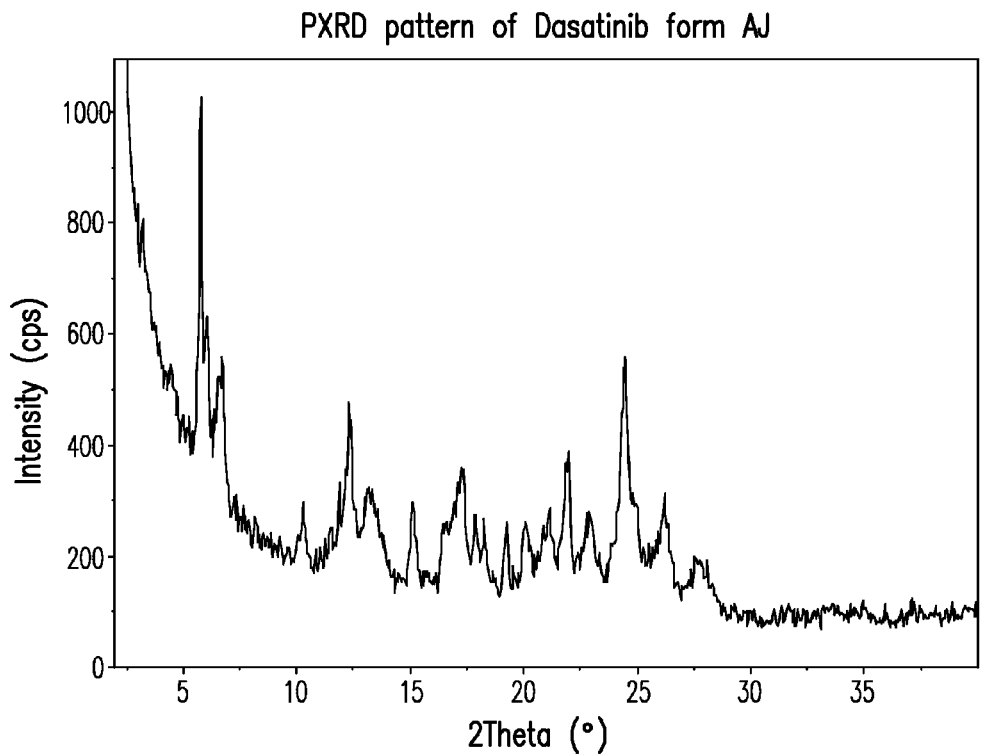
FIG. 34 shows a powder XRD pattern of crystalline dasatinib form AJ

In another embodiment, the present invention encompasses an isopropylacetate solvate of dasatinib characterized by data selected from the group consisting of: a PXRD pattern having any 3 peaks selected from the list consisting of: 5.8, 10.3, 12.3, 17.3, 21.9 and 24.4±0.2 degrees 2-theta, a powder XRD pattern as depicted in FIG. 34, and a combination thereof. This form can be designated as form AJ.

In a preferred embodiment, the present invention encompasses an isopropylacetate solvate of dasatinib designated Form AJ characterized by a PXRD pattern having peaks at about 12.3 and 17.3±0.2 degrees 2-theta and any 3 peaks selected from the list consisting of: 5.8, 10.3, 21.9 and 24.4±0.2 degrees 2-theta.

The above isopropylacetate solvate of dasatinib designated Form AJ can be further characterized by data selected from the group consisting of: a powder XRD pattern with peaks at about 10.3, 12.3, 17.3 and 21.9±0.2 degrees 2-theta; a powder XRD pattern with peaks at about 5.8, 12.3, 21.9 and 24.4±0.2 degrees 2-theta; and a weight loss on drying in two steps one of about 6% and the second of about 4%, as measured by TGA.

Form AJ can be prepared by a process comprising suspending form A21 of dasatinib in isopropylacetate.

Preferably, the suspension is heated to a temperature of about 40° C. to about 60° C., preferably to about 50° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 15° C. to about 30° C., preferably of about 25° C.

Form AJ can then be recovered from the suspension by evaporating the solvent. Preferably, the solvent is removed at about room temperature. Preferably, the solvent is removed at atmospheric pressure.

Preferably, form AJ is maintained at atmospheric pressure, preferably, at about room temperature, preferably, for a period of overnight.

Figure 36:
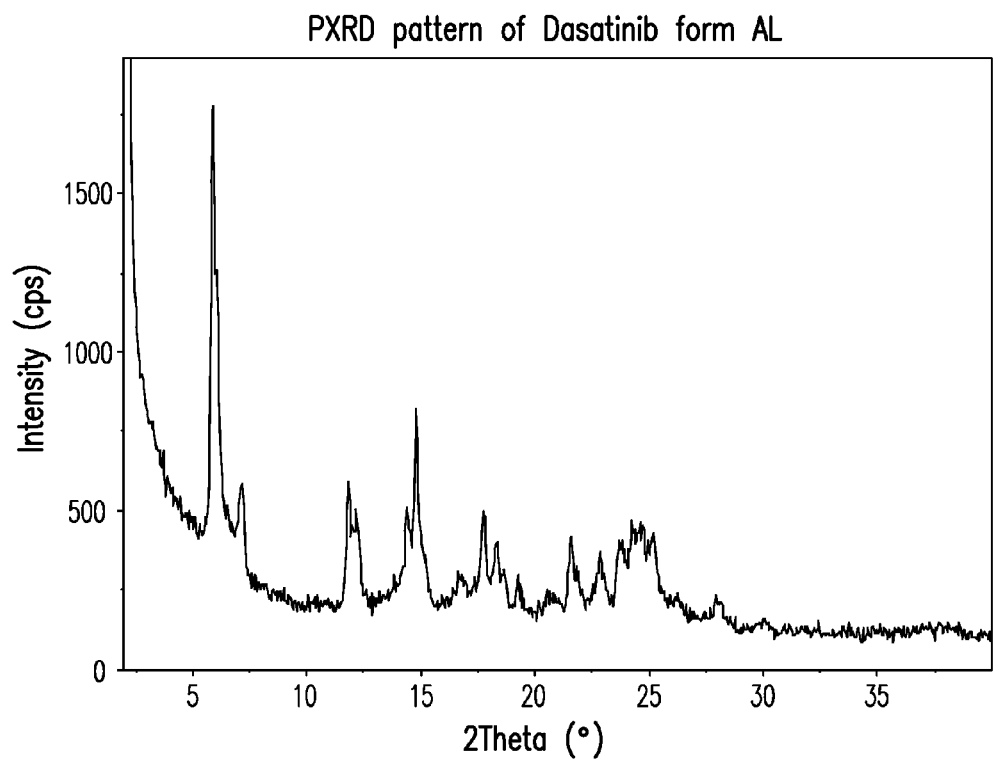
FIG. 36 shows a powder XRD pattern of crystalline dasatinib form AL

In another embodiment, the present invention encompasses a dichloromethane solvate of dasatinib characterized by data selected from the group consisting of: a PXRD pattern having any 3 peaks selected from the list consisting of: 5.9, 7.1, 11.8, 14.4, 14.8, 18.3 and 22.9±0.2 degrees 2-theta, a powder XRD pattern as depicted in FIG. 36, and a combination thereof. This form can be designated as form AL.

In a preferred embodiment, the present invention encompasses a dichloromethane solvate of dasatinib designated Form AL characterized by a PXRD pattern having peaks at about 7.1 and 14.4±0.2 degrees 2-theta and any 3 peaks selected from the list consisting of: 5.9, 11.8, 14.8, 18.3 and 22.9±0.2 degrees 2-theta.

The above dichloromethane solvate of dasatinib designated Form AL can be further characterized by data selected from the group consisting of: a powder XRD pattern with peaks at about 5.9, 7.1, 14.4, 18.3 and 22.9±0.2 degrees 2-theta; a powder XRD pattern with peaks at about 7.1, 11.8, 14.4, 14.8 and 18.3±0.2 degrees 2-theta; and a weight loss on drying of about 10% to about 12% by weight, preferably of about 11% by weight, as measured by TGA Form AL can be prepared by a process comprising suspending form A21 of dasatinib in dichloromethane.

Preferably, the suspension is heated to a temperature of about 25° C. to about 40° C., preferably to about 30° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 10° C. to about 25° C., preferably to about 25° C.

Form AL can then be recovered from the suspension by evaporating the solvent. Preferably, the solvent is removed at about room temperature. Preferably, the solvent is removed at atmospheric pressure.

Preferably, form AL is maintained at atmospheric pressure, preferably, at about room temperature, preferably, for a period of overnight.

Figure 37:
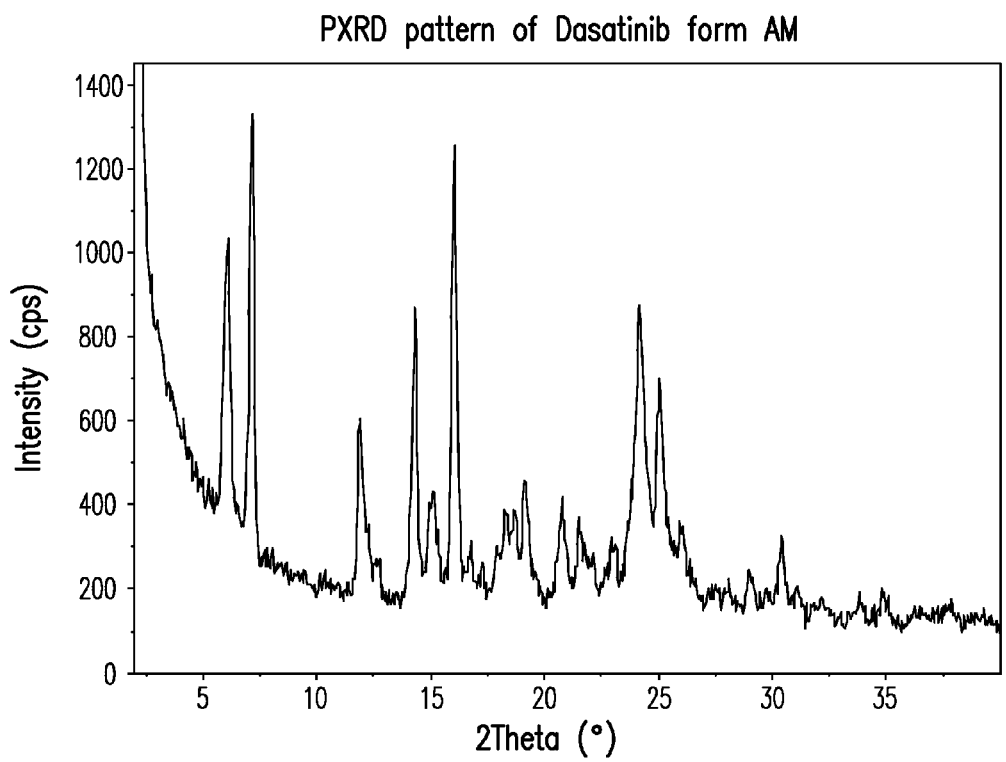
FIG. 37 shows a powder XRD pattern of crystalline dasatinib form AM

In another embodiment, the present invention encompasses a methylformate solvate of dasatinib characterized by data selected from the group consisting of: a PXRD pattern having any 3 peaks selected from the list consisting of: 6.0, 7.1, 11.9, 14.3, 16.0, 24.2 and 25.1±0.2 degrees 2-theta, a powder XRD pattern as depicted in FIG. 37, and a combination thereof. This form can be designated as form AM.

In a preferred embodiment, the present invention encompasses a methylformate solvate of dasatinib designated Form AM characterized by a PXRD pattern having peaks at about 7.1 and 16.0±0.2 degrees 2-theta and any 3 peaks selected from the list consisting of: 6.0, 11.9, 14.3, 24.2 and 25.1±0.2 degrees 2-theta.

The above methylformate solvate of dasatinib designated Form AM can be further characterized by data selected from the group consisting of: a powder XRD pattern with peaks at about 6.1, 7.1, 11.9, 14.3 and 16.0±0.2 degrees 2-theta; a powder XRD pattern with peaks at about 7.1, 14.3, 16.0, 24.2 and 25.1±0.2 degrees 2-theta; and a weight loss on drying in two steps, one of about 3% and the second of about 8%, as measured by TGA.

Form AM can be prepared by a process comprising suspending form A21 of dasatinib in methylformate.

Preferably, the suspension is heated to a temperature of about 25° C. to about 40° C., preferably of about 30° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 10° C. to about 25° C., preferably to about 25° C.

Form AM can then be recovered from the suspension by evaporating the solvent. Preferably, the solvent is removed at about room temperature. Preferably, the solvent is removed at atmospheric pressure.

Preferably, form AM is maintained at atmospheric pressure, preferably, at about room temperature, preferably, for a period of overnight.

Figure 38:
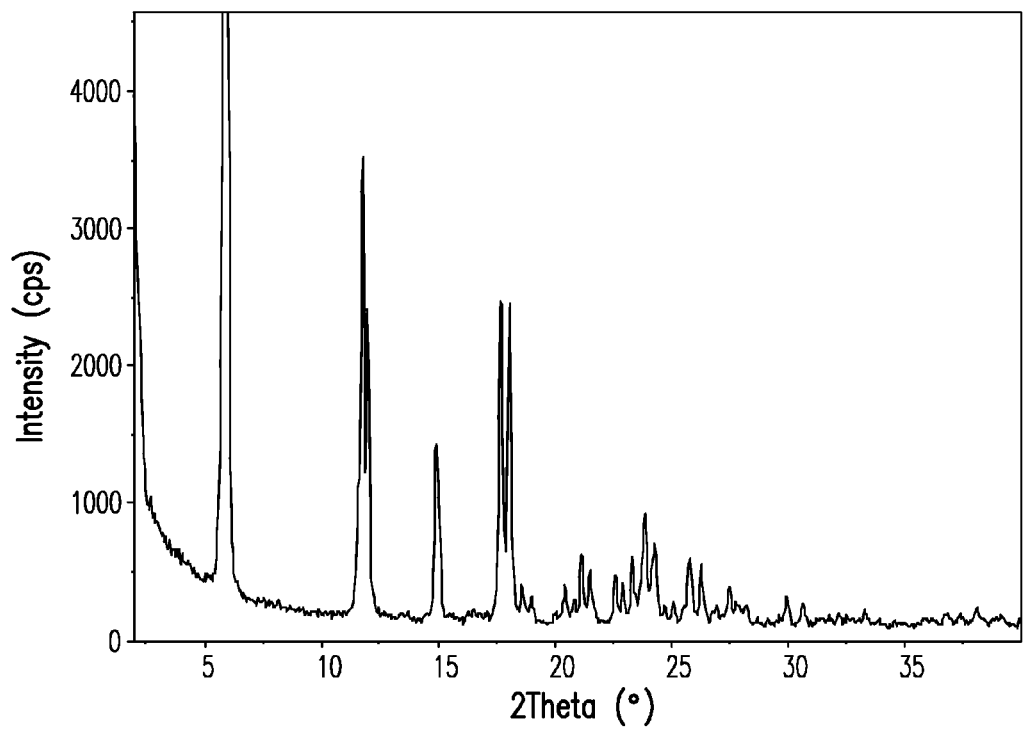
FIG. 38 shows a powder XRD pattern of crystalline dasatinib form AN

In another embodiment, the present invention encompasses a tert-butanol solvate of dasatinib characterized by data selected from the group consisting of: a PXRD pattern having any 3 peaks selected from the list consisting of: 5.9, 11.8, 12.0, 15.0, 17.7, 18.1 and 26.3±0.2 degrees 2-theta, a powder XRD pattern as depicted in FIG. 38, and a combination thereof. This form can be designated as form AN.

In a preferred embodiment, the present invention encompasses a tert-butanol solvate of dasatinib designated Form AN characterized by a PXRD pattern having peaks at about 11.8 and 18.1±0.2 degrees 2-theta and any 3 peaks selected from the list consisting of: 5.9, 12.0, 15.0, 17.7, and 26.3±0.2 degrees 2-theta.

The above tert-butanol solvate of dasatinib designated Form AN can be further characterized by data selected from the group consisting of: a powder XRD pattern with peaks at about 11.8, 12.0, 17.7, 18.1 and 26.3±0.2 degrees 2-theta; a powder XRD pattern with peaks at about 5.9, 12.0, 15.0, 17.7 and 18.1±0.2 degrees 2-theta; and a weight loss on drying of about 12% to about 15% by weight, preferably of about 13% by weight, as measured by TGA.

Form AN can be prepared by a process comprising suspending form A21 of dasatinib in tert-butanol.

Preferably, the process further comprises heating the suspension to a temperature of about 40° C. to about 60° C., preferably to about 50° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 15° C. to about 30° C., preferably to about 25° C.

Form AN can then be recovered from the cooled suspension by evaporating the solvent. Preferably, the solvent is removed at about room temperature. Preferably, the solvent is removed at atmospheric pressure.

Preferably, the removal of the solvent is done by maintaining form AN at atmospheric pressure, preferably, at about room temperature, preferably, for a period of overnight.

Figure 39:
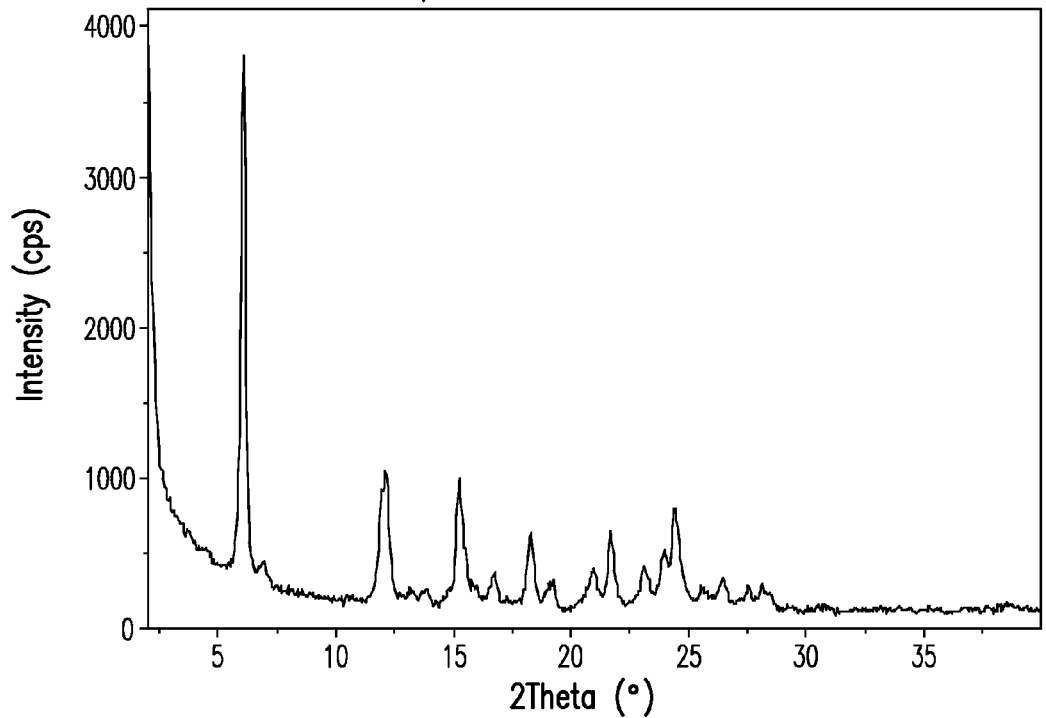
FIG. 39 shows a powder XRD pattern of crystalline dasatinib form AP

In another embodiment, the present invention encompasses a dimethoxyethane solvate of dasatinib characterized by data selected from the group consisting of: a PXRD pattern having any 3 peaks selected from the list consisting of: 6.1, 12.1, 15.3, 21.0, 23.1 and 24.4±0.2 degrees 2-theta, a powder XRD pattern as depicted in FIG. 39, and a combination thereof. This form can be designated as form AP.

In a preferred embodiment, the present invention encompasses a dimethoxyethane solvate of dasatinib designated Form AP characterized by a PXRD pattern having peaks at about 21.0 and 24.4±0.2 degrees 2-theta and any 3 peaks selected from the list consisting of: 6.1, 12.1, 15.3 and 23.1±0.2 degrees 2-theta.

The above dimethoxyethane solvate of dasatinib designated Form AP can be further characterized by data selected from the group consisting of: a powder XRD pattern with peaks at about 6.1, 12.1, 15.3, 21.0 and 24.4±0.2 degrees 2-theta; a powder XRD pattern with peaks at about 6.1, 15.3, 21.0, 23.1 and 24.4±0.2 degrees 2-theta; and a weight loss on drying of about 10% to about 12% by weight, preferably about 11% by weight, as measured by TGA.

Form AP can be prepared by a process comprising drying crystalline dasatinib form AB.

Preferably, drying is done at a temperature of about 50° C. to about 60° C., preferably of about 55° C., preferably, for a period of overnight.

Figure 40:
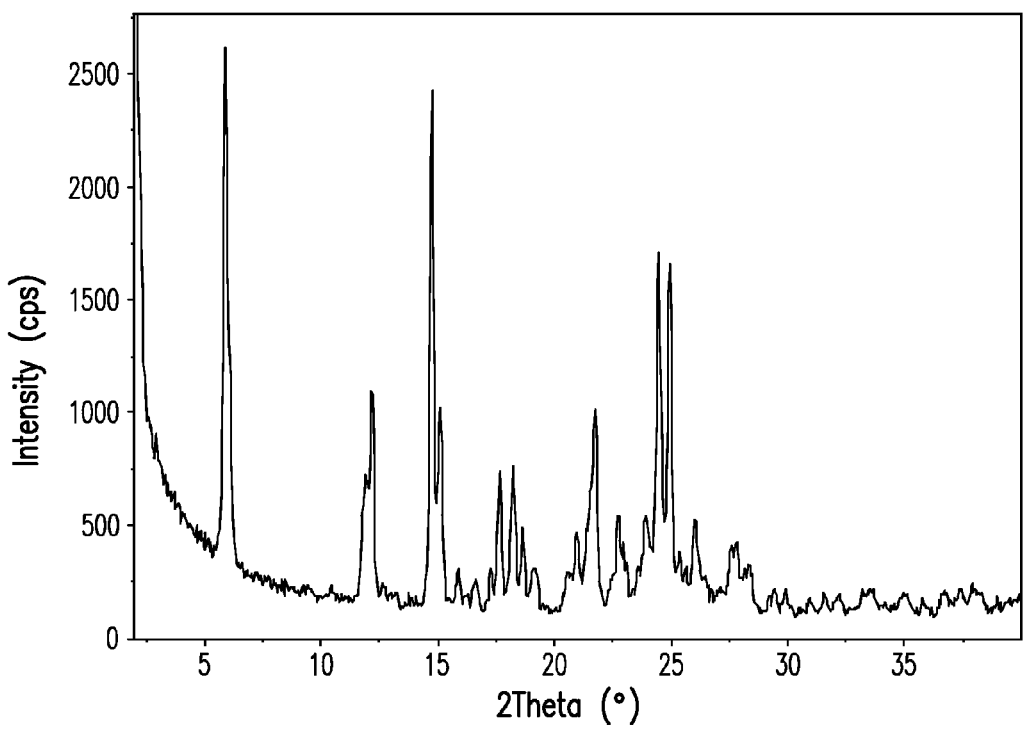
FIG. 40 shows a powder XRD pattern of crystalline dasatinib form AQ

In another embodiment, the present invention encompasses a MEK solvate of dasatinib characterized by data selected from the group consisting of: a PXRD pattern having any 3 peaks selected from the list consisting of: 5.9, 12.2, 14.7, 15.1, 21.7, 24.5 and 24.9±0.2 degrees 2-theta, a powder XRD pattern as depicted in FIG. 40, and a combination thereof. This form can be designated as form AQ.

In a preferred embodiment, the present invention encompasses a MEK solvate of dasatinib designated Form AQ characterized by a PXRD pattern having peaks at about 14.7 and 24.9±0.2 degrees 2-theta and any 3 peaks selected from the list consisting of: 5.9, 12.2, 15.1, 21.7 and 24.5±0.2 degrees 2-theta.

The above MEK solvate of dasatinib designated Form AQ can be further characterized by data selected from the group consisting of: a powder XRD pattern with peaks at about 5.9, 12.2, 14.7, 21.7 and 24.5±0.2 degrees 2-theta; a powder XRD pattern with peaks at about 12.2, 15.1, 21.7, 24.5 and 24.9±0.2 degrees 2-theta; and a weight loss on drying of about 9% to about 11% by weight, preferably about 10% by weight, as measured by TGA.

Form AQ can be prepared by a process comprising suspending form A21 of dasatinib in MEK.

Preferably, the process further comprises heating the suspension to a temperature of about 40° C. to about 60° C., preferably to about 50° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 15° C. to about 30° C., preferably to about 25° C.

Form AQ can then be recovered from the cooled suspension by evaporating the solvent. Preferably, the solvent is removed at about room temperature. Preferably, the solvent is removed at atmospheric pressure.

Preferably, the removal of the solvent is done by maintaining form AQ at atmospheric pressure, preferably, at about room temperature, preferably, for a period of overnight.

Figure 41:
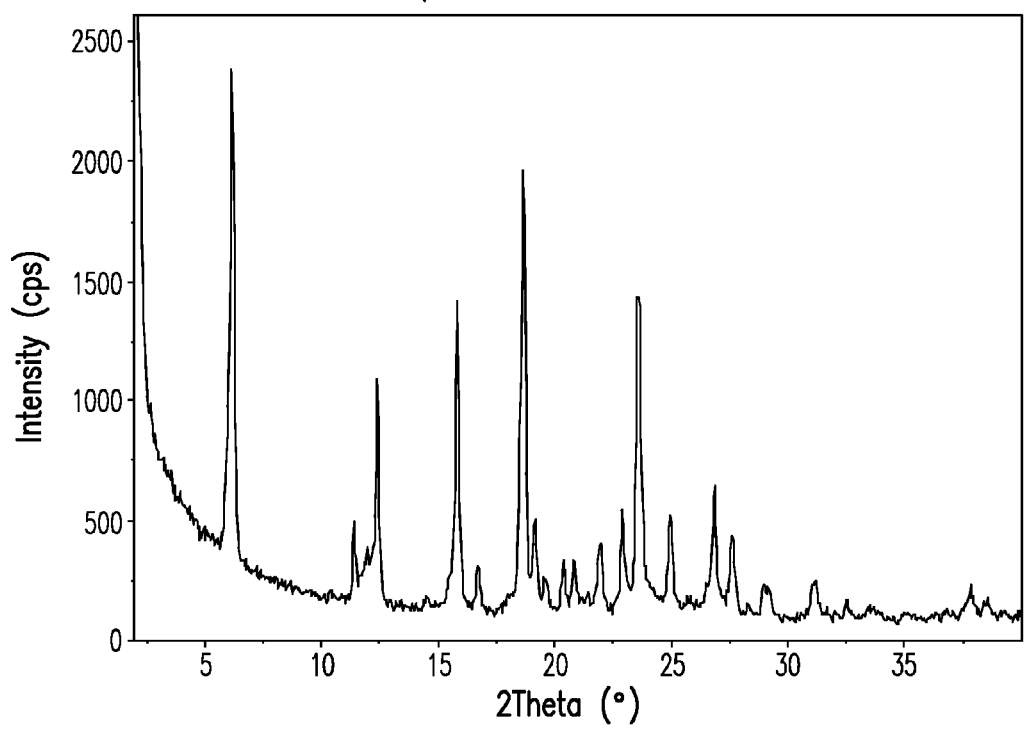
FIG. 41 shows a powder XRD pattern of crystalline dasatinib form AR

In another embodiment, the present invention encompasses a monochlorobenzene solvate of dasatinib characterized by data selected from the group consisting of: a PXRD pattern having any 3 peaks selected from the list consisting of: 6.2, 12.4, 15.8, 18.7, 23.6 and 26.8±0.2 degrees 2-theta, a powder XRD pattern as depicted in FIG. 41, and combination thereof. This form can be designated as form AR.

In a preferred embodiment, the present invention encompasses a monochlorobenzene solvate of dasatinib designated Form AR characterized by a PXRD pattern having peaks at about 12.4 and 15.8±0.2 degrees 2-theta and any 3 peaks selected from the list consisting of: 6.2, 18.7, 23.6 and 26.8±0.2 degrees 2-theta.

The above monochlorobenzene solvate of dasatinib designated Form AR can be further characterized by data selected from the group consisting of: a powder XRD pattern with peaks at about 6.2, 12.4, 15.8, 18.7 and 23.6±0.2 degrees 2-theta; a powder XRD pattern with peaks at about 12.4, 15.8, 18.7, 23.6 and 26.8±0.2 degrees 2-theta; and a weight loss on drying in two steps, one of about 30% and the second of about 6%, as measured by TGA.

Form AR can be prepared by a process comprising suspending form A21 of dasatinib in monochlorobenzene at a temperature of about 50° C. for a period of about 6 hours, and cooling the suspension to a temperature of about of 25° C. for a period of about overnight.

Form AR can then be recovered from the cooled suspension by evaporating the solvent. Preferably, the solvent is removed at about room temperature. Preferably, the solvent is removed at atmospheric pressure.

Preferably, the removal of the solvent is done by maintaining form AR at atmospheric pressure, preferably, at about room temperature, preferably, for a period of overnight.

Figure 42:
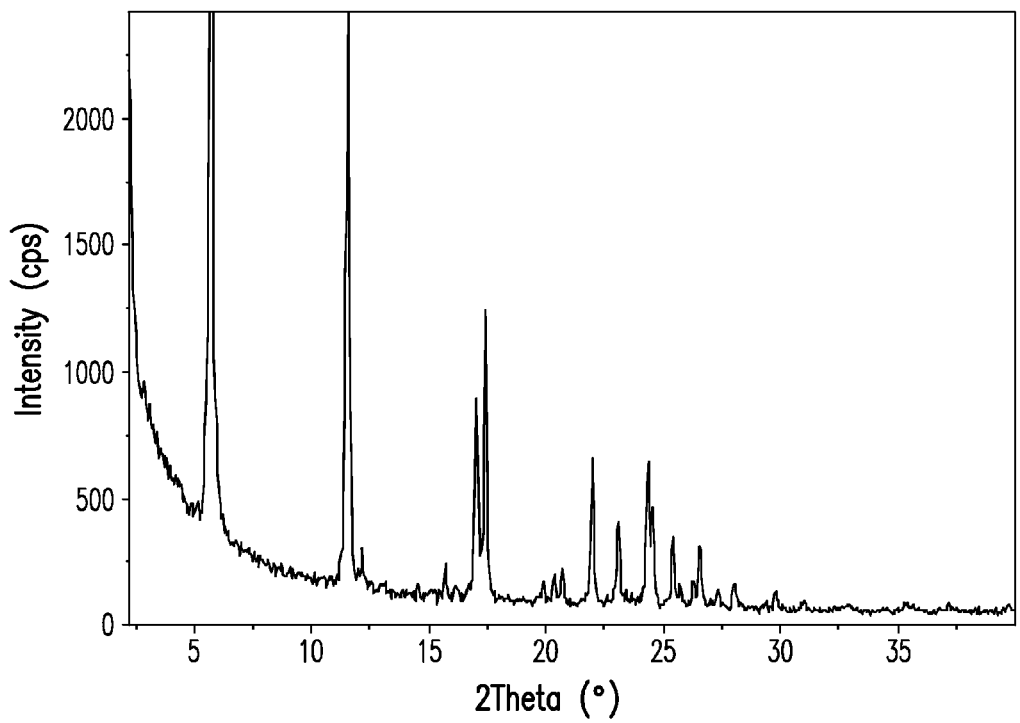

In another embodiment, the present invention encompasses a PGME solvate of dasatinib characterized by data selected from the group consisting of: a PXRD pattern having any 3 peaks selected from the list consisting of: 5.7, 11.5, 17.0, 17.4, 22.0, 23.1 and 24.3±0.2 degrees 2-theta, a powder XRD pattern as depicted in FIG. 42, and a combination thereof. This form can be designated as form AS.

In a preferred embodiment, the present invention encompasses a PGME solvate of dasatinib designated Form AS characterized by a PXRD pattern having peaks at about 11.5 and 23.1±0.2 degrees 2-theta and any 3 peaks selected from the list consisting of: 5.7, 17.0, 17.4, 22.0 and 24.3±0.2 degrees 2-theta.

The above PGME solvate of dasatinib designated Form AS can be further characterized by data selected from the group consisting of: a powder XRD pattern with peaks at about 5.7, 11.5, 17.0, 17.4 and 23.1±0.2 degrees 2-theta; a powder XRD pattern with peaks at about 11.5, 17.0, 22.0, 23.1 and 24.4±0.2 degrees 2-theta; and a weight loss on drying of about 12% to about 15% by weight, preferably of about 14% by weight, as measured by TGA.

Form AS can be prepared by a process comprising suspending form A21 of dasatinib in PGME.

Preferably, the process further comprises heating the suspension to a temperature of about 40° C. to about 60° C., preferably of about 50° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 15° C. to about 30° C., preferably to about 25° C.

Form AS can then be recovered from the suspension by evaporating the solvent. Preferably, the solvent is removed at about room temperature. Preferably, the solvent is removed at atmospheric pressure.

Preferably, the removal of the solvent is done by maintaining form AS at atmospheric pressure, preferably, at about room temperature, preferably, for a period of overnight.

Figure 44:
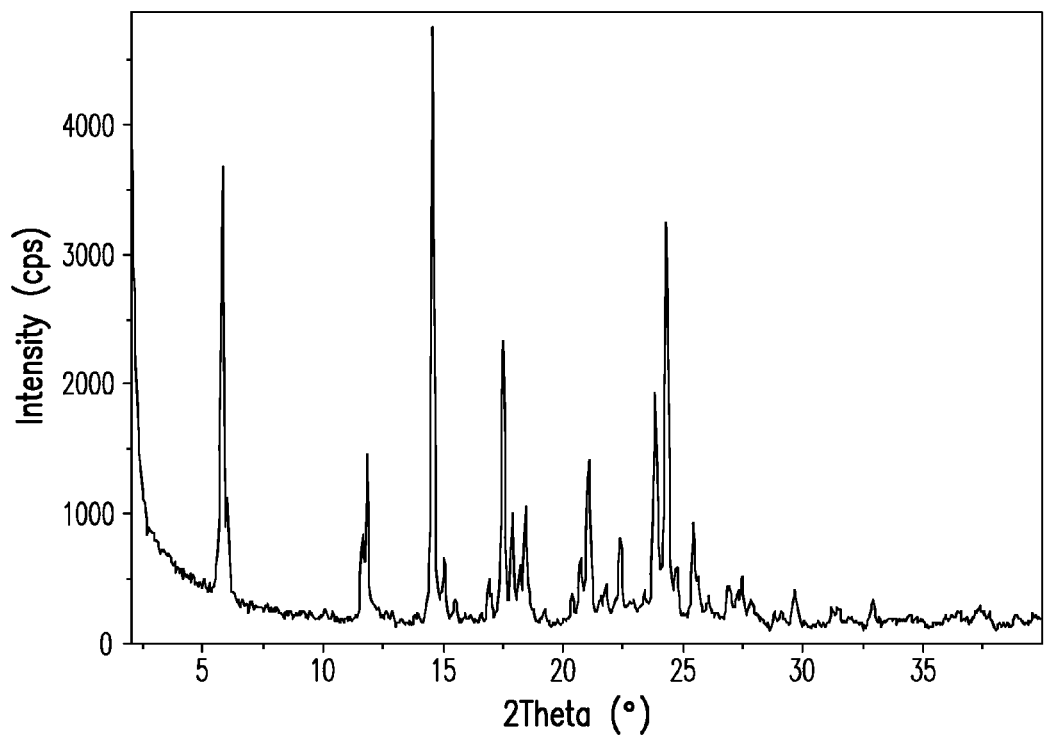
FIG. 44 shows a powder XRD pattern of crystalline dasatinib form AU

In another embodiment, the present invention encompasses a cyclopentyl methyl ether solvate of dasatinib characterized by data selected from the group consisting of: a PXRD pattern having any 3 peaks selected from the list consisting of: 5.8, 14.6, 17.5, 21.1, 22.4, 23.9 and 24.3±0.2 degrees 2-theta, a powder XRD pattern as depicted in FIG. 44, and a combination thereof. This form can be designated as form AU.

In a preferred embodiment, the present invention encompasses a cyclopentyl methyl ether solvate of dasatinib designated Form AU characterized by a PXRD pattern having peaks at about 17.5 and 23.9±0.2 degrees 2-theta and any 3 peaks selected from the list consisting of: 5.8, 14.6, 21.1, 22.4 and 24.3±0.2 degrees 2-theta.

The above cyclopentyl methyl ether solvate of dasatinib designated Form AU can be further characterized by data selected from the group consisting of: a powder XRD pattern with peaks at about 14.6, 17.5, 21.1, 22.4 and 24.3±0.2 degrees 2-theta; a powder XRD pattern with peaks at about 5.8, 14.6, 21.1, 22.4 and 23.9±0.2 degrees 2-theta; and a weight loss on drying by TGA of about 9% to about 11% by weight, preferably about 10% by weight.

Form AU can be prepared by a process comprising suspending form A21 of dasatinib in cyclopentyl methyl ether.

Preferably, the process further comprises heating the suspension to a temperature of about 40° C. to about 60° C., preferably of about 50° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 15° C. to about 30° C., preferably of about 25° C.

Form AU can then be recovered from the suspension by evaporating the solvent. Preferably, the solvent is removed at about room temperature. Preferably, the solvent is removed at atmospheric pressure.

Preferably, the removal of the solvent is done by maintaining form AU at atmospheric pressure, preferably, at about room temperature, preferably, for a period of overnight.

Figure 45:
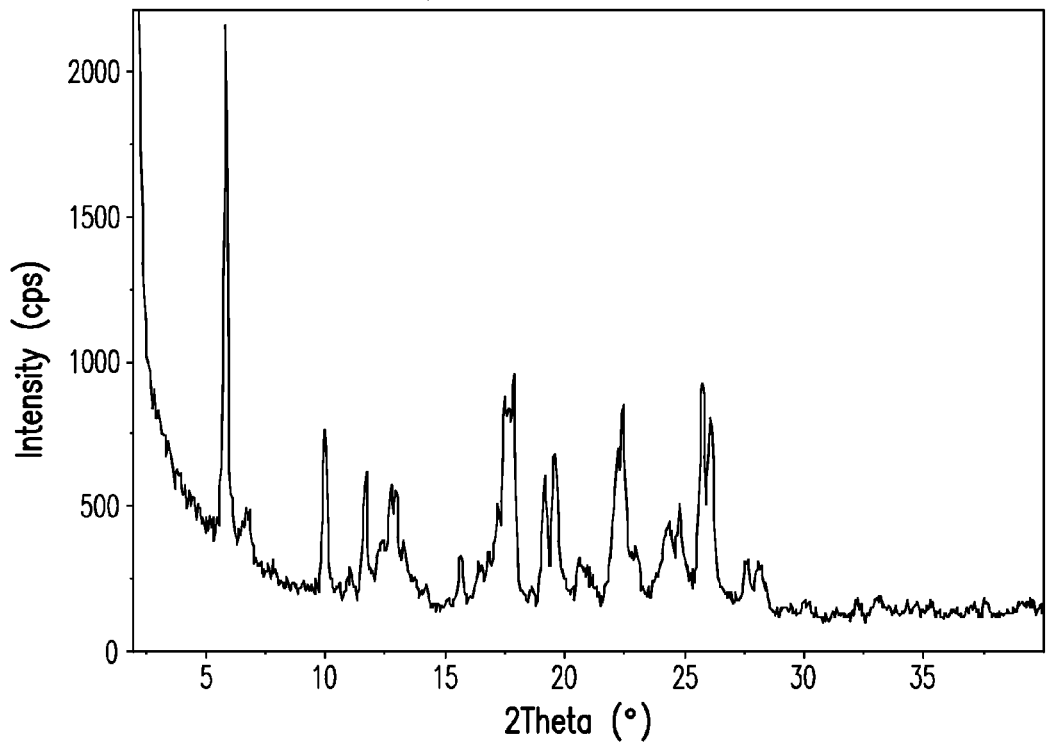
FIG. 45 shows a powder XRD pattern of crystalline dasatinib form AV

In another embodiment, the present invention encompasses a MTBE solvate of dasatinib characterized by data selected from the group consisting of: a PXRD pattern having any 3 peaks selected from the list consisting of: 5.8, 10.0, 19.2, 19.6, 22.4, 25.7 and 26.1±0.2 degrees 2-theta, a powder XRD pattern as depicted in FIG. 45, and a combination thereof. This form can be designated as form AV.

In a preferred embodiment, the present invention encompasses a MTBE solvate of dasatinib designated Form AV characterized by a PXRD pattern having peaks at about 10.0 and 22.4±0.2 degrees 2-theta and any 3 peaks selected from the list consisting of: 5.8, 19.2, 19.6, 25.7 and 26.1±0.2 degrees 2-theta.

The above MTBE solvate of dasatinib designated Form AV can be further characterized by data selected from the group consisting of: a powder XRD pattern with peaks at about 5.8, 10.0, 19.6, 25.7 and 26.1±0.2 degrees 2-theta; a powder XRD pattern with peaks at about 10.0, 19.2, 22.4, 25.7 and 26.1±0.2 degrees 2-theta; and a weight loss on drying by TGA of about 7% to about 9% by weight, preferably of about 8% by weight.

Form AV can be prepared by a process comprising suspending form A21 of dasatinib in MTBE.

Preferably, the process further comprises heating the suspension to a temperature of about 40° C. to about 60° C., preferably of about 50° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 15° C. to about 30° C., preferably of about 25° C.

Form AV can then be recovered from the suspension by evaporating the solvent. Preferably, the solvent is removed at about room temperature. Preferably, the solvent is removed at atmospheric pressure.

Preferably, the removal of the solvent is done by maintaining form AV at atmospheric pressure, preferably, at about room temperature, preferably, for a period of overnight.

Figure 46:
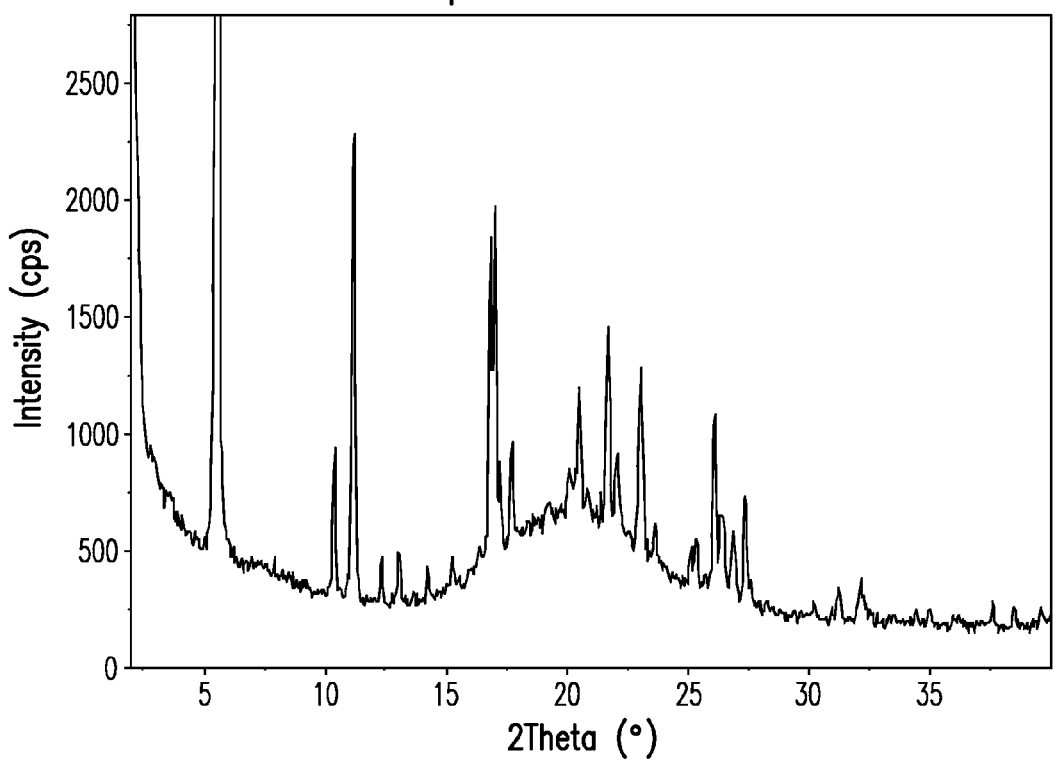
FIG. 46 shows a powder XRD pattern of crystalline dasatinib form AH

In another embodiment, the present invention encompasses an amylalcohol solvate of dasatinib characterized by data selected from the group consisting of: a PXRD pattern having any 3 peaks selected from the list consisting of: 5.6, 10.4, 11.2, 21.7, 23.1 and 26.1±0.2 degrees 2-theta, a powder XRD pattern as depicted in FIG. 46, and a combination thereof. This form can be designated as form AH.

In a preferred embodiment, the present invention encompasses an amylalcohol solvate of dasatinib designated Form AH characterized by a PXRD pattern having peaks at about 10.4 and 11.2±0.2 degrees 2-theta and any 3 peaks selected from the list consisting of: 5.6, 21.7, 23.1 and 26.1±0.2 degrees 2-theta.

The above amylalcohol solvate of dasatinib designated Form AH can be further characterized by data selected from the group consisting of: a powder XRD pattern with peaks at about 5.6, 10.4, 21.7, 23.1 and 26.1±0.2 degrees 2-theta; a powder XRD pattern having a double peak at about 16.8 and 17.0±0.2 degrees 2-theta; and a weight loss on drying in two steps one of about 72% and the second of about 3%, as measured by TGA.

Form AH can be prepared by a process comprising suspending form A21 of dasatinib in amylalcohol.

Preferably, the process further comprises heating the suspension to a temperature of about 40° C. to about 60° C., preferably of about 50° C. Preferably, the suspension is maintained at this temperature for about 4 hours to about 12 hours, preferably for about 6 hours.

The heated suspension is then cooled and maintained for overnight. Preferably, the heated suspension is cooled and maintained at a temperature of about 15° C. to about 30° C., preferably of about 25° C.

Form AH can then be recovered from the suspension by evaporating the solvent. Preferably, the solvent is removed at about room temperature. Preferably, the solvent is removed at atmospheric pressure.

Preferably, the removal of the solvent is done by maintaining form AH at atmospheric pressure, preferably, at about room temperature, preferably, for a period of overnight.

Figure 47:
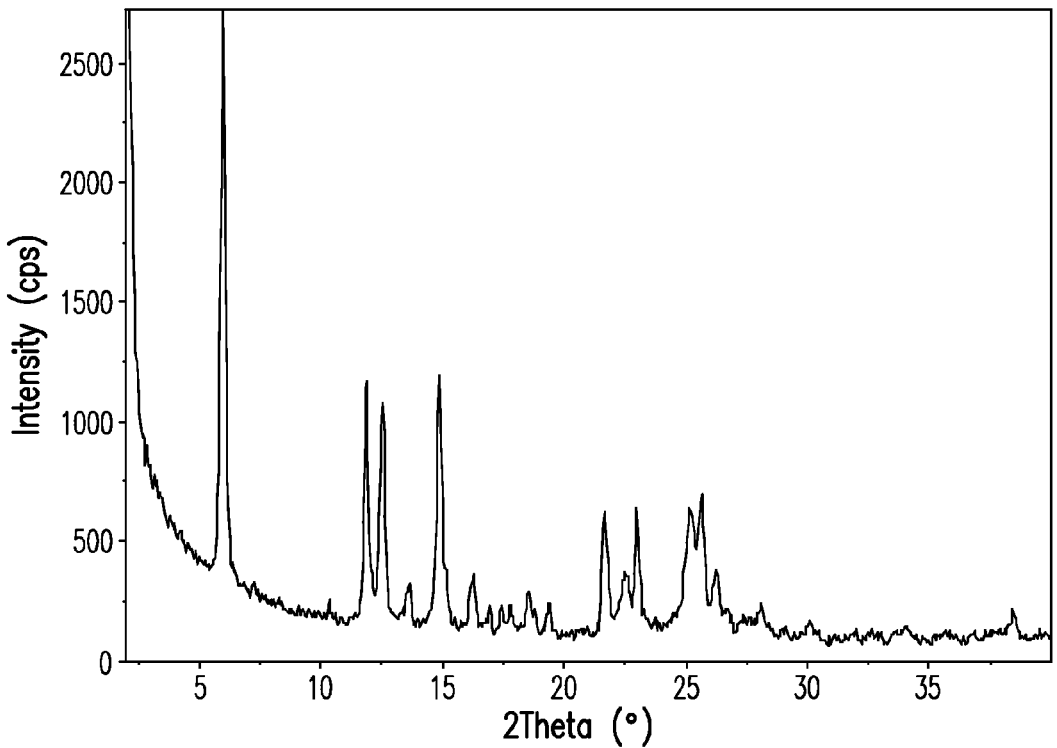
FIG. 47 shows a powder XRD pattern of crystalline dasatinib form AY

In one embodiment, the present invention encompasses a dimethyl carbonate solvate of dasatinib characterized by data selected from the group consisting of: a PXRD pattern having any 3 peaks selected from the list consisting of: 12.5, 13.6, 16.2, 21.7 and 25.6±0.2 degrees 2-theta, a powder XRD pattern as depicted in FIG. 47, and a combination thereof. This form can be designated as form AY.

In a preferred embodiment, the present invention encompasses a dimethyl carbonate solvate of dasatinib characterized by a PXRD pattern having peaks at about 12.5, 13.6, 16.2, 21.7 and 25.6±0.2 degrees 2-theta.

The above dimethyl carbonate solvate of dasatinib designated Form AY can be further characterized by data selected from the group consisting of: a powder XRD pattern with peaks at about 13.6, 16.2, 21.7 and 25.6±0.2 degrees 2-theta; a powder XRD pattern with peaks at about 12.5, 13.6, 16.2 and 25.6±0.2 degrees 2-theta; and a weight loss on drying by TGA of about 8% to about 10% by weight, preferably about 9% by weight.

Form AY can be prepared by a process comprising drying dasatinib form AI.

Preferably, drying is done at a temperature of about 50° C. to about 60° C., preferably of about 55° C., preferably, for a period of overnight.

Figure 48:
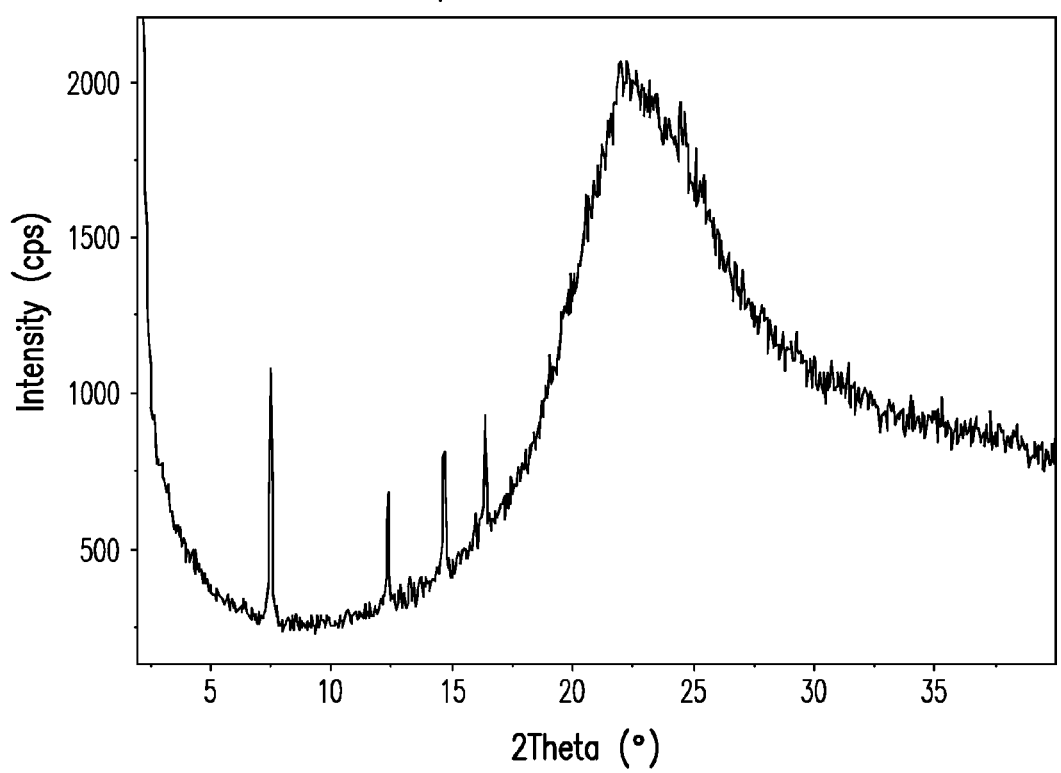
FIG. 48 shows a powder XRD pattern of crystalline dasatinib form AW
Figure 49:
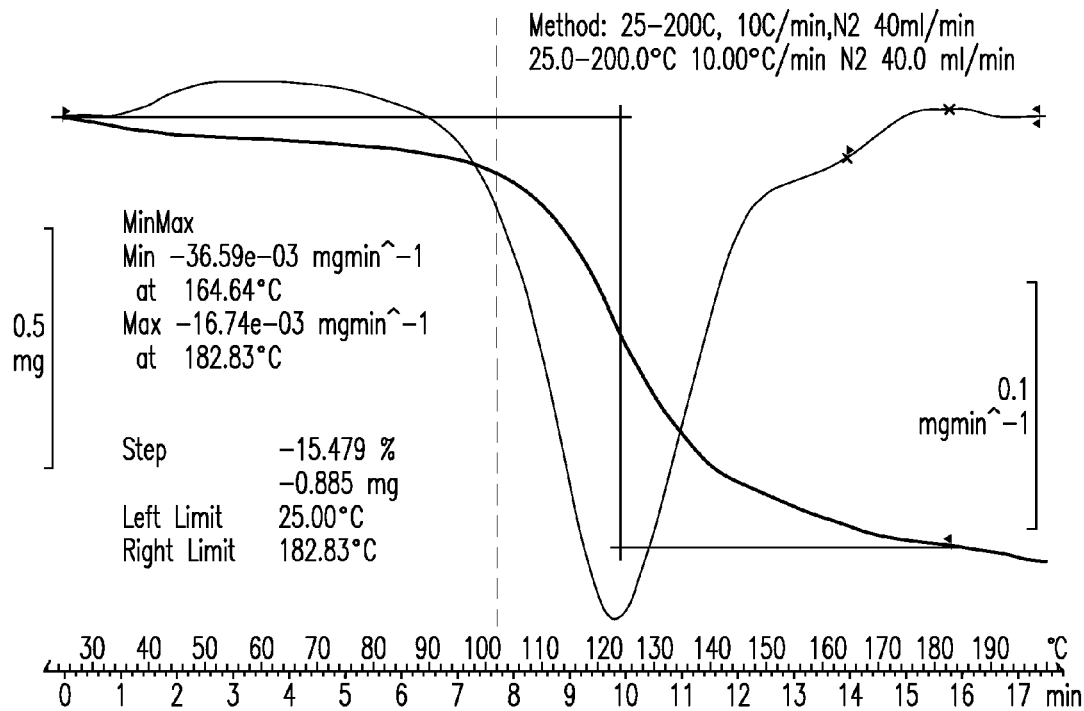
FIG. 49 shows a TGA thermogram of crystalline Dasatinib form AA
Figure 50:
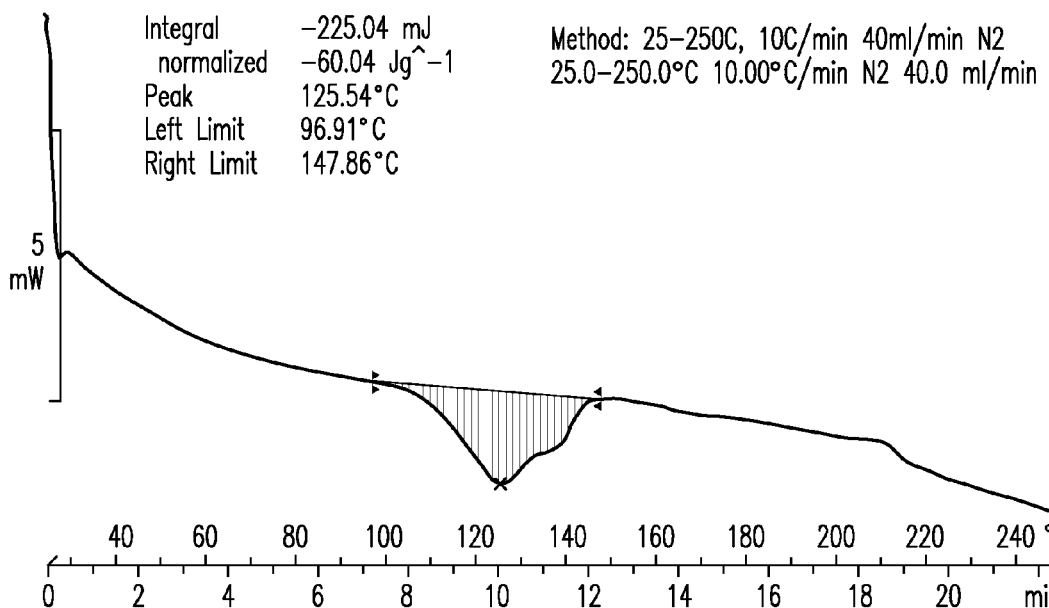
FIG. 50 shows a DSC thermogram of crystalline Dasatinib form AA
Figure 51:
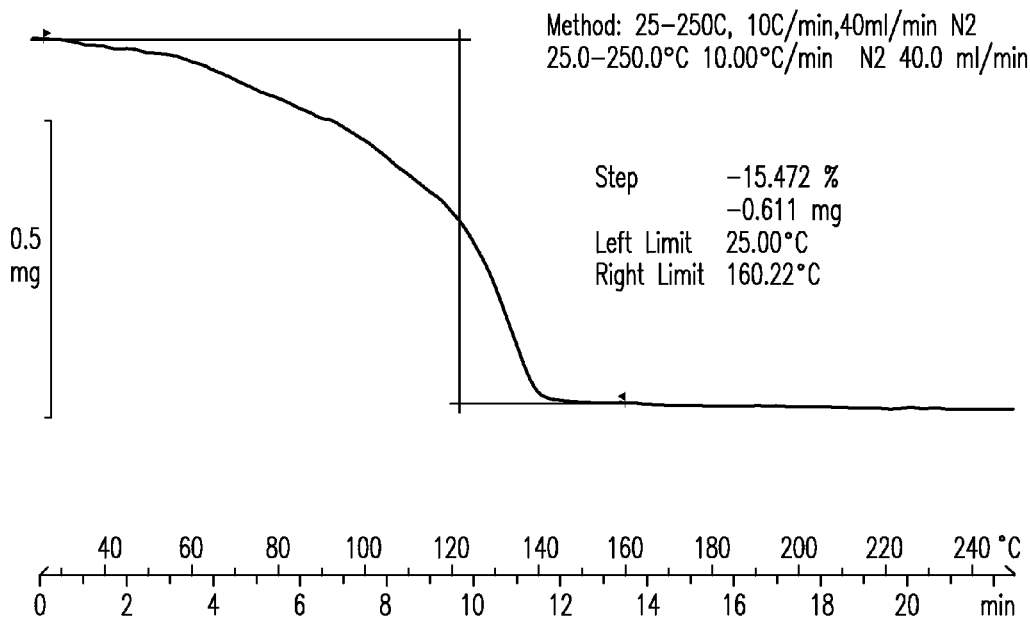
FIG. 51 shows a TGA thermogram of crystalline Dasatinib form AB
Figure 52:
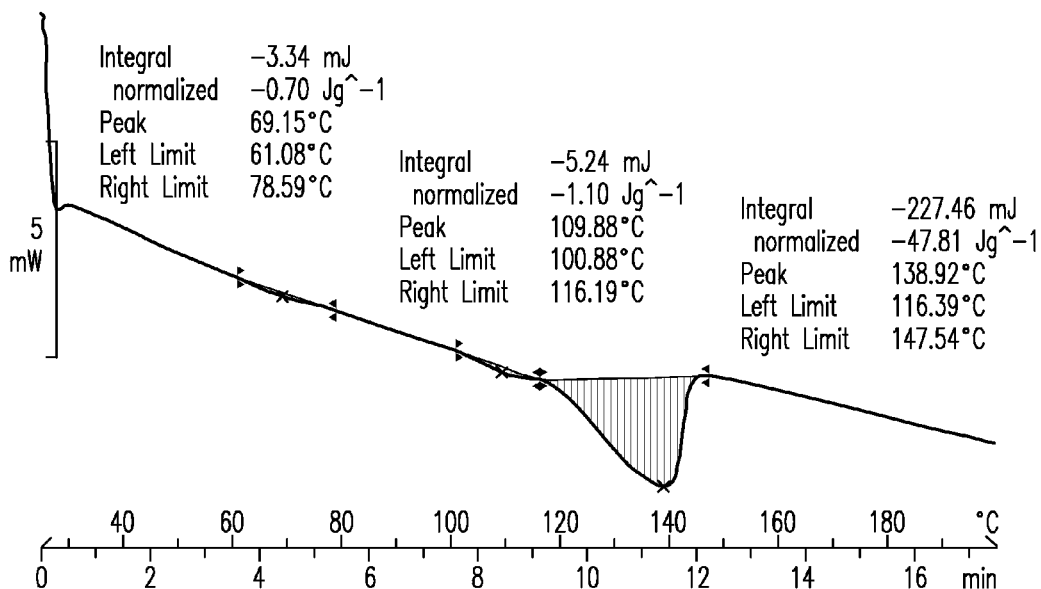
FIG. 52 shows a DSC thermogram of crystalline Dasatinib form AB
Figure 53:
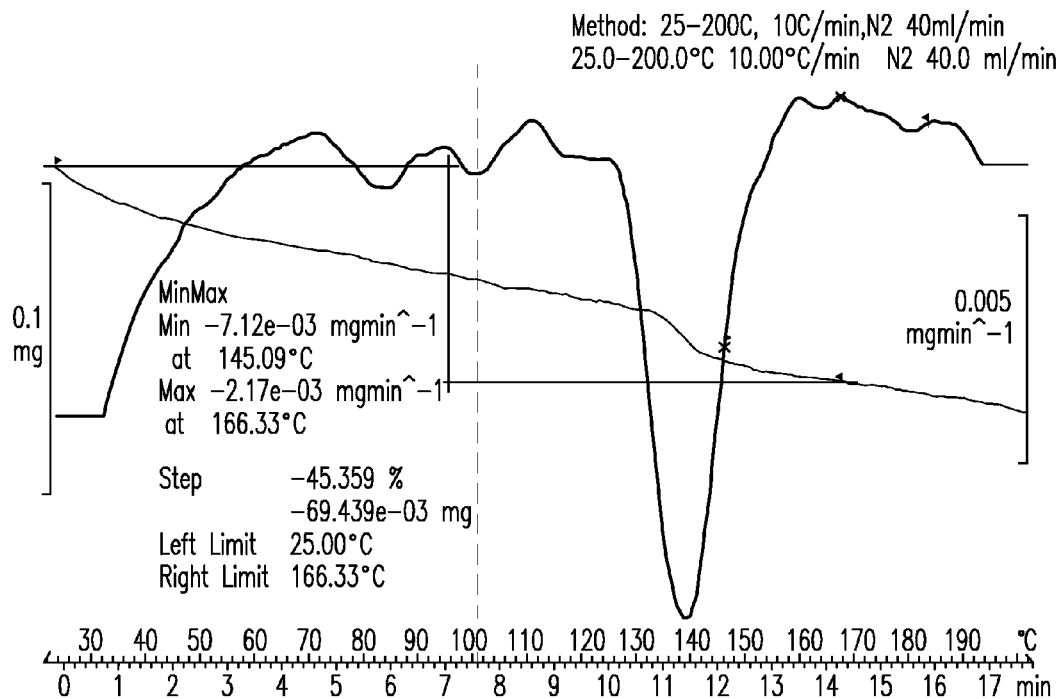
FIG. 53 shows a TGA thermogram of crystalline Dasatinib form AC
Figure 54:
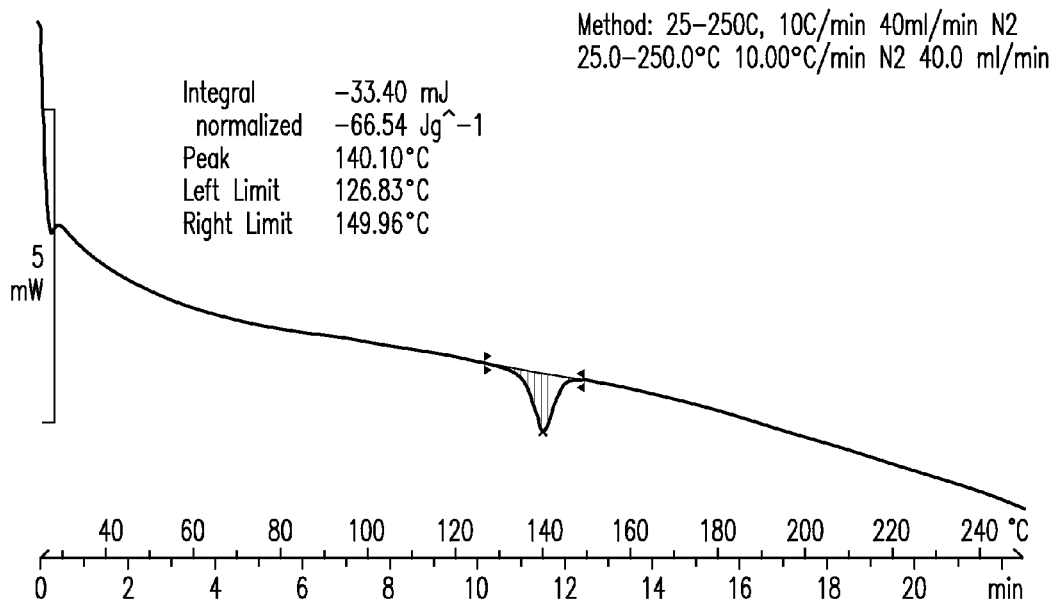
FIG. 54 shows a DSC thermogram of crystalline Dasatinib form AC
Figure 55:
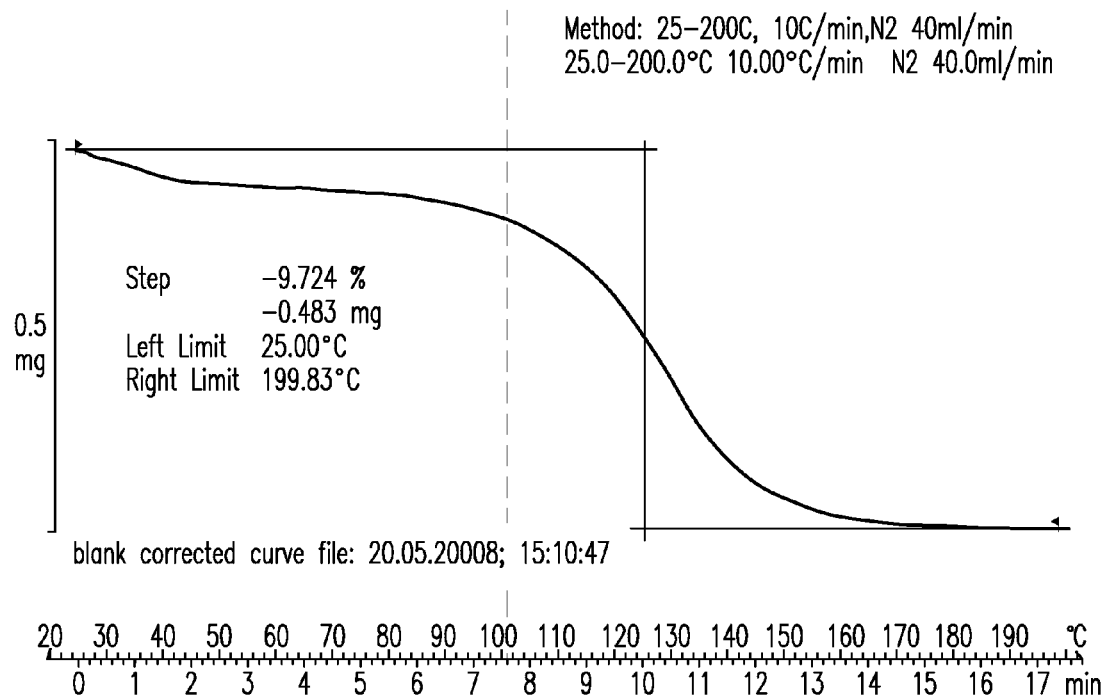
FIG. 55 shows a TGA thermogram of crystalline Dasatinib form AD
Figure 56:
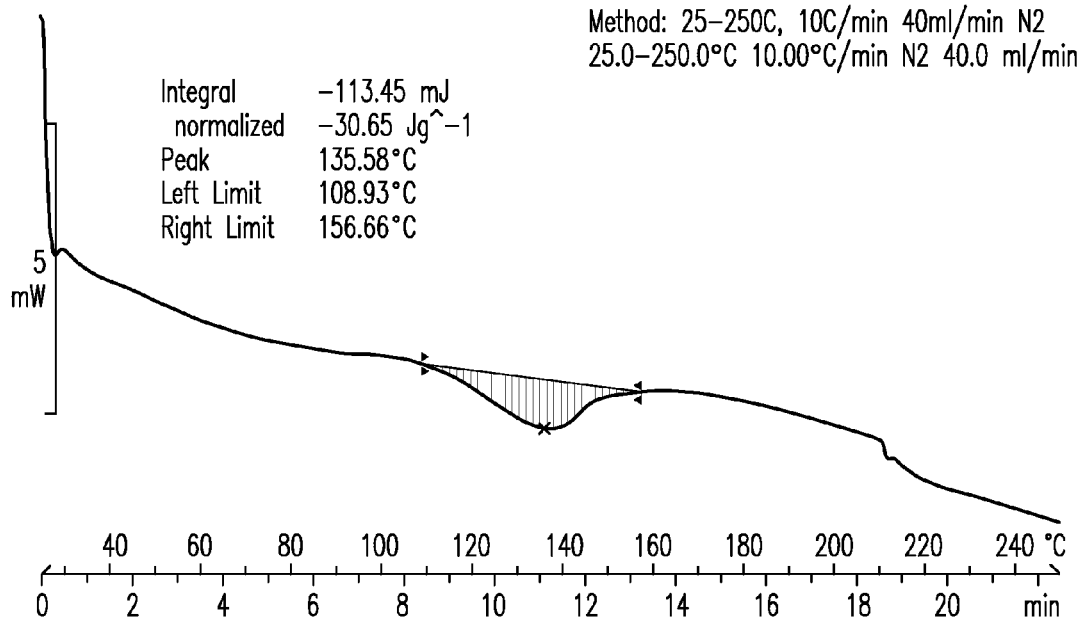
FIG. 56 shows a DSC thermogram of crystalline Dasatinib form AD
Figure 57:
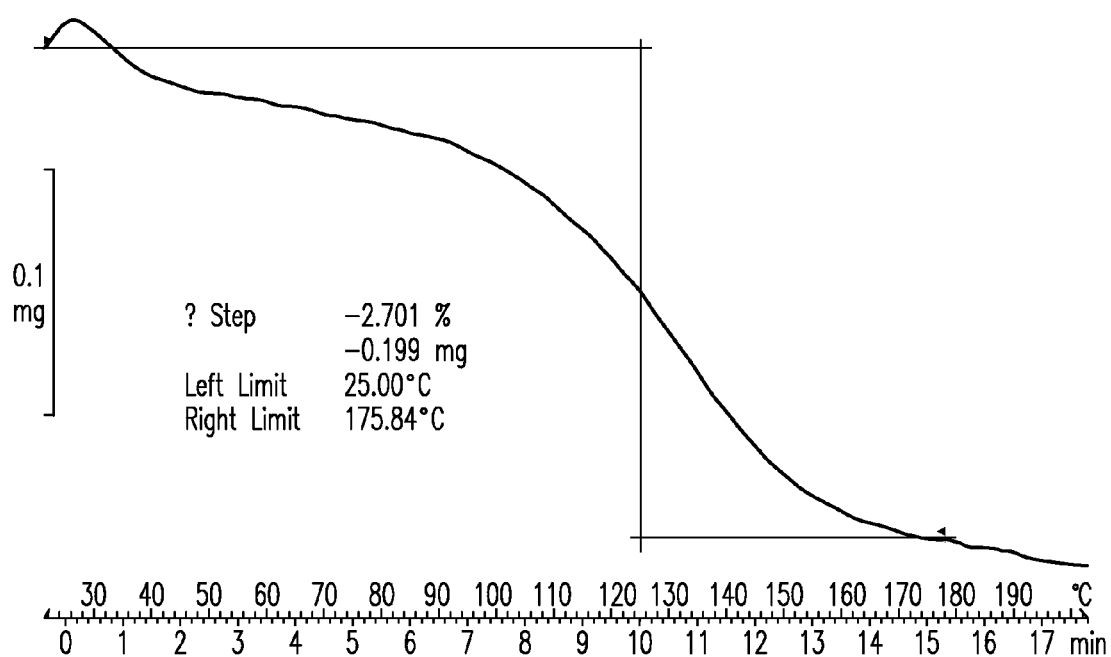
FIG. 57 shows a TGA thermogram of crystalline Dasatinib form AE
Figure 58:
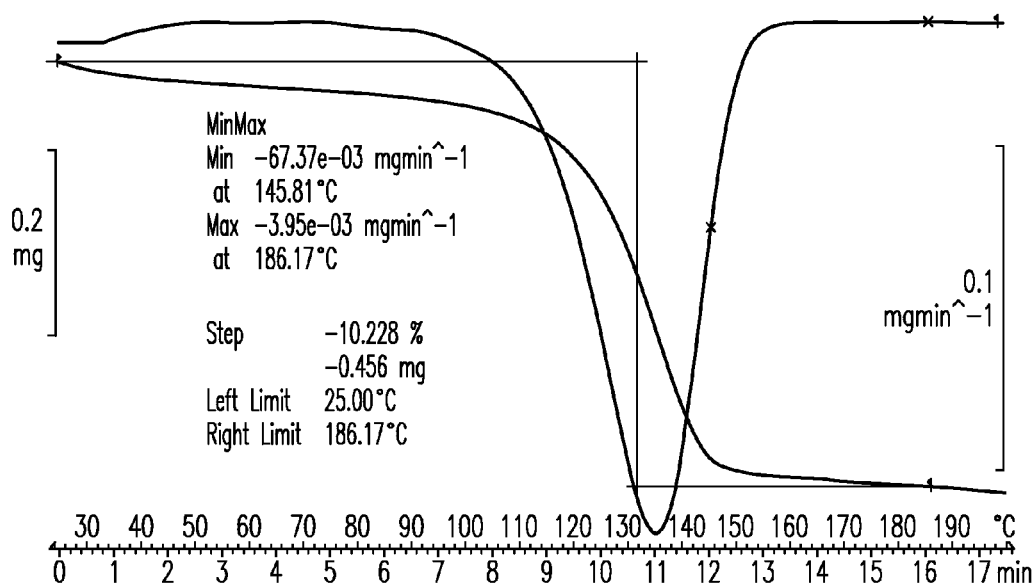
FIG. 58 shows a TGA thermogram of crystalline Dasatinib form AF
Figure 59:
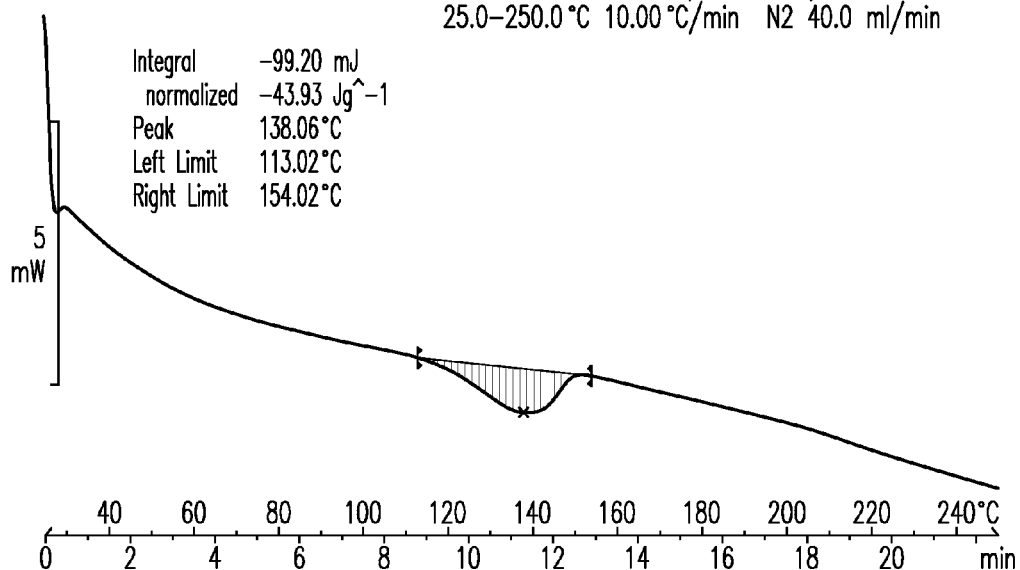
FIG. 59 shows a DSC thermogram of crystalline Dasatinib form AF
Figure 60:
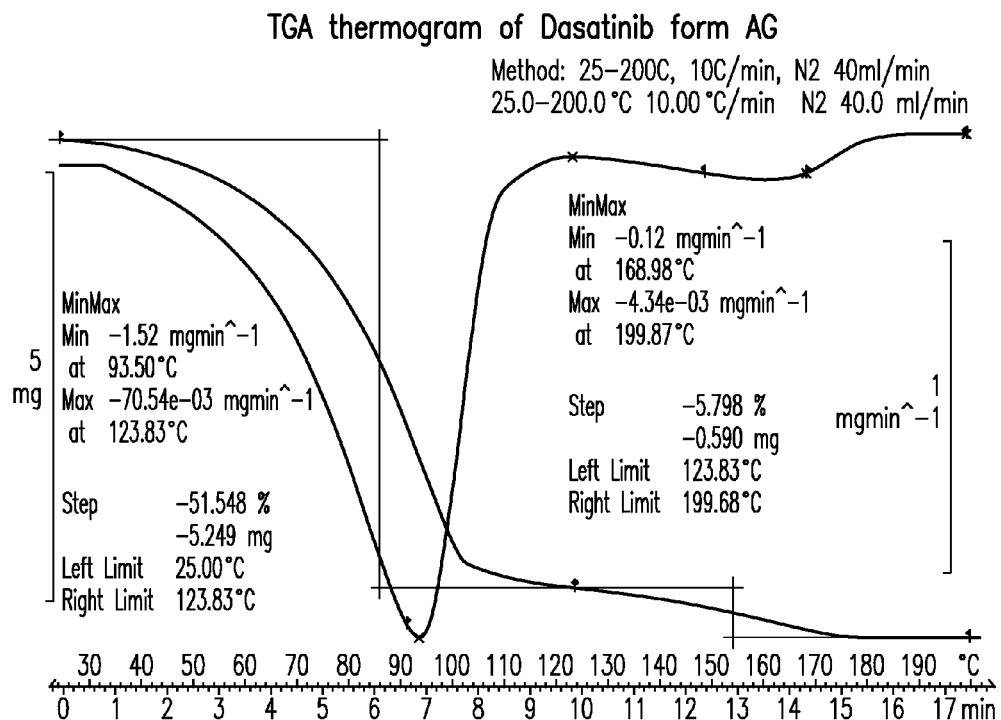
FIG. 60 shows a TGA thermogram of crystalline Dasatinib form AG
Figure 61:
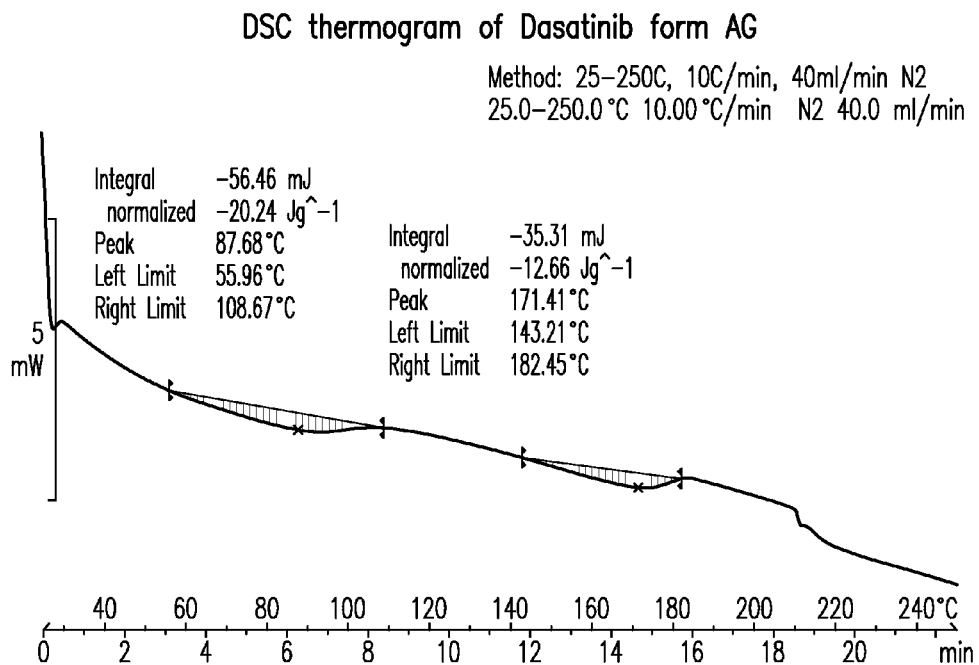
FIG. 61 shows a DSC thermogram of crystalline Dasatinib form AG
Figure 62:
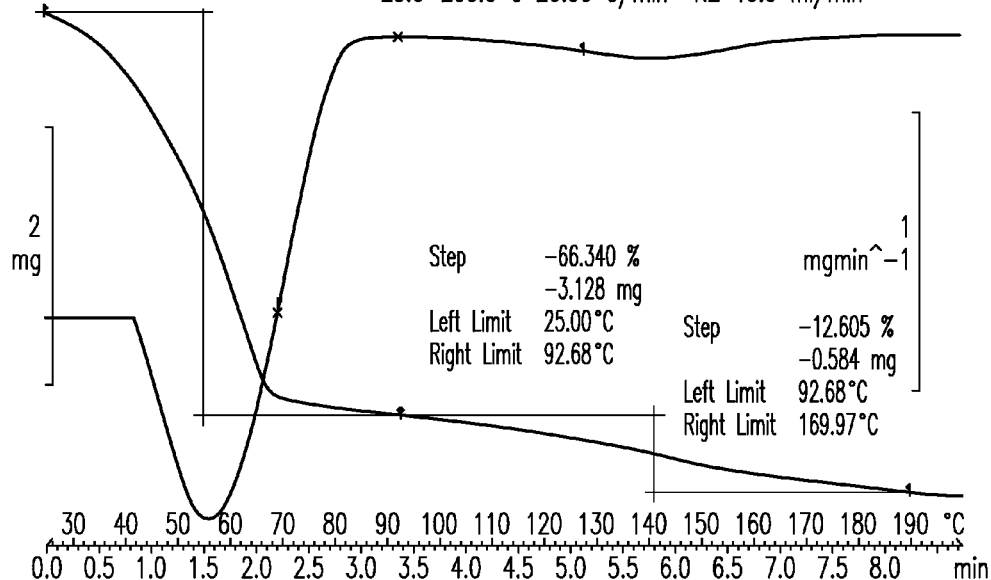
FIG. 62 shows a TGA thermogram of crystalline Dasatinib form AI
Figure 63:
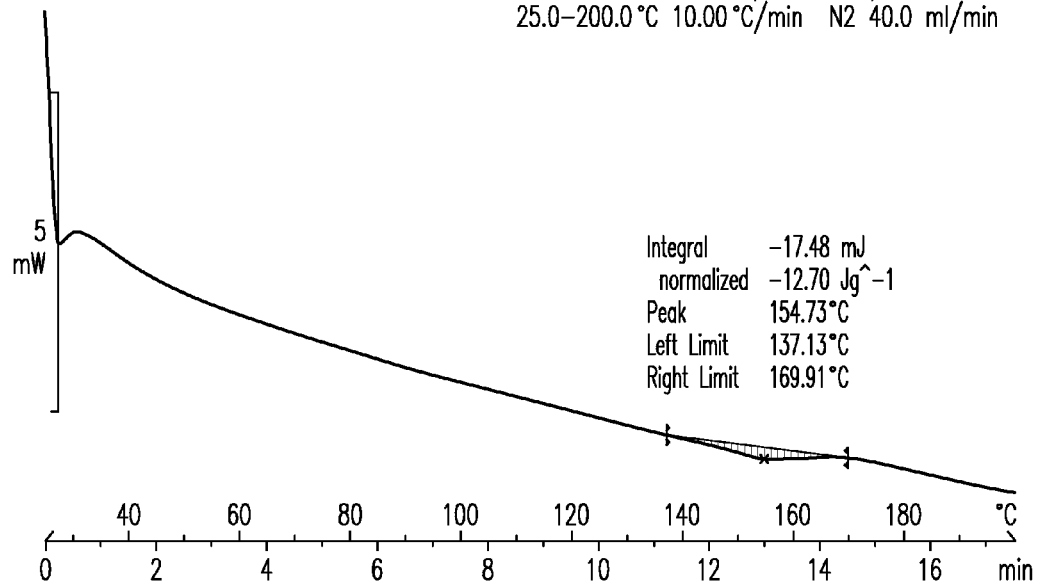
FIG. 63 shows a DSC thermogram of crystalline Dasatinib form AI
Figure 64:
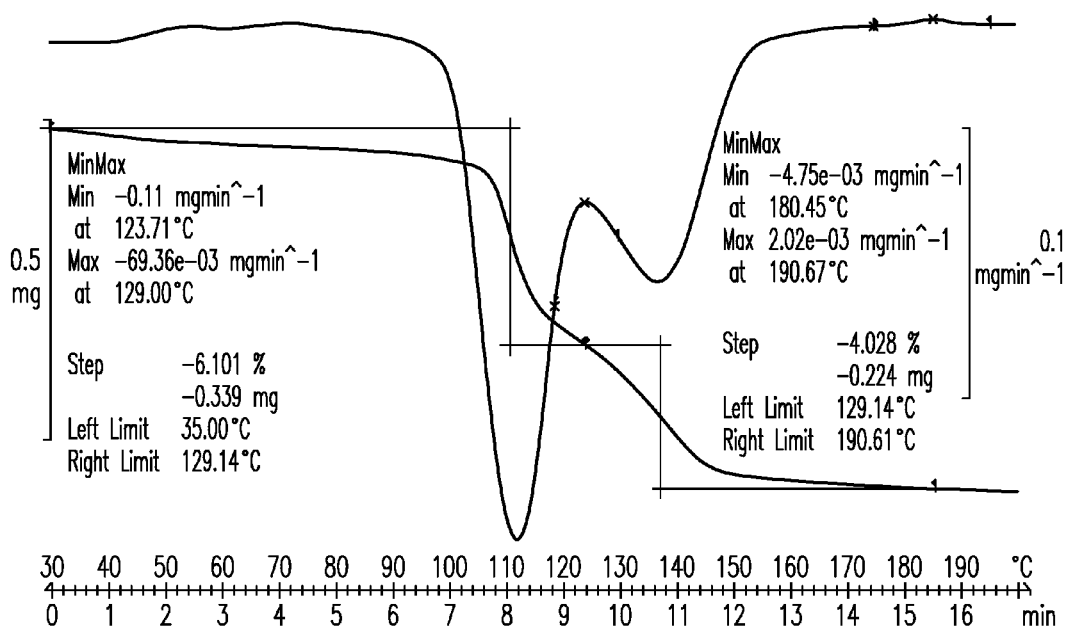
FIG. 64 shows a TGA thermogram of crystalline Dasatinib form AJ
Figure 65:
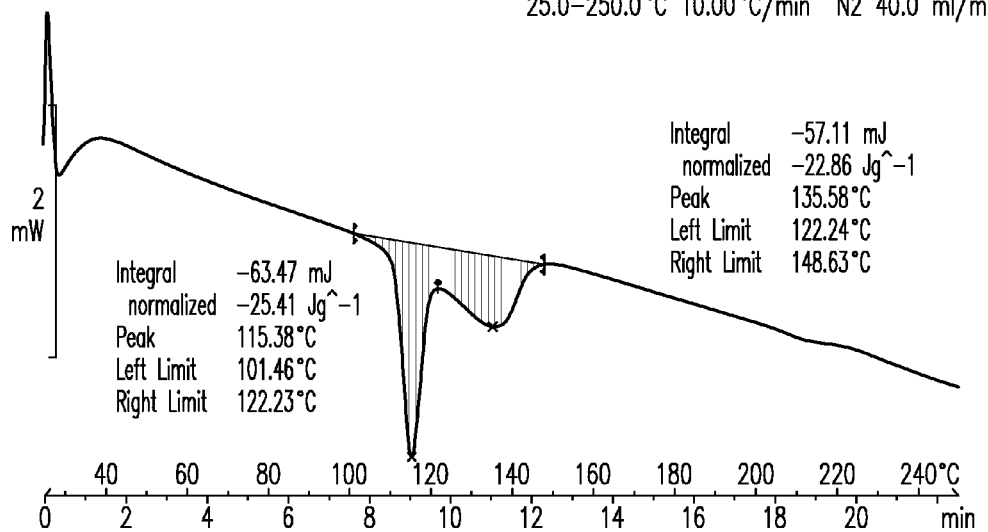
FIG. 65 shows a DSC thermogram of crystalline Dasatinib form AJ
Figure 66:
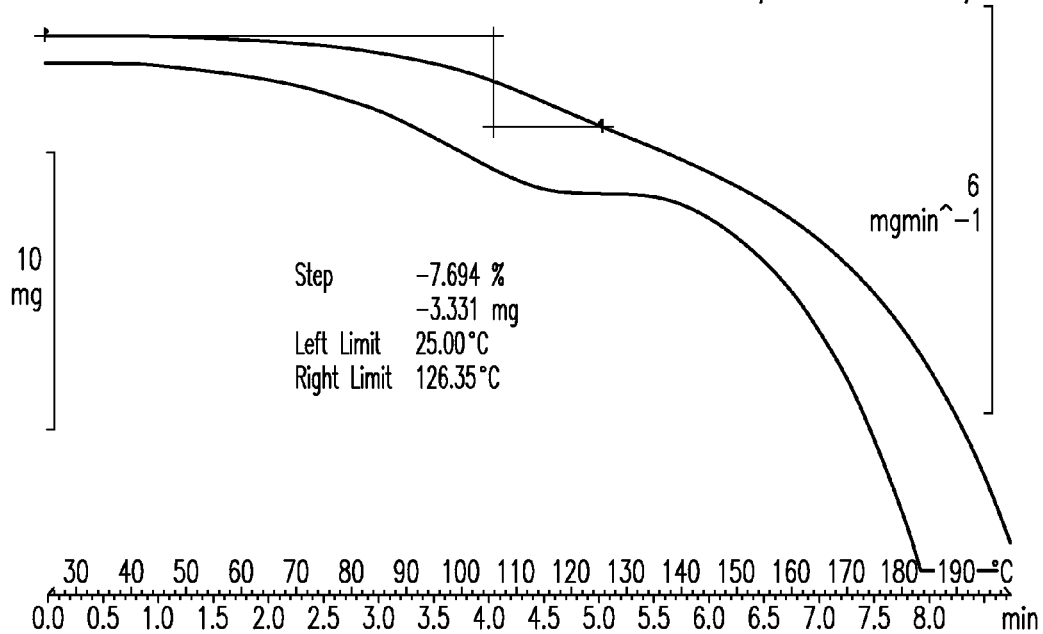
FIG. 66 shows a TGA thermogram of crystalline Dasatinib form AK
Figure 67:
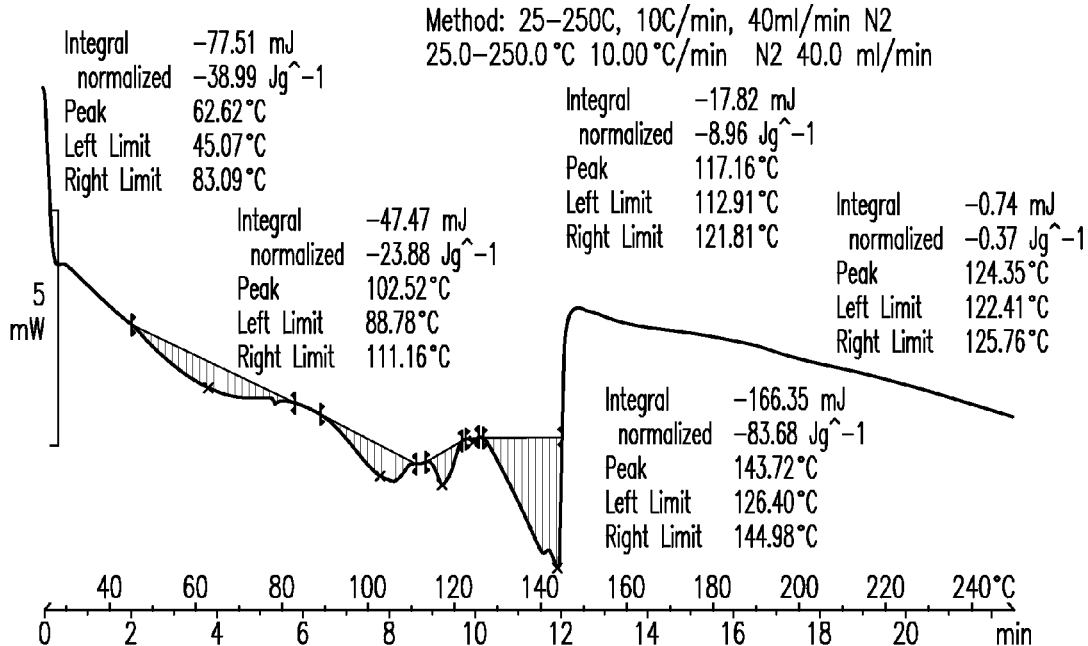
FIG. 67 shows a DSC thermogram of crystalline Dasatinib form AK
Figure 68:
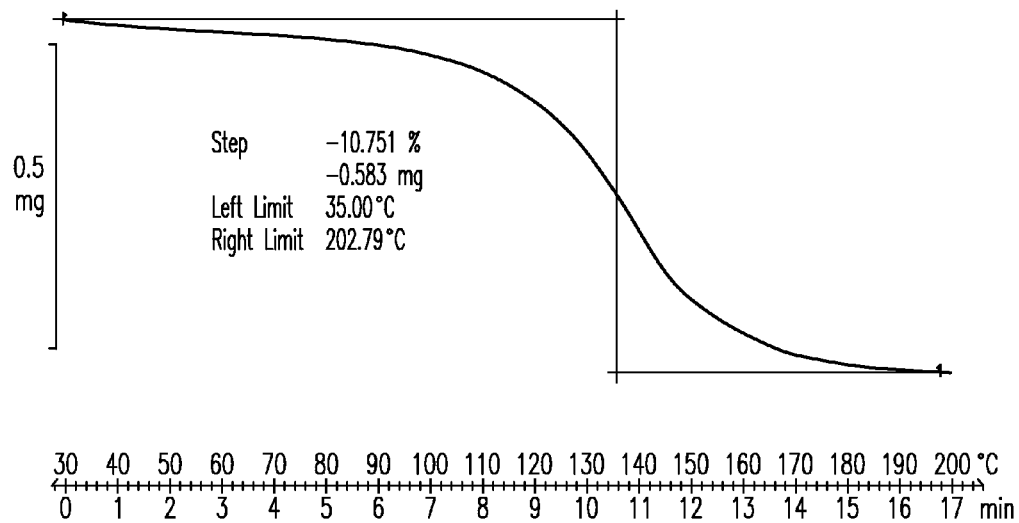
FIG. 68 shows a TGA thermogram of crystalline Dasatinib form AL
Figure 69:
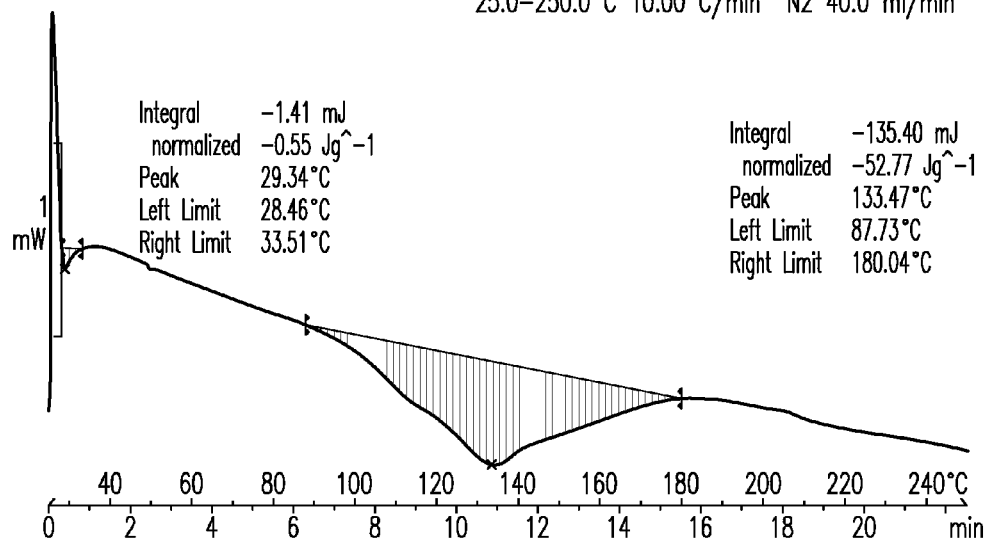
FIG. 69 shows a DSC thermogram of crystalline Dasatinib form AL
Figure 70:
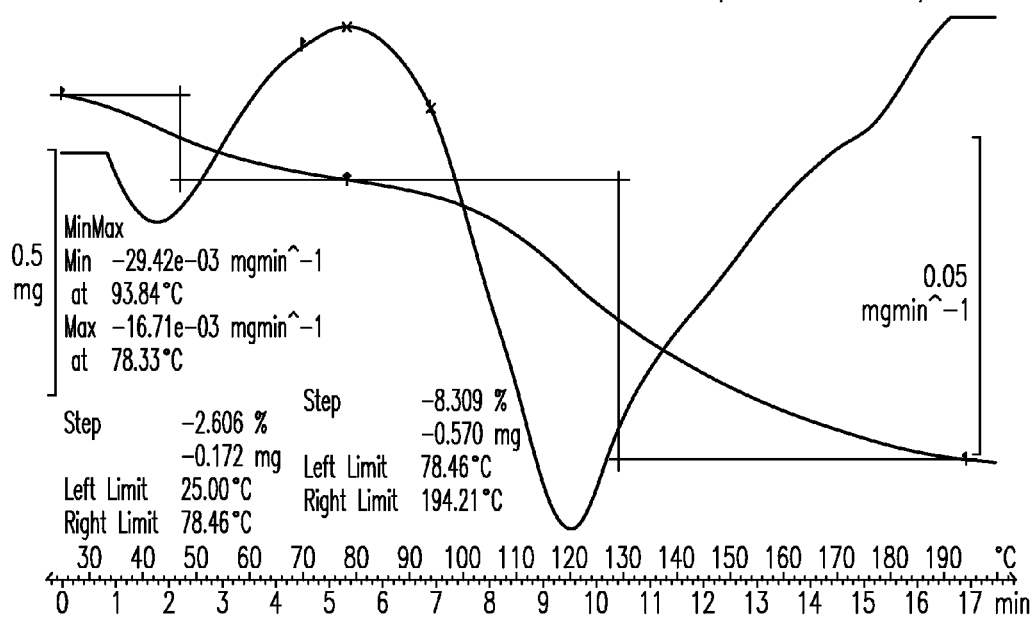
FIG. 70 shows a TGA thermogram of crystalline Dasatinib form AM
Figure 71:
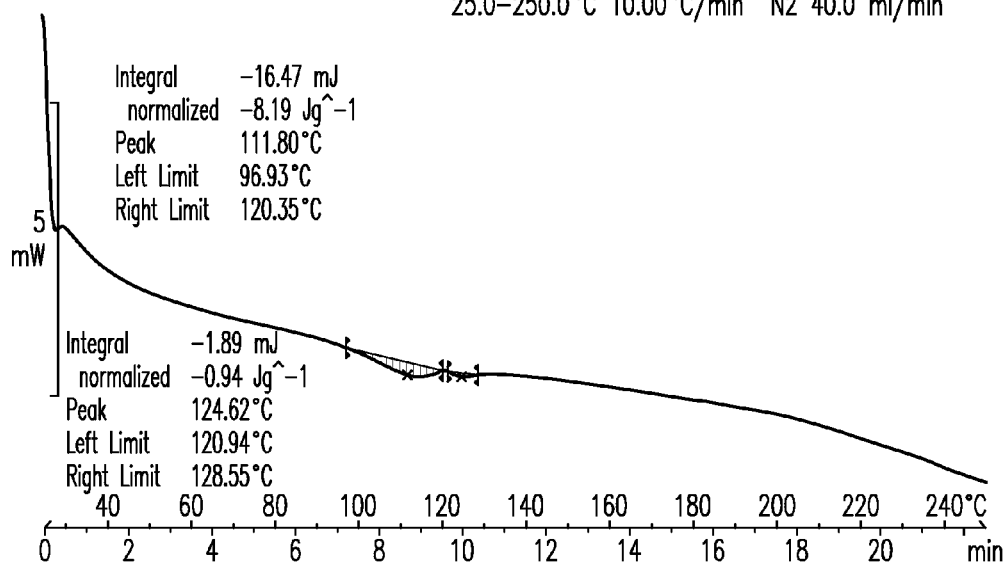
FIG. 71 shows a DSC thermogram of crystalline Dasatinib form AM
Figure 72:
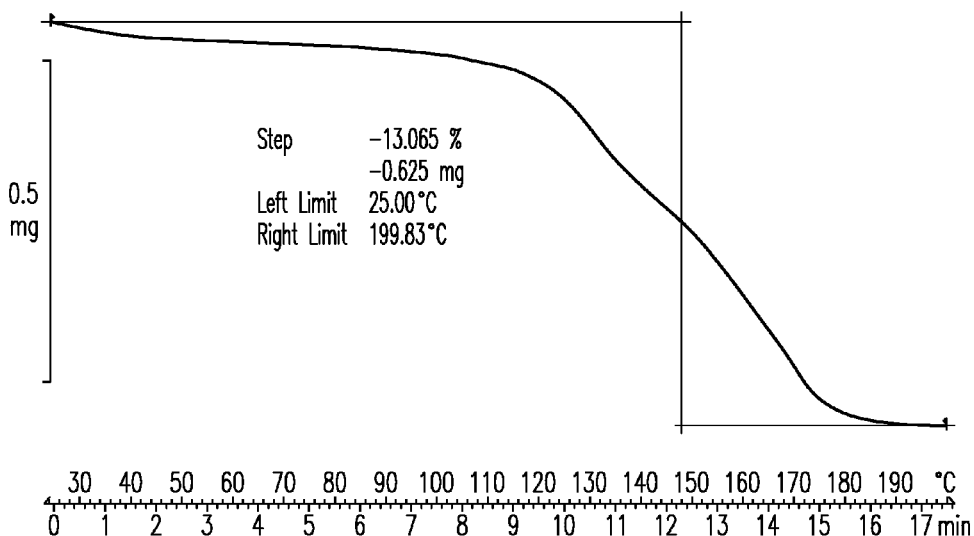
FIG. 72 shows a TGA thermogram of crystalline Dasatinib form AN
Figure 73:
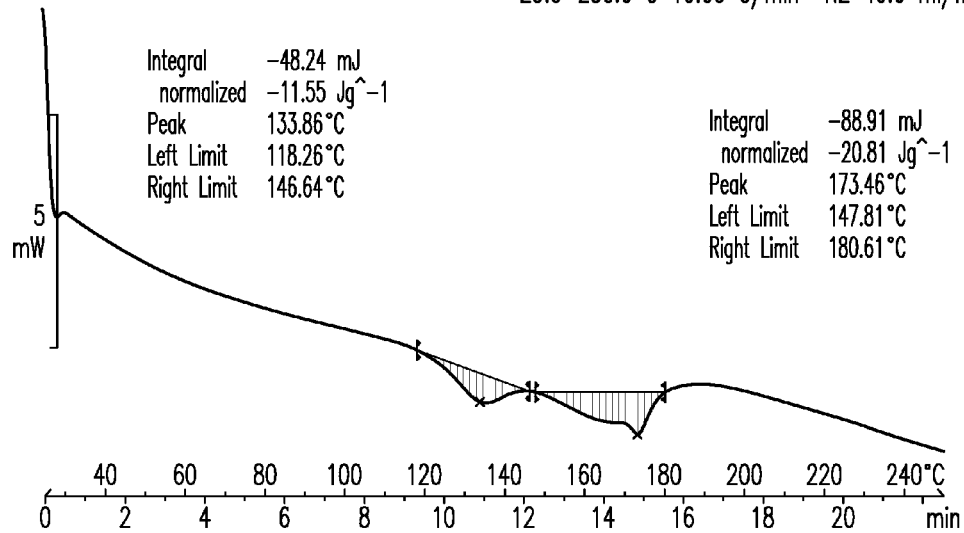
FIG. 73 shows a DSC thermogram of crystalline Dasatinib form AN
Figure 74:
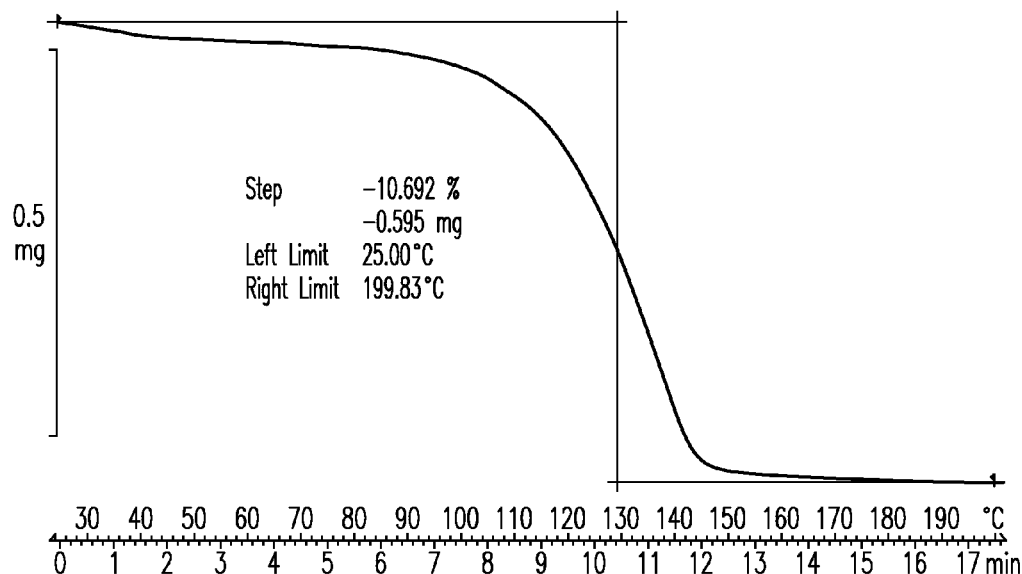
FIG. 74 shows a TGA thermogram of crystalline Dasatinib form AP
Figure 75:
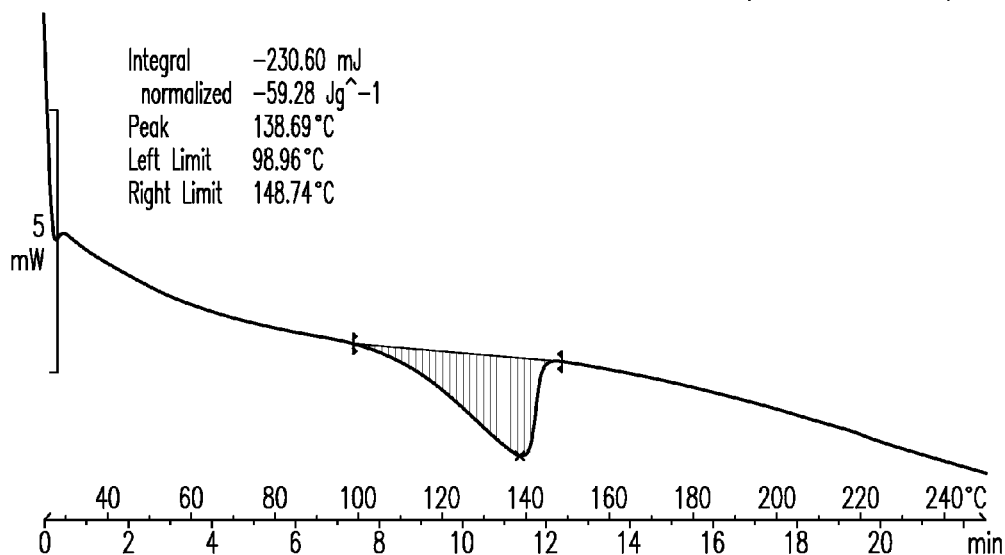
FIG. 75 shows a DSC thermogram of crystalline Dasatinib form AP
Figure 76:
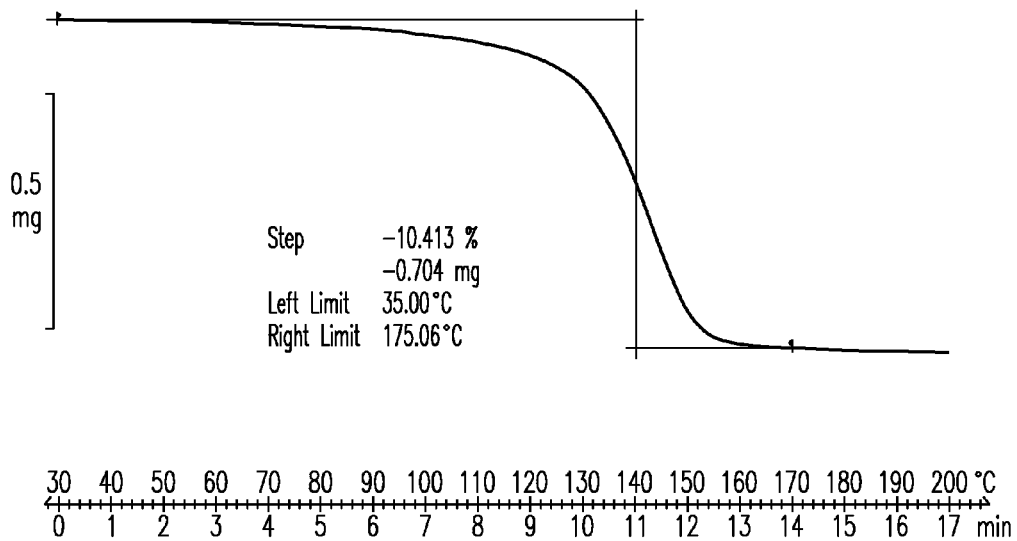
FIG. 76 shows a TGA thermogram of crystalline Dasatinib form AQ
Figure 77:
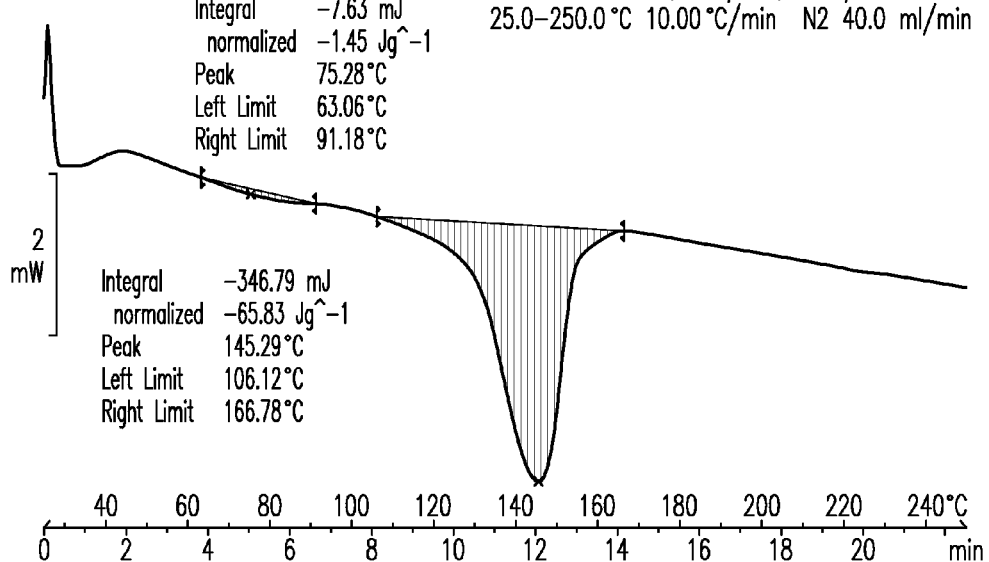
FIG. 77 shows a DSC thermogram of crystalline Dasatinib form AQ
Figure 78:
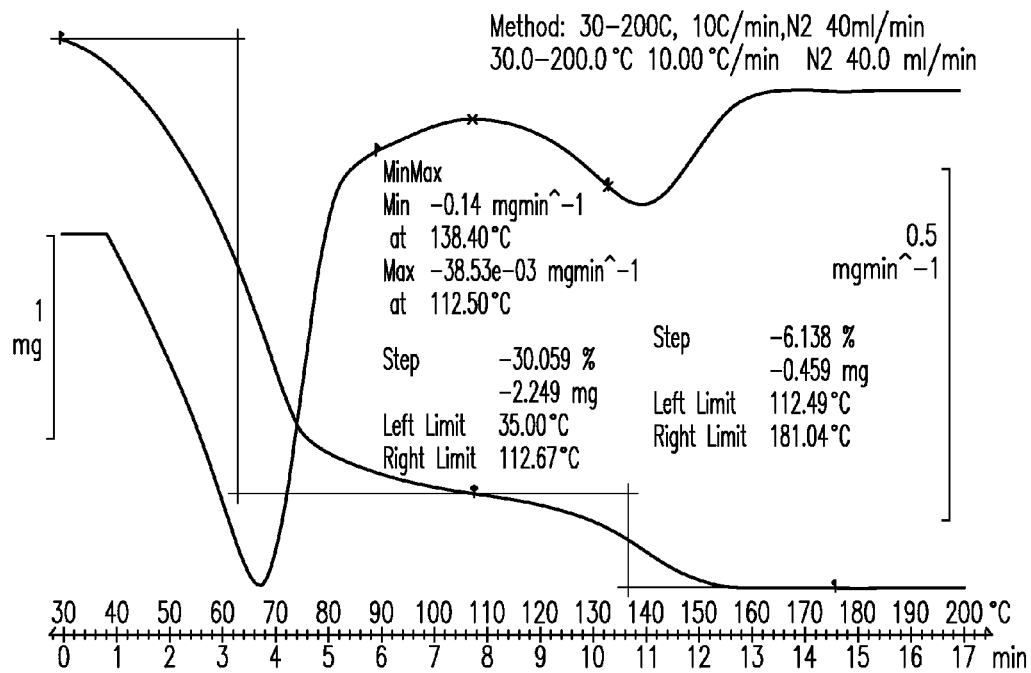
FIG. 78 shows a TGA thermogram of crystalline Dasatinib form AR
Figure 79:
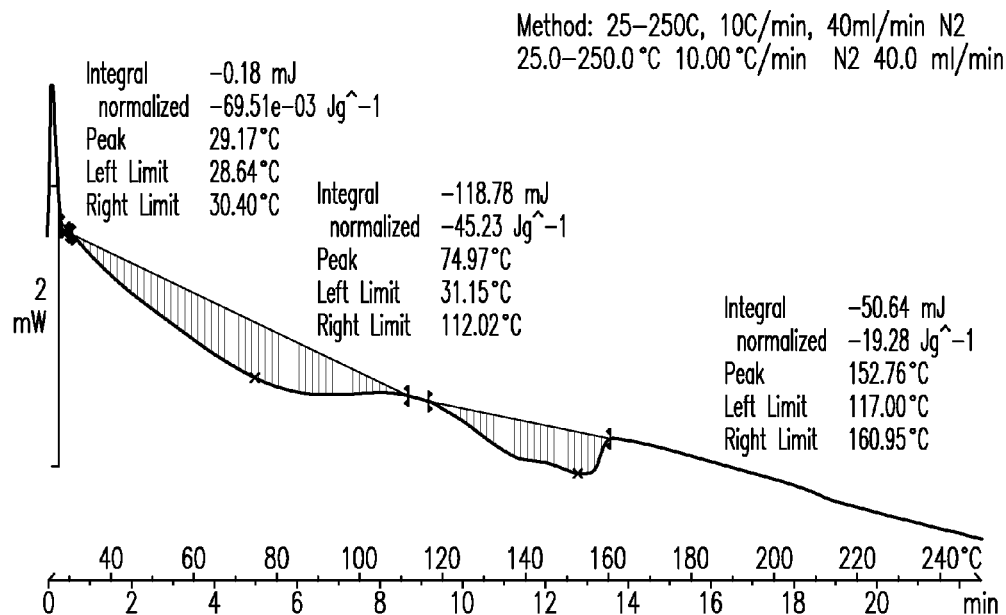
FIG. 79 shows a DSC thermogram of crystalline Dasatinib form AR
Figure 80:
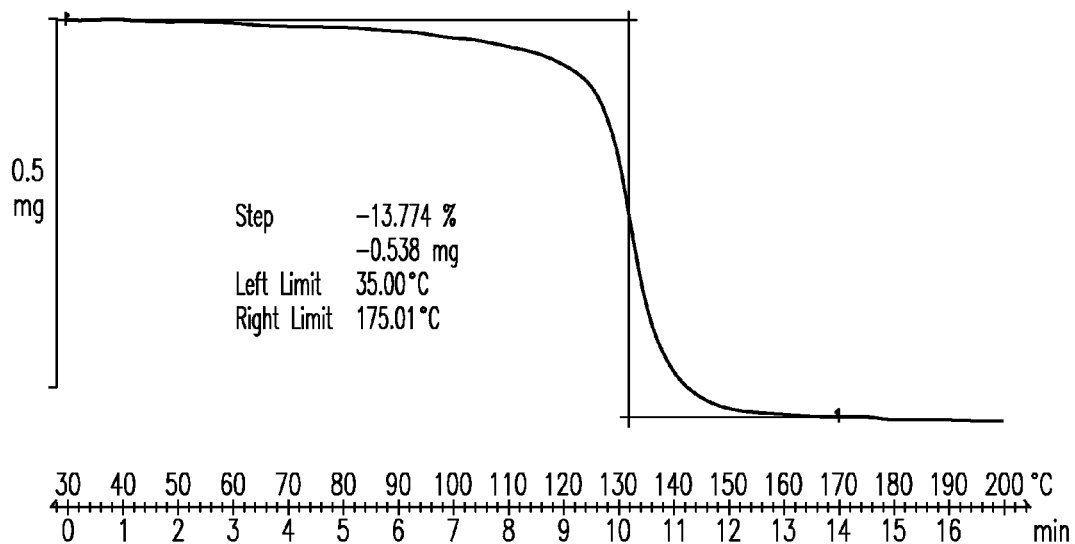
Figure 81:
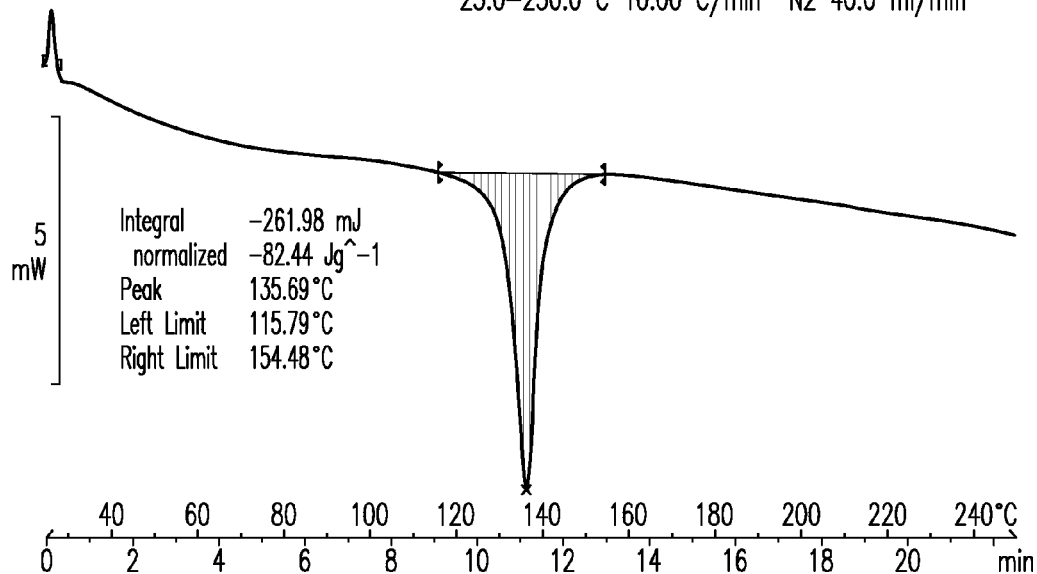
Figure 82:
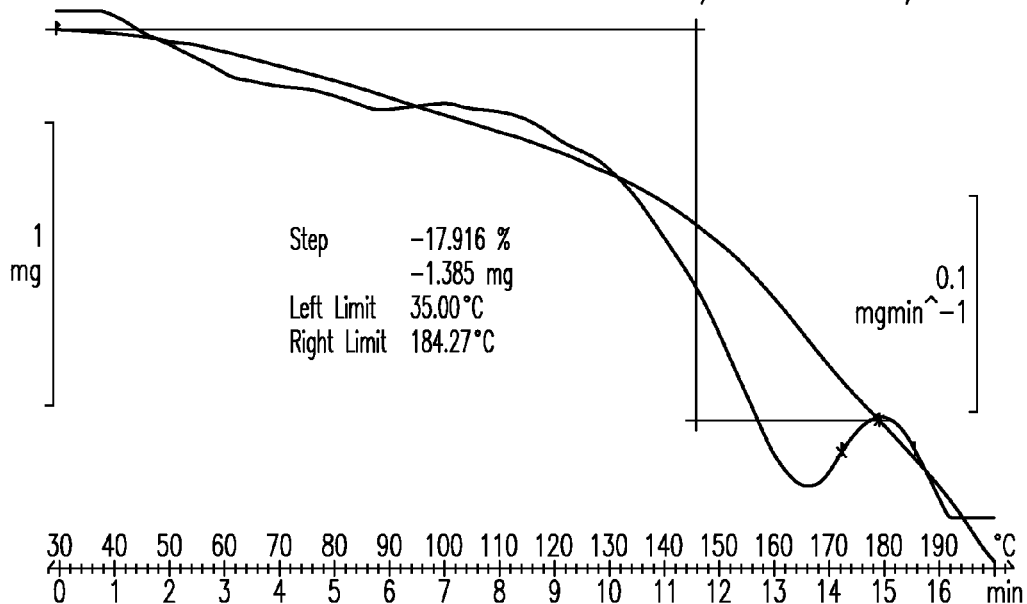
Figure 83:
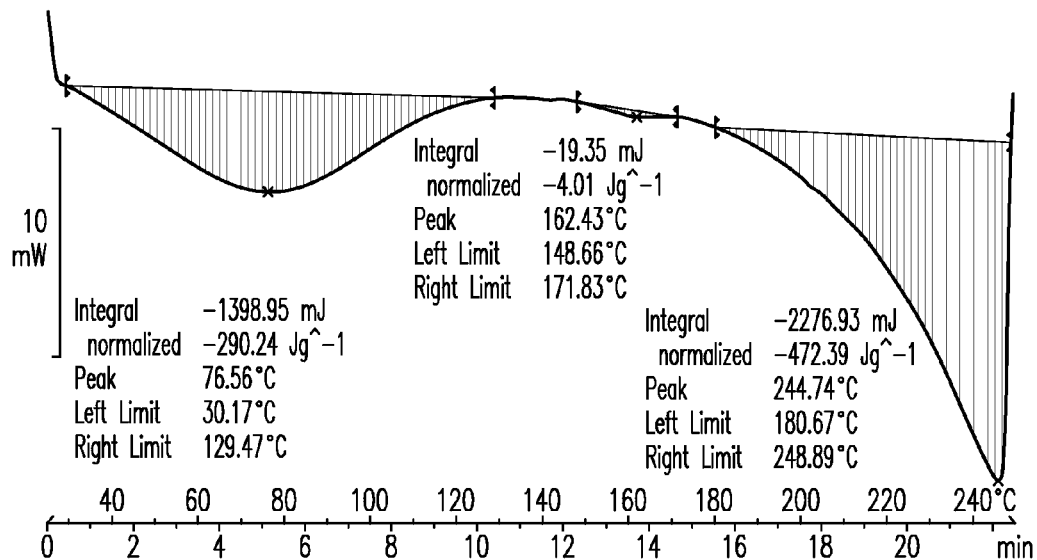
Figure 84:
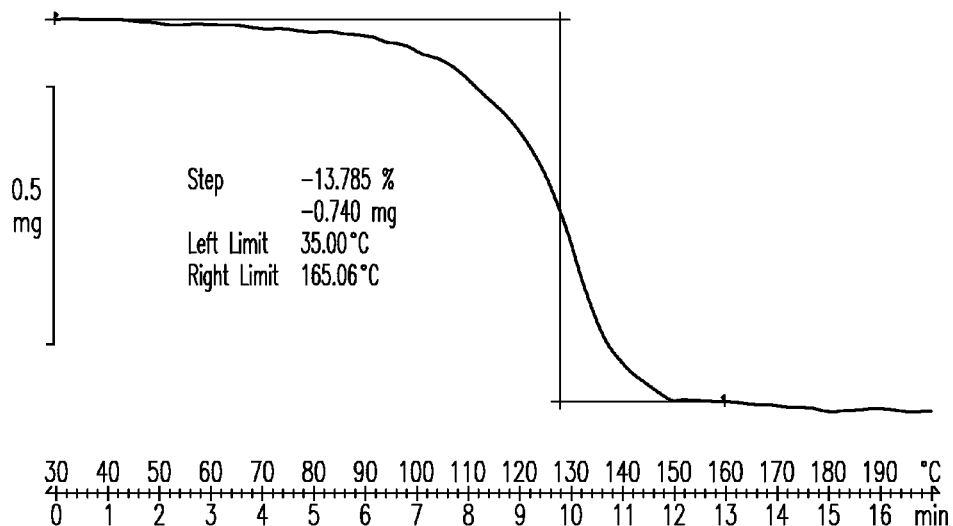
FIG. 84 shows a TGA thermogram of crystalline Dasatinib form AU
Figure 85:
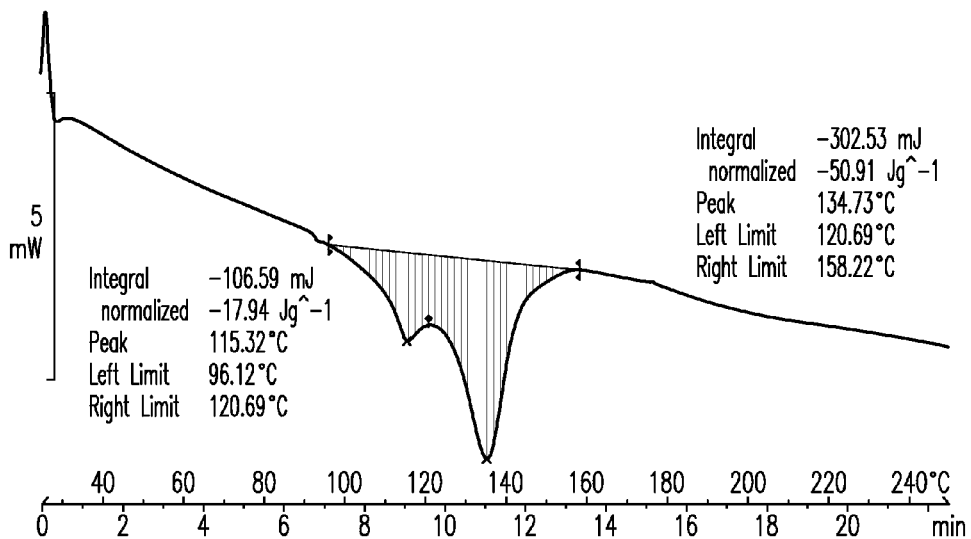
FIG. 85 shows a DSC thermogram of crystalline Dasatinib form AU
Figure 86:
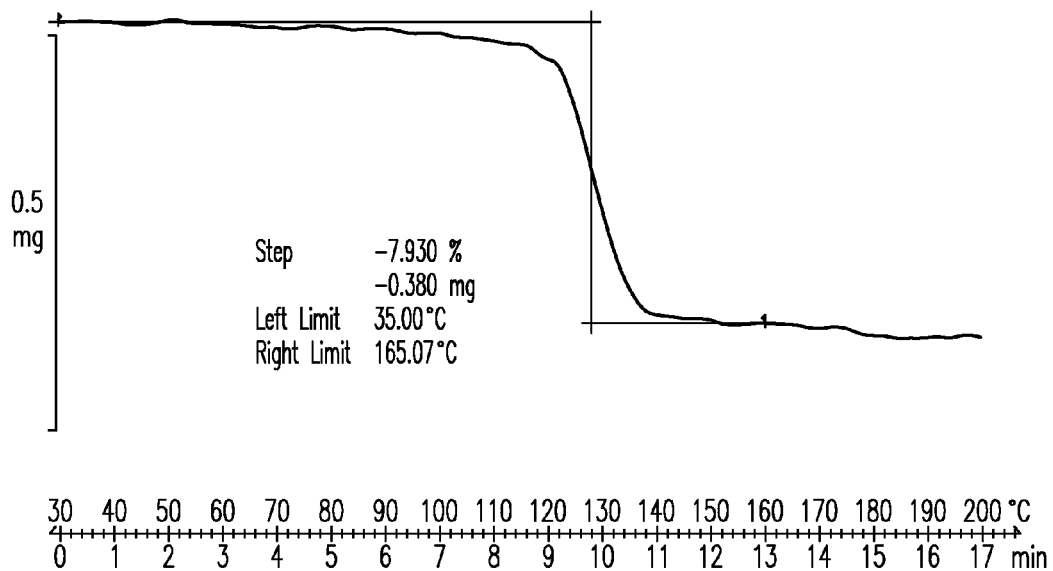
FIG. 86 shows a TGA thermogram of crystalline Dasatinib form AV
Figure 87:
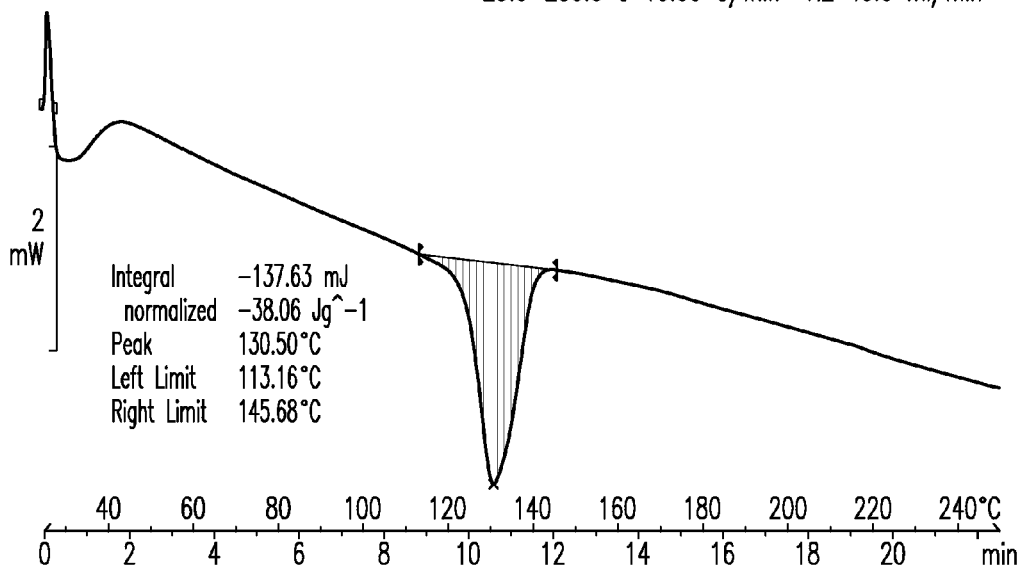
FIG. 87 shows a DSC thermogram of crystalline Dasatinib form AV
Figure 88:
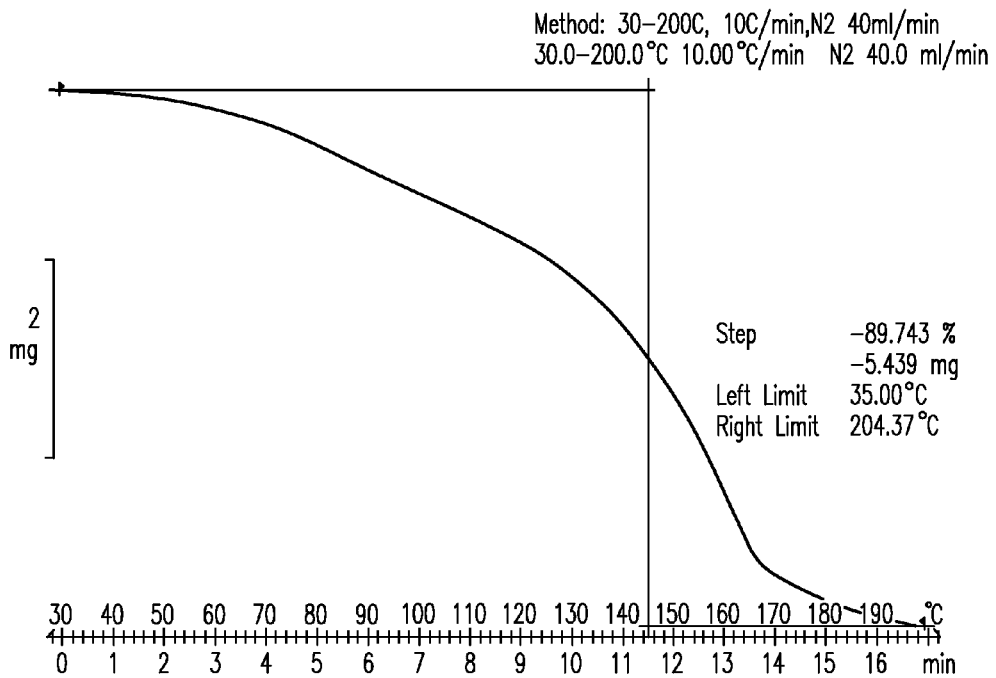
FIG. 88 shows a TGA thermogram of crystalline Dasatinib form AW
Figure 89:
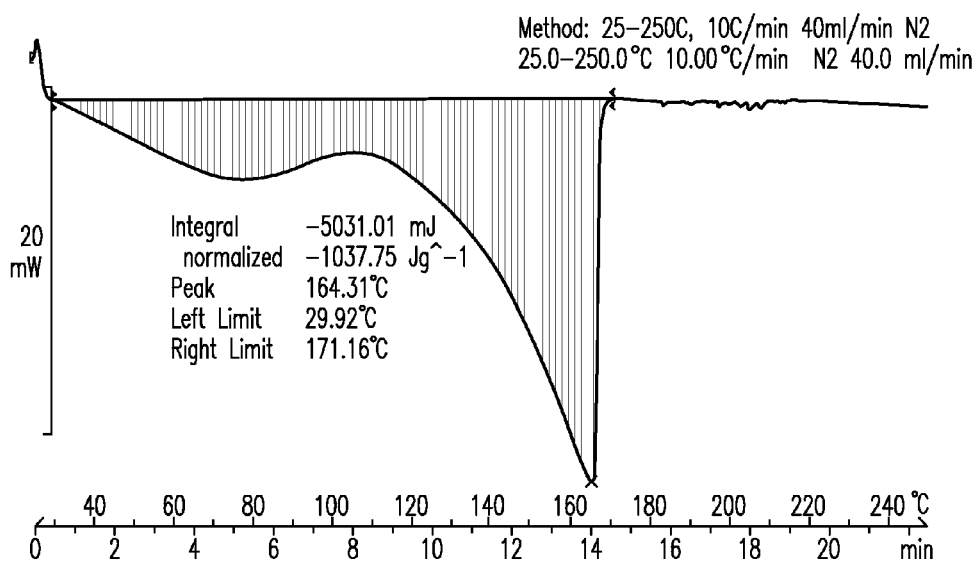
FIG. 89 shows a DSC thermogram of crystalline Dasatinib form AW
Figure 90:
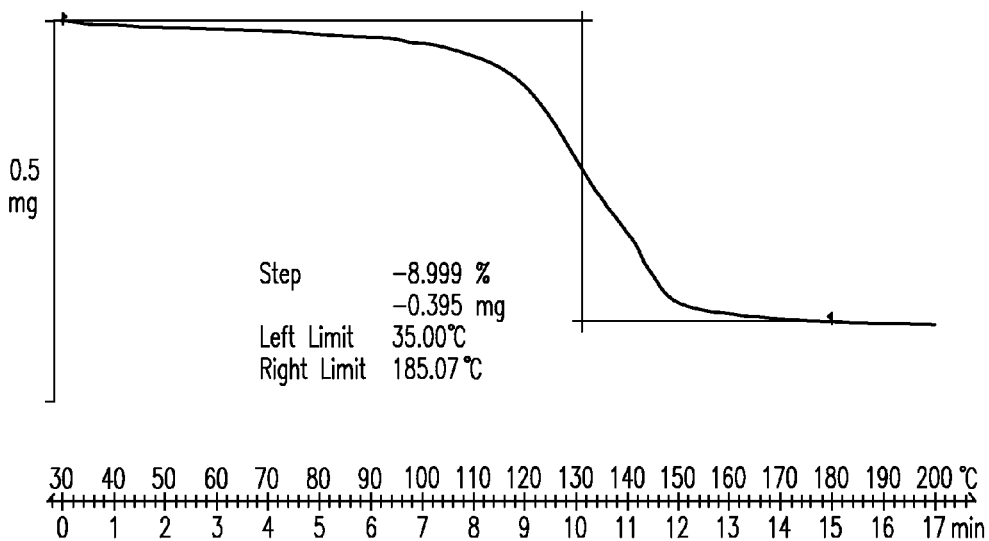
FIG. 90 shows a TGA thermogram of crystalline Dasatinib form AY
Figure 91:
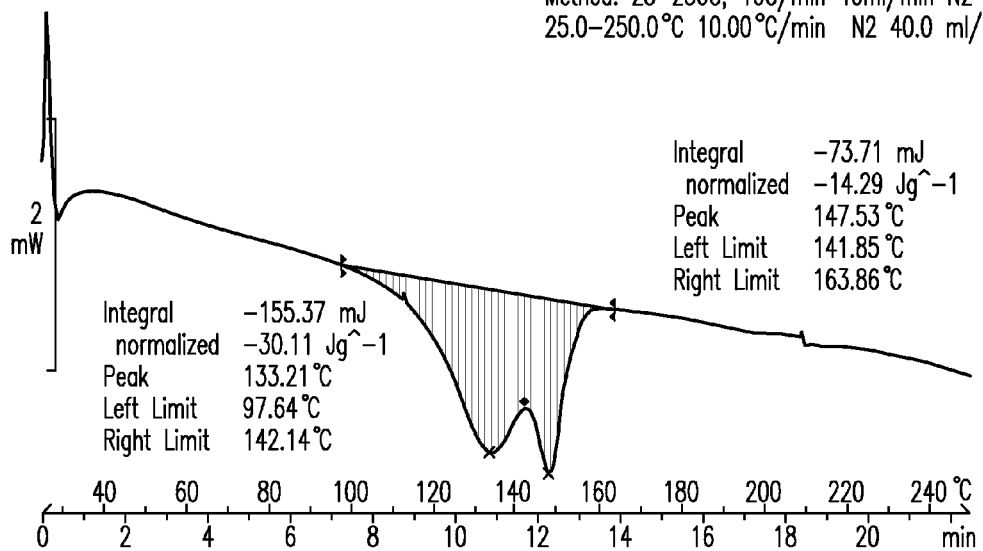
FIG. 91 shows a DSC thermogram of crystalline Dasatinib form AY
Figure 92:
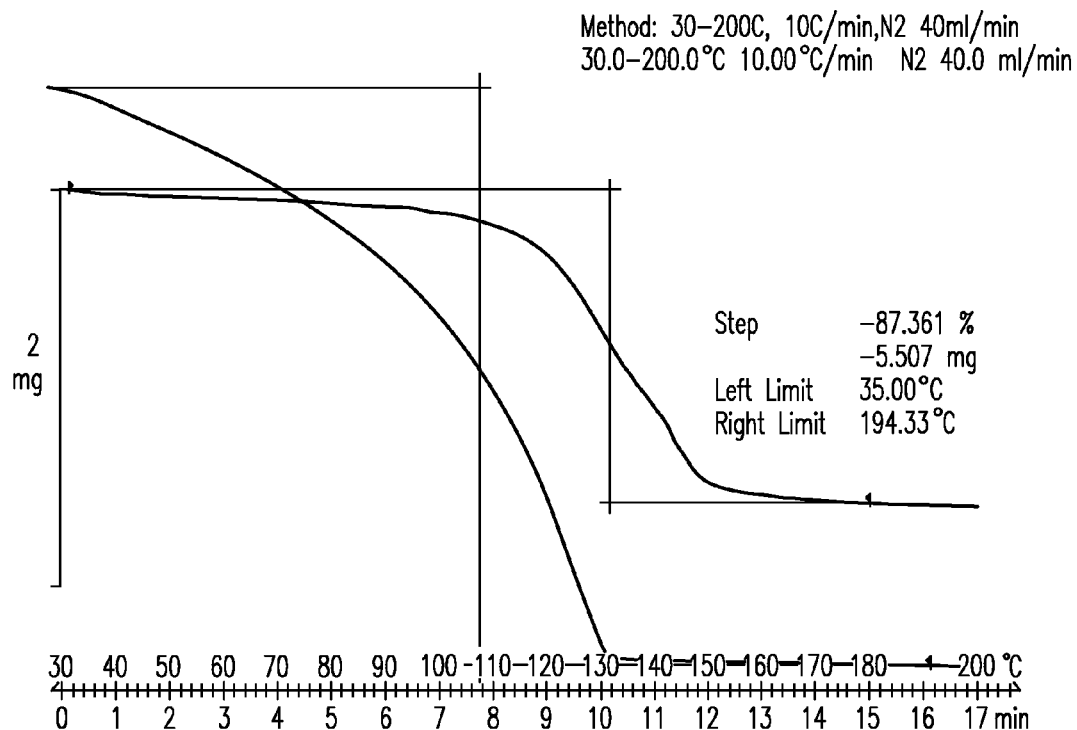
FIG. 92 shows a TGA thermogram of crystalline Dasatinib amorphous
Figure 93:
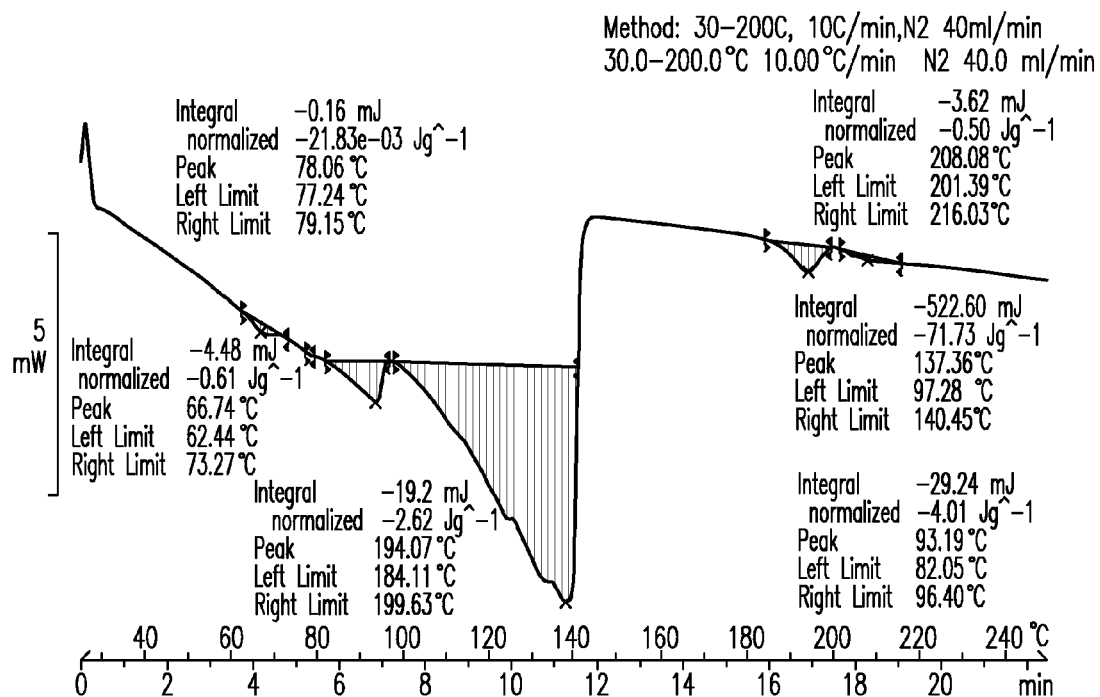
FIG. 93 shows a DSC thermogram of crystalline Dasatinib amorphous
Figure 94:
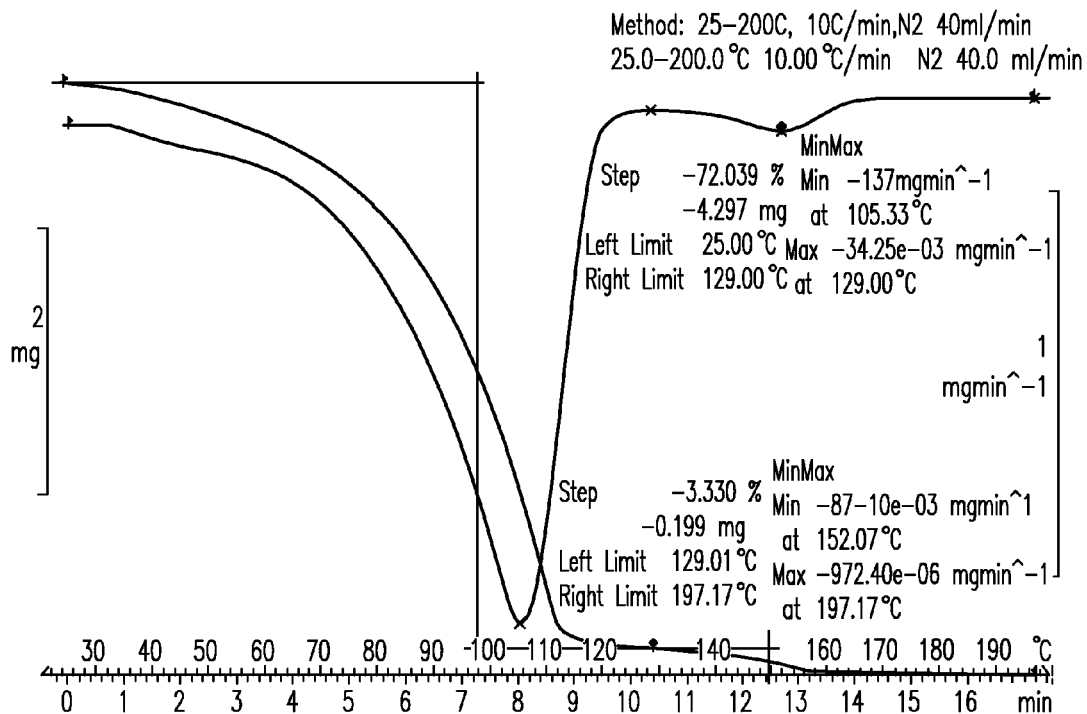
FIG. 94 shows a TGA thermogram of crystalline Dasatinib form AH
Figure 95:
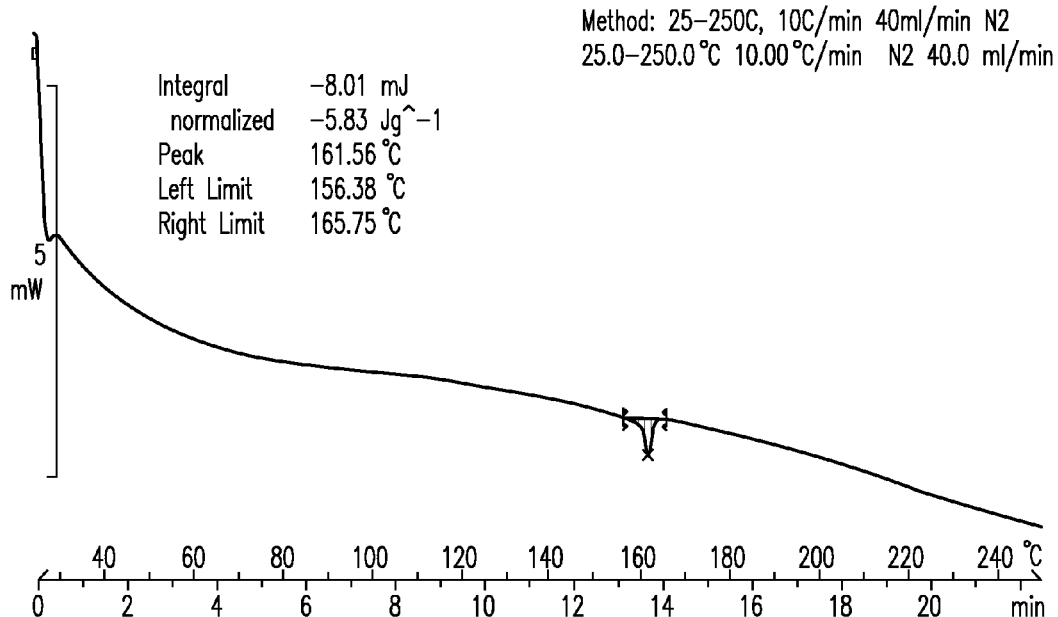
FIG. 95 shows a TGA thermogram of crystalline Dasatinib form AH

In one embodiment, the present invention encompasses an ethylene glycol solvate of dasatinib characterized by data selected from the group consisting of: a PXRD pattern having any 3 peaks selected from the list consisting of: 7.5, 12.3, 14.7 and 16.4±0.2 degrees 2-theta, a powder XRD pattern as depicted in FIG. 48, and a combination thereof. This form can be designated as form AW.

In a preferred embodiment, the present invention encompasses an ethylene glycol solvate of dasatinib characterized by a PXRD pattern having peaks at about 7.5, 12.3, 14.7 and 16.4±0.2 degrees 2-theta.

The above ethylene glycol solvate of dasatinib designated Form AW can be further characterized by data selected from the group consisting of: a powder XRD pattern with peaks at about 7.5, 12.3 and 16.4±0.2 degrees 2-theta; a powder XRD pattern with peaks at about 7.5, 14.7 and 16.4±0.2 degrees 2-theta; and a weight loss on drying by TGA of about 85% to about 90%, preferably about 90% by weight.

The above ethylene glycol solvate of dasatinib designated Form AW may contain traces of amorphous dasatinib.

Form AW can be prepared by a process comprising drying dasatinib form AK.

Preferably, drying is done at a temperature of about 50° C. to about 60° C., preferably of about 55° C., preferably, for a period of overnight.

Figure 97:
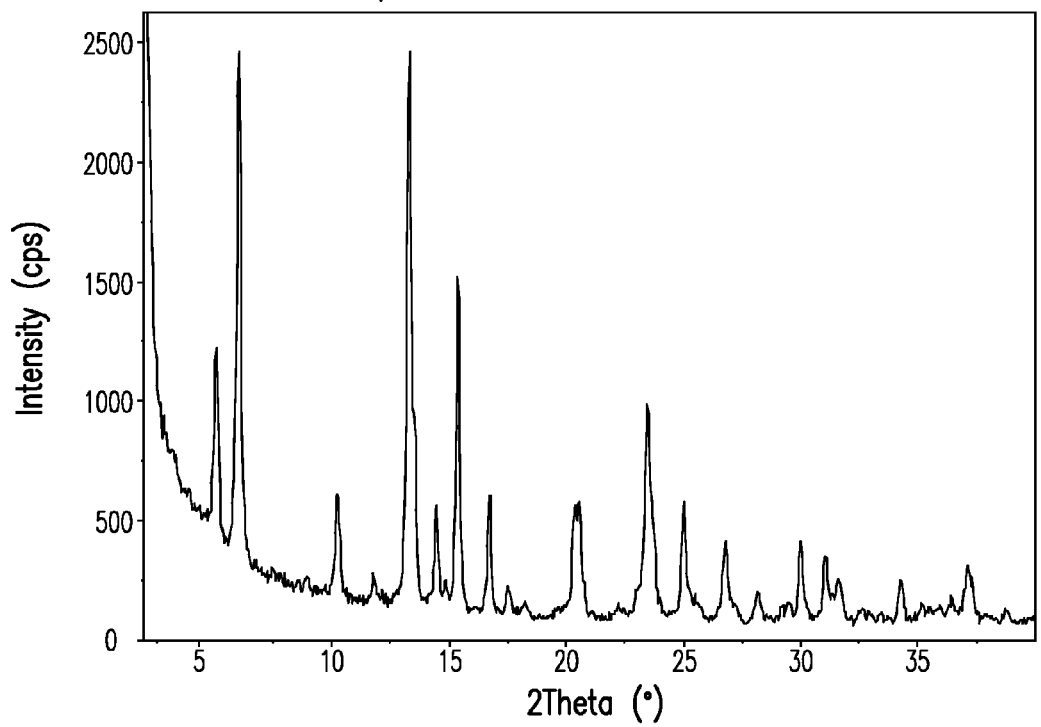
FIG. 97 shows a powder XRD pattern of crystalline dasatinib form BA

In one embodiment, the present invention encompasses an anhydrous form of dasatinib characterized by data selected from the group consisting of: a PXRD pattern having peaks at about 5.1 and 10.2±0.2 degrees 2-theta and any 3 peaks selected from the list consisting of: 5.1, 6.0, 10.2, 20.3, 20.5, 23.5 and 26.8±0.2 degrees 2-theta, a powder XRD pattern as depicted in FIG. 97, and a combination thereof. This form can be designated as form BA.

The above anhydrous form of dasatinib designated Form BA can be further characterized by data selected from the group consisting of: a powder XRD pattern with peaks at about 5.1, 6.0, 10.2, 23.5 and 26.8±0.2 degrees 2-theta; a powder XRD pattern having a double peak at about 20.3 and 20.5±0.2 degrees 2-theta; and a weight loss on drying by TGA of about 2% by weight or less.

Form BA can be prepared by a process comprising drying amorphous form of dasatinib.

Preferably, drying is done at a temperature of about 50° C. to about 60° C., preferably of about 55° C., preferably, for a period of overnight.

Figure 98:
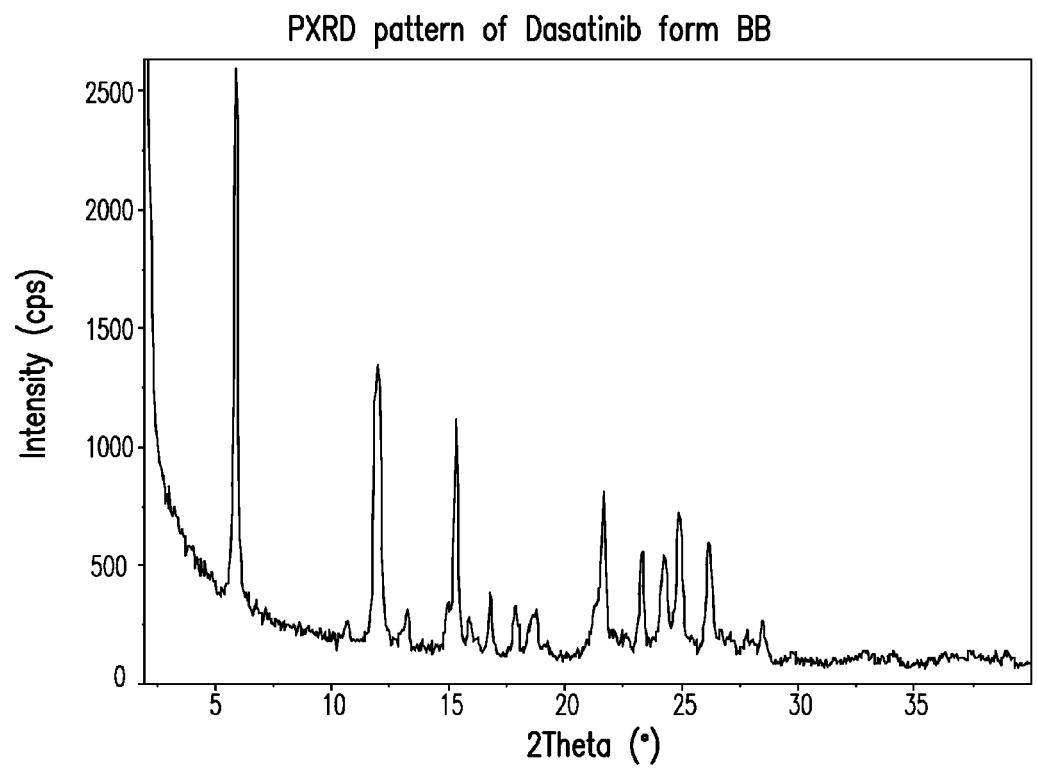
FIG. 98 shows a powder XRD pattern of crystalline dasatinib form BB

In one embodiment, the present invention encompasses a monochlorobenzene solvate of dasatinib characterized by data selected from the group consisting of: a PXRD pattern having any 3 peaks selected from the list consisting of: 5.9, 12.0, 15.3, 17.9, 24.3 and 26.2±0.2 degrees 2-theta, a powder XRD pattern as depicted in FIG. 98, and a combination thereof. This form can be designated as form BB.

In a preferred embodiment, the present invention encompasses a monochlorobenzene solvate of dasatinib designated Form BB and characterized by a PXRD pattern having peaks at about 15.3 and 26.2±0.2 degrees 2-theta and any 3 peaks selected from the list consisting of: 5.9, 12.0, 17.9 and 24.3±0.2 degrees 2-theta.

The above monochlorobenzene solvate of dasatinib designated Form BB can be further characterized by data selected from the group consisting of: a powder XRD pattern with peaks at about 5.9, 12.0, 15.3, 17.9 and 24.3±0.2 degrees 2-theta; a powder XRD pattern with peaks at about 12.0, 15.3, 17.9, 24.3 and 26.2±0.2 degrees 2-theta; and a weight loss on drying by TGA of about 9% to about 11% by weight, preferably about 10% by weight.

Form BB can be prepared by a process comprising drying dasatinib form AR, dasatinib form BJ, or mixtures thereof.

Preferably, drying is done at a temperature of about 50° C. to about 60° C., preferably of about 55° C., preferably, for a period of overnight.

Figure 109:
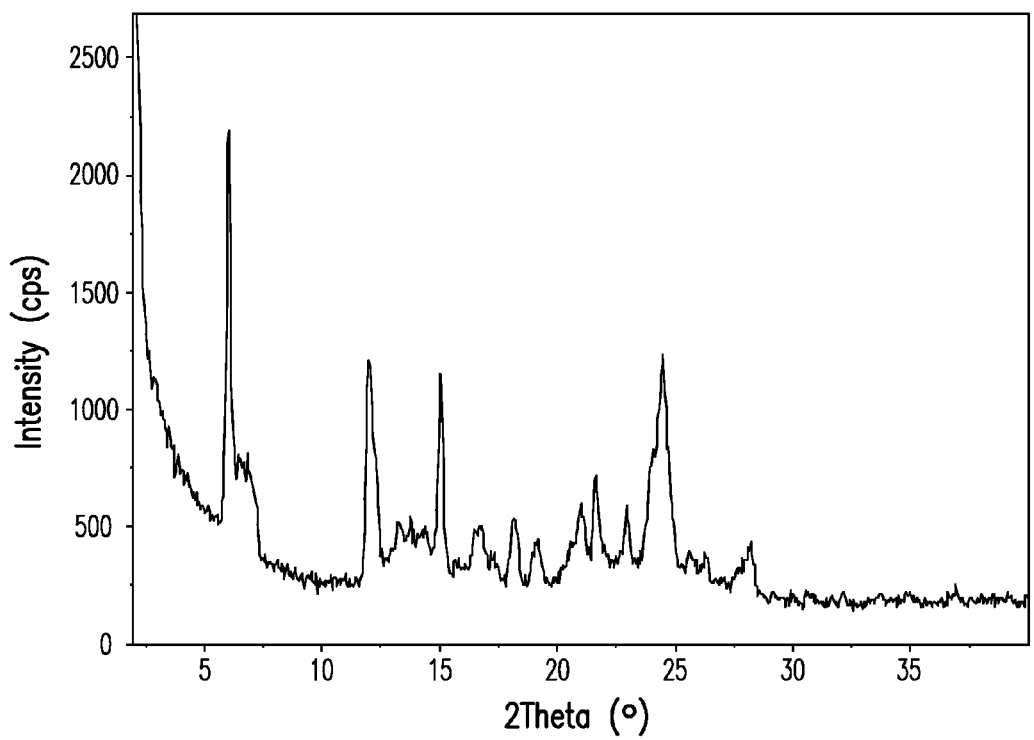
FIG. 109 shows a PXRD pattern of crystalline Dasatinib form BD

In one embodiment, the present invention encompasses a dimethyl carbonate solvate of dasatinib characterized by data selected from the group consisting of: a PXRD pattern having any 3 peaks selected from the list consisting of: 12.0, 16.7, 19.1, 21.0, 21.6, 23.0 and 24.5±0.2 degrees 2-theta, a powder XRD pattern as depicted in FIG. 109, and a combination thereof. This form can be designated as form BD.

In a preferred embodiment, the present invention encompasses a dimethyl carbonate solvate of dasatinib designated Form BD characterized by a PXRD pattern having peaks at about 16.7 and 21.6±0.2 degrees 2-theta and any 3 peaks selected from the list consisting of: 12.0, 19.1, 21.0, 23.0 and 24.5±0.2 degrees 2-theta.

The above dimethyl carbonate solvate of dasatinib designated Form BD can be further characterized by data selected from the group consisting of: a powder XRD pattern with peaks at about 16.7, 19.1, 21.0, 23.0 and 24.5±0.2 degrees 2-theta; a powder XRD pattern with peaks at about 12.0, 19.1, 21.0, 21.6 and 24.5±0.2 degrees 2-theta; and a weight loss on drying by TGA of about 1.3% by weight at a temperature of about 25° C. to about 67° C.

Form BD can be prepared by a process comprising suspending form A21 of dasatinib in dimethyl carbonate at a temperature of about 50° C. for a period of about 4 hours, and cooling the suspension to a temperature of about of 25° C. for a period of about 3 days.

Form BD can then be recovered from the suspension by evaporating the solvent, and drying. Preferably, the solvent is removed for a period of about 2 days.

Preferably, drying is done at a temperature of about 50° C. to about 60° C., preferably of about 55° C., preferably, for a period of overnight.

Figure 110:
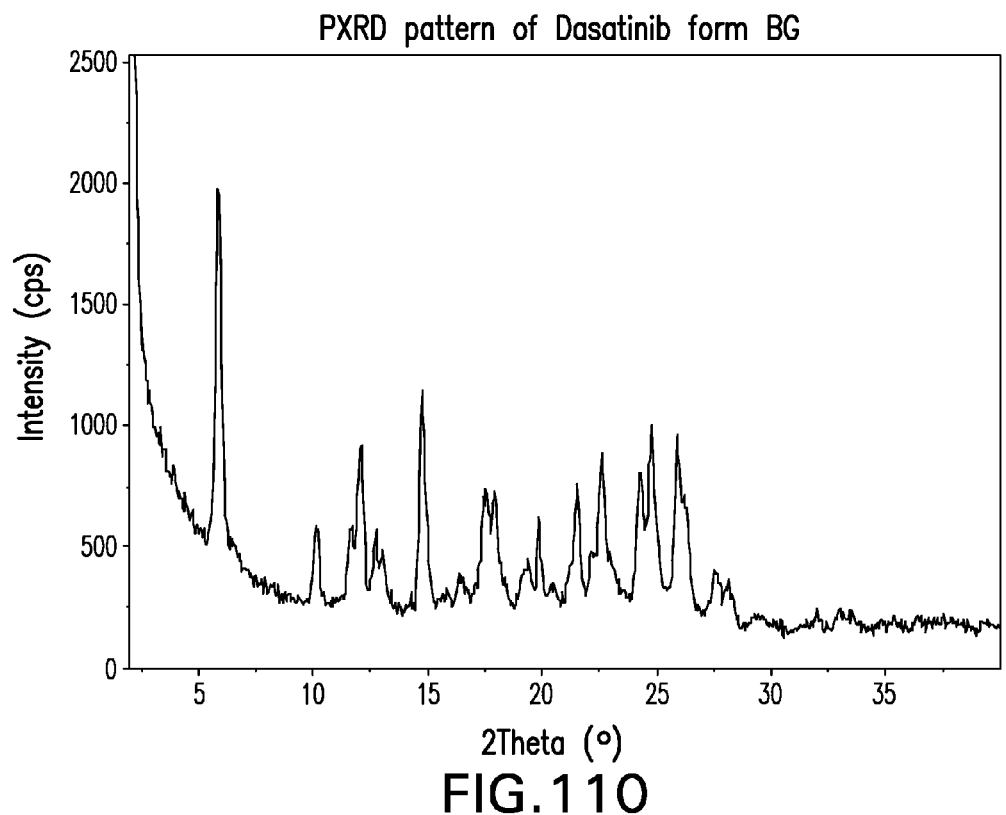
FIG. 110 shows a PXRD pattern of crystalline Dasatinib form BG

In one embodiment, the present invention encompasses a methyl isopropyl ketone ("MIPK") solvate of dasatinib characterized by data selected from the group consisting of: a PXRD pattern having any 3 peaks selected from the list consisting of: 10.1, 12.1, 12.7, 17.5, 17.9, 19.9 and 25.9±0.2 degrees 2-theta, a powder XRD pattern as depicted in FIG. 110, and a combination thereof. This form can be designated as form BG.

In a preferred embodiment, the present invention encompasses methyl isopropyl ketone ("MIPK") solvate of dasatinib characterized by a PXRD pattern having peaks at about 10.1 and 12.7±0.2 degrees 2-theta and any 3 peaks selected from the list consisting of: 12.1, 17.5, 17.9, 19.9 and 25.9±0.2 degrees 2-theta.

The above methyl isopropyl ketone solvate of dasatinib designated Form BG can be further characterized by data selected from the group consisting of: a powder XRD pattern with peaks at about 12.1, 12.7, 17.9, 19.9 and 25.9±0.2 degrees 2-theta; a powder XRD pattern with peaks at about 10.1, 12.1, 17.5, 19.9 and 25.9±0.2 degrees 2-theta; and a weight loss on drying in three steps, one of about 2% by weight, the second of about 7% by weight and the third of about 6% by weight as measured by TGA.

Form BG can be prepared by a process comprising suspending form A21 of dasatinib in methyl isopropyl ketone ("MIPK") at a temperature of about 50° C. for a period of about 4 hours, and cooling the suspension to a temperature of about of 25° C. for a period of about 3 days.

Form BG can then be recovered from the suspension by evaporating the solvent, and drying. Preferably, the solvent is removed over a period of about 2 days.

Preferably, drying is done at a temperature of about 50° C. to about 60° C., preferably of about 55° C., preferably, for a period of overnight.

Figure 111:
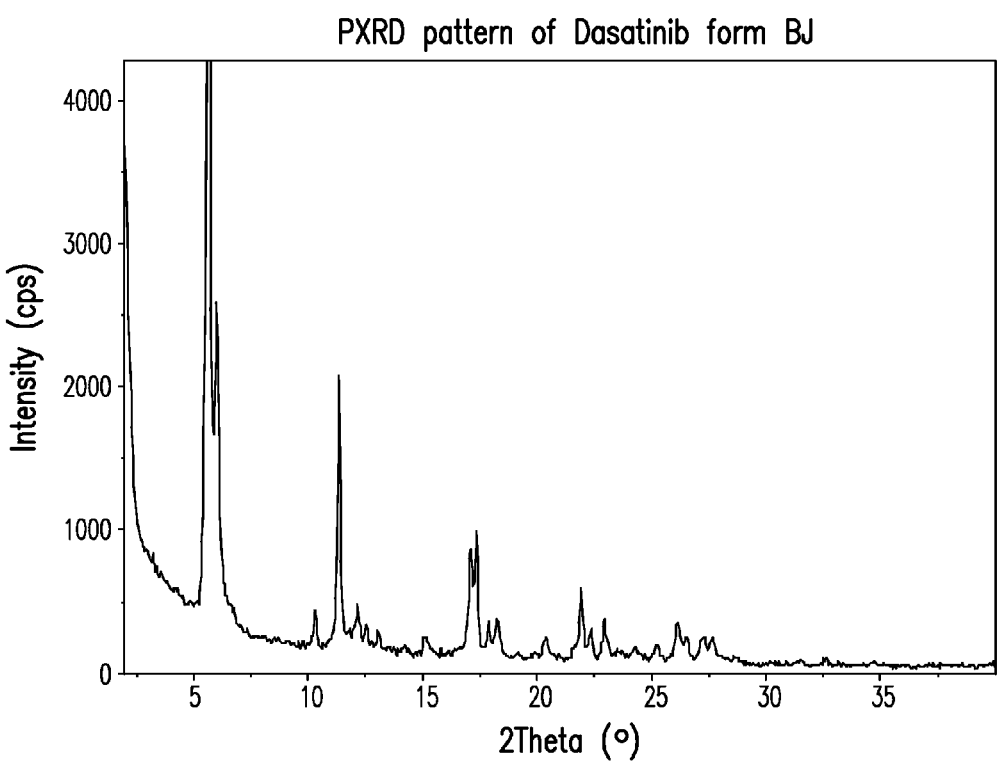
FIG. 111 shows a PXRD pattern of crystalline Dasatinib form BJ
Figure 112:
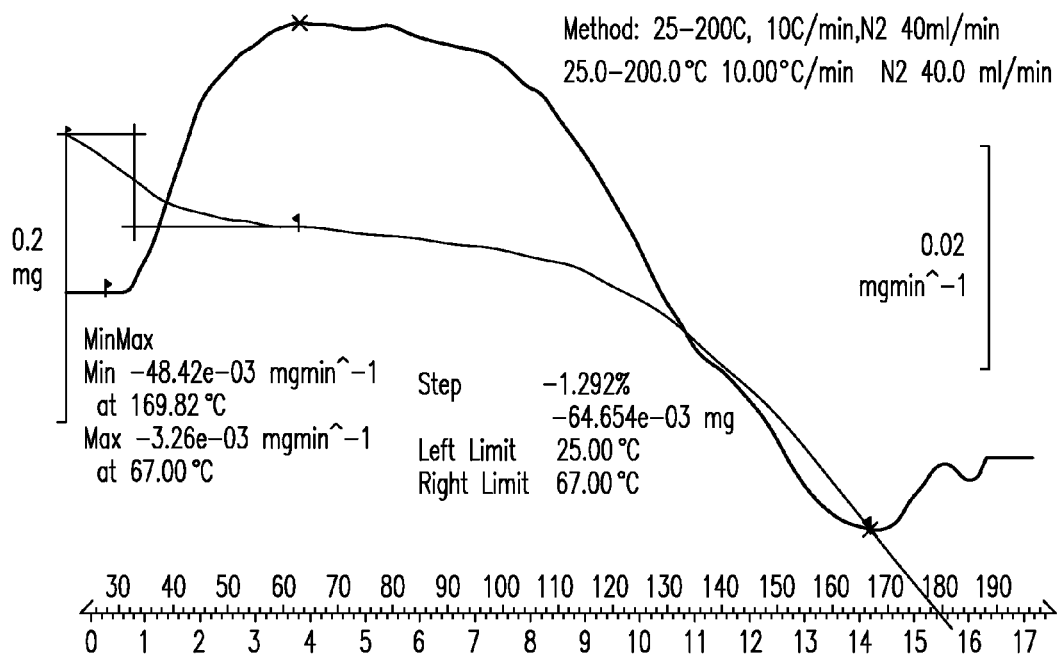
FIG. 112 shows a TGA thermogram of crystalline Dasatinib form BD
Figure 113:
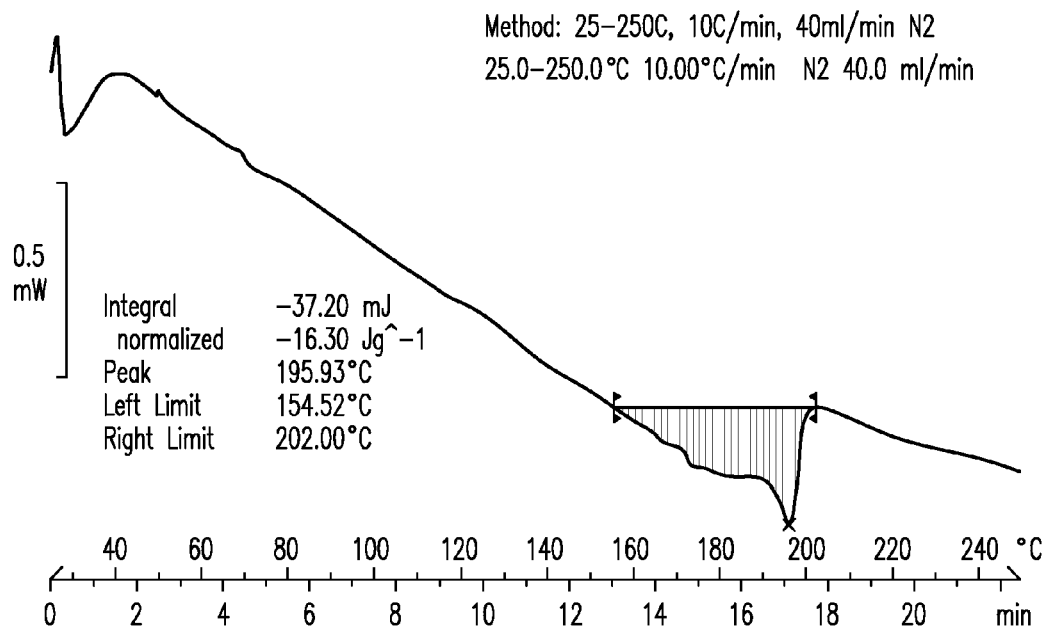
FIG. 113 shows a DSC thermogram of crystalline Dasatinib form BD
Figure 114:
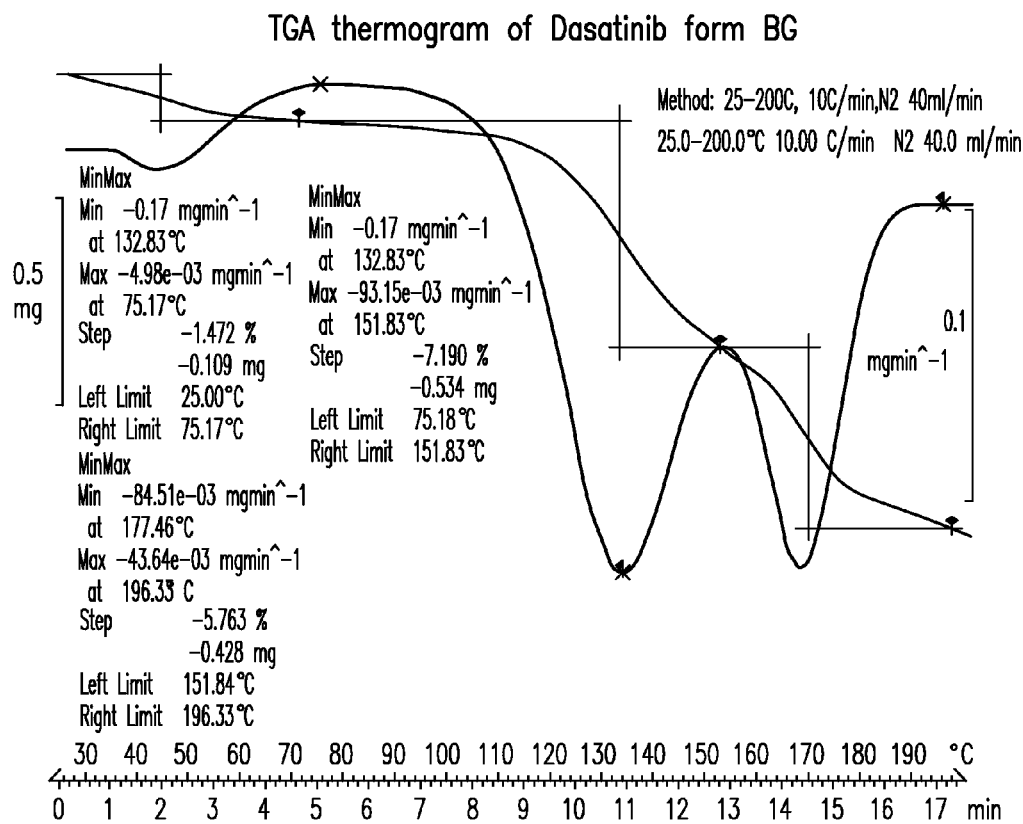
FIG. 114 shows a TGA thermogram of crystalline Dasatinib form BG
Figure 115:
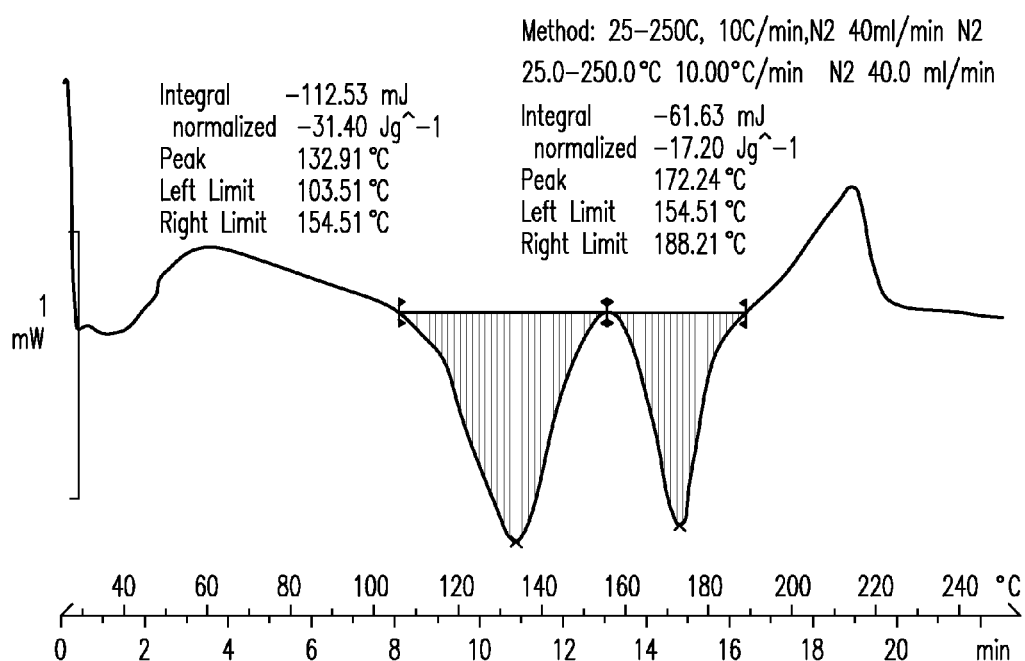
FIG. 115 shows a DSC thermogram of crystalline Dasatinib form BG
Figure 116:
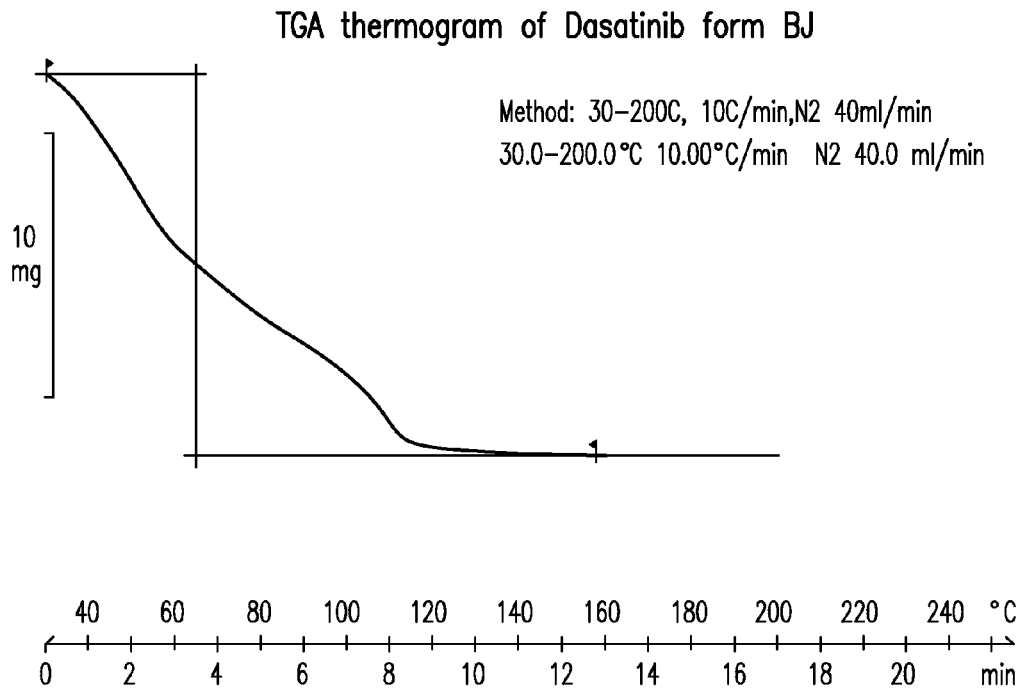
FIG. 116 shows a TGA thermogram of crystalline Dasatinib form BJ
Figure 117:
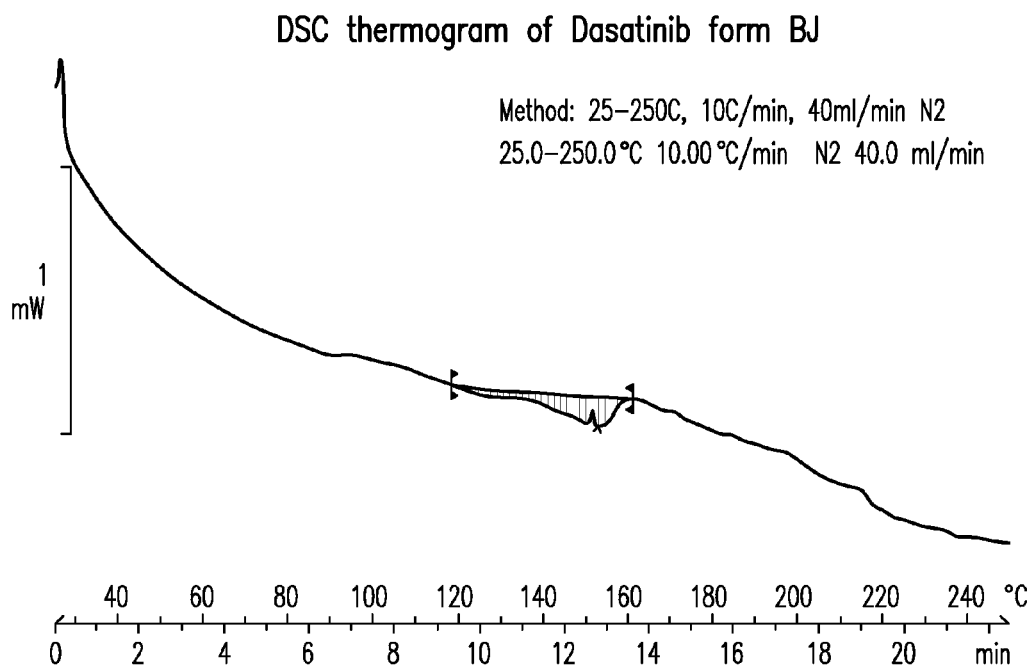
FIG. 117 shows a DSC thermogram of crystalline Dasatinib form BJ

In one embodiment, the present invention encompasses a monochlorobenzene solvate of dasatinib characterized by data selected from the group consisting of: a PXRD pattern having any 3 peaks selected from the list consisting of: 5.6, 10.3, 11.3, 17.3, 22.3 and 26.1±0.2 degrees 2-theta, a powder XRD pattern as depicted in FIG. 111, and a combination thereof. This form can be designated as form BJ.

In a preferred embodiment, the present invention encompasses a monochlorobenzene solvate of dasatinib characterized by a PXRD pattern having peaks at about 10.3 and 17.3±0.2 degrees 2-theta and any 3 peaks selected from the list consisting of: 5.6, 11.3, 22.3 and 26.1±0.2 degrees 2-theta.

The above monochlorobenzene solvate of dasatinib designated Form BJ can be further characterized by data selected from the group consisting of: a powder XRD pattern with peaks at about 5.6, 10.3, 17.3, 22.3 and 26.1±0.2 degrees 2-theta; a powder XRD pattern with peaks at about 5.6, 10.3, 11.3, 17.3 and 26.1±0.2 degrees 2-theta; and a weight loss on drying by TGA of about 73% by weight.

Form BJ can be prepared by a process comprising suspending form A21 of dasatinib in monochlorobenzene at a temperature of about 50° C. for a period of about 4 hours, and cooling the suspension to a temperature of about of 25° C. for a period of about 3 days.

Form BJ can then be recovered from the suspension by evaporating the solvent. Preferably, the solvent is removed over a period of about 2 days.

In one embodiment, the present invention encompasses a glycerol formal solvate of dasatinib characterized by a PXRD pattern having any 3 peaks selected from the list consisting of: 5.9, 11.8, 17.8, 18.6, 20.5, 23.8 and 24.3±0.2 degrees 2-theta.

Figure 125:
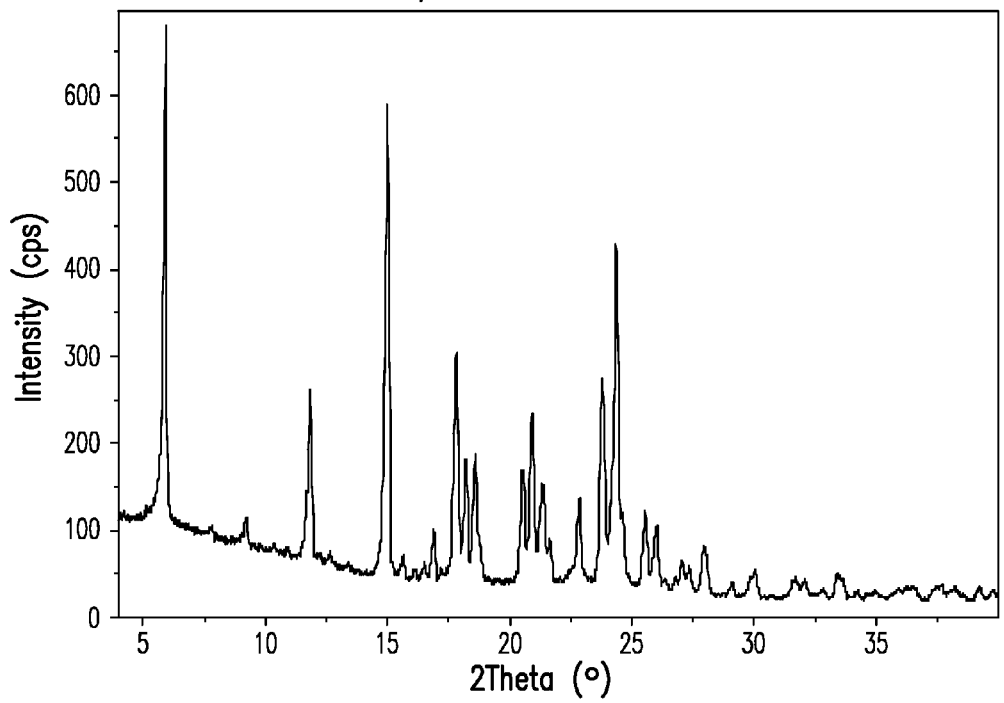
Figure 126:
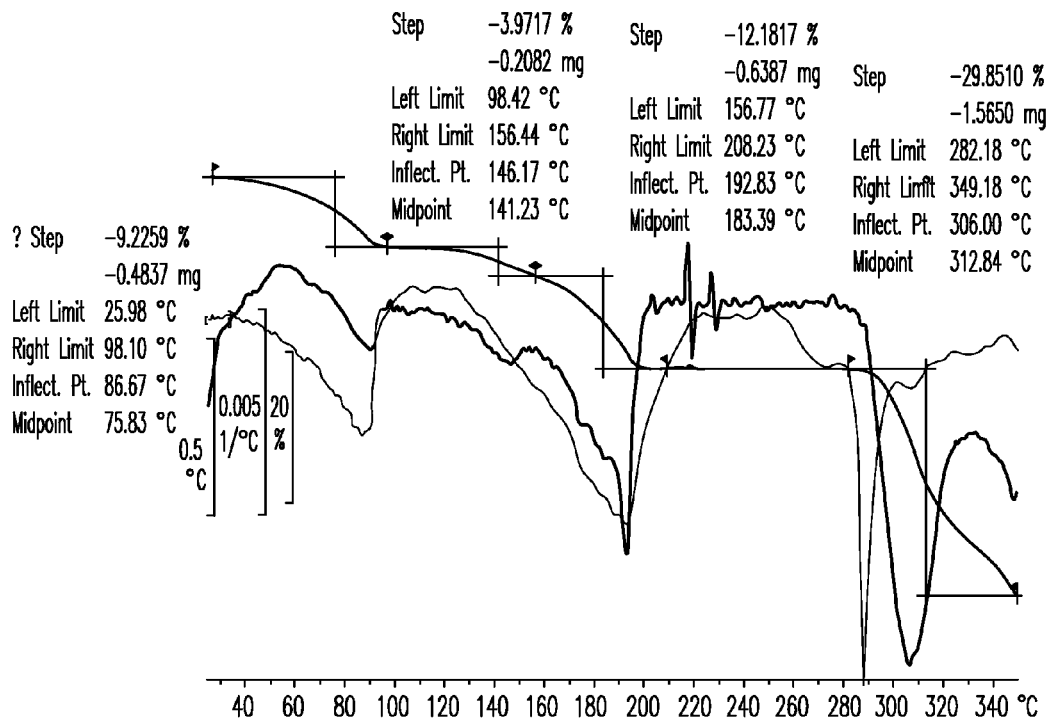
Figure 127:
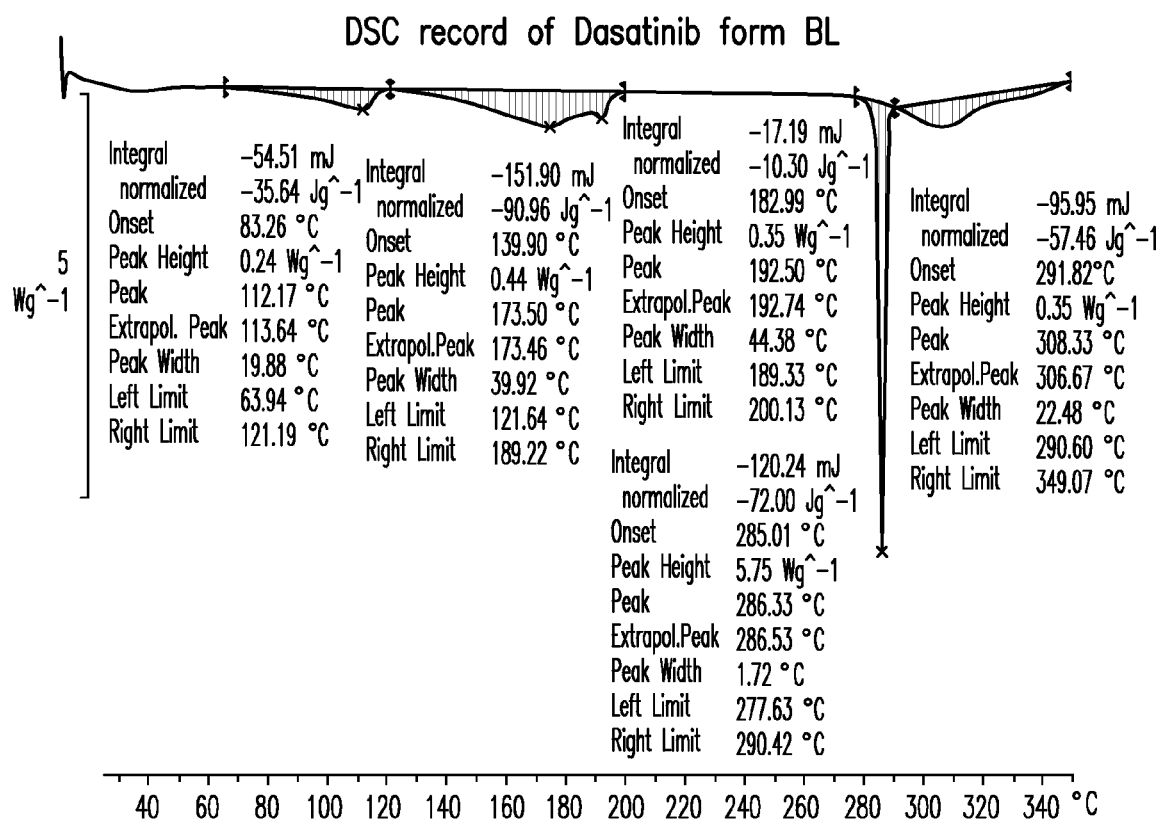

In one embodiment, the present invention encompasses a glycerol formal solvate of dasatinib characterized by data selected from the group consisting of: a PXRD pattern having peaks at about 17.8 and 23.8±0.2 degrees 2-theta and any 3 peaks selected from the list consisting of: 5.9, 11.8, 17.8, 18.6, 20.5, 23.8 and 24.3±0.2 degrees 2-theta, a powder XRD pattern as depicted in FIG. 125, and combination thereof. This form can be designated as form BL.

The above glycerol formal solvate of dasatinib designated Form BL can be further characterized by data selected from the group consisting of: a powder XRD pattern with peaks at about 5.9, 17.8, 18.6, 23.8 and 24.3±0.2 degrees 2-theta; a powder XRD pattern with peaks at about 11.8, 17.8, 18.6, 20.5 and 23.8±0.2 degrees 2-theta; and a weight loss on drying of about 15% to about 17% by weight, preferably about 16% by weight, by TGA in the temperature range 100-210° C.

Form BL of dasatinib can be prepared by a process comprising crystallizing dasatinib from glycerol formal.

The crystallization comprises providing a solution of dasatinib in glycerol formal, and precipitating said crystalline form to obtain a suspension.

Preferably, the solution is provided by combining dasatinib and glycerol formal, and heating the combination. Preferably, heating is to about 120° C. to about 140° C., preferably to about 130° C.

Preferably, precipitation is obtained by cooling the solution. Preferably, cooling is to a temperature of about 10° C. to about 25° C., preferably about 20° C.

The process for preparing form BL of dasatinib can further comprise recovering said form. The recovery can be done for example, by filtering the suspension, washing, and drying.

Figure 131:
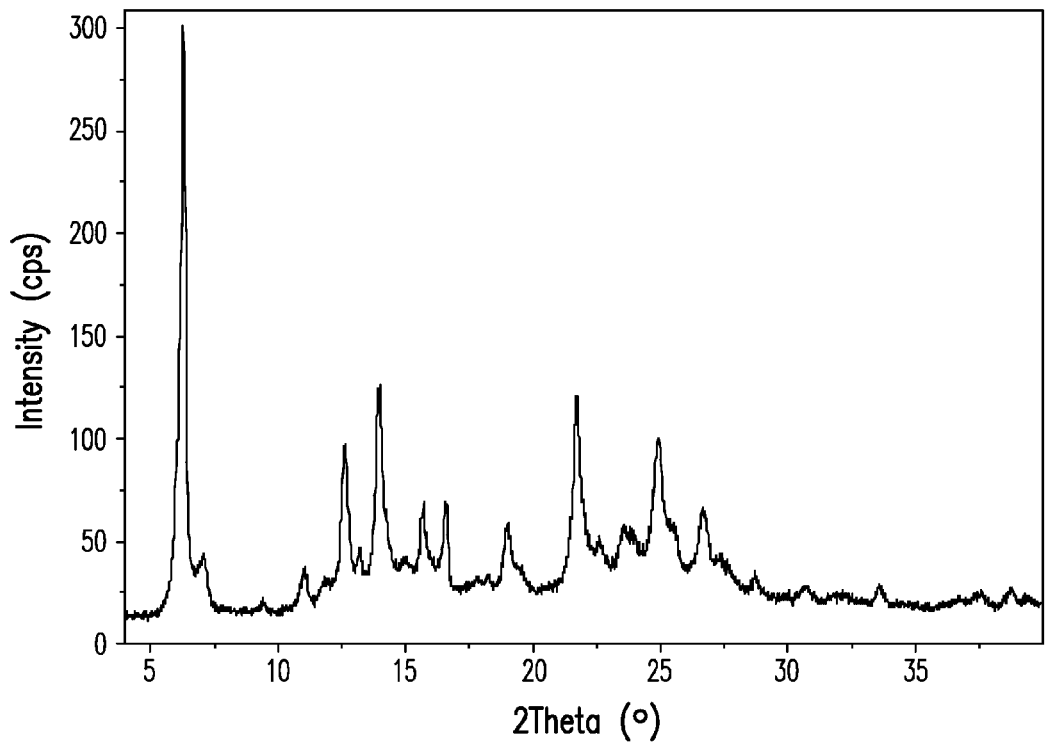

In one embodiment, the present invention encompasses dasatinib characterized by data selected from the group consisting of: a PXRD pattern having peaks at about 6.4 and 14.0±0.2 degrees 2-theta and any 3 peaks selected from the list consisting of: 6.4, 12.7, 14.0, 19.0, 21.7 and 25.0±0.2 degrees 2-theta, a powder XRD pattern as depicted in FIG. 131, and combination thereof. This form can be designated as form BM.

The above dasatinib designated Form BM can be further characterized by data selected from the group consisting of: a powder XRD pattern with peaks at about 6.4, 12.7, 14.0, 19.0 and 25.0±0.2 degrees 2-theta; a powder XRD pattern with peaks at about 6.4, 12.7, 14.0, 19.0 and 21.7±0.2 degrees 2-theta; and a weight loss on drying about 1% by weight or less by TGA.

In addition, crystalline Dasatinib Form BM has less than about 15% by weight, preferably, less about than 10% by weight, more preferably, less than about 5% by weight of crystalline Dasatinib forms N-6 and H1-7 or mixtures thereof.

Typically, the amount of form N-6 in form BM is measured by PXRD using any peaks selected from the group consisting of peaks at: 6.9, 17.3, 21.1 and 24.4 deg±0.2 degrees 2-theta and the amount of form H1-7 in form BM is measured by PXRD using any peaks selected from the group consisting of peaks at: 4.6, 9.2, 12.3, 15.2, 17.9, 18.4, 19.6 and 21.2 deg±0.2 degrees 2-theta.

Form BM of dasatinib can be prepared by a process comprising providing a solution of dasatinib in methanol, and precipitating said crystalline form by cooling to a temperature of about 0° C. to about −15° C. to obtain a suspension.

Preferably, the solution is provided by combining dasatinib and methanol, and heating the combination. Preferably, heating is to about 60° C. to about 70° C., preferably to about 64° C.-65° C.

Preferably, precipitation is obtained by cooling the solution. Preferably, cooling is to a temperature of about 0° C. to about −115° C.

The process for preparing form BM of dasatinib can further comprise recovering said form. The recovery can be done for example, by filtering the suspension, and drying.

The present invention also provides a process for preparing crystalline form H1-7 comprising reacting compound 1, N-(2-hydroxyethyl)piperazine, and N-ethyldiisopropylamine in DMF to obtain a solution comprising dasatinib, adding water to obtain a precipitate, and cooling to obtain said crystalline form.

Preferably, the reaction of a mixture of compound 1, N-(2-hydroxyethyl)piperazine, and N-ethyldiisopropylamine in DMF is done at a temperature of about 90° C. to about 100° C., more preferably, at a temperature of about 100° C. Preferably, the reaction is done for about 2.5 hours to about 4 hours, more preferably, for about 2.5 hours.

Preferably, water is added at a temperature of about 100° C.

Preferably, the cooling is to a temperature of about 25° C. to about 10° C., more preferably, of about room temperature.

The process for preparing Form H1-7 form of dasatinib can further comprise recovering said form. The recovery can be done for example, by filtering the suspension and drying.

Figure 106:
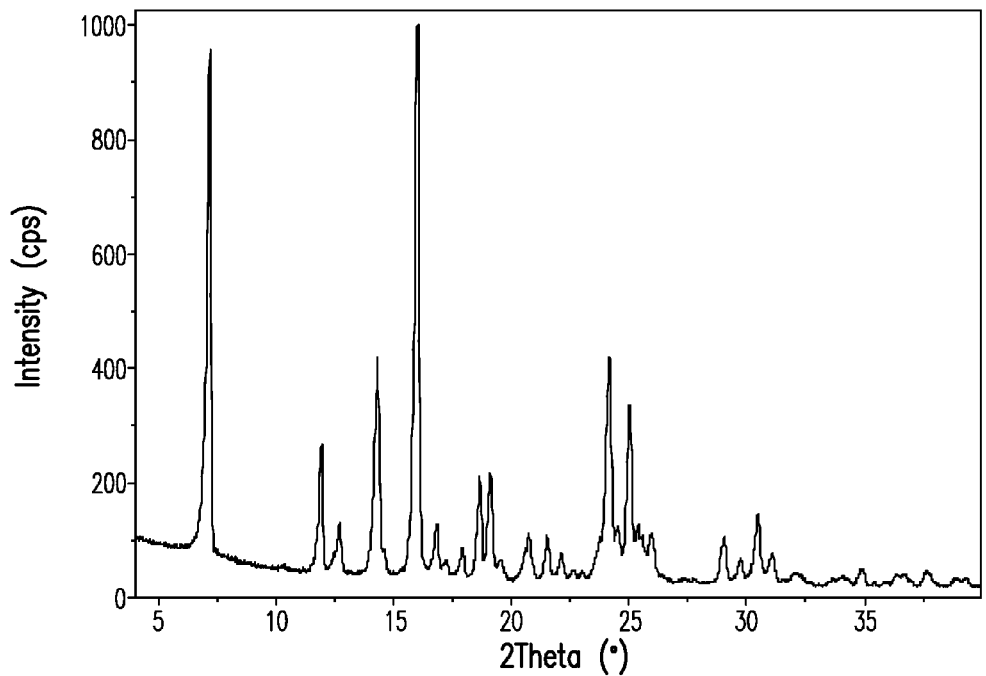
FIG. 106 shows a PXRD pattern of pure crystalline Dasatinib form T1E2-1 as obtained in examples 64-71

In another embodiment, the present invention encompasses a pure crystalline form T1E2-1 of dasatinib, characterized by a powder XRD pattern as depicted in FIG. 106.

As used herein, the term "pure crystalline" in reference to crystalline form T1E2-1 of Dasatinib corresponds to crystalline form T1E2-1 of Dasatinib containing less than about 5% by weight, preferably, less than 2% by weight, more preferably, less than about 1% by weight of crystalline Dasatinib diethanolate.

The content of crystalline dasatinib diethanolate in crystalline T1E2-1 is measured by PXRD using the peak at about 6.0°±0.2 degrees 2-theta-theta.

The pure crystalline form T1E2-1 can be prepared by a process comprising mixing crystalline dasatinib selected from the group consisting of crystalline form K2, crystalline form A2, and mixtures thereof with ethanol.

Preferably, mixing is done at about room temperature. Preferably, the obtained mixture is stirred. Preferably, stirring is done for about 2 hours to about 6 hours, preferably for about 4 hours.

The process for preparing pure crystalline form T1E2-1 can further comprise recovering said form. The recovery can be done for example, by filtering the suspension.

The present invention also provides another process for preparing pure crystalline form T1E2-1 providing a solution of dasatinib in a mixture of ethanol and water, and precipitating said crystalline form to obtain a suspension.

Preferably, the solution is provided by suspending dasatinib in ethanol, heating the suspension, and adding water to obtain the said solution. Preferably, the suspended Dasatinib is crystalline form L2 of Dasatinib, i.e., Dasatinib 2-butanol, crystalline form BU-2, i.e., n-butanol solvate or crystalline Dasatinib n-propanolate.

Preferably, the heating is to a temperature of about 70° C. to about 90° C., preferably about 80° C.

Optionally, the solution can be seeded prior to precipitation of the crystalline form. Preferably, when the starting material is form BU-2, the obtained solution is seedes with anhydrous Dasatinib. Preferably, the solution is seeded with N-6 anhydrous dasatinib.

Preferably, the precipitation is done by cooling the solution to a temperature of less than about 5° C. to about 0° C., more preferably, to about 5° C. to about 0° C.

The process for preparing pure crystalline form T1E2-1 can further comprise recovering said form. The recovery can be done for example, by filtering the suspension and drying.

The present invention provides an additional process for preparing pure crystalline form T1E2-1 comprising suspending dasatinib form A21 in a mixture comprising ethanol and water.

Preferably, dasatinib form A21 is suspended in said solvent mixture at a temperature of about 25° C. to about 75° C., more preferably, at about 75° C.

Preferably, the suspension is maintained at the above mentioned temperature for about 0.5 hours to about 2 hours, preferably about 1 hour.

The process for preparing pure crystalline form T1E2-1 can further comprise recovering said form. The recovery can be done for example, by cooling the heated suspension and filtering the suspension.

Preferably, the cooling is to a temperature of about 5° C. to about −10° C., preferably to about 5° C.

The present invention also provides a process for preparing crystalline form T1E2-1 comprising crystallizing dasatinib from a mixture comprising the compound of formula 1, N-(2-hydroxyethyl) piperazine, N-ethyldiisopropylamine and a mixture of DMSO and ethanol.

The crystallization comprises reacting compound 1, N-(2-hydroxyethyl)piperazine, and N-ethyldiisopropylamine in DMSO to obtain a solution comprising dasatinib, adding ethanol, and precipitating said crystalline form to obtain a suspension.

Preferably, the reaction of a mixture of compound 1, N-(2-hydroxyethyl)piperazine, and N-ethyldiisopropylamine in DMSO is done at a temperature of about 40° C. to about 150° C., more preferably, at about 40° C. to about 100° C., most preferably, at about 60° C. to about 80° C. Preferably, the reaction is done for about 1 hour to about 2 hours depending on the reaction temperature.

Preferably, ethanol is added at a temperature of about 60° C. to about 80° C., providing a second solution. Optionally, water can be added after adding ethanol, providing a third solution. Preferably, water is added at a temperature of about 60° C. to about 80° C.

Preferably, the cooling is to a temperature of about 25° C. to about 10° C., more preferably, of about room temperature.

The process for preparing form T1E2-1 of dasatinib can further comprise recovering said form. The recovery can be done for example, by filtering the suspension and drying.

The present invention also provides a process for preparing crystalline form N-6 comprising dying form P of dasatinib.

Preferably, drying is done at a temperature of about 200° C.

The present invention provides an additional process for preparing pure crystalline form N-6 comprising heating form A3 of dasatinib.

Preferably, heating is done to a temperature of about 200° C. to about 210° C., more preferably, at 208° C.

Preferably, drying is done for a period of about 15 minutes.

The above forms of dasatinib can be used to prepare pharmaceutical compositions. Preferably, the formulated polymorph is selected from the group consisting of: crystalline forms A3, A21, B, C and amorphous, more preferably, forms A3, A21 and B.

In yet another embodiment, the invention encompasses a pharmaceutical composition comprising at least one of the above described polymorphs of dasatinib, and at least one pharmaceutically acceptable excipient.

The present invention also encompasses a pharmaceutical composition comprising at least one of the above described polymorphs of dasatinib prepared according to the processes of the present invention, and at least one pharmaceutically acceptable excipient.

In another embodiment, the invention encompasses a process for preparing a pharmaceutical composition comprising at least one of the above-described polymorphs of dasatinib, and at least one pharmaceutically acceptable excipient.

In another embodiment, the invention encompasses a method of treating chronic yelogenous leukemia after imatinib treatemant, and Philadelphia chromosome-positive acute lymphoblastic leukemia comprising administering the pharmaceutical composition comprising at least one of the above described polymorphs of dasatinib to a patient in need thereof.

One embodiment of the invention provides the use of the above crystalline forms of dasatinib of the present invention for the manufacture of a pharmaceutical composition.

EXAMPLES

PXRD

XRD diffraction was performed on X-Ray powder diffractometer: Philips X'pert Pro powder diffractometer, CuK$_\alpha$ radiation, λ=1.5418 Å. X'Celerator detector active length (2 theta)=2.122°, laboratory temperature 22-25° C. Zero background sample holders. Prior to analysis the samples were gently ground by means of mortar and pestle in order to obtain a fine powder. The ground sample was adjusted into a cavity of the sample holder and the surface of the sample was smoothed by means of a cover glass.

A silicon internal standard can be used to calibrate peak positions and to eliminate an effect of a sample preparation. The internal standard possesses a diffraction with defined position at 28.44 degrees 2-theta. The internal standard can be mixed with a sample, PXRD is then acquired and the current position of the aforementioned internal standard diffraction peak is determined. The difference between the current position of the diffraction and its nominal value of 28.44 degrees 2-theta is calculated. The current positions of all relevant sample peaks are then re-calculated by means of the difference to obtain true positions of the sample diffractions.

$^{13}$C NMR

The CP/MAS $^{13}$C NMR measurements were made at Bruker Avance 500 NMR US/WB spectrometer in 4-mm ZrO2 rotor. Magic angle spinning (MAS) speed was 10 kHz. As used herein, the term "$^{13}$C NMR chemical shifts" refers to the shifts measured under above specified conditions, however, these shifts can slightly differ instrument to instrument and can be shifted either upfield or downfield due to the different instrumental setup and calibration used. Nevertheless the sequence of individual peaks remains identical.

DSC

DSC measurements were performed on Differential Scanning Calorimeter DSC823e (Mettler Toledo). Al crucibles 40 μl with PIN were used for sample preparation. Usual weight of sample was 1.5-3.5 mg.
Program: temperature range 25° C.-250° C., 10° C./min.

Water Content by KF

Water content was determined by Karl Fischer titrator TIT-RANDO 841, software Tiamo 1.1 (Metrohm). Solution used for determination: Hydranal Composite 2 (Riedel de Haen). Sampling: 100 mg, 2 repeats.

TGA

DSC measurements were performed on Differential Scanning Calorimeter DSC823e (Mettler Toledo). Alumina crucibles 70 μl were used for sample preparation. Usual weight of sample was 7-13 mg.
Program: temperature range 25° C.-250° C., 10° C./min; or 25° C.-350° C., 10° C./min.

GC

Residual solvents were determined by gas chromatography using head-space sampling. Headspace instrument HP7694 together with Gas chromatograph A6890 equipped with FID detector (Agilent technologies).

Crystal Structure Determination

Powder diffraction pattern was measured using synchrotron radiation at wavelength 0.80809(8) Å. Data were collected from 4 to 41 degrees 2theta at 15 degrees per minute, thus 3 minute per scan, step size 0.004 degrees. Crystal structure determination from powder diffraction data was solved using FOX program.

MIBK and Pyridine:

Sample amount 50.0 mg with 0.5 ml of N-Methylpyrrolidone is mixed in 20-ml headspace vial, after equilibration (30 min.) in the headspace oven (80° C.) 1 ml of vapour phase is injected into GC. GC column: Equity-5: 30 m×0.53 mm ID×5 μm (5%—Phenylmethylpolysiloxane); Injector temperature: 200° C., split 1:4; FID detector temperature: 250° C.; GC oven: 40° C. (10 min.)-10° C./min. to 120° C. (0 min.)-40° C./min. to 220° C. (2 min.), He: 23 kPa (40° C.), 33 cm/sec., constant flow.

Other Solvents:

Sample amount 50.0 mg with 0.5 ml of N-Methylpyrrolidone is mixed in 20-ml headspace vial, after equilibration (20 min.) in the headspace oven (90° C.) 1 ml of vapour phase is injected into GC. GC column: RES-SOLV (624—Agilent for fast GC): 30 m×0.53 mm ID×1 μm (94%—methylpolysiloxane, 6%—cyanopropyl); Injector temperature: 220° C., split 1:4; FID detector temperature: 250° C.; GC oven: 40° C. (4.2 min.)—25° C./min. to 180° C. (0 min.), He: 24 kPa (40° C.), 35 cm/sec., constant flow 4.8 ml/min.

Example 1

Procedure for the Preparation of Dasatinib Form K1

A mixture of compound 1 (394.3 mg, 1 mmol), N-(2-hydroxyethyl)piperazine (390.6 mg, 3 mmol) and N-ethyldiisopropylamine (0.348 ml, 2 mmol) in DMF (1 ml) was stirred at 100° C. for 2.75 h. n-propyl alcohol (10 ml) was slowly added through a condenser and mild reflux was maintained for 10 min. The reaction mixture was cooled to room temperature. The product was filtered after 1 hour and washed with n-PrOH (2×) and dried on the filter. Yield: 350 mg.

Example 2

Procedure for the Preparation of Dasatinib Form K2

A mixture of compound 1 (591.4 mg, 1.5 mmol), N-(2-hydroxyethyl)piperazine (390.6 mg, 3 mmol) and N-ethyldiisopropylamine (0.525 ml, 3 mmol) in DMSO (1.5 ml) was stirred at 80° C. for 1.5 h. n-propyl alcohol was added to the stirred solution at the same temperature. The product started precipitating after the addition of about 5 ml of n-propyl alcohol. Additional 1 ml of n-propyl alcohol was added, the suspension was stirred at 80° C. for 5 min and slowly cooled to room temperature. The product was filtered off after overnight stirring at room temperature, washed with n-propyl alcohol (2×) and dried on the filter and under reduced pressure at 40° C. for 6 hours. Yield: 640 mg.

Example 3

Procedure for the Preparation of Dasatinib Form K2

A mixture of compound 1 (5.91 g, 15 mmol), N-(2-hydroxyethyl)piperazine (3.91 g, 30 mmol) and N-ethyldiisopropylamine (5.25 ml, 30 mmol) in DMSO (15 ml) was stirred at 80° C. for 60 min. n-Propyl alcohol (46 ml) was slowly added and the temperature was maintained at 80° C. The product started precipitating after the given amount of n-PrOH had been added. The suspension was stirred at 80° C. for 10 min, then slowly cooled to room temperature during 90 min and stirred at room temperature for 20 min. The suspension was cooled to 10° C. and after 15 min the product was filtered off, washed with isopropyl alcohol (3×10 ml) and dried on the filter. Yield: 5.18 g.

Example 4

Procedure for the Preparation of Dasatinib Form B

A mixture of compound 1 (0.45 g, 1.14 mmol), N-(2-hydroxyethyl)piperazine (0.30 g, 2.30 mmol) and N-ethyldiisopropylamine (0.30 ml, 1.75 mmol) in DMSO (5 ml) was stirred at 60-65° C. for 2 h. MeOH (35 ml) was slowly added at this temperature followed by H$_2$O (55 ml). The solution was slowly cooled to 0-5° C. The precipitated product was filtered off, washed with MeOH (5.0 ml) and dried on the filter. Yield: 0.42 g.

Example 5

Procedure for the Preparation of Dasatinib Form B

Dasatinib butanolate (form BU-2, 1.00 g, 2.05 mmol) was heated in a mixture of ethanol (22 ml) and water (3 ml) at 75-80° C. to achieve complete dissolution. Water was added (8 ml) at the same temperature. The solution was cooled to 70° C. and maintained at 70° C. for 1 h. Temperature was lowered from 70° C. to 5° C. during 2 h, and maintained between 0-5° C. for 2 h. The product was filtered and washed with EtOH/$H_2O$ (1:1, 2×10 ml) and dried under reduced pressure at 40° C./8 h. Yield: 0.61 g.

Example 6

Procedure for the Preparation of Dasatinib Form C

A mixture of compound 1 (0.30 g, 0.76 mmol), N-(2-hydroxyethyl)piperazine (0.49 g, 3.76 mmol) and N-ethyldiisopropylamine (0.26 ml, 1.52 mmol) in DMSO (1.5 ml) was stirred at 40° C. for 3 hours. $H_2O$ was slowly added at the same temperature. The solution was slowly cooled to 0-5° C. The product was filtered off, washed with $H_2O$ and dried under reduced pressure at 40° C. for 6 hours. Yield: 0.40 g.

Example 7

Procedure for the Preparation of Dasatinib Form C

A mixture of compound 1 (0.45 g, 1.14 mmol), N-(2-hydroxyethyl)piperazine (0.30 g, 2.30 mmol) and N-ethyldiisopropylamine (0.30 ml, 1.75 mmol) in DMSO (5 ml) was stirred at 60° C. for 2 h. $H_2O$ (4 ml) was slowly added and the solution was heated at 60° C. for 30 min. The solution was slowly cooled to 0-5° C. The product was filtered off, washed with $H_2O$ and dried on the filter. Yield: 0.39 g.

Example 8

Procedure for the Preparation of Dasatinib Form D

A mixture of compound 1 (0.21 g, 0.53 mmol), N-(2-hydroxyethyl)piperazine (0.36 g, 2.77 mmol) and N-ethyldiisopropylamine (0.17 ml, 1.0 mmol) in THF (2.5 ml) was refluxed for 8 hours. The solution was slowly cooled to 0-5° C. The product was filtered off, washed with THF and dried under reduced pressure at 40° C. Yield: 0.29 g.

Example 9

Procedure for the Preparation of Dasatinib Form E

A mixture of compound 1 (0.30 g, 0.76 mmol), N-(2-hydroxyethyl)piperazine (0.52 g, 3.99 mmol) and N-ethyldiisopropylamine (0.26 ml, 1.52 mmol) in 2-methyl-THF (1.0 ml) was refluxed for 3 hours. The solution was slowly cooled to 0-5° C. Product was filtered off and washed with 2-methyl-THF and dried on the filter. Yield: 0.45 g.

Example 10

Procedure for the Preparation of Dasatinib Form F

A mixture of compound 1 (0.30 g, 0.76 mmol), N-(2-hydroxyethyl)piperazine (0.49 g, 3.76 mmol) and N-ethyldiisopropylamine (0.26 ml, 1.52 mmol) in dioxane (1.0 ml) was refluxed for 3 hours. The suspension was slowly cooled to 0-5° C. The product was filtered off, washed with dioxane and dried on the filter. Yield: 0.43 g.

Example 11

Procedure for the Preparation of Dasatinib Form G

A mixture of compound 1 (394.3 mg, 1 mmol), N-(2-hydroxyethyl)piperazine (260.4 mg, 2 mmol) and N-ethyldiisopropylamine (0.35 ml, 2 mmol) in pyridine (2 ml) was stirred at 90° C. for 3 h. Acetone (7 ml) was slowly added to the stirred solution through a condenser at the same temperature maintaining a mild reflux. The suspension was cooled to room temperature and after 1 h the product was filtered off washed with acetone (3×) and dried on the filter. Yield: 550 mg.

Example 12

Procedure for the Preparation of Dasatinib Form G

A mixture of compound 1 (394.3 mg, 1 mmol), N-(2-hydroxyethyl)piperazine (260.4 mg, 2 mmol) and N-ethyldiisopropylamine (0.35 ml, 2 mmol) in pyridine (2 ml) was stirred at 100° C. for 2.5 h. Ethyl acetate (6 ml) was added through a condenser to the stirred solution at the same temperature. The suspension was stirred and refluxed for 5 min and then slowly cooled to room temperature. The product was filtered off after 3 h and washed with ethyl acetate (2×) and dried on the filter. Yield: 660 mg.

Example 13

Procedure for the Preparation of Dasatinib Form H

A mixture of compound 1 (0.34 g, 0.86 mmol), N-(2-hydroxyethyl)piperazine (0.55 g, 4.22 mmol) and N-ethyldiisopropylamine (0.29 ml, 1.7 mmol) in toluene (6 ml) was refluxed for 9 h. The suspension was slowly cooled to 0-5° C. The product was filtered off, washed with toluene and dried on the filter, than dried under reduced pressure at 40° C. for 6 hours. Yield: 0.43 g.

Example 14

Procedure for the Preparation of Dasatinib Form I

A mixture of compound 1 (394.3 mg, 1 mmol), N-(2-hydroxyethyl)piperazine (260.4 mg, 2 mmol) and N-ethyldiisopropylamine (0.35 ml, 2 mmol) in pyridine (2 ml) was stirred at 100° C. for 2.5 h. Methyl isobutyl ketone (7 ml) was added to the stirred solution at the same temperature. The suspension was slowly cooled to room temperature. After 1 h the product was filtered off washed with methyl isobutyl ketone (2×) and dried on the filter. Yield: 660 mg.

Example 15

Procedure for the Preparation of Dasatinib Form J

A mixture of compound 1 (0.45 g, 1.14 mmol), N-(2-hydroxyethyl)piperazine (0.30 g, 2.30 mmol) and N-ethyldiisopropylamine (0.30 ml, 1.75 mmol) in DMSO (5 ml) was stirred at 60-65° C. for 2 hours. Acetone (20 ml) was slowly added at this temperature followed by $H_2O$ (30 ml). The solution was slowly cooled to 0-5° C. The product was filtered off and washed with acetone (5 ml) and dried on the filter, than dried under reduced pressure at 40° C. for 6 hours. Yield: 0.44 g.

Example 16

Procedure for the Preparation of Dasatinib Form J

A mixture of compound 1 (591.4 mg, 1.5 mmol), N-(2-hydroxyethyl)piperazine (390.6 mg, 3 mmol) and N-ethyldiisopropylamine (0.525 ml, 3 mmol) in DMSO (1.5 ml) was stirred at 80° C. for 1.5 h. Acetone (15 ml) was added to the stirred solution through a condenser at the same temperature and refluxed. The product started precipitating after 3 min. The reflux continued for 5 more min and the mixture was slowly cooled to room temperature. The product was filtered off after 4 h, washed with acetone (3×) and dried on the filter. Yield: 600 mg.

Example 17

Procedure for the Preparation of Dasatinib Form J (Acetone Solvate)

A mixture of compound 1 (394.3 mg, 1 mmol), N-(2-hydroxyethyl)piperazine (390.6 mg, 3 mmol) and N-ethyldiisopropylamine (0.348 ml, 2 mmol) in DMF (1 ml) was stirred at 100° C. for 2.5 h. Acetone (15 ml) was slowly added through a condenser and mild reflux was maintained for 10 min. The suspension was cooled to room temperature. The product was filtered after 1 hour and washed with acetone (3×) and dried on the filter. Yield: 360 mg.

Example 18

Procedure for the Preparation of Dasatinib Form A2

A mixture of compound 1 (591.4 mg, 1.5 mmol), N-(2-hydroxyethyl)piperazine (390.6 mg, 3 mmol) and N-ethyldiisopropylamine (0.525 ml, 3 mmol) in DMSO (1.5 ml) was stirred at 80° C. for 1.5 h. Isopropyl alcohol was added to the stirred solution at the same temperature. The product started precipitating after the addition of about 5 ml of isopropyl alcohol. Additional 1 ml of isopropyl alcohol was added, the suspension was stirred at 80° C. for 5 min and slowly cooled to room temperature. The product was filtered off after overnight stirring at room temperature, washed with isopropyl alcohol (2×) and dried on the filter. Yield: 640 mg.

Example 19

Procedure for the Preparation of Dasatinib Form A2

A mixture of compound 1 (5.91 g, 15 mmol), N-(2-hydroxyethyl)piperazine (3.91 g, 30 mmol) and N-ethyldiisopropylamine (5.25 ml, 30 mmol) in DMSO (15 ml) was stirred at 80° C. for 60 min. Isopropyl alcohol (46 ml) was slowly added and the temperature was maintained at 80° C. The product started precipitating after 1-2 min. The suspension was stirred at 80° C. for 5 min and slowly cooled to room temperature. The product was filtered off after overnight stirring at room temperature, washed with isopropyl alcohol (2×15 ml) and dried on the filter. Yield: 6.18 g.

Example 20

Procedure for the Preparation of Dasatinib Form A1

A mixture of compound 1 (394.3 mg, 1 mmol), N-(2-hydroxyethyl)piperazine (390.6 mg, 3 mmol) and N-ethyldiisopropylamine (0.348 ml, 2 mmol) in DMF (1 ml) was stirred at 100° C. for 2.5 h. Isopropyl alcohol (10 ml) was slowly added through a condenser and mild reflux was maintained for 10 min. The suspension was cooled to room temperature. The product was filtered after 1 hour and washed with i-PrOH (3×) and dried on the filter. Yield: 370 mg.

Example 21

Procedure for the Preparation of Dasatinib Form L2

A mixture of compound 1 (0.50 g, 1.27 mmol), N-(2-hydroxyethyl)piperazine (0.33 g, 2.54 mmol) and N-ethyldiisopropylamine (0.43 ml, 2.54 mmol) in DMSO (1.3 ml) was stirred at 80-85° C. for 2 hours. Butan-2-ol (7 ml) was slowly added at this temperature. The solution was slowly cooled to 0-5° C. The product was filtered off, washed with butan-2-ol (10 ml) and dried on the filter, than dried under reduced pressure at 40° C. for 6 hours. Yield: 0.56 g.

Example 22

Procedure for the Preparation of Dasatinib Mixture of Form G+M

A mixture of compound 1 (394.3 mg, 1 mmol), N-(2-hydroxyethyl)piperazine (260.4 mg, 2 mmol) and N-ethyldiisopropylamine (0.35 ml, 2 mmol) in pyridine (2 ml) was stirred at 80° C. for 5 h. $H_2O$ was added to the stirred solution at the same temperature. The product precipitated from the resulting solution after 5-7 min. The suspension was slowly cooled to room temperature. After 1 h the product was filtered off washed with $H_2O$ (4×) and dried on the filter. Yield: 470 mg.

Example 23

Procedure for the Preparation of Dasatinib Form H1-7 (Monohydrate)

A mixture of compound 1 (133.9 mg, 0.5 mmol), N-(2-hydroxyethyl)piperazine (260.4 mg, 2 mmol) and N-ethyldiisopropylamine (0.174 ml, 1 mmol) in DMF (0.5 ml) was stirred at 100° C. for 2.5 h. $H_2O$ (3 ml) was added to the solution at the same temperature. A gummy product precipitated. The suspension was allowed to cool slowly to room temperature and stirred for 2 h at room temperature. The product was filtered washed with $H_2O$ (2×) and dried on the filter. Yield: 140 mg.

Example 24

Procedure for the Preparation of Dasatinib Form T1E2-1 (Hemi-Ethanolate)

A mixture of compound 1 (591.4 mg, 1.5 mmol), N-(2-hydroxyethyl)piperazine (390.6 mg, 3 mmol) and N-ethyldiisopropylamine (0.525 ml, 3 mmol) in DMSO (1.5 ml) was stirred at 80° C. for 1.5 h. EtOH (10 ml) was added at the same temperature. The resulting solution was slowly cooled. The product started precipitating at 68° C. The mixture was cooled to room temperature. The product was filtered after 4 h, washed with EtOH (3×) and dried on the filter. Yield: 550 mg.

Example 25

Procedure for the Preparation of Dasatinib Form T1E2-1 (Hemi-Ethanolate)

A mixture of compound 1 (0.45 g, 1.14 mmol), N-(2-hydroxyethyl)piperazine (0.30 g, 2.30 mmol) and N-ethyldiisopropylamine (0.30 ml, 1.75 mmol) in DMSO (5 ml) was stirred at 60-65° C. for 2 hours. EtOH (30 ml) was slowly added at this temperature followed by $H_2O$ (40 ml). The solution was slowly cooled to 0-5° C. The product was filtered off and washed with ethanol (5 ml) and dried on the filter. Yield: 0.38 g.

Example 26

Procedure for the Preparation of Dasatinib Amorphous Substance

A mixture of compound 1 (591.4 mg, 1.5 mmol), N-(2-hydroxyethyl)piperazine (390.6 mg, 3 mmol) and N-ethyldiisopropylamine (0.525 ml, 3 mmol) in DMF (1.5 ml) was stirred at 90° C. for 2.5 h. The solution was cooled down to 0° C. Than, water (20 ml) was added in to the mixture and the mixture was stirred for 1 hour at 0° C. The product was filtered and washed with water (3×) and dried on the filter. Yield: 670 mg.

Example 27

Procedure for the Preparation of Dasatinib Form K1

A mixture of compound 1 (1.5 mmol), N-(2-hydroxyethyl)piperazine (3 mmol) and N-ethyldiisopropylamine (3 mmol) in DMF was stirred at 100° C. for 4 h, n-propanol was added at this temperature. The suspension was slowly cooled to 0-5° C. The product was filtered off, washed by i-propanol and dried on the filter.

Example 28

Procedure for the Preparation of Dasatinib Form K3

Dasatinib (form H1-7, 1 g) was dissolved in a mixture of n-PrOH (30 ml) and $H_2O$ (5 ml) under reflux. The resulting solution was quickly cooled to 0-5° C. (ice bath). The product was filtered off after 1 h, washed with n-PrOH and dried under reduced pressure at 50° C. for 2 h. Yield 620 mg.

Example 29

Procedure for the Preparation of Dasatinib Form A1

A mixture of compound 1 (1.5 mmol), N-(2-hydroxyethyl)piperazine (3 mmol) and N-ethyldiisopropylamine (3 mmol) in DMF was stirred at 100° C. for 4 h, i-propanol was added at this temperature. The suspension was slowly cooled to 0-5° C. The product was filtered off, washed by i-propanol and dried on the filter.

Example 30

Procedure for the Preparation of Dasatinib Form A3

Dasatinib (form H1-7, 1 g) was dissolved in a mixture of iso-PrOH (30 ml) and $H_2O$ (14 ml) under reflux. The resulting solution was quickly cooled to 0-5° C. (ice bath). The product was filtered off after 1 h, washed with iso-PrOH and dried under reduced pressure at 50° C. for 2 h. Yield 620 mg.

Example 31

Procedure for the Preparation of Dasatinib Form A3

Dasatinib (form H1-7, 1 g) was dissolved in a mixture of iso-PrOH (30 ml) and H2O (8 ml) under reflux. The resulting solution was quickly cooled to 0-5° C. (ice bath). The product was filtered off after 1 h, washed with iso-PrOH and dried under reduced pressure at 50° C. for 2 h. Yield 620 mg.

Example 32

Procedure for the Preparation of Dasatinib Form L1

A mixture of compound 1 (1.5 mmol), N-(2-hydroxyethyl)piperazine (3 mmol) and N-ethyldiisopropylamine (3 mmol) in DMF was stirred at 100° C. for 4 h, 2-butanole was added at this temperature. The suspension was slowly cooled to 0-5° C. The product was filtered off, washed by 2-butanol and dried on the filter.

Example 33

Procedure for the Preparation of Dasatinib Form L3

Dasatinib (form L2, 1.0 g, 2.05 mmol) was suspended in 2-BuOH (30 ml) and heated to reflux. Water (2.0 ml) was slowly added at these conditions to achieve complete dissolution. The resulting solution was refluxed 60 more minutes. The resulting solution was slowly cooled to 0-5° C. The product was filtered off and dried on the filter. Yield: 0.85 g, 85%.

Example 34

Procedure for the Preparation of Dasatinib Form N2

A mixture of compound 1 (1.5 mmol), N-(2-hydroxyethyl)piperazine (3 mmol) and N-ethyldiisopropylamine (3 mmol) was heated in DMSO (1.3 ml) at 80-85° C. for 1.5 hours. n-Butanol (7.0 ml) was slowly added at this temperature. The suspension was slowly cooled to 0-5° C. Product was filtered off and washed with n-butanol (10.0 ml) and dried on the filter.

Example 35

Procedure for the Preparation of Dasatinib Form P

Dasatinib i-propanolate (form A3, 4.74 g) was dissolved in DMF (23.7 ml) at 100° C. After water (23.7 ml) was added at 100° C. The suspension was cooled to room temperature. The product was filtered off, washed with water (3×) and dried on the filter.

Example 36

Procedure for the Preparation of Dasatinib Form Q

Dasatinib Form P was dried under flow of nitrogen at 70° C. for 2 hours.

Example 37

Procedure for the Preparation of Dasatinib Form AA

Dasatinib Form A21 (40 mg) [the detailed description has that these and all following methods were using Form C, please confirm that this should be Form A21. Also please clarify whether the method could be practiced with either form C or form A21.] was slurried in 1 ml MIPK and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AA. The wet sample was dried in a bottle in a conventional oven overnight on 55° C._The obtained sample was analyzed by XRD and found to be Form AA.

Example 38

Procedure for the Preparation of Dasatinib Form AB

Dasatinib Form A21 (40 mg) was slurried in 1 ml dimethoxyethane and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AB.

Example 38a

Procedure for the Preparation of Dasatinib Form AP

Dasatinib Form AB obtained by example 38 was dried in a bottle in a conventional oven overnight on 55° C._The obtained sample was analyzed by XRD and found to be Form AP.

Example 39

Procedure for the Preparation of Dasatinib Form AC

Dasatinib Form A21 (40 mg) was slurried in 1 ml cellosolve and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AC. The wet sample was dried in a bottle in a conventional oven overnight on 55° C. The obtained sample was analyzed by XRD and found to be Form AC.

Example 40

Procedure for the Preparation of Dasatinib Form AD

Dasatinib Form A21 (40 mg) was slurried in 1 ml methylacetate and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AD. The wet sample was dried in a bottle in a conventional oven overnight on 55° C._The obtained sample was analyzed by XRD and found to be Form AD.

Example 41

Procedure for the Preparation of Dasatinib Form AE 40 mg Dasatinib Form A21 was slurried in 1 ml MeOH and heated from 25 to 65° C. with 0.1 deg/min heating rate till total dissolution. It was mixed on 65° C. during 1 hour and cooled to 5° C. with 1 deg/min, than filtrated washed with 5 ml MeOH. Wet sample was obtained and analyzed by XRD and found to be Form AE. The wet sample was dried in a conventional oven overnight on 55° C._The obtained sample was analyzed by XRD and found to be Form AE.

Example 42

Procedure for the Preparation of Dasatinib Form AF

Dasatinib Form A21 (40 mg) was slurried in 1 ml ethylacetate and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AF. The wet sample was dried in a bottle in a conventional oven overnight on 55° C. The obtained sample was analyzed by XRD and found to be Form AF.

Example 43

Procedure for the Preparation of Dasatinib Form AG

Dasatinib Form A21 (40 mg) was slurried in 1 ml 2-pentanole and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AG. The wet sample was dried in a bottle in a conventional oven overnight on 55° C. The obtained sample was analyzed by XRD and found to be Form AG.

Example 44

Procedure for the Preparation of Dasatinib Form AI

Dasatinib Form A21 (40 mg) was slurried in 1 ml dimethyl carbonate and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AI.

Example 44a Procedure for the Preparation of Dasatinib Form AY

Dasatinib Form AI obtained by example 44 was dried in a bottle in a conventional oven overnight on 55° C. The obtained sample was analyzed by XRD and found to be Form AY.

Example 45

Procedure for the Preparation of Dasatinib Form AJ

Figure 107:
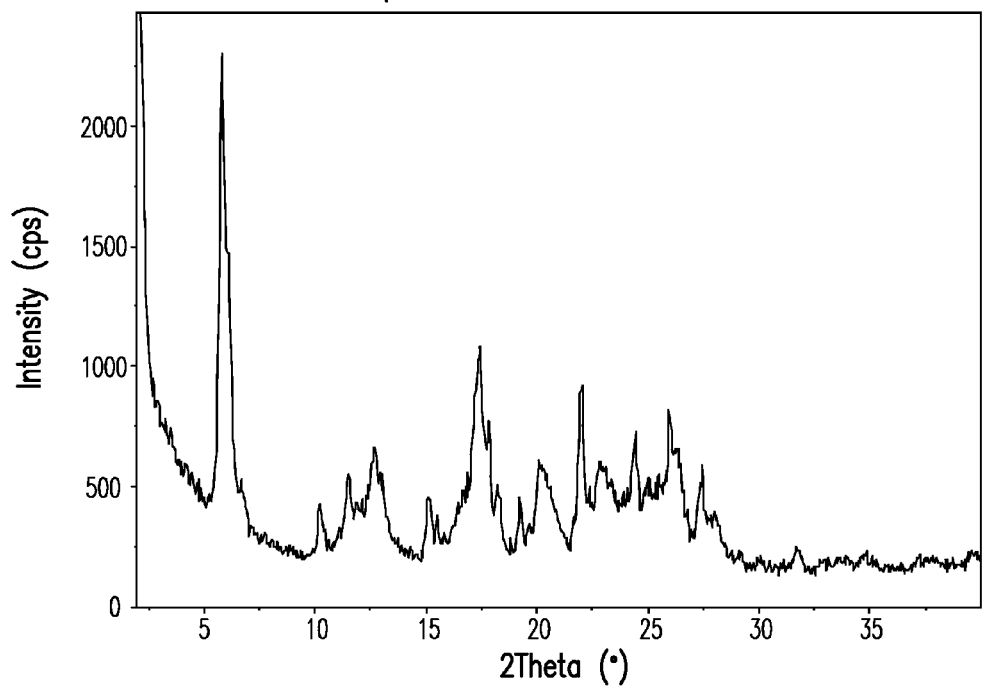
FIG. 107 shows a PXRD pattern of wet crystalline Dasatinib form AJ

Dasatinib Form A21 (40 mg) was slurried in 1 ml isopropylacetate and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AJ. The wet sample was analyzed by PXRD providing the following characteristics peaks at about 5.8, 10.2, 11.5, 12.7, 17.4 and 22.0±0.2 degrees 2-theta and a PXRD pattern depicted in FIG. 107. The wet sample was dried in a bottle in a conventional oven overnight on 55° C. The obtained sample was analyzed by PXRD and found to be Form AJ.

Example 46

Procedure for the Preparation of Dasatinib Form AK

Dasatinib Form A21 (40 mg) was slurried in 1 ml ethyleneglycol and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AK.

Example 46a

Procedure for the Preparation of Dasatinib Form AW

Dasatinib Form AK obtained by example 46 was dried in a bottle in a conventional oven overnight on 55° C. The obtained sample was analyzed by XRD and found to be Form AW.

Example 47

Procedure for the Preparation of Dasatinib Form AL

Figure 108:
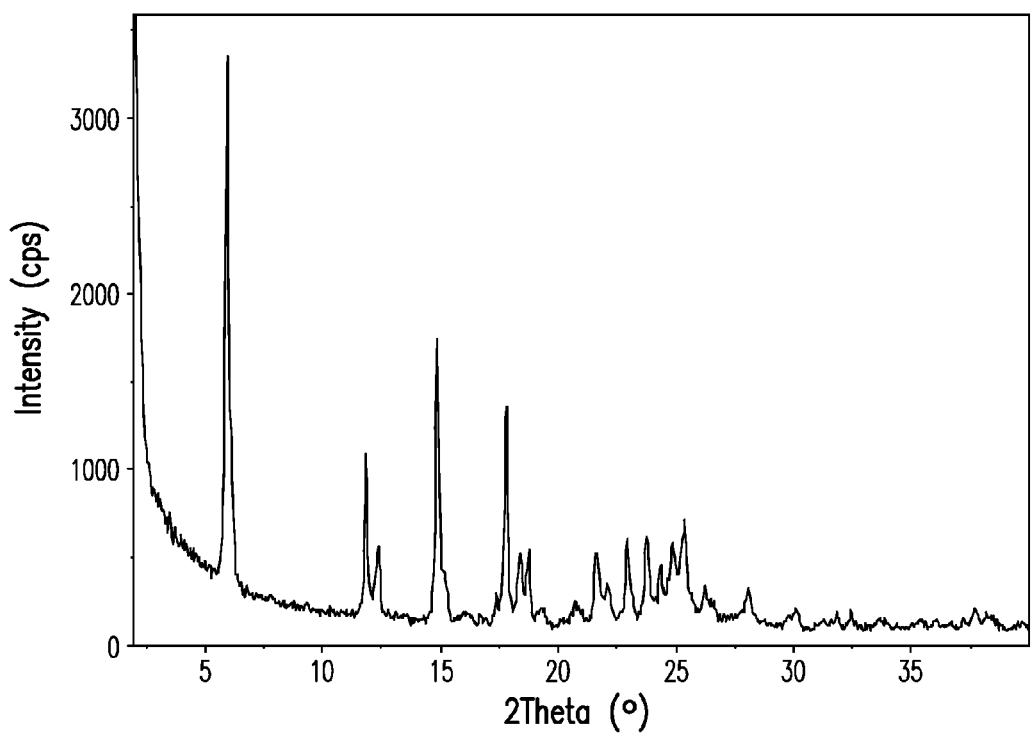
FIG. 108 shows a PXRD pattern of wet crystalline Dasatinib form AL

Dasatinib Form A21 (40 mg) was slurried in dichloromethane and heated from 25° C. till 50° C. with 0.5° C./min heating rate. The sample with the solvent was slurried at 30° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AL. The wet sample was analyzed by PXRD providing the following characteristics peaks at about 5.9, 12.3, 17.8, 18.4, 18.7, 23.0 and 23.8±0.2 degrees 2-theta, and a PXRD pattern depicted in FIG. 108. The wet sample was dried in a bottle in a conventional oven overnight on 55° C. The obtained sample was analyzed by XRD and found to be Form AL.

Example 48

Procedure for the Preparation of Dasatinib Form AM

Dasatinib Form A21 (40 mg) was slurried in 1 ml methylformate and heated from 25° C. till 50° C. with 0.5° C./min heating rate. The sample with the solvent was slurried at 30° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AM. The wet sample was dried in a bottle in a conventional oven overnight on 55° C. The obtained sample was analyzed by XRD and found to be Form AM.

Example 49

Procedure for the Preparation of Dasatinib Form AN

Dasatinib Form A21 (40 mg) was slurried in 1 ml tert-butanol and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AN. The wet sample was dried in a bottle in a conventional oven overnight on 55° C. The obtained sample was analyzed by XRD and found to be Form AN.

Example 50

Procedure for the Preparation of Dasatinib Amorphous

Dasatinib Form A21 (40 mg) was slurried in 1 ml 1,2-dichlorobenzene and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Amorphous Form.

Example 50a

Procedure for the Preparation of Dasatinib Form BA

Dasatinib amorphous obtained by example 50 was dried in a bottle in a conventional oven overnight on 55° C. The obtained sample was analyzed by XRD and found to be Form BA.

Example 51

Procedure for the Preparation of Dasatinib Form K3

Dasatinib Form A21 (40 mg) was slurried in 1 ml n-propanol and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form K3. The wet sample was dried in a bottle in a conventional oven overnight on 55° C. The obtained sample was analyzed by XRD and found to be Form K3.

Example 52

Procedure for the Preparation of Dasatinib Form AE

Dasatinib Form A21 (40 mg) was dissolved in 200 μl DMSO and heated from 25° C. till 65° C. with 0.05° C./min heating rate. The sample with the solvent was mixed at 65° C.

and 800 µl MeOH was injected into the system. Then it was cooled down to 5° C. with 1° C./min heating rate. The suspension was filtered and washed with ~5 ml MeOH. Wet sample was obtained and analyzed by XRD and found to be Form AE.

Example 53

Procedure for the Preparation of Dasatinib Form AE 40 mg Dasatinib Form A21 was slurried in 1 ml MeOH and heated from 25 to 65° C. with 0.1 deg/min heating rate till total dissolution. It was mixed on 65° C. during 1 hour and cooled to 5° C. with 0.1 deg/min, then filtrated washed with 5 ml MeOH. Wet sample was obtained and analyzed by XRD and found to be Form AE.

Example 54

Procedure for the Preparation of Dasatinib Form AE 40 mg Dasatinib Form A21 was dissolved in 200 µl DMSO and slurried on 25. On 25° C. 800 µl MeOH was injected into the system, than spontaneous crystallization was observed. The obtained crystals were filtrated and washed with ~5 ml MeOH. Wet sample was obtained and analyzed by XRD and found to be Form AE.

Example 55

Procedure for the Preparation of Dasatinib Form AH

Dasatinib Form A21 (40 mg) was slurried in 1 ml tert-butanol and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AH. The wet sample was dried in a bottle in a conventional oven overnight on 55° C. The obtained sample was analyzed by XRD and found to be Form AH.

Example 56

Procedure for the Preparation of Dasatinib Amorphous

Dasatinib Form A21 (40 mg) was slurried in 1 ml benzyl alcohol and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Amorphous Form.

Example 57

Procedure for the Preparation of Dasatinib Form AQ

Dasatinib Form A21 (40 mg) was slurried in 1 ml methyl-ethylketone ("MEK") and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AQ. The wet sample was dried in a bottle in a conventional oven overnight on 55° C. The obtained sample was analyzed by XRD and found to be Form AQ.

Example 58

Procedure for the Preparation of Dasatinib Form AR

Dasatinib Form A21 (40 mg) was slurried in 1 ml monochlorobenzene and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AR.

Example 58a Procedure for the Preparation of Dasatinib Form BB

Dasatinib form AR obtained by example 58 was dried in a bottle in a conventional oven overnight on 55° C. The obtained sample was analyzed by XRD and found to be Form BB.

Example 59

Procedure for the Preparation of Dasatinib Form AS

Dasatinib Form A21 (40 mg) was slurried in 1 ml propylene glycol monoethyl ether ("PGME") and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AS. The wet sample was dried in a bottle in a conventional oven overnight on 55° C. The obtained sample was analyzed by XRD and found to be Form AS.

Example 60

Procedure for the Preparation of Dasatinib Amorphous

Dasatinib Form A21 (40 mg) was slurried in 1 ml propylene glycol and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Amorphous Form.

Example 61

Procedure for the Preparation of Dasatinib Form AT

Dasatinib Form A21 (40 mg) was slurried in 1 ml glycerol and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AT.

Example 61a Procedure for the Preparation of Dasatinib Form BC

Dasatinib form AT obtained by example 61 was dried in a bottle in a conventional oven overnight on 55° C. The obtained sample was analyzed by XRD and found to be Form BC.

Example 62

Procedure for the Preparation of Dasatinib Form AU

Dasatinib Form A21 (40 mg) was slurried in 1 ml cyclopentyl methyl ether and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AU. The wet sample was dried in a bottle in a conventional oven overnight on 55° C. The obtained sample was analyzed by XRD and found to be Form AU.

Example 63

Procedure for the Preparation of Dasatinib Form AV

Dasatinib Form A21 (40 mg) was slurried in 1 ml methyl tert butyl ether ("MTBE") and heated from 25° C. till 50° C. with 0.5° C./min heating rate. The sample with the solvent was slurried at 50° C. for 6 hours, cooled to 25° C. with 0.5° C./min cooling rate, slurried overnight at 25° C. The sample was kept in a hood at atmospheric pressure and room temperature overnight. Wet sample was obtained and analyzed by XRD and found to be Form AV. The wet sample was dried in a bottle in a conventional oven overnight on 55° C. The obtained sample was analyzed by XRD and found to be Form AV.

Example 64

Procedure for the Preparation of Pure Dasatinib Form T1E2-1 (Hemi-Ethanolate)

Dasatinib Form K2 (solvate of n-propanol and DMSO) (500 mg) was stirred in 10 ml EtOH at r.t. for 4 h.

Example 65

Procedure for the Preparation of Pure Dasatinib Form T1E2-1 (Hemi-Ethanolate)

Dasatinib Form K2 (solvate of n-propanolate and DMSO) (500 mg) was refluxed in 10 ml EtOH for 4 h.

Example 66

Procedure for the Preparation of Pure Dasatinib Form T1E2-1 (Hemi-Ethanolate)

Dasatinib Form A2, (solvate of i-propanolate and DMSO) solvate (500 mg) was stirred in 10 ml EtOH at r.t. for 4 h.

Example 67

Procedure for the Preparation of Pure Dasatinib Form T1E2-1 (Hemi-Ethanolate)

Dasatinib 2-butanolate (form L2, 1.0 g, 2.05 mmol) was suspended in EtOH (8.1 ml). After heating at 80° C. was added next portion EtOH (4.0 ml). Then water was added (2.05 ml) to achieve complete dissolution. The solution was cooled to 0-5° C. The product was filtered off and dried on the filter. Yield: 0.50 g, 71.4%.
EtOH—W (6:1).

Example 68

Procedure for the Preparation of Pure Dasatinib Form T1E2-1 (Hemi-Ethanolate)

Dasatinib n-propanolate (form K2, 0.60 g, 1.23 mmol) was suspended in EtOH (7.0 ml). After heating at 80° C. was added next portion EtOH (3.4 ml). Then water was added (1.8 ml) to achieve complete dissolution. The solution was cooled to 0-5° C. The product was filtered off and dried on the filter. Yield: 0.43 g, 71.7%.
EtOH—W (6:1)

Example 69

Procedure for the Preparation of Pure Dasatinib Form T1E2-1 (Hemi-Ethanolate)

Dasatinib n-butanolate (form BU-2, 1.0 g) was refluxed in EtOH (22 ml). After water (3 ml) was added at these conditions to achieve complete dissolution. To the solution was added dasatinib anhydrous (50 mg) at 68° C. The suspension was slowly cooled to room temperature. The product was filtered off and dried on the filter.

Example 70

Procedure for the Preparation of Pure Dasatinib Form T1E2-1 (Hemi-Ethanolate)

40 mg DAS (Form A21)+880 µl EtOH+120 µl water heating 25-75° C. with 0.1 deg/min, slurry on 75° C. during 1 hour, cooling till 5° C. with 1 deg/min, filtration, washing with ~5 ml EtOH, than XRD.

Example 71

Procedure for the Preparation of Pure Dasatinib Form T1E2-1 (Hemi-Ethanolate)

40 mg DAS (Form A21)+880 µl EtOH+120 µl water heating 25-65° C. with 0.05 deg/min, slurry on 65° C. during 1 hour, injection of 320 µl water cooling till 5° C. with 1 deg/min, washing with ~5 ml EtOH, than XRD.

Example 72

Procedure for the Preparation of Dasatinib Form A3

Dasatinib (form A3, 3.50 g) was dissolved in a mixture of i-PrOH—H2O 30:8 (in 140 ml) under reflux. The solution was slowly cooled to about 70° C. The product started to crystallized at 65-70° C. Temperature was kept at this value for about 20 min then it was decreased to 50° C. and kept for 15 min. The mixture was slowly cooled to room temperature and stirred at room temperature for 1 h. The product was filtered off, washed with i-PrOH (2×) and dried under reduced pressure at 50° C. for 3 h. Yield: 2.44 g.

Example 73

Procedure for the Preparation of Crude Dasatinib form A21 in 1-g Scale

A mixture of compound 1 (1.58 g, 4 mmol) and N-(2-hydroxyethyl)piperazine (1.56 g, 12 mmol) was stirred in DMSO (4 ml) at 70° C. for 3 h. i-PrOH (12 ml) was added at the same temperature to precipitate the product. The mixture was cooled to room temperature during 30 min and stirred at room temperature for 1 h. The product was filtered, washed with i-PrOH (2×) and dried. Yield: 1.37 g, 70%.

Example 74

Procedure for the Preparation of Dasatinib Form A3 in 1-g Scale

Crude Dasatinib (form A21, 800 mg, example 73) was dissolved in a mixture of i-PrOH—H$_2$O 30:8 (32 ml) under reflux. The solution was slowly cooled to about 70° C. The product started to crystallize at 65-70° C. Temperature was kept at this value for about 20 min then it was decreased to 50° C. and kept for 15 min. The mixture was slowly cooled to room temperature and stirred at room temperature for 1 h. The product was filtered off, washed with i-PrOH (2×) and dried under reduced pressure at 50° C. for 3 h. Yield: 580 mg, 73%.

Example 75

Procedure for the preparation of crude Dasatinib form A21 in 1-kg scale

A mixture of compound 1 (1000 g, 2.54 mol) and N-(2-hydroxyethyl)piperazine (991 g, 7.61 mol) was stirred in DMSO (2.54 l) under nitrogen at 70° C. for 3 h. i-PrOH (7.62 l) was added at the same temperature during 15 min to precipitate the product. The mixture was cooled to 20° C. during 30 min and stirred at 20° C. for 1 h. The product was filtered, washed with i-PrOH (2×3.5 l) and dried. Yield: 866 g, 70%.

Example 76

Procedure for the preparation of Dasatinib Form A3 in 1-kg scale

Crude Dasatinib (form A21, 800 g, example 75) was dissolved in a mixture of i-PrOH—H$_2$O 30:8 (32 l) under reflux under nitrogen. The solution was cooled to about 70° C. The product started to crystallize at 65-70° C. Temperature was kept at this value for about 20 min then it was decreased to 50° C. and kept for 15 min. The mixture was slowly cooled to room temperature and stirred at room temperature for 1 h. The product was filtered off, washed with i-PrOH (2×3 l) and dried under reduced pressure at 50° C. for 3 h. Yield: 580 g, 73%.

Example 77

Procedure for the preparation of Dasatinib Form BD 40 mg DAS (Form A21)+1 ml DiMeCarbonate heating till 50° C. with 0.5° C./min heating rate, slurry on 50° C. during 4 hours, cooling to 25° C. with 0.1° C./min cooling rate, slurry during 3 days on 25° C. and evaporation of the solvent in the hood during 2 days. Then drying in oven on 55° C. overnight.

Example 78

Procedure for the preparation of Dasatinib Form BG 40 mg DAS (Form A21)+1 ml MIPK heating till 50° C. with 0.5° C./min heating rate, slurry on 50° C. during 4 hours, cooling to 25° C. with 0.1° C./min cooling rate, slurry during 3 days on 25° C. and evaporation of the solvent in the hood during 2 days, then drying in oven on 55° C. overnight.

Example 79

Procedure for the preparation of Dasatinib Form BJ 40 mg DAS (Form A21)+1 ml monochlorobenzene heating till 50° C. with 0.5° C./min heating rate, slurry on 50° C. during 4 hours, cooling to 25° C. with 0.1° C./min cooling rate, slurry during 3 days on 25° C. and evaporation of the solvent in the hood during 2 days.

Example 79a Procedure for the preparation of Dasatinib Form BB

Dasatinib form BJ obtained by example 79 was dried in a bottle in a conventional oven overnight on 55° C. The obtained sample was analyzed by XRD and found to be Form BB.

Example 80

Preparation of a pharmaceutical formulation of Dasatinib form A3

Dasatinib form A3, having the main PXRD peaks at 6.0, 11.9, 12.0, 14.9, 17.9, 18.3, 18.8, 21.4, 22.9, 24.2 and 24.7±0.2 degrees two-theta, and all the components presented in the below table were weighed together and blended.

| Component | Weight (mg) |
| --- | --- |
| Dasatinib Form A3 | 70 |
| Lactose monohydrate | 100 |
| Magnesium stearate | 5 |
| Microcrystalline celulose | 50 |
| Hydroxypropylmethyl celulose | 50 |
| Total weight | 275 |

The above blend was pressed in order to form a tablet which was then analyzed by PXRD providing the following main PXRD peaks: 6.0, 11.9, 14.9, 17.9, 18.3, 24.2 and 24.7±0.2 belonging to form A3.

Example 81

Procedure for the preparation of Dasatinib Form B

Dasatinib Form C (1 g) and 25 ml of methanol were mixed and the blend was gradually heated up to 65° C. during 1 hour. The obtained opalescent solution was kept at 65° C. for 1 hour. Then the solution was gradually cooled down to 5° C.

during 1 hour. The product was filtered off, washed with methanol and dried at 55° C. overnight.

Example 82

Preparation of a Pharmaceutical Formulation of Dasatinib Amorphous

Dasatinib amorphous and all the components presented in the below table are weighed together and blended.

| Component | Weight (mg) |
| --- | --- |
| Dasatinib amorphous | 70 |
| Lactose monohydrate | 100 |
| Magnesium stearate | 5 |
| Microcrystalline celulose | 50 |
| Hydroxypropylmethyl celulose | 50 |
| Total weight | 275 |

The above blend is pressed in order to form a tablet which is then analyzed by PXRD to provide amorphous phase with peaks of excipients.

Example 83

Preparation of a Pharmaceutical Formulation of Dasatinib Form B

Dasatinib form B, having the main PXRD peaks at 7.2, 11.9, 14.4, 16.5, 17.3, 19.1, 20.8, 22.4, 23.8, 25.3 and 29.1±0.2 degrees two-theta, and all the components presented in the below table were weighed together and blended.

| Component | Weight (mg) |
| --- | --- |
| Dasatinib Form B | 70 |
| Lactose monohydrate | 100 |
| Magnesium stearate | 5 |
| Microcrystalline celulose | 50 |
| Hydroxypropylmethyl celulose | 50 |
| Total weight | 275 |

The above blend was pressed in order to form a tablet which was then analyzed by PXRD providing main PXRD peaks 7.2 and 14.4 degrees two-theta.

Example 84

Preparation of a Pharmaceutical Formulation of Dasatinib Form C

Dasatinib form C having the main PXRD peaks at 6.1, 11.8, 15.1, 16.6, 18.2, 19.3, 20.8, 21.6, 23.0, 23.8, 24.3, 24.8 and 25.5±0.2 degrees 2-theta, and all the components presented in the below table are weighed together and blended.

| Component | Weight (mg) |
| --- | --- |
| Dasatinib Form C | 70 |
| Lactose monohydrate | 100 |
| Magnesium stearate | 5 |
| Microcrystalline celulose | 50 |
| Hydroxypropylmethyl celulose | 50 |
| Total weight | 275 |

The above blend is pressed in order to form a tablet which is then analyzed by PXRD to provide main PXRD peaks 6.1, 11.8, 15.1, 18.2 and 24.3 degrees two-theta.

Example 85

Preparation of a pharmaceutical formulation of Dasatinib form A21

Dasatinib form A21 having the main PXRD peaks at 6.0, 11.9, 15.1, 18.2, 20.8, 23.9, 24.3 and 25.5±0.2 degrees 2-theta, and all the components presented in the below table were weighed together and blended.

| Component | Weight (mg) |
| --- | --- |
| Dasatinib Form A21 | 70 |
| Lactose monohydrate | 100 |
| Magnesium stearate | 5 |
| Microcrystalline celulose | 50 |
| Hydroxypropylmethyl celulose | 50 |
| Total weight | 275 |

The above blend was pressed in order to form a tablet which was then analyzed by PXRD providing main PXRD peaks 6.0, 11.9, 15.1, 18.2 and 24.3 degrees two-theta.

Example 86

Procedure for the preparation of Dasatinib Form BL

Crude dasatinib form A21(240 mg) was dissolved in glycerol formal (1.25 ml) by heating to 130° C. for 1 min. The solution was allowed to cool spontaneously to 20° C. within about 20 min and than the sample was allowed to stand at 20° C. for additional 20 min. Crystals formed were recovered by filtration, washed by TBME (15 ml) and dried on air for 1 h.

Example 87

Procedure for the preparation of Dasatinib Form N-6

Dasatinib (form P) was dried at 200° C. under nitrogen for 2 hours.

Example 88

Procedure for the preparation of Dasatinib Form N-6

Dasatinib (200 mg, form A3) was heated on oil bath gradually up to 208° C. at final 0.7 Pa for about 15 min. None sublimation was observed. MS proved that the sample was pure dasatinib (without any chemical change).

Example 89

Procedure for the preparation of Dasatinib Form BM

Suspension 30 mg of Dasatinib (form C) in MeOH (1 ml) was dissolved by heating at 64° C. for 30 minutes and then the temperature was slashed down to 0° C. during 1-2 minutes. Crystalline phase was created immediately after the temperature drop-off. The solid was separated by filtration and dried up on filter under stream of N2.

Example 90

Procedure for the preparation of Dasatinib Form BM

Suspension 40 mg Dasatinib (form C) at 1 ml MeOH was cooled from R.T. to (−15° C.) during 5 min. Then heating to 65° C. during 170 min., 10 min. keeping 65° C. and then cooling to (−15° C.) during 170 min. Filtration under N2.

Example 91

Conversion of form N6 to form B

Dasatinib (form N-6, 75 mg) was put into vial and 1 ml of methanol was added. The slurry was then left at 0° C. for 2 days. The solid phase was filtered off and left to dry on air. The sample was analyzed by PXRD and provided form N-6 containing about 10% of form B.

Example 92

Conversion of form N6 to form B

Dasatinib (form N-6, 75 mg) was put into vial and 1 ml of methanol was added. The slurry was then left at 20° C. for 2 days respectively. The solid phase was filtered off and left to dry on air. The sample was analyzed by PXRD and provided form N-6 containing about 1% of form B.

The invention claimed is:

1. An isopropyl alcohol solvate of dasatinib characterized by data selected from a group consisting of: a powder x-ray diffraction pattern having any three peaks selected from the group consisting of: 6.0, 11.9, 12.0, 14.9, 17.9, 18.3, 18.8, 21.4, 22.9, 24.2 and 24.7±0.2 degrees 2-theta, a powder x-ray diffraction pattern as depicted in FIG. 18, a solid-state $^{13}$C NMR spectrum having signals at 139.2 and 127.6±0.2 ppm; a solid-state $^{13}$C NMR spectrum having chemical shift differences between the signal exhibiting the lowest chemical shift and another in the chemical shift range of 100 to 180 ppm of 14.2 and 2.6±0.1 ppm; and a unit cell with the following parameters as determined by crystal structure determination using synchrotron powder diffraction data:

| Cell dimensions | |
|---|---|
| Cell length a | 14.9942(5) Å |
| Cell length b | 8.45434(22) Å |
| Cell length c | 22.6228(16) Å |
| Cell angle alpha | 90.0° |
| Cell angle beta | 95.890(4)° |
| Cell angle gamma | 90.0° |
| Cell volume | 2852.67(21) Å$^3$ |
| Symmetry cell setting | monoclinic |
| Symmetry space group name | P 2$_1$/c | a powder x-ray diffraction pattern and calculated powder x-ray diffraction pattern as depicted in FIG. 96, and combinations thereof.

2. The isopropyl alcohol solvate of dasatinib of claim 1, characterized by the powder x-ray diffraction pattern having any three peaks selected from the group consisting of: 6.0, 11.9, 12.0, 14.9, 17.9, 18.3, 18.8, 21.4, 22.9, 24.2 and 24.7±0.2 degrees 2-theta.

3. The isopropyl alcohol solvate of dasatinib of claim 1, characterized by a powder x-ray diffraction pattern as depicted in FIG. 18.

4. The isopropyl alcohol solvate of dasatinib of claim 1, characterized by a solid-state $^{13}$C NMR spectrum having signals at 139.2 and 127.6±0.2 ppm.

5. The isopropyl alcohol solvate of dasatinib of claim 1, characterized by a solid-state $^{13}$C NMR spectrum having chemical shift differences between the signal exhibiting the lowest chemical shift and another in the chemical shift range of 100 to 180 ppm of 14.2 and 2.6±0.1 ppm.

6. The isopropyl alcohol solvate of dasatinib of claim 2, characterized by a powder x-ray diffraction pattern having any five peaks selected from the group consisting of 6.0, 11.9, 12.0, 14.9, 17.9, 18.3, 18.8, 21.4, 22.9, 24.2 and 24.7±0.2 degrees 2-theta.

7. The isopropyl alcohol solvate of dasatinib of claim 2, characterized by a powder x-ray diffraction pattern having peaks at 6.0 and 17.9±0.2 degrees 2-theta and any three peaks at positions selected from the group consisting of: 11.9, 14.9, 21.4, 24.2 and 24.7±0.2 degrees 2-theta.

8. The isopropyl alcohol solvate of dasatinib of claim 2, further characterized by data selected from the group consisting of: a powder x-ray diffraction pattern with peaks at 6.0, 11.9, 12.0, 14.9, 17.9 and 18.3±0.2 degrees 2-theta and a powder x-ray diffraction pattern with peaks at 11.9, 12.0, 21.4, 22.9 and 24.7±0.2 degrees 2-theta.

9. The isopropyl alcohol solvate of dasatinib of claim 1, further characterized by a content of isopropyl alcohol of about 9% to about 13% by weight.

10. The isopropyl alcohol solvate of dasatinib of claim 1, having less than about 15% by weight of crystalline dasatinib forms: N-6 characterized by a powder x-ray diffraction pattern having peaks at 6.9, 12.4, 13.2, 13.8, 16.8, 17.2, 21.1, 24.4, 24.9 and 27.8±0.2 degrees 2-theta, and H1-7 characterized by a powder x-ray diffraction pattern having peaks at 4.6, 9.2, 11.2, 13.8, 15.2, 17.9, 19.5, 23.1, 23.6, 25.9 and 28.0±0.2 degrees 2-theta.

11. A formulation comprising the isopropyl alcohol solvate of dasatinib of claim 1 and at least one pharmaceutically acceptable excipient.

12. A pharmaceutical composition comprising the isopropyl alcohol solvate of dasatinib according to claim 1, and at least one pharmaceutically acceptable excipient.

13. A method for preparing an isopropyl alcohol solvate of dasatinib characterized by data selected from a group consisting of: a powder x-ray diffraction pattern having any three peaks selected from the group consisting of: 6.0, 11.9, 12.0, 14.9, 17.9, 18.3, 18.8, 21.4, 22.9, 24.2 and 24.7±0.2 degrees 2-theta, a powder x-ray diffraction pattern as depicted in FIG. 18, a solid-state $^{13}$C NMR spectrum having signals at 139.2 and 127.6±0.2 ppm; a solid-state $^{13}$C NMR spectrum having chemical shift differences between the signal exhibiting the lowest chemical shift and another in the chemical shift range of 100 to 180 ppm of 14.2 and 2.6±0.1 ppm; and a unit cell with the following parameters as determined by crystal structure determination using synchrotron powder diffraction data:

| Cell dimensions: | |
|---|---|
| Cell length a | 14.9942(5) Å |
| Cell length b | 8.45434(22) Å |
| Cell length c | 22.6228(16) Å |
| Cell angle alpha | 90.0° |
| Cell angle beta | 95.890(4)° |
| Cell angle gamma | 90.0° |
| Cell volume | 2852.67(21) Å$^3$ |
| Symmetry cell setting | monoclinic |
| Symmetry space group name | P 2$_1$/c | a powder x-ray diffraction pattern and calculated powder x-ray diffraction pattern as depicted in FIG. 96, and combinations thereof, said method comprising crystallizing dasatinib from a mixture of isopropyl alcohol and water.

14. The method of claim 13, wherein the crystallization comprises providing a solution of dasatinib in a mixture of isopropyl alcohol and water, and precipitating the isopropyl alcohol solvate of dasatinib to obtain a suspension.

15. The method of claim 14, wherein the solution is provided by combining dasatinib, isopropyl alcohol and water, and heating the combination.

16. The method of claim 15, wherein the heating is to about reflux temperature.

17. The method of claim 14, wherein the precipitation is performed by cooling the solution 18. The method of claim 17, wherein the cooling is to a temperature of about 20° C. to about 0° C.

19. The method of claim 13, further comprising recovering the isopropyl alcohol solvate of dasatinib 20. A process for preparing a pharmaceutical composition comprising combining the dasatinib of claim 1, and at least one pharmaceutically acceptable excipient.

\* \* \* \* \*